US012433263B2

(12) United States Patent
Prather et al.

(10) Patent No.: US 12,433,263 B2
(45) **Date of Patent: *Oct. 7, 2025**

(54) METHODS FOR PROTECTING PORCINE FETUSES FROM INFECTION WITH PORCINE REPRODUCTIVE AND RESPIRATORY SYNDROME VIRUS (PRRSV)

(71) Applicant: The Curators of the University of Missouri, Columbia, MO (US)

(72) Inventors: Randall S. Prather, Rocheport, MO (US); Kevin D. Wells, Columbia, MO (US); Kristin M. Whitworth, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 895 days.

This patent is subject to a terminal disclaimer.

(21) Appl. No.: 17/490,765

(22) Filed: Sep. 30, 2021

(65) Prior Publication Data

US 2022/0015340 A1 Jan. 20, 2022

Related U.S. Application Data

(63) Continuation of application No. 16/386,901, filed on Apr. 17, 2019, now Pat. No. 11,160,260.

(60) Provisional application No. 62/658,740, filed on Apr. 17, 2018.

(51) Int. Cl.

| | |
|---|---|
| ***A01K 67/0276*** | (2024.01) |
| ***A01K 67/02*** | (2006.01) |
| ***C07K 14/705*** | (2006.01) |
| ***C12N 9/22*** | (2006.01) |
| ***C12N 15/11*** | (2006.01) |

(52) U.S. Cl.

CPC .......... *A01K 67/0276* (2013.01); *A01K 67/02* (2013.01); *C07K 14/70596* (2013.01); *C12N 9/22* (2013.01); *C12N 15/11* (2013.01); *A01K 2217/075* (2013.01); *A01K 2227/108* (2013.01); *C12N 2310/20* (2017.05); *C12N 2800/80* (2013.01)

(58) Field of Classification Search

CPC ................ A01K 67/0276; A01K 67/02; A01K 2217/075; A01K 2227/108; C07K 14/70596; C12N 9/22; C12N 15/11; C12N 2310/20; C12N 2800/20

USPC ..................................... 800/17, 22; 435/455

See application file for complete search history.

(56) References Cited

U.S. PATENT DOCUMENTS

| | | | | |
|---|---|---|---|---|
| 5,945,577 | A | 8/1999 | Stice et al. | |
| 6,211,429 | B1 | 4/2001 | Machaty et al. | |
| 9,820,475 | B2 * | 11/2017 | Prather | A01K 67/0276 |
| 10,080,353 | B2 * | 9/2018 | Prather | A01K 67/0276 |
| 10,091,975 | B2 * | 10/2018 | Prather | C12N 15/8509 |
| 10,405,526 | B2 * | 9/2019 | Prather | C12N 15/8509 |
| 10,827,730 | B2 * | 11/2020 | Prather | C07K 14/70596 |
| 11,019,809 | B2 * | 6/2021 | Prather | A01K 67/0276 |
| 11,160,260 | B2 * | 11/2021 | Prather | C12N 15/11 |
| 2003/0237106 | A1 | 12/2003 | Gorczynski | |
| 2005/0120400 | A1 | 6/2005 | Day et al. | |
| 2005/0260176 | A1 | 11/2005 | Ayares et al. | |
| 2009/0104147 | A1 | 4/2009 | Delputte et al. | |
| 2010/0158947 | A1 | 6/2010 | Delputte et al. | |
| 2011/0016543 | A1 | 1/2011 | Weinstein et al. | |
| 2011/0016546 | A1 | 1/2011 | Bedell et al. | |
| 2011/0038841 | A1 | 2/2011 | Ayares | |
| 2012/0180141 | A1 | 7/2012 | Welsh et al. | |
| 2013/0309263 | A1 | 11/2013 | Calvert et al. | |
| 2014/0096275 | A1 | 4/2014 | Prather | |
| 2016/0046963 | A1 | 2/2016 | May et al. | |
| 2017/0035035 | A1 * | 2/2017 | Prather | A01K 67/0276 |
| 2018/0027783 | A1 | 2/2018 | Prather et al. | |
| 2019/0082662 | A1 | 3/2019 | Prather et al. | |
| 2020/0137992 | A1 | 5/2020 | Prather et al. | |

FOREIGN PATENT DOCUMENTS

| | | | |
|---|---|---|---|
| CN | 104593422 | A | 5/2015 |
| JP | 09-298981 | A | 12/2009 |
| KR | 20140034229 | A | 3/2014 |
| KR | 20180033548 | A | 4/2018 |
| WO | 96/07732 | A1 | 3/1996 |
| WO | 97/07668 | A1 | 3/1997 |
| WO | 97/07669 | A1 | 3/1997 |

(Continued)

OTHER PUBLICATIONS

Prather et al. (Oct. 17, 2017) Scientific Reports, vol. 7:1331.doi. 10.1038/s41598-017-13794-2, pp. 1-5.*
Karniychuk et al. (2013) vol. 44(95), pp. 1-14.*
Whitworth et al. (2016) Nat. Biotech., vol. 34(1), 20-22; dx.doi. org/10.1038/nbt.3434.*
Salamone et al. (2017) Reproduction, vol. 154, F111-F124.*
Shimozawa, et al., "Abnormalities in Cloned Mice Are Not Transmitted to the Progeny", Genesis, 2002, pp. J03-J207, vol. 34.
Shi, et al., "Phylogeny-based evolutionary, demographical, and geographical dissection of North American type 2 porcine reproductive and respiratory syndrome viruses", Journal of Virology, 2010, vol. 84, pp. 8700-8711.

(Continued)

*Primary Examiner* — Anne S Wehbe
(74) *Attorney, Agent, or Firm* — Steven T. Kazmierski; Sandberg Phoenix & von Gontard, PC

(57) ABSTRACT

Methods for protecting porcine fetuses from infection with Porcine Reproductive and Respiratory Syndrome Virus (PRRSV). The methods comprise breeding a female porcine animal with a male porcine animal. The female porcine animal comprises modified chromosomal sequences in both alleles of its CD163 gene, wherein the modified chromosomal sequences reduce the susceptibility of the female porcine animal to infection by PRRSV, as compared to the susceptibility to infection by PRRSV of a female porcine animal that does not comprise any modified chromosomal sequences in the alleles of its CD163 gene. The male porcine animal comprises at least one wild-type CD163 allele.

20 Claims, 29 Drawing Sheets

Specification includes a Sequence Listing.

(56) References Cited

FOREIGN PATENT DOCUMENTS

| | | | |
|---|---|---|---|
| WO | 2005/104835 | A2 | 11/2005 |
| WO | 2008/106986 | A1 | 9/2008 |
| WO | 2012/158828 | A1 | 11/2012 |
| WO | 2015/011483 | A1 | 1/2015 |
| WO | 2015/153647 | A1 | 10/2015 |
| WO | 2016/110214 | A1 | 7/2016 |
| WO | 2017/023570 | A1 | 2/2017 |
| WO | 2017023337 | A1 | 2/2017 |

OTHER PUBLICATIONS

Smit, et al., RepeatMasker Open-3.0. 1996-2010. Current Version: open-4.0.5 (RMLib: Jan. 31, 2014 and Dfam: 1.2). http:// www. repeatmasker.org&gt. CD163: accessed Jul. 25, 2014; CD1D: accessed Aug. 27, 2013.
Snijder, et al., "The Molecular Biology of Arteriviruses [Review]", Journal of General Virology, 1998, pp. 961-979, vol. 79, Part 5.
Soares, et al., "Heme Oxygenase-1: From Biology to Therapeutic Potential, Trends in Molecular Medicine", 2009, pp. 50-58, vol. 15, No. 2.
Stein, et al., "Interleukin 4 Potently Enhances Murine Macrophage Mannose Receptor Activity: A Marker of Alternative Immunologic Macrophage Activation", The Journal of Experimental Medicine, Jul. 1992, pp. 287-292, vol. 176, No. 1.
Stephen, et al., "Scavenger Receptors and Their Potential as Therapeutic Targets in the Treatment of Cardiovascular Disease", International Journal of Hypertension, 2010, 21 pages, vol. 2010, Article ID 646929.
Stephenson, et al., Multiplex Serology for Common Viral Infections in Feral Pigs (*Sus scrota*) in Hawaii Between 2007 and 2010, Journal of Wildlife, 2015, pp. 239-243, vol. 51, No. 1.
Suarez, et al., "Open Reading Frame 5 of Porcine Reproductive and Respiratory Syndrome Virus as a Cause of Virus-Induced Apoptosis", Journal of Virology, May 1996, pp. 2876-2882, vol. 70, No. 5.
Sulahian, et al., "Human Monocytes Express CD163, Which is Upregulated by IL-10 and Identifical to p155", Cytokine, Sep. 2000, pp. 1312-1321, vol. 12, No. 9.
Sur, et al., "In Vivo Detection of Porcine Reproductive and Respiratory Syndrome Virus RNA by in Situ Hybridization at Different Times Postinfection", Journal of Clinical Microbiology, Sep. 1996, pp. 2280-2286, vol. 34, No. 9.
Sur, et al.,"Porcine Reproductive and Respiratory Syndrome Virus Replicates in Testicular Germ Cells, Alters Spermatogenesis, and Induces Germ Cell Death by Apoptosis", Journal of Virology, Dec. 1997, pp. 9170-9179, vol. 71, No. 12.
Tait-Burkard, et al., "Livestock 2.0—Genome Editing for Fitter, Healthier, and More Productive Farmed Animals", Genome Biology, 2018, pp. 1-11, vol. 19, No. 1.
Terns, et al., "CRISPR-Based Adaptive Immune Systems, Current Opinion in Microbiology", Jun. 2011, p. 321-327, vol. 14, No. 3.
Tian, et al.,"Emergence of fatal PRRSV variants: unparalleled outbreaks of atypical PRRS in China and molecular dissection of the unique hallmark", PLoS One, 2007, vol. 2, p. e526.
Trible, et al., "Recognition of the Different Structural Forms of the Capsid Protein Determines the Outcome following Infection with Porcine Circovirus Type 2, Journal of Virology", Dec. 2012, pp. 13508-13514, vol. 36, No. 24.
U.S. Department of Agriculture and U.S. Department of Health and Human Services, Dietary Guidelines for Americans J010, 7th Edition, 112 pages.
Vadori, et al., "The Immunological Barriers to Xenotransplantation, Tissue Antigen"s, 2015, pp. 239-253, vol. 86, No. 4.
Van Breedam, et al., "Porcine Reproductive and Respiratory Syndrome Virus Entry into the Porcine Macrophage", Journal of General Virology, 2010, pp. 1659-1667, vol. 91, Part 7.
Van Breedam, et al., "The M/GP{5) Glycoprotein Complex of Porcine Reproductive and Respiratory Syndrome Virus Binds the Sialoadhesin Receptor in a Sialic Acid-Dependent Manner", PLoS Pathogens, 2010, e1000730, pp. 1-11, vol. 6, No. 1.
Van Den Heuvel, et al., "Regulation of CD163 on Human Macrophages: Cross-linking of CD163 Induces Signaling and Activation", Journal of Leukocyte Biology, Nov. 1999, pp. 858-866, vol. 66, No. 5.
Van Den Hoff, et al., "Electroporation in 'Intracellular' Buffer Increases Cell Survival", Nucleic Acids Research, 1992, p. 2902, vol. 20, No. 11.
Yoshioka, et al., "Birth of Piglets Derived from Porcine Zygotes Cultured in a Chemically Defined Medium", Biology of Reproduction, 2002, pp. 112-119, vol. 66.
Van Gorp, et al., Identification of the CD163 Protein Domains Involved in Infection of the Porcine Reproductive and Respiratory Syndrome Virus, Journal of Virology, Mar. 2010, pp. 3101-3105, vol. 84, No. 6.
Van Gorp, et al., Sialoadhesin and CD163 Join Forces During Entry of the Porcine Reproductive and Respiratory Syndrome Virus, Journal of General Virology, 2008, pp. 2943-2953, vol. 89, Part 12.
Van Gorp, et al., Scavenger Receptor CD163, A Jack-of-all-trades and Potential Target for Cell-Directed Therapy, Molecular Immunology, 2010, pp. 1650-1660, vol. 47, Nos. 7-8.
Vanderheijden, et al., "Involvement of Sialoadhesin in Entry of Porcine Reproductive and Respiratory Syndrome Virus into Porcine Alveolar Macrophages", Journal of Virology, Aug. 2003, pp. 8207-8215, vol. 77, No. 15.
Vinson, et al., "Characterization of the Sialic Acid-Binding Site in Sialoadhesin by Site-Directed Mutagenesis, Journal of Biological Chemistry", 1996, pp. 9267-9272, vol. 271, No. 16.
Walters, et al., "Advancing Swine Models for Human Health and Diseases", Missouri Medicine, May/Jun. 2013, pp. 212-215, vol. 110, No. 3.
Wakchaure, et al., "Transgenic Animals: A Review on its Various Dimensions and Applications in Animal Biotechnolog"y; International Journal of Emerging Technology and Advanced Engineering; 2015, vol. 5, No. 11, pp. 210-213.
Wang, et al., "One-Step Generation of Mice Carrying Mutations in Multiple Genes by CRISPR/Cas-Mediated Benome Engineering", Cell, 2013, pp. 910-918, vol. 153, No. 4.
Watanabe, et al., "Knockout of Exogenous EGFP Gene in Porcine Somatic Cells Using Zinc-finger Nucleases, Biochemical and Biophysical Research Communications", Nov. 2010, pp. 14-18, vol. 402, Issue 1.
Welch, et al., "A Brief Review of CD163 and its Role in PRRSV Infection, Virus Research", 2010, pp. 98-103, vol. 154.
Wells, et al.,"Use of the CRISPR/Cas9 system to produce genetically engineered pigs from in vitro-derived oocytes and embryos", Biol Reprod, 2014, vol. 91,p. 78.
Wells, et al., "Replacement of Porcine CD163 Scavenger Receptor Cysteine-Rich Domain 5 with a CD163-like Homolog Confers Restistance of Pigs to Genotype 1 but Not Genotype 2 Porcine Reproductive and Respiratory Syndrome Virus", Journal of Virology, Jan. 2017, pp. 1-11, vol. 91, Issue 2, Article e01521-16.
Wensvoort, et al., "Mystery Swine Disease in the Netherlands: The Isolation of Lelystad Virus", Veterinary Quarterly, 1991, pp. 121-130, vol. 13.
Whitworth, et al., "Gene-edited Pigs are Protected From Porcine Reproductive and Respiratory Syndrome Virus, Nature Biotechnology", Jan. 2016, pp. 20-22, vol. 34, No. 1.
Whitworth, et al., "Disruption the Sialoadhesin and CD163 Genes to Create Pigs Resistant to PRRSV Infectivity", Abstract, Swine in Biomedical Research in Chicago, Illinois, Jul. 17-19, 2011, S1-25, pp. 39-40.
Whitworth, et al., "Method of Oocyte Activation Affects Cloning Efficiency in Pigs, Molecular Reproduction and Development", May 2009, pp. 490-500, vol. 76, No. 5.
Whitworth, et al., "Activation Method Does Not Alter Abnormal Placental Gene Expression and Development in Cloned Pigs", Molecular Reproduction and Development, 2010, pp. 1016-1030, vol. 77, No. 12.
Whitworth, et al., "Pigs Resistant to PRRSV Infectivity", Poster Presented at Swine in Biomedical Research n Chicago, Illinois, Jul. 18, 2011, 1 page.

(56) References Cited

OTHER PUBLICATIONS

Whitworth, et al., "Scriptaid Corrects Gene Expression of a Few Aberrantly Reprogrammed Transcripts in Nuclear Transfer Pig Blastocyst Stage Embryos", Cellular Reprogramming, 2011, pp. 191-204, vol. 13, No. 3.
Whitworth, et al.,Pigs Resistant to PRRSV Infectivity, University of Missouri Technology Transfer Showcase, 2012, 1 page.
Niu, et al., "Generation of Gene-Modified Cynomolgus Monkey via Cas9/RNA-Modified Gene Targeting in One-Cell Embryos", Cell, Feb. 13, 2014, pp. 836-843, vol. 156.
Nussbaum, et al., "Differential Effects of Protein Synthesis Inhibitors on Porcine Oocyte Activation", Molecular Reproduction and Development, 1995, pp. 70-75, vol. 41.
Oetke, et al., "Sialoadhesin-Deficient Mice Exhibit Subtle Changes in B- and T-Cell Populations and Reduced Immunoglobulin M Levels", Molecular and Cellular Biology, Feb. 2006, pp. 1549-1557, vol. 26, No. 4.
Schurgers, et al., "Discrepancy Between the In Vitro and In Vivo Effects of Murine Mesenchymal Stem Cells on T-cell Proliferation and Collagen-Induced Arthritis, Arthritis Research & Therapy, 2010", pp. 1-11, vol. 12, No. 1.
Paris, et al., "Equine embryos and embryonic stem cells: Defining reliable markers of pluripotency"; Theriogenology, 2010, vol. 74, pp. 516-524.
Park, et al., "Developmental Potential of Porcine Nuclear Transfer Embryos Derived from Transgenic Fetal Fibroblasts Infected with the Gene for the Green Fluorescent Protein: Comparison of Different Fusion/Activation Conditions", Biology of Reproduction, 2001, pp. 1681-1685, vol. 65, No. 6.
Park, et al., "Production of Nuclear Transfer-Derived Swine That Express the Enhanced Green Fluorescent Protein", Animal Biotechnology, 2001, pp. 173-181, vol. 12.
Patience, et al., Nutrition of the Breeding Herd, Swine Nutrition Guide, 1989, Chapter 6, pp. 149-171, Prairie Swine Centre, University of Saskatchewan, Saskatoon, Saskatchewan, Canada.
Patton, et al., "Modulation of CD163 Receptor Expression and Replication of Porcine Reproductive and Respiratory Syndrome Virus in Porcine Macrophages", Virus Research, 2009, pp. 161-171, vol. 140.
Plagemann, et al., "Lactate Dehydrogenase-Elevating Virus and Related Viruses", in Fields Virology, 3rd Edition, Fields, Bet al., ed, 1996, Chapter 36, pp. 1105-1120.
Popescu, et al., "Genetically Edited Pigs Lacking CD163 Show No Resistance Following Infection with the Africar Swine Fever Virus Isolate", Georgia Jan. 2007, Virology, 2017, pp. 102-106, vol. 501.
Prather, et al., "Genetic Engineering Alveolar Macrophages for Host Resistance to PRRSV, Veterinary Microbiology", 2017, pp. 124-129, vol. 209.
Prather, et al., "Knockout of Maternal CD163 Protects Fetuses from Infection with Porcine Reproductive and Respiratory Syndrome Virus (PRRSV)", Scientific Reports, 2017, pp. 1-5, vol. 7, No. 1, Article 13371.
Prather, et al., Genetic Engineering of Pigs for PRRSV Resistance, National Swine Improvement B Federation—International PRRS Symposium, Marriott Kansas City, Kansas City, Missouri, Nov. 29-30, 2012, 43 pages.
Prather, et al., An Intact Sialoadhesin (Sn/SIGLEC1/CD169) Is Not Required for Attachment/Internalization of the Porcine Reproductive and Respiratory Syndrome Virus, Journal of Virology, Sep. 2013, pp. 9538-9546, vol. 87, No. 17.
Prather, et al., Genetic Engineering of Pigs for PRRSV Resistance, North American Porcine Reproductive and Respiratory Syndrome Symposium, Chicago, Illinois, Dec. 6, 2014, 55 pages.
Prather, et al., Genetic Engineering the Pig to Better Understand PRRSv Infection, 2014 North American PRRS Symposium, Final Program, Chicago, Illinois, Dec. 5-6, 2014, p. 33.
Prather, et al., Genetic Engineering for Profitable Pork Production: Is Resistance to PRRSv Possible? Virginia Polytechnic Institute, Blacksburg, Virginia, May 1, 2015, 70 pages.
Prather, et al., CRISPR/Cas9-Mediated Genetic Engineering: Is CD163 an Entry Mediator for PRRSv Infection? International Plant and Animal Genome Conference XXIII, Abstract, Jan. 9-15, 2015, 1 page.
Provost, et al., "Identification of a New Cell Line Permissive to Porcine Reproductive and Respiratory Syndrome 9 Virus Infection and Replication Which is Phenotypically Distinct from MARC-145 Cell Line", Virology Journal, 2012, 14 pages, vol. 9.
Reed, et al.,"A Simple Method of Estimating Fifty Percent Endpoints", The American Journal of Hygiene, May 1938, pp. 493-497, vol. 27, No. 3.
Shanmukhappa, et al., "Role of CD151, A Tetraspanin, in Porcine Reproductive and Respiratory Syndrome Virus Infection", Virology Journal, 2007, pp. 1-12, vol. 4.
Rezaee, et al., "The Importance of Translatability in Drug Discovery", Expert Opinion on Drug Discovery, 2017, pp. 237-239, vol. 12, No. 3.
Ritter, et al., "The Scavenger Receptor CD163: Regulation, Promoter Structure and Genomic Organization", Pathobiology, 1999, pp. 257-261, vol. 67, Nos. 5-6.
Ritter, et al., "Genomic Organization and Chromosomal Localization of the Human CD163 (M130) Gene: A 20 Member of the Scavenger Receptor Cysteine-Rich Superfamily", Biochemical and Biophysical Research Communications, 1999, pp. 466-474, vol. 260, No. 2.
Robl, et al., "Nuclear Transplantation in Bovine Embryos", Journal of Animal Science, Feb. 1987, pp. 542-647, vol. 64, No. 2.
Ropp, et al., "Characterization of Emerging European-Like Porcine Reproductive and Respiratory Syndrome Virus Isolates in the United States", Journal of Virology, Apr. 2004, pp. 3684-3703, vol. 78, No. 7.
Ross, et al., "Optimization of Square-wave Electroporation for Transfection of Porcine Fetal Fibroblasts", Transgenic Research, Aug. 2010, pp. 611-620, vol. 19, No. 4.
Rowland, et al., "Control of Porcine Reproductive and Respiratory Syndrome (PRRS) Through Genetic Improvements in Disease Resistance and Tolerance, Frontiers in Genetics", Dec. 2012, pp. 1-6, vol. 3, article 260.
Rowland, et al., The "Evolution of Porcine Reproductive and Respiratory Syndrome Virus: Quasispecies and Emergence of a Virus Subpopulation During Infection of Pigs with VR-2332", Virology, 1999, pp. 262-266, vol. 259.
Rowland, et al., "Lymphotropism of porcine reproductive and respiratory syndrome virus replication during persistent infection of pigs originally exposed to virus in utero", Veterinary Microbiology 2003, vol. 96, pp. 219-235.
Rowland, et al.,"The interaction between PRRSV and the late gestation pig fetus", Virus Research, 20210, vol. 154, pp. 114-122.
Saeidnia, et al., "From In Vitro Experiments to In Vivo and Clinical Studies; Pros and Cons, Current Drug Discovery Technologies", 2015, pp. 218-224, vol. 12, No. 4.
Sanchez, et al., "The porcine 2A10 antigen is homologous to human CD163 and related to macrophage differentiation", Journal of Immunology, 1999, vol. 162, pp. 5230-5237.
Sanchez-Torres, et al., "Expression of Porcine CD163 on Monocytes/Macrophages Correlates with Permissiveness to African Swine Fever Infection, Archives of Virology", 2003, pp. 2307-2323, vol. 148, No. 12.
Sangamo BioSciences, Inc., Sangamo BioSciences Announces Efficient Generation of Transgenic Pigs Using Zinc Finger Nuclease (ZFN) Technology, Press Release, Jul. 21, 2011, 2 pages.
Schaer, et al., "Constitutive Endocytosis of CD163 Mediates Hemoglobin-Heme Uptake and Determines the Noninflammatory and Protective Transcriptional Response of Macrophages to Hemoglobin", Circulation Research, 2006, pp. 943-950, vol. 99.
Schaer, et al., "CD163 is the Macrophage Scavenger Receptor for Native and Chemically Modified Hemoglobins in the Absence of Haptoglobin", Blood, Jan. 1, 2006, pp. 373-380, vol. 107, No. 1.
Schaer, et al., "Hemophagocytic Macrophages Constitute a Major Compartment of Heme Oxygenase Expression in Sepsis", European Journal of Haematology, 2006, pp. 432-436, vol. 77.

(56) References Cited

OTHER PUBLICATIONS

Aigner, et al., "Transgenic Pigs as Models for Translational Biomedical Research", Journal of Molecular Medicine, 2010, vol. 88, No. 7, pp. 653-664.
Albina, et al., "Immune Response and Persistance of the Porcine Reproductive and Respiratory Syndrome Virus in Infected Pigs and Farm Units", The Veterinary Record, May 1994, vol. 134, No. 22, pp. 567-573.
Allende, et al., "Porcine Reproductive and Respiratory Syndrome Virus: Description of Persistance in Individual Pigs Upon Experimental Infection", Journal of Virology, Nov. 2000, vol. 74, No. 22, pp. 10834-10837.
Allende, et al., N"orth American and European Porcine Reproductive and Respiratory Syndrome Viruses Differ in Non-Structural Protein Coding Regions"; Journal of General Virology, 1999, vol. 80, pp. 307-315.
American Society for Cell Biology, Small Details Between "In Vivo" and "In Vitro" Studies Make for Big Differences, Science Daily, Dec. 13, 2010, <www.sciencedaily.com/releases/2010/12/101213101804.htm>, 3 pages.
An, et al., "Porcine Reproductive and Respiratory Syndrome Virus Attachment is Mediated by the N-Terminal Domain of the Sialoadhesin Receptor," Veterinary Microbiology, 2010, vol. 143, No. 2-4, pp. 371-378.
Andreyev, et al., "Genetic Variation and Phylogenetic Relationships of 22 Porcine Reproductive and Respiratory Syndrome Virus (Prrsv) Field Strains Based on Sequence Analysis of Open Reading Frame 5"; Archives of Virology, 1997, vol. 142, No., 5, pp. 993-1001.
ATCC 293T (ATCC(R) CRL-3216(TM)), accessed from <htlps://www.atcc.org/Products/AII/CRL-3216.aspx> on Sep. 29, 2016, 2 pages.
Bauer, et al., "Arginine Supplementation in Vitro Increases Procine Embryo Development and Affects mRNA Transcript Expression"; Reproduciton, Fertililty, and Development, 2010, vol. 23, p. 107.
Beaton, et al., "Compound Transgenics: Recombinase-Mediated Gene Stacking", Transgenic Animal Technology, 2014, Chapter 21, Elsevier, pp. 565-578.
Benfield, et al., "Characterization of Swine Infertility and Respiratory Syndrome (SIRS) Virus (Isolate ATCC VR-2332)", Journal of Veterinary Diagnostic Investigation, 1992, vol. 4, pp. 127-133.
Benfield, et al., "Pathogenesis and Persistence of PRRS", Proceedings, Allen D. Leman Swine Conference, 1998, pp. 169-171.
Berg, H., "500-Biological Implications of Electric Field Effects, Part V. Fusion of Blastomeres and Blastocysts of Mouse Embryos", Bioelectrochemistry and Bioenergetics, 1982, vol. 9, pp. 223-228.
Dee, et al., "Elimination of Porcine Reproductive and Respiratory Syndrome Virus Using a Test and Removal Process", The Veterinary Record, 1998, , vol. 143, No. 17, pp. 474-476.
Boddicker, et al., "Genome-wide Association and Genomic Prediction for Host Response to Porcine Reproductive and Respiratory Syndrome Virus Infection", Genetics Selection Evolution, 2014, vol. 46, No. 18, 14-pages.
Bookstein, et al., "Promoter Deletion and Loss of Retinoblastoma Gene Expression in Human Prostate Carcinoma", Proceedings of the National Academy of Sciences of the United States of America, Oct. 1990, , vol. 87, No., 19, pp. 7762-7766.
Borg, et al., "CD1d-lipid-antigen Recognition by the Semi-invariant NKT T-cell Receptor", Nature, Jul. 2007, vol. 448, No. 7149, pp. 44-49.
Brevini, et al., "No shortcuts to pig embryonic stem cells"; Theriogenology, 2010, vol. 74, pp. 544-550.
Brinster, et al., "Factors Affecting the Efficiency of Introducing Foreign DNA Into Mice by Microinjecting Eggs", Proceedings of the National Academy of Sciences of the United States of America, Jul. 1985, vol. 82, No. 13, pp. 1438-4442.
Burkard, et al., "Pigs Lacking the Scavenger Receptor Cysteine-Rich Domain 5 of CD163 Are Resistant to Porcine Reproductive and Respiratory Syndrome Virus 1 Infection", Journal of Virology, 2018, vol. 92, No. 16, 17-pages.
Burkard, et al., "Precision Engineering for PRRSV Resistance in Pigs: Macrophages from Genome Edited Pigs Lacking CD163 SRCR5 Domain are Fully Resistant to Both PRRSV Genotypes While Maintaining Biological Function", PLoS Pathogens, 2017, vol. 13, No. 2, pp. 1-28.
Burlak, et al., "Identification of Human Preformed Antibody Targets in GTKO Pigs, Xenotransplantation", Mar.-Apr. 2012, vol. 19, No. 2, pp. 92-101.
Cafruny, et al., Trojan "Horse macrophages: studies with the murine lactate dehydrogenase-elevating virus and implications for sexually transmitted virus infection". J. Gen. Virol., 1996, vol. 77, No. 12, pp. 3005-3012.
Calvert, et al.,"CD163 Expression Confers Susceptibility to Porcine Reproductive and Respiratory Syndrome Viruses"; Journal of Virology, Jul. 2007, vol. 81, No. 14, pp. 7371-7379.
Carter et al., "Phenotyping of Transgenic Cloned Piglets,' Cloning and Stem Cells", 2002, vol. 4, No. 2, pp. 131-145.
Cao, et al., "Isolation and Culture of Primary Bovine Embryonic Stem Cell Colonies by a Novel Method"; Journal of Experimental Zoology, 2009, vol. 311A, pp. 368-376.
Chin, et al., "The sup(-104)G Nucleotide of the Human CYP21 Gene is Important for CYP21 Transcription Activity and Protein Interaction", Nucleic Acids Research, 1998, vol. 26, No. 8, pp. 1959-1964.
Christianson, et al., "Experimental reproduction of swine infertility and respiratory syndrome in pregnant sows". American Journal of Veterinary Research, 1992, vol. 53, pp. 485-488.
Christopher-Hennings, et al., "Persistence of Porcine Reproductive and Respiratory Syndrome Virus in Serum and Semen of Adult Boars", Journal of Veterinary Diagnostic Investigation, 1995, Vo. 7, No. 4, pp. 456-464.
Christopher-Hennings, et al., "Effects of a Modified-Live Virus Vaccine Against Porcine Reproductive and Respiratory Syndrome in Boars", American Journal of Veterinary Research, 1997, vol. 58, No. 1, pp. 40-45.
Ciotti, et al., "Coding Defect and a TATA Box Mutation at the Bilirubin UDP-Glucuronosyltransferase Gene Cause Crigler-Najjar Type I Disease", Biochimica et Biophysica ACTA, 1998, vol. 1407, pp. 40-50.
Clark, et al., "A future for transgenic livestock; Nature Reviews/Genetics"; Oct. 2003, vol. 4, pp. 825-833.
Cooper, et al., "Modifying the Sugar Icing on the Transplantation Cake, Glycobiology", Jun. 2016, vol. 26, No. 6, pp. 571-581.
Cong, et al.,"Multiplex Genome Engineering Using CRISPR/Cas Systems", Science, 2013, vol. 339, No. 6121, pp. 819-823.
Crocker, et al., "Properties and Distribution of a Lectin-Like Hemagglutinin Differentially Expressed by Murine Stromal Tissue Macrophages", The Journal of Experimental Medicine, 1986, vol. 164, pp. 1862-1875.
Crocker, et al., "Molecular Analysis of Sialoside Binding to Sialoadhesin by NMR and Site-Directed Mutagenesis", Biochemical Journal, 1999, vol. 341 (Part 2), pp. P355-P361.
Dai, et al., "Targeted Disruption of the alpha1 ,3-galactosyltransferase Gene in Cloned Pigs", Nature Biotechnology, Mar. 2002, vol. 20, No. 3, pp. 251-255.
Das, et al., "The Minor Envelope Glycoproteins GP2a and GP4 of Porcine Reproductive and Respiratory Syndrome Virus Interact with the Receptor CD163", Journal of Virology, 2010, vol. 84, pp. 1731-1740.
Delputte, et al., "Effect of Virus-Specific Antibodies on Attachment, Internalization and Infection of Porcine 17 Reproductive and Respiratory Syndrome Virus in Primary Macrophages, Veterinary Immunology and Immunopathology", 2004, vol. 102, No. r 3, pp. 179-188.
Delputte, et al., "Porcine Arterivirus Infection of Alveolar Macrophages is Mediated by Sialic Acid on the Virus, Journal of Virology", 2004, vol. 78, No. 15, pp. 8094-8101.
Delputte, et al., "Porcine Arterivirus Attachment to the Macrophage-Specific Receptor Sialoadhesin is Dependent on the Sialic Acid-Binding Activity of the N-Terminal Immunoglobulin Domain of Sialoadhesin", Journal of Virology, 2007, vol. 81, No. 17, pp. 9546-9550.

(56) References Cited

OTHER PUBLICATIONS

Delputte, et al., "Porcine Sialoadhesin (CD169/Siglec-1) is an Endocytic Receptor that Allows Targeted Delivery of Toxins and Antigens to Macrophages", PLoS One, Feb. 2011, e16827, vol. 6, No. 2, pp. 1-12.
Delputte, et al., "Involvement of the matrix protein in attachment of porcine reproductive and respiratory syndrome virus to a heparin-like receptor on porcine alveolar macrophages". J Virol., 2002, vol. 76, pp. 4312-4320.
Lai, et al., "Alpha-1,3-Galactosyltransferase Knockout Pigs by Nuclear Transfer Cloning", Science, Feb. 2002, pp. 1089-1092, vol. 295, No. 5557.
Lai, et al., "Creating Genetically Modified Pigs by Using Nuclear Transfer", Reproductive Biology and Endocrinology, 2003, pp. 1-6, vol. 1, No. 82.
Lai, et al., "Generation of Cloned Transgenic Pigs Rich in Omega-3 Fatty Acids", Nature Biotechnology, Apr. 2006, pp. 435-436, vol. 24, No. 4.
Lai, et al., "Methods Paper—Production of Cloned Pigs by Using Somatic Cells as Donors", Cloning and Stem Cells, 2003, pp. 233-241, vol. 5, No. 4.
Lai, et al., "A Method for Producing Cloned Pigs by Using Somatic Cells as Donors", Methods in Molecular Biology, J004, pp. 149-163, vol. 254.
Lawson, et al., "Porcine Reproductive and Respiratory Syndrome Virus Infection of Gnotobiotic Pigs: Sites of Virus replication and Co-localization with MAC-387 Staining at 21 Days Post-infection", Virus Research, 1997, pp. 105-113, vol. 51.
Lee, et al., "Engraftment of Human iPS Cells and Allogeneic Porcine Cells into Pigs with Inactivated RAG2 and Accompanying Severe Combined Immunodeficiency", Proceedings of the National Academy of Sciences of the United States of America, 2014, pp. 7260-7265, vol. 111.
Lee, et al., "Piglets Produced from Cloned Blastocysts Cultured In Vitro with GM-CSF", Molecular Reproduction and Development, 2013, pp. 145-154, vol. 80, No. 2.
Li, et al., "Heritable Gene Targeting in the Mouse and Rat Using a CRISPR-Cas System, Nature Biotechnology", pp. 681-683, vol. 31.
Li, et al., "Cloned Transgenic Swine Via In Vitro Production and Cryopreservation, Biology of Reproduction", 2006, pp. 226-230, vol. 75, No. 2.
Li, et al., "Regulation of Human NAD(P)H:Quinone Oxidoreductase Gene", The Journal of Biological Chemistry, 1992, pp. 15097-15104, vol. 267, No. 21.
Lillico, et al., "Live Pigs Produced From Genome Edited Zygotes", Scientific Reports, 2013, pp. 1-4, vol. 3, No. 2847.
Van Gorp, H., et al., "Identification of the CD163 Protein Domains Involved in Infection of the Porcine Reproductive and Respiratory Syndrome Virus," Journal of Virology, Supplemental Material, Mar. 2010, 4 pages, vol. 84, No. 6, Accessed from <http://jvi.asm.org/content/84/6/3101/suppl/DC1>.
Loudianos, et al., "Molecular Characterization of Wilson Disease in the Sardinian Population—Evidence of a rounder Effect, Human Mutation", 1999, pp. 294-303, vol. 14, No. 4, Abstract Only.
Lunney, et al.,"Genetic Control of Host Resistance to Porcine Reproductive and Respiratory Syndrome Virus (PRRSV) Infection", Virus Research, 2010, pp. 161-169, vol. 154.
Machaty, et al., "Complete Activation of Porcine Oocytes Induced by the Sulfhydryl Reagent, Thimerosa", Biology of Reproduction, 1997, pp. 1123-1127, vol. 57, No. 5.
Machaty, et al., "Development of Early Porcine Embryos In Vitro and In Vivo, Biology of Reproduction", 1998, pp. 451-455, vol. 59.
Madsen, et al., "Molecular Characterization of the Haptoglobin-Hemoglobin Receptor CD163", The Journal of Biological Chemistry, Dec. 3, 2004, pp. 51561-51567, vol. 279, No. 49.
Mansour, et al., "Disruption of the Proto-Oncogene int-2 in Mouse Embryo-Derived Stem Cells: A General Strategy for Targeting Mutations to Nonselectable Genes", Nature, 1988, pp. 348-352, vol. 336.
Meng, X. J., et al., "Sequence Comparison of Open Reading Frames 2 to 5 of Low and High Virulence United States Isolates of Porcine Reproductive and Respiratory Syndrome Virus," Journal of General Virology, 1995, pp. 3181-3188, vol. 76, Part 12.
Mayes, et al., "Parthenogenic Activation of Pig Oocytes by Protein Kinase Inhibition, Biology of Reproduction", 1995, pp. 270-275, vol. 53, No. 2.
McGrath, et al., "Nuclear Transplantation in the Mouse Embryo by Microsurgery and Cell Fusion", Science, Jun. 1983, pp. 1300-1302, vol. 220, No. 4603.
Meng, et al., "Heterogeneity of Porcine Reproductive and Respiratory Syndrome Virus: Implications for Current Vaccine Efficacy and Future Vaccine Development [Review]", Veterinary Microbiology, 2000, pp. 309-329, vol. 74, No. 4.
Menon, K. P., et al., "Architecture of the Canine IDUA Gene and Mutation Underlying Canine Mucopolysaccharidosis I.," Genomics, 1992, pp. 763-768, vol. 14, No. 3, Abstract Only.
Zhang, et al., "PRRS Virus Receptors and Their Role for Pathogenesis, Veterinary Microbiology", 2015, pp. J29-J241, vol. 177.
Misinzo, et al., "Involvement of Proteases in Porcine Reproductive and Respiratory Syndrome Virus Uncoating Upon Internalization in Primary Macrophages", Veterinary Research, 2008, 14 pages, vol. 39, No. 55.
Mengeling, et al., "Identification and Clinical Assessment of Suspected Vaccine-Related Field Strains of Porcine Reproductive and Respiratory Syndrome Virus, American Journal of Veterinary Research", 1999, pp. 334-340, vol. 60, No. 3.
Mengeling, et al., "Clinical Consequences of Exposing Pregnant Gilts to Strains of Porcine Reproductive and Respiratory Syndrome (PRRS) Virus Isolated from Field Cases of "Atypical" PRRS", American Journal of Veterinary Research, 1998, pp. 1540-1544, vol. 59, No. 12.
Merck & Co, Inc., Normal Rectal Temperature Ranges chart, The Merck Veterinary Manual 2009-2015, accessed ram <http://www.merckvetmanual.com/mvm/appendixes/reference_guides/normal_rectal_temperature_ranges.html?~t=normal%20rectal%2otemperature%20ranges&alt=sh>, 1 page.
Miao, et al., "Centrosome Abnormalities During Porcine Oocyte Aging, Environmental and Molecular Mutagenesis", 2009, pp. 666-671, vol. 50.
Molitor, et al.,"Immunity to PRRSV—Double-Edged Sword", Veterinary Microbiology, 1997, pp. 265-276, vol. 55, Nos. 1-4.
Morgan, et al., "Pathology and Virus Distribution in the Lung and Lymphoid Tissues of Inoculated with Three Distinct Type 1 PRRS Virus Isolates of Varying Pathogenicity", Transboundary and Emerging Diseases, 2016, pp. 285-295, vol. 63.
Munoz, et al., "Conventional pluripotency markers are unspecific for bovine embryonic-derived cell-lines"; Theriogenology, 2008, vol. 69, pp. 1159-1164.
Murtaugh, et al., "Comparison of the Structural Protein Coding Sequences of the VR-2332 and Lelystad Virus Strains of the PRRS Virus", Archives of Virology, 1995, pp. 1451-1460, vol. 140, No. 8.
Nath, et al., "The Amino-Terminal Immunoglobulin-Like Domain of Sialoadhesin Contains the Sialic Acid Binding Site, Comparison with CD22", The Journal of Biological Chemistry, 1995, pp. 26184-26191, vol. 270, No. 14.
Nauwynck, et al., "Entry of Porcine Reproductive and Respiratory Syndrome Virus into Porcine Alveolar 7 Macrophages Via Receptor-Mediated Endocytosis", Journal of General Virology, 1999, pp. 297-305, vol. 80, Part 2.
Niemann, H., Transgenic Farm Animals Get Off the Ground, Transgenic Research, 1998, vol. 7, pp. 73-75.
Nelsen, et al.,"Porcine Reproductive and Respiratory Syndrome Virus Comparison: Divergent Evolution on Two Continents", Journal of Virology, Jan. 1999, pp. 270-280, vol. 73, No. 1.
Neumann, et al., "Assessment of the Economic Impact of Porcine Reproductive and Respiratory Swine Production in the United States," Journal of the American Veterinary Medical Association, Aug. 1, 2005, pp. 385-392, vol. 227, No. 3.
Nielsen, et al., "Generation of an Infectious Clone of VR-2332, a Highly Virulent North American-Type Isolate of Porcine Reproductive and Respiratory Syndrome Virus", Journal of Virology, Mar. 2003, pp. 3702-3711, vol. 77, No. 6.

(56) References Cited

OTHER PUBLICATIONS

Nielsen, et al., "The Macrophage Scavenger Receptor CD163: Endocytic Properties of Cytoplasmic Tail Variants", Journal of Leukocyte Biology, Apr. 2006, pp. 837-845, vol. 79, No. 4.
Etzerodt, et al., "Plasma Clearance of Hemoglobin and Haptoglobin in Mice and Effect of DC163 Gene Targeting Disruption, Antioxidants and Redox Signaling", 2013, vol. 18, No. 17, pp. 2352-2363.
Etzerodt, et al., "CD163 and Inflammation: Biological, Diagnostic, and Therapeutic Aspects, Antioxidants and Redox Signaling", 2013, vol. 18, No. 17, pp. 2352-2363.
Fabriek, et al., The "Macrophage Scavenger Receptor CD163, Immunobiology", 2005, vol. 210, No. 2-4, pp. 153-160.
Fabriek, et al., "The Macrophage Scavenger Receptor CD163 Functions as an Innate Immune Sensor for Bacteria, Blood", Jan. 22, 2009, vol. 113, No. 4, pp. 887-892.
Fisher, et al., "Membrane Fusion by Viruses and Chemical Agents", Techniques in Cellular Physiology, 1981, vol. P115, pp. 1-36.
Flagiello, et al., "Mutation in the Nerve-Specific 5'non-coding Region of Cx32 Gene and Absence of Specific mRNA in A CMTX1 Italian Family," Human Mutation, 1998, vol. 12, No. 5, p. 361, Abstract Only.
Fridman et al., "Critical Pathways in Cellular Senescence and Immortalization Revealed by Gene Expression Profiling", Oncogene, 2008, pp. 5975-5987, vol. 27, No. 46.
Gaj. et al., "ZFN, TALEN and CRISPR/Cas-based Methods for Genome Engineering", Trends in Biotechnology, 2013, pp. 397-405, vol. 31, No. 7.
Galili, U., "Xenotransplantation and ABO Incompatible Transplantation: The Similarities They Share", Transfusion and Apheresis Science, 2006, pp. 45-58, vol. 35, No. 1.
Gaudreault, et al., "Factors Affecting the Permissiveness of Porcine Alveolar Macrophages for Porcine Reproductive and Respiratory Syndrome Virus", Archives of Virology, 2009, pp. 133-136, vol. 154, No. 1.
Gerrits, et al., "Perspectives for Artificial Insemination and Genomics to Improve Global Swine Populations", Theriogenology, Jan. 2005, pp. 283-299, vol. 63, No. 2.
Gómez, et al., "Derivation of cat embryonic stem-like cells from in vitro-produced blastocysts on homologous and heterologous feeder cells"; Theriogenology, 2010, vol. 74, pp. 498-515.
Goryanin, et al., "Applications of Whole Cell and Large Pathway Mathematical Models in the Pharmaceutical Industry", Metabolic Engineering in the Post Genomic Era, 2004, p. 344.
Graham, et al.,"The Fusion of Cells with One- and Two-Cell Mouse Embryos", The Wistar Institute Symposium Monograph, 1969, pp. 19-33.
Graham, et al., "Resources for the design of CRISPR gene editing experiments"; Graham and Root Genome Biology: 2015, pp. 1-21, vol. 16.
Graversen, et al., "Targeting the Hemoglobin Scavenger Receptor CD163 in Macrophages Highly Increases the Anti-inflammatory Potency of Dexamethasone", Molecular Therapy, 2012, pp. 1550-1558, vol. 20, No. 8.
Groenen, et al., "Analyses of Pig Genomes Provide Insight Into Porcine Demography and Evolution", Nature, 2012, pp. 393-398, vol. 491, No. 7424.
Hai, et al., "One-step Generation of Knockout Pigs by Zygote Injection of CRISPR/Cas System", Cell Research, 2014, pp. 372-375, vol. 24, No. 3.
Halbur, et al., "Comparison of the Pathogenicity of Two US Porcine Reproductive and Respiratory Syndrome Virus Isolates with that of the Lelystad Virus", Veterinary Pathology, 1995, pp. 648-660, vol. 32.
Halbur, et al., "Update on abortion storms and sow mortality", Journal of Swine Health and Production, 1997, vol. 5, p. 73.
Hammer, et al., "Production of Transgenic Rabbits, Sheep and Pigs by Microinjection", Nature, Jun. 1985, pp. 680-683, vol. 315, No. 6021.
Hao, et al., "Production of Endothelial Nitric Oxide Synthase (eNOS) Over-Expressing Piglets", Transgenic Research, 2006, pp. 739-750, vol. 15, No. 6.
Hauschild, et al., "Efficient Generation of a Biallelic Knockout in Pigs Using Zinc-Finger Nucleases", Proceedings of the National Academy of Sciences of the United States of America, 2011, pp. 12013-12017, vol. 108, No. 29.
Holtkamp, et al., "Assessment of the Economic Impact of Porcine Reproductive and Respiratory Syndrome Virus on United States Pork Producers", Journal of Swine Health and Production, Mar. and Apr. 2013, pp. 72-84, vol. 21, No. 2.
Huang, et al., "Porcine DC-SIGN: Molecular Cloning, Gene Structure, Tissue Distribution and Binding Characteristics", Developmental and Comparative Immunology, 2009, pp. 464-480, vol. 33.
Hwang, et al., "Efficient genome editing in zebrafish using a CRISPR-Cas system", Nat Biotechnol, 2013; vol. 31, pp. 227-229.
Hyder, et al., "Identification of an Estrogen Response Element in the 3'-Flanking Region of the Murine c-fos Drotooncogene", The Journal of Biological Chemistry, 1992, pp. 18047-18054, vol. 267, No. 25.
Im, et al.,"In Vitro Development of Preimplantation Porcine Nuclear Transfer Embryos Cultured in Different Media and Gas Atmosphere",Theriogenology, 2004, pp. 1125-1135, vol. 61.
Jean, et al., "Pluripoent genes in avian stem cells"; Develop. Growth Differ., 2013, vol. 55, pp. 41-51.
Jeney, et al., "Pro-Oxidant and Cytotoxic Effects of Circulating Heme, Blood", Aug. 1, 2002, pp. 879-887, vol. 100, No. 3.
Keffaber, et al., "Reproductive Failure of Unknown Etiology", American Association of Swine Practitioners Newsletter, 1989, pp. 1-9, vol. 1.
Key, et al., "Genetic variation and phylogenetic analyses of the ORF5 gene of acute porcine reproductive and respiratory syndrome virus isolates", Veterinary Microbiology, 2001, vol. 83, pp. 249-263.
Kim, et al., "Enhanced Replication of Porcine Reproductive and Respiratory Syndrome {PRRS) Virus in a Homogeneous Subpopulation of MA-104 Cell Line", Archives of Virology, 1993, pp. 477-483, vol. 133.
Kim, et al.,"Defining the Cellular Target{s) of Porcine Reproductive and Respiratory Syndrome Virus Blocking Monoclonal Antibody 7G10, Journal of Virology", Jan. 2006, pp. 689-696, vol. 80, No. 2.
Kim, et al., "A guide to genome engineering with programmable nucleases"; Nature Reviews/Genetics; May 2014, vol. 15, pp. 321-334.
Kleinjan, et al., "Cis-ruption Mechanisms: Disruption of cis-regulatory Control as a Cause of Human Genetic Disease", Briefings in Functional Genomics and Proteomics, 2009, pp. 317-332, vol. 8, No. 4.
Kolston, et al., "Comparing In Vitro, In Situ, and In Vivo Experimental Data in a Three-Dimensional Model of Mammalian Cochlear Mechanics, Proceedings of the National Academy of Sciences of the United States of America"., Mar. 1999, pp. 3676-3681, vol. 96, No. 7.
Kristiansen, M., et al., "Identification of the Haemoglobin Scavenger Receptor," Nature, Jan. 2001, pp. 198-201, vol. 409, No. 6817.
Kwon, et al., "Production of Biallelic CMP-Neu5Ac Hydroxylase Knock-out Pigs," Scientific Reports, 2013, p. 1981, vol. 3.
Lading, et al., "Pathogenicity of Three Type 2 Porcine Reproductive and Respiratory Syndrome Virus Strains in Experimentally Inoculated Pregnant Gills", Virus Research, 2015, pp. 24-35, vol. 203.
Lager, et al., "Evaluation of Protective Immunity in Gilts Inoculated with the NADC-8 Isolate of Porcine Reproductive and Respiratory Syndrome Virus (PRRSV) and Challenge-Exposed with an Antigenically Distinct PRRS Isolate", American Journal of Veterinary Research, 1999, pp. 1022-1027, vol. 60, No. 8.
Whitworth, et al., Use of the CRISPR/Cas9 System to Produce Genetically Engineered Pigs from In Vitro-Derived Oocytes and Embryos; Biology of Reproduction, 2014, vol. 91, No. 3, 78, pp. 1-13.
Whitworth, et al., Gene-edited pigs are protected from porcine reproductive and respiratory syndrome virus; Nature Biology, Jan. 2016, vol. 34, No. 1, pp. 20-22.

(56) References Cited

OTHER PUBLICATIONS

Whitworth, et al., "Gene Editing as Applied to Prevention of Reproductive Porcine Reproductive and Respiratory Syndrome", Molecular Reproduction and Development, 2017, pp. 926-933, vol. 84, No. 9.
Whitworth, et al., "Use of the CRISPR/Cas9 System to Produce Genetically Engineered Pigs from In Vitro-Derived Oocytes and Embryos", Biology of Reproduction, 2014, pp. 1-13, vol. 91, No. 3.
Whitworth, et al., "Use of the CRISPR/Cas9 System to Produce Pigs With a Genetically Modified CD163 Gene by Using Somatic Cell Nuclear Transfer of In Vitro Derived Oocytes", Abstract, Swine in Biomedical Research Conference, Raleigh, North Carolina, Jul. 20-22, 2014, p. 103.
Whitworth, et al., "Use of the CRISPR/Cas9 System to Produce Pigs With a Genetically Gene by Using Somatic Cell Nuclear Transfer of In Vitro Derived Oocytes", Poster, Swine in Biomedical Research Conference, Raleigh, North Carolina, Jul. 20-22, 2014.
Whitworth, et al., "CD163 facilitates both entry and replication of porcine reproductive and respiratory syndrome virus. Nature Biotech", 2016, vol. 34, pp. 20-22.
Whitworth, et al., "Zygote Injection of CRISPR/Cas9 RNA Successfully Modifies the Target Gene Without Delaying Blastocyst Development or Altering the Sex Ratio in Pigs", Transgenic Research, 2017, pp. 97-107, vol. 26, Issue 1.
Whitworth, et al., "Gene Editing of CD163 Protects Pigs from PRRSV Infectivity", Abstracts from the UC Davis Transgenic Animal Research Conference XI (Aug. 13-17, 2017), Transgenic Research, 2018, pp. 473-474, vol. 27.
Whyte, et al., "Genetic modifications of pigs for medicine and agriculture", Mol Reprod Dev., 2011, vol. 78, No. 10-11, pp. 879-891.
Whyte, et al., "Gene Targeting With Zinc Finger Nucleases to Produce Cloned eGFP Knockout Pigs", Molecular Reproduction and Development, Jan. 2011, p. 2, vol. 78, Issue 1.
Wiedenheft, et al., "RNA-guided Genetic Silencing Systems in Bacteria and Archaea", Nature, Feb. 2012, pp. 331-338, vol. 482, No. 7385.
Wikipedia, "In vitro," accessed from <hllps://en.wikipedia.org/wiki/In_vitro> on Sep. 29, 2016, 6 pages.
Wilkinson, et al., "Genome-wide analysis of the transcriptional response to porcine reproductive and respiratory syndrome virus infection at the maternal/fetal interface and in the fetus", BMC Genomics, 2016, vol. 17, p. 383.s.
Wills, et al., "Porcine Reproductive and Respiratory Syndrome Virus—A Persistent Infection, Veterinary Microbiology", 1997, pp. 231-240, vol. 55, Nos. 1-4.
Winckler, et al., "The Reliability and Repeatability of a Lameness Scoring System for Use as an Indicator of 20 Melfare in Dairy Cattle, Acta Agriculturae Scandinavica", Section A—Animal Science, 2001, pp. 103-107, vol. 51, Supplement 30.
Wissink, et al., "Identification of Porcine Alveolar Macrophage Glycoproteins Involved in Infection of Porcine Respiratory and Reproductive Syndrome Virus, Archives of Virology", 2003, pp. 177-187, vol. 148, No. 1.
Yang, et al., "Generation of PPAR(Gamma) Mono-Allelic Knockout Pigs Via Zinc-Finger Nucleases and Nuclear transfer Cloning", Cell Research, 2011, pp. 979-982, vol. 6.
Yoon, et al., "Persistent and Contact Infection in Nursery Pigs Experimentally Infected with PRRS Virus", Swine Health and Production, 1993, pp. 5-8, vol. 1.
Zhao, et al., "Histone Deacetylase Inhibitors Improve In Vitro and In Vivo Developmental Competence of Somatic Cell Nuclear Transfer Porcine Embryos", Cellular Reprogramming, 2010, pp. 75-83, vol. 12, No. 1.
Zhao, et al., "Significant Improvement in Cloning Efficiency of an Inbred Miniature Pig by Histone Deacetylase Ihibitor Treatment After Somatic Cell Nuclear Transfer", Biology of Reproduction, 2009, pp. 525-530, vol. 81.
International Search Report and Written Opinion issued for PCT/US2018/27944, dated Jul. 3, 2018, 10 pages.
International Search Report and Written Opinion issued for PCT/US2015/044113, dated Jan. 6, 2016, 13 pages.
International Search Report and Written Opinion issued for PCT/US2016/043467, dated Oct. 25, 2016, 15 pages.

* cited by examiner

C

| | SEQ ID NO | |
|---|---|---|
| WT | 16 | GGTCGCCACCATGGTGAGCAAGGGCGAGGAGCTGTTCACCGGGGTGGTGCCCATC |
| #1 | 17 | GGTCGCCACCATGG**CCA**TGAGCAAGGGCGAGGAGCTGTTCACCGGGGTGGTGCC (+3 bp) |
| #2 | 18 | GGTCGCCACCATGG------TGAGCAAGGGCGAGGAGCTGTTCACCGGGGTGGT (-6 bp) |
| #3 | 19 | GGTCGCCACCATGGT**T**GAGCAAGGGCGAGGAGCTGTTCACCGGGGTGGTGCCCAT (+1 bp) |

A

| | SEQ ID NO | |
|---|---|---|
| WT | 20 | TGCAGGGAACTACAGTGCGGCACTGTGGTTTCCCTCCTGGGGG |
| #1-1 | 21 | TGCAGGGAACTACAGTGCGGCACTG(+16 bp)TGGTTTCCCTCCTGGGGGG |
| #1-4 | 22 | TGCAGGGAACTACAGTGCGGC--TGTGGTTTCCCTCCTGGGGG |
| #2-2 | 23 | TGCAGGGAACTACAGTGCGG-AACTACTGTGGTTTCCCTCCTGGGGG |

B

FIG. 6
A
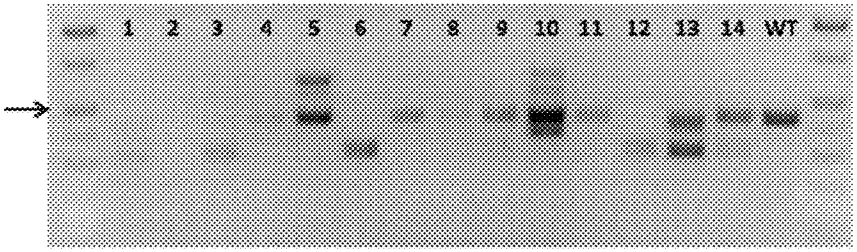
B
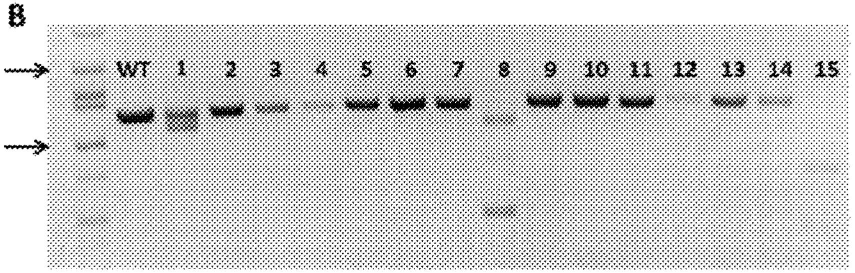
C
| | *CD163* | *SEQ ID NO* | *eGFP* | *SEQ ID NO* |
|---|---|---|---|---|
| WT | GAAACCCAGGCTGGTTGGAGGGGACATTCCC | 24 | GGTCGCCACCATGGTGAGCAAGGGCGAGGAG | 28 |
| #1 | GAAACCCAGGCTGG---------GGACATTCCC | 25 | GGTCGCCACCATGGCTGAGCAAGGGCGAGGAG<br>GGTCGCCACCATGGTGAG--AGGGCGAGGAG | 29<br>30 |
| #2 | –(Δ83 bp)----------AGGGGACATTCCC | 26 | GGTCGCCACCATGGTTGAGCAAGGGCGAGGAG | 31 |
| #3 | GAAACCCA-----------------TTCCC | 27 | GGTCGCCACCATGGTGAGCAAGGGCGAGGAG+ (17 bp) | 32 |

FIG. 7
A
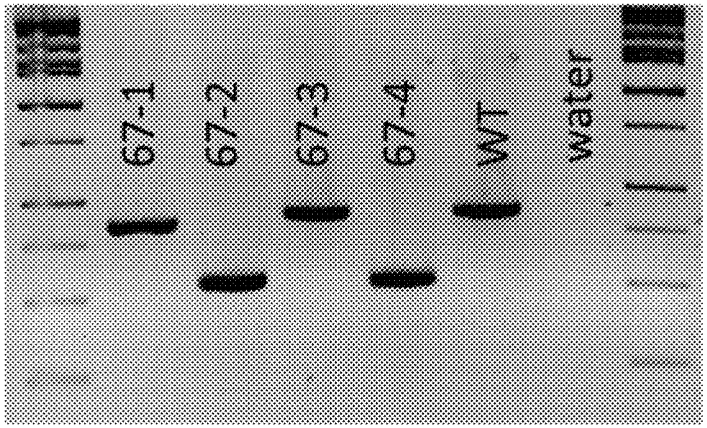
B
C
| | SEQ ID NO | |
|---|---|---|
| WT | 33 | TGCTGTGCAGGGAACTACAGTGCGGCACTGTGGTTTCCCTCCTGGGGGG |
| #67-1 | 34 | TGCTGTGCAGGGAACT-----------CTGTGGTTTCCCTCCTGGGGGG |
| #67-2 | 35<br>36 | -(Δ124 bp)-----------------CTGTGGTTTCCCTCCTGGGGGG<br>-(Δ123 bp)----------------ACTGTGGTTTCCCTCCTGGGGGG |
| #67-3 | 37 | TGCTGTGCAGGGAACTACAGTGCGGCAACTGTGGTTTCCCTCCTGGGGGG |
| #67-4 | 38<br>39 | -(Δ130 bp)----------------------------TCCTGGGGGG<br>-(Δ132 bp)------------------------------CTGGGGGG |

FIG. 8

A

B

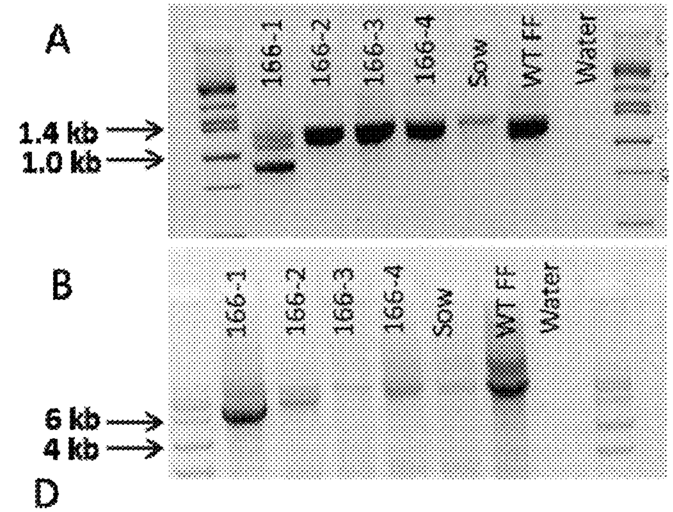

C

D

| | SEQ ID NO | |
|---|---|---|
| WT | 40 | AGAGAGCAGAGCCAGCGACTCGCCCAGCGACatgGGGTACCTGCCGTTTGTG |
| #166-1 | <br>41<br>42 | ------------------------------------------------ (-632 bp deletion)<br>AGAGAGCAGAGCCAGCGACTCGCCCAGCGAGat------------ (-27 bp deletion)<br>AGAGAGCAGAGCCAGCGACTCGCCCAGCGA--------------- (-24 bp deletion) |
| #166-2 | 43 | AGAGCCAGCCTCGCCCAGCAGGGGTACCatgGGGTACCTGCCGTTTGTGT (AG mismatch+Δ6 bp)<br>-------------------------------------------------(-1598 bp deletion) |
| #166-3 | 44<br>45 | AGAGAGCAGAGCCAGCGACTCGCCCAGCGAGCagtGGGTACCTGCCGTTTGTG (+Δ1 bp)<br>AGAGAGCAGAGCCAGCGACTCGCCCAGCGATCagtGGGTACCTGCCGTTTGTG (+Δ1 bp) |
| #166-4 | 46 | AGAGAGCAGAGCCAGCGACTCGCCCAGCGAACatgGGGTACCTGCCGTTTGTG (+Δ1 bp) |

Uncharacterized A

FIG. 16

SEQ ID NO. 47

```
LOCUS       WT_CD163_Referen        4990 bp ds-DNA     linear
DEFINITION  Reference CD163 gene:  3000 bp upstream of exon 7 to the last base of
exon 10
ACCESSION
VERSION
SOURCE      .
  ORGANISM  . pig
COMMENT
COMMENT     ApEinfo:methylated:1
FEATURES             Location/Qualifiers
    misc_feature     1..3000
                     /label=intron 6

    misc_feature     3001..3315
                     /label=exon 7

    misc_feature     3316..3412
                     /label=intron 7

     misc_feature    3413..3727
                     /label=exon 8

     misc_feature    3728..4501
                    /label=intron 8

     misc_feature    4502..4594
                     /label=exon 9

     misc_feature    4595..4676
                     /label=intron 9

     misc_feature    4676..4989
                     /label=exon 10

ORIGIN
        1 tatagatgac aaggctttgt gtctgatagg ggccagcgaa ctcagtaaag agggaagatg
       61 agaaagataa tggcaagaat ttatccctga agtgtagttt tgacaaacca gtcacaaaga
      121 ggtctaagaa attttggtca caaagttgtt ttgaatccca ggcattttat ttgcaatgat
      181 tgcatatgtt ctggaaagga catctgaacc taagaaatag ttcatttgca ttgtgttata
      241 ttttactaag gtctgagaaa taatcttgag atgagaatga actctacttc ttcagagtct
      301 ggaaggaata aattatgaaa atgtattaat gcttctttaa accatattgt atatttatct
      361 attactaaac aaaaagaagt agctctattt atttatttat ttatttattt atttatgtct
      421 tttgtctctt tagggccaca cctgtggcat atggaggttc ccaggctaga ggtccaattg
      481 gagatgtagc agccagccta tgccagagcc accgcaacac gggatctgag ccacgtctgt
      541 gacttacacc acagctcaca gcaacgcctg atcctcaacc cactgagcga ggccagggat
      601 cgaacccatg tcctcatgga tgctagttgg gttcgttaac tgctgagcca tgatgggaac
      661 tccaaattaa ttatttctta tatttgttct tcatatattc atttctatag aaagaaataa
      721 atacagattc agttaatgat ggcaggtaaa agcttaactt attaatcaaa ggagttaatc
      781 caggcacaaa aattcaattc atggctctct gttaaaattt aggtataggt ttagcaggaa
      841 gaaaaggtta gtagatgcag actattacat ttagaatgga tggacaatga agtcctacta
      901 tacagcacag ggaactatat ccaatctctt gggatagaat atgatggaag acaaaatcag
      961 aacaagagag tatatatata tgtgtgtgtg tgtgtgtgtg tgtgtgtgtg tgtgtgtgtg
     1021 tgtgtgactg ggtcaccctg cggcacagca gaaattggca gaacattgta aatcaactat
     1081 actttaatag gaaaaatact tttaagggct aaatttccaa tattctaacc atgtacacag
     1141 agtaaatgtc ataaggatgc cagtctgtgt agagattgat gtgttactag cagattcatg
     1201 aaataaaggc tgaggatgta gtccccaagt cacttctgag tggaagaatt tctcctttgt
     1261 cctggactca aatattttag gataaaggaa aaaagaagat atttatagaa gggacttgtt
     1321 ttcaagtact tgacaaaatt tcaccattaa agagaaattt gtgggagttc ccatcgtggc
     1381 tcagtggaaa caaatccaac taggaaccat gaggttgtgg gtttgatccc tggcctcact
     1441 cagtgggtta aggatccggt gttgccgtga gctgtggtgt aggttgcaga cacggttctg
     1501 atcctgcgtt gctgtggctg tggctgtggt gtaggccagc agcaaacagc tctgattaga
     1561 cccctagcct ggaaacctcc atatgccaca ggtgcagccc taaaaagaca aaaaaagaga
```

FIG. 16 cont.

```
1621 aaagacaaaa aaaaaaaaaa aaaaaaaaaa aaaaaaaaaa aaaaaaaaaa gaacccccag
1681 aggtatttat ttgtttttgc ctttttttcac tgactgttct ttgtttgttt gtttgagact
1741 gatctagaag actagagatt acaagaaata tggatttggc tcactctaag aaactgcttt
1801 cattccaagg tttgggtcta tccaaaagtg gaatagaatc atatgaatac tagtttatga
1861 gtatttagtg agaggaattt caagctcaaa taatgattca gcaagattaa attaaggagg
1921 gaattttcct tgtggctgag tgggttaagg acccaatgtt gtctctgtga ggatgtaggt
1981 tccatcctgg gctttgctca ttaggttaag gatctggcat tgctgcagct cagacccagt
2041 gctgccctgg ttgtggctta ggccaaagct gcagctccaa ttcaatctct ggcctgggaa
2101 cctccatgtg ctacaaggtg cggccttaaa aggaaaaaaa aaaaattaaa tcaaggactc
2161 aagagtcttt cattatttgt gttgtggaag ctatatttgt tttaaagtct tagttgtgtt
2221 tagaaagcaa gatgttcttc aactcaaatt tgggagggaa cttgtttcat acatttttaa
2281 tggataagtg gcaaaatttt catgctgagg tgatctatag tgttgtaatg cagaatatag
2341 tcagatcttg aacattttag gaagttggtg agggccaatt gtgtatctgt gccatgctga
2401 taagaatgtc aagggatcac aagaattcgt gttatttgac agcagtcatc tttaaaaggc
2461 atttgagaaa gtccaatttc aaatgcattt cctttcttta aaagataaat tgaagaaaat
2521 aagtctttat ttcccaagta aattgaattg cctctcagtc tgttaaaaga aactcttacc
2581 ttgatgattg cgctcttaac ctggcaaaga ttgtctttaa aatctgagct ccatgtcttc
2641 tgctttattt ctggtgtgcc tttgactcca gattacagta aatggaggac tgagtatagg
2701 gctaaaaagt agagagaatg gatgcatatt atctgtggtc tccaatgtga tgaatgaagt
2761 aggcaaatac tcaaaggaaa gagaaagcat gctccaagaa ttatgggttc cagaaggcaa
2821 agtcccagaa ttgtctccag ggaaggacag ggaggtctag aatcggctaa gcccactgta
2881 ggcagaaaaa ccaagaggca tgaatggctt ccctttctca cttttcactc tctggcttac
2941 tcctatcatg aaggaaaata ttggaatcat attctccctc accgaaatgc tatttttcag
3001 CCCACAGGAA ACCCAGGCTG GTTGGAGGGG ACATTCCCTG CTCTGGTCGT GTTGAAGTAC
3061 AACATGGAGA CACGTGGGGC ACCGTCTGTG ATTCTGACTT CTCTCTGGAG GCGGCCAGCG
3121 TGCTGTGCAG GGAACTACAG TGCGGCACTG TGGTTTCCCT CCTGGGGGGA GCTCACTTTG
3181 GAGAAGGAAG TGGACAGATC TGGGCTGAAG AATTCCAGTG TGAGGGGCAC GAGTCCCACC
3241 TTTCACTCTG CCCAGTAGCA CCCCGCCCTG ACGGGACATG TAGCCACAGC AGGGACGTCG
3301 GCGTAGTCTG CTCAAgtgag acccagggaa tgtgttcact ttgttcccat gccatgaaga
3361 gggtagggtt aggtagtcac agacatcttt ttaaagccct gtctccttcc agGATACACA
3421 CAAATCCGCT TGGTGAATGG CAAGACCCCA TGTGAAGGAA GAGTGGAGCT CAACATTCTT
3481 GGGTCCTGGG GGTCCCTCTG CAACTCTCAC TGGGACATGG AAGATGCCCA TGTTTTATGC
3541 CAGCAGCTTA AATGTGGAGT TGCCCTTTCT ATCCCGGGAG GAGCACCTTT TGGGAAAGGA
3601 AGTGAGCAGG TCTGGAGGCA CATGTTTCAC TGCACTGGGA CTGAGAAGCA CATGGGAGAT
3661 TGTTCCGTCA CTGCTCTGGG CGCATCACTC TGTTCTTCAG GGCAAGTGGC CTCTGTAATC
3721 TGCTCAGgta agagaataag ggcagccagt gatgagccac tcatgacggt gccttaagag
3781 tgggtgtacc taggagttcc cattgtggct cagtggtaac aaactcgact ggtatccatg
3841 agggtatggg tttgatccct ggccttgctc aatgggttaa ggatccagca ttgctgtgag
3901 ctgtggtata ggttgcagac tctgctcagg tcccatgttg ctgtgattgt ggtgtaggct
3961 gactgctgca gcttcaattt gacccctagc ccgggaattt ccataggcca cacgtgcagc
4021 actaaggaag gaaaaaaaGa aaaaaaaaaa aaaagagtgg gtgtgcctat agtgaagaac
4081 agatgtaaaa gggaagtgaa agggattccc ccattctgag ggattgtgag aagtgtgcca
4141 gaatattaac ttcatttgac ttgttacagg gaaagtaaac ttgactttca cggacctcct
4201 agttacctgg tgcttactat atgtcttctc agagtacctg attcattccc agcctggttg
4261 acccatcccc ctatctctat ggctatgttt atccagagca catctatcta acactccagc
4321 tgatcttcct gacacagctg tggcaaccct ggatccttta accaactgtg ccaggctgga
4381 gatcaaacct aagcctctgc agcaacccaa gctgctgcag tcagattttt aaccccctgt
4441 gccactgtgg gtatctccga tattttgtat cttctgtgac tgagtggttt gctgtttgca
4501 gGGAACCAGA GTCAGACACT ATCCCCGTGC AATTCATCAT CCTCGGACCC ATCAAGCTCT
4561 ATTATTTCAG AAGAAAATGG TGTTGCCTGC ATAGgtgaga atcagtgacc aacctatgaa
4621 aatgatctca atcctctgaa atgcatttta ttcatgtttt atttcctctt tgcagGGAGT
4681 GGTCAACTTC GCCTGGTCGA TGGAGGTGGT CGTTGTGCTG GGAGAGTAGA GGTCTATCAT
4741 GAGGGCTCCT GGGGCACCAT CTGTGATGAC AGCTGGGACC TGAATGATGC CCATGTGGTG
4801 TGCAAACAGC TgAGCTGTGG ATGGGCCATT AATGCCACTG GTTCTGCTCA TTTTGGGGAA
4861 GGAACAGGGC CCATTTGGCT GGATGAGATA AACTGTAATG GAAAAGAATC TCATATTTGG
4921 CAATGCCACT CACATGGTTG GGGGCGGCAC AATTGCAGGC ATAAGGAGGA TGCAGGAGTC
4981 ATCTGCTCGG
```

METHODS FOR PROTECTING PORCINE FETUSES FROM INFECTION WITH PORCINE REPRODUCTIVE AND RESPIRATORY SYNDROME VIRUS (PRRSV)

CROSS REFERENCE TO RELATED APPLICATIONS

This application is a U.S. Continuation Application of U.S. application Ser. No. 16/386,901 filed Apr. 17, 2019, claiming priority to U.S. Provisional Application No. 62/658,740 filed Apr. 17, 2018, the disclosures of which are hereby incorporated by reference in their entirety.

REFERENCE TO SEQUENCE LISTING SUBMITTED ELECTRONICALLY

The official copy of the sequence listing is submitted electronically via EFS-Web as an ASCII-formatted sequence listing with a file named "SEQ LISTING 18054US", created on Mar. 27, 2018 and having a size of 175.5 kilobytes, and is filed concurrently with the specification. The sequence listing contained in this ASCII-formatted document is part of the specification and is herein incorporated by reference in its entirety.

FIELD OF THE INVENTION

The present invention relates to methods for protecting porcine fetuses from infection with Porcine Reproductive and Respiratory Syndrome Virus (PRRSV).

BACKGROUND OF THE INVENTION

Porcine reproductive and respiratory syndrome (PRRS) is the most economically important disease of swine in North America, Europe and Asia, costing North American producers approximately S600 million annually (Holtkamp et al., 2013). Clinical disease syndromes caused by infection with porcine reproductive and respiratory syndrome virus (PRRSV) were first reported in the United States in 1987 (Keffaber, 1989) and later in Europe in 1990 (Wensvoort et al., 1991). Infection with PRRSV results in respiratory disease including cough and fever, reproductive failure during late gestation, and reduced growth performance. The virus also participates in a variety of polymicrobial disease syndrome interactions while maintaining a life-long sub-clinical infection (Rowland et al., 2012). Losses are the result of respiratory disease in young pigs, poor growth performance, reproductive failure, and in utero infection (Keffaber, 1989).

The reproductive form of the disease accounts for an estimated 45% of losses, the result of abortions, dead fetuses, and respiratory disease in newborns. In its severest form, reproductive PRRS can result in 90% mortality of fetuses/neonates, along with increased mortality for the dams. The reproductive form of PRRS occurs following the infection of pregnant gilts or sows at about 90 days of the 114 day gestation period (Christianson et al., 1993; Rowland, 2010). After an initial phase of replication in maternal macrophages, the virus crosses the placenta and begins to productively infect fetuses. The virus initially infects only a small number of fetuses, followed by horizontal transmission of virus from fetus to fetus (Wilkinson et al., 2016). The exact mechanism of how the virus crosses the placenta remains unknown, but could be similar to the infected "Trojan Horse" macrophage, previously described for lactate dehydrogenase-elevating virus (LDV) (Cafruny, 1996). Unlike the alveolar macrophages in adult animals, the primary site of PRRSV replication in the fetus is the thymus (Rowland, 2003). Since the pig fetus becomes immunocompetent at about 70 days of gestation, PRRSV infection occurs in a fetal immune environment containing functional B and T cells (Rowland, 2003; Rowland, 2010).

Pigs that survive in utero infection become continuous sources of virus in downstream production phases, resulting in endemically infected herds (Rowland, et al., 2003). The severest form of reproductive disease is associated with a group of highly virulent isolates referred to as atypical PRRSV (Halbur et al., 1997; Mengeling et al., 1998). Interestingly, many of the atypical PRRSV isolates emerged from PRRS-vaccinated farms (Key et al., 2001). In 2006, an atypical virus, called high pathogenic PRRSV (HP-PRRSV), appeared in China and continues to decimate pig populations in that country (Tian et al., 2007). Since the standard commercial breeding facility contains about 5,000 sows, an outbreak of high mortality reproductive PRRS can have a devastating impact. To ensure sustainability of pork production and food security, solutions for the control of reproductive PRRS remain a priority. Vaccines have been unable to control the disease, largely because of genetic diversity within the structural proteins of the virus (Shi et al., 2010). In practice, intensive biosecurity measures provide the only means of protecting the reproductive herd.

Porcine reproductive and respiratory syndrome virus (PRRSV) belongs to the family Arterividae along with murine lactate dehydrogenase-elevating virus, simian hemorrhagic fever virus, and equine arteritis virus. Structurally, the arteriviruses resemble togaviruses, but similar to coronaviruses, replicate via a nested 3'-co-terminal set of subgenomic mRNAs, which possess a common leader and a poly-A tail. The arteriviruses share important properties related to viral pathogenesis, including a tropism for macrophages and the capacity to cause severe disease and persistent infection (Plagemann, 1996). Molecular comparisons between North American and European viruses place all PRRSV isolates into one of two genotypes, Type 2 or Type 1, respectively. Even though the two genotypes possess only about 70% identity at the nucleotide level (Nelsen et al., 1999), both share a tropism for CD163-positive cells, establish long-term infections, and produce similar clinical signs.

CD163 is a 130 kDa type 1 membrane protein composed of nine scavenger receptor cysteine-rich (SRCR) domains and two spacer domains along with a transmembrane domain and a short cytoplasmic tail (Fabriek et al., 2005). Porcine CD163 contains 17 exons that code for a peptide signal sequence followed by nine SRCR domains, two linker domains (also referred to as proline serine threonine (PST) domains, located after SRCR 6 and SRCR 9), and a cytoplasmic domain followed by a short cytoplasmic tail. Surface expression of CD163 is restricted to cells of the monocyte-macrophage lineage. In addition to functioning as a virus receptor, CD163 exhibits several important functions related to maintaining normal homeostasis. For instance, following infection or tissue damage, CD163 functions as a scavenger molecule, removing haptoglobin-hemoglobin complexes from the blood (Kristiansen et al., 2001). The resulting heme degradation products regulate the associated inflammatory response (Fabriek et al., 2005). HbHp scavenging is a major function of CD163 and locates to SRCR 3 (Madsen et al., 2004). Metabolites released by macrophages following HbHp degradation include bilirubin, CO, and free iron. One important function of CD163 the prevention of oxidative toxicity that results from free hemoglobin (Kristiansen et al., 2001; Soares et al., 2009).

Other important functions of C163 include erythroblast adhesion (SRCR2), being a TWEAK (tumor necrosis factor-like weak inducer of apoptosis) receptor (SRCR1-4 & 6-9), being a bacterial receptor (SRCR5), and being an African Swine Virus receptor (Sanchez-Torres et al. 2003). CD163 also has a potential role as an immune-modulator (discussed in Van Gorp et al. 2010).

CD163 was first described as a receptor for PRRSV by Calvert et. al. (2007). Transfection of non-permissive cell lines with CD163 cDNAs from a variety of species, including simian, human, canine, and mouse, can make cells permissive for PRRSV infection (Calvert et al., 2007). In addition to CD163, a second receptor protein, CD169 (also known as sialoadhesin or SIGLEC1), was identified as being a primary PRRSV receptor involved in forming the initial interaction with the GP5-matrix (M) heterodimer, the major protein on the surface of the virion (Delputte et al., 2002). In this model, the subsequent interaction between CD163 and the GP2, 3, 4 heterotrimer in an endosomal compartment mediates uncoating and the release of the viral genome into the cytoplasm (Van Breedam et al., 2010, Allende et al., 1999). A previous model describing PRRSV infection of alveolar macrophages identified SIGLEC1 (CD169) as the primary viral receptor on the surface of macrophages; however, previous work using SIGLEC1$^{-/-}$ pigs showed no difference in virus replication compared to wild type pigs (Prather et al., 2013). These results supported previous in vitro studies showing that PRRSV-resistant cell lines lacking surface CD169 and CD163 supported virus replication after transfection with a CD163 plasmid (Welch et al., 2010).

Many characteristics of both PRRSV pathogenesis (especially at the molecular level) and epizootiology are poorly understood, thus making control efforts difficult. Currently, producers often vaccinate swine against PRRSV with modified-live attenuated strains or killed virus vaccines, however, current vaccines often do not provide satisfactory protection. This is due to both the strain variation and inadequate stimulation of the immune system. In addition to concerns about the efficacy of the available PRRSV vaccines, there is strong evidence that the modified-live vaccine currently in use can persist in individual pigs and swine herds and accumulate mutations (Mengeling et al. 1999), as has been demonstrated with virulent field isolates following experimental infection of pigs (Rowland et al., 1999). Furthermore, it has been shown that vaccine virus is shed in the semen of vaccinated boars (Christopher-Hennings et al., 1997). As an alternative to vaccination, some experts are advocating a "test and removal" strategy in breeding herds (Dee et al., 1998). Successful use of this strategy depends on removal of all pigs that are either acutely or persistently infected with PRRSV, followed by strict controls to prevent reintroduction of the virus. The difficulty, and much of the expense, associated with this strategy is that there is little known about the pathogenesis of persistent PRRSV infection and thus there are no reliable techniques to identify persistently infected pigs.

As can be seen, a need exists in the art for the development of strategies to induce PRRSV resistance in animals. There is also a particular need for techniques for protecting fetuses from PRRSV infection while in utero and for preventing transmission of PRRSV from mother to fetus.

BRIEF SUMMARY OF THE INVENTION

A method for protecting a porcine fetus from infection with porcine reproductive and respiratory syndrome virus (PRRSV) is provided. The method comprises breeding a female porcine animal with a male porcine animal. The female porcine animal comprises modified chromosomal sequences in both alleles of its CD163 gene, wherein the modified chromosomal sequences reduce the susceptibility of the female porcine animal to infection by PRRSV, as compared to the susceptibility to infection by PRRSV of a female porcine animal that does not comprise any modified chromosomal sequences in the alleles of its CD163 gene. The male porcine animal comprises at least one wild-type CD163 allele.

Other objects and features will be in part apparent and in part pointed out hereinafter.

BRIEF DESCRIPTION OF THE DRAWINGS

FIG. 6. Effect of CRISPR/Cas9 system when introduced with two types of CRISPRs. A) PCR amplification of CD163 in blastocysts injected with CRISPR/Cas9 as zygotes. Lanes 1, 3, 6, and 12 show the designed deletion between two different CRISPRs. B) PCR amplification of CD1D in blastocysts injected with CRISPR/Cas9 as zygotes. CD1D had a lower frequency of deletion as determined by gel electrophoresis when compared to CD163 (3/23); lanes 1, 8, and 15 show obvious deletions in CD1D. C) CRISPR/Cas9 system successfully targeted two genes when the system was provided with two CRISPRs targeting CD163 and eGFP. The modifications of CD163 and eGFP are shown: CD163 WT (SEQ ID NO:24), CD163 #1 (SEQ ID NO:25), CD163 #2 (SEQ ID NO:26), CD163 #3 (SEQ ID NO:27), eGFP WT (SEQ ID NO:28), eGFP #1-1 (SEQ ID NO:29), eGFP #1-2 (SEQ ID NO: 30), eGFP #2 (SEQ ID NO:31), and eGFP #3 (SEQ ID NO:32).

FIG. 7. CD163 knockout pigs generated by CRISPR/Cas9 system injected into zygotes. A) PCR amplification of CD163 from the knockout pigs; a clear sign of deletion was detected in litters 67-2 and 67-4. B) Image of CD163 knockout pigs with a surrogate. All the animals are healthy and show no signs of abnormalities. C) Genotype of CD163 knockout pigs. Wild-type (WT) sequence is shown as SEQ ID NO: 33. Two animals (from litters 67-1 (SEQ ID NO:34) and 67-3 (SEQ ID NO:37)) are carrying a homozygous deletion or insertion in CD163. The other two animals (from litters 67-2 and 67-4) are carrying a biallelic modification of CD163: #67-2 A1 (SEQ ID NO:35), #67-2 A2 (SEQ ID NO:36), #67-4 A1 (SEQ ID NO:38), and #67-4 a2 (SEQ ID NO:39). The deletion was caused by introducing two different CRISPRs with Cas9 system. No animals from the zygote injection for CD163 showed a mosaic genotype.

FIG. 8. CD1D knockout pigs generated by CRISPR/Cas9 system injected into zygotes. A) PCR amplification of CD1D from knockout pigs; 166-1 shows a mosaic genotype for CD1D. 166-2, 166-3, and 166-4 do not show a change in size for the amplicon, but sequencing of the amplicon revealed modifications. WT FF=wild-type fetal fibroblasts. B) PCR amplification of the long-range assay showed a clear deletion of one allele in piglets 166-1 and 166-2. C) Image of CD1D knockout pigs with surrogate. D) Sequence data of CD1D knock out pigs; WT (SEQ ID NO:40), #166-1.1 (SEQ ID NO: 41), #166-1.2 (SEQ ID NO:42), #166-2 (SEQ ID NO:43), #166-3.1 (SEQ ID NO:44), #166-3.2 (SEQ ID NO:45), and #166-4 (SEQ ID NO:46). The atg start codon in exon 3 is shown in bold and also lower case.

FIG. 16. Genomic Sequence of wild type CD163 exons 7-10 used as a reference sequence (SEQ ID NO: 47). The sequence includes 3000 bp upstream of exon 7 to the last base of exon 10. The underlined regions show the locations of exons 7, 8, 9, and 10, respectively.

Figure 20:
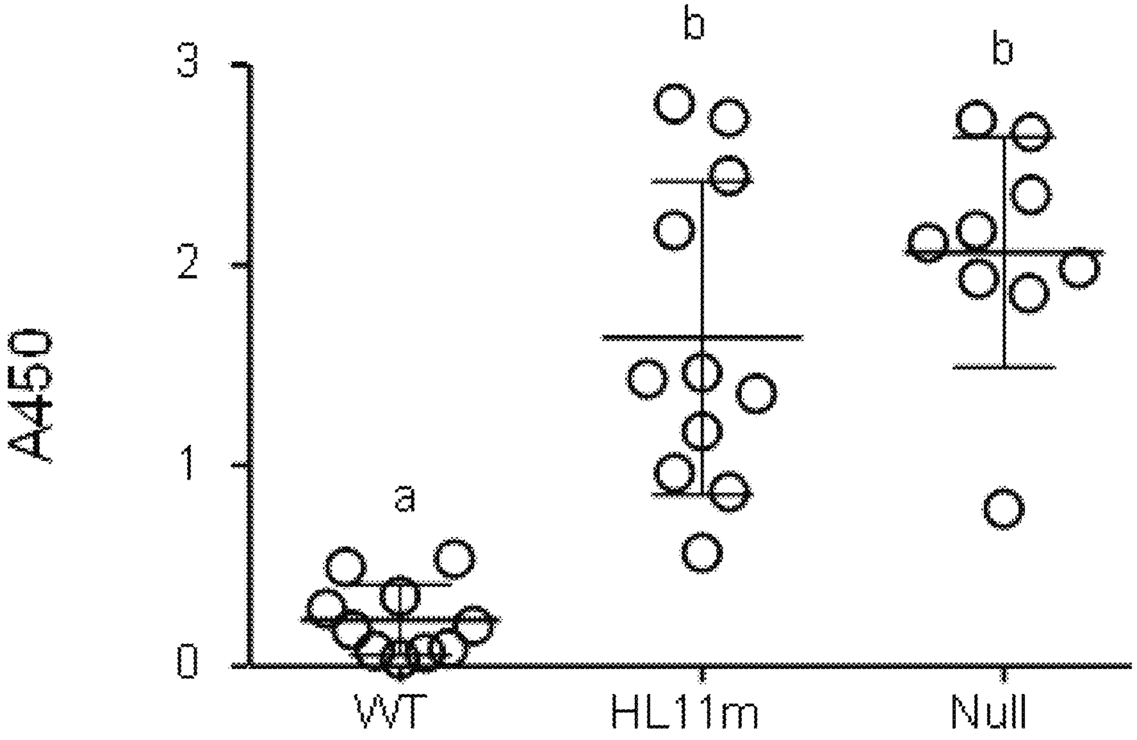

FIG. 20. Serum haptoglobin levels in wild-type and CD163-modified pigs.

Figure 21:
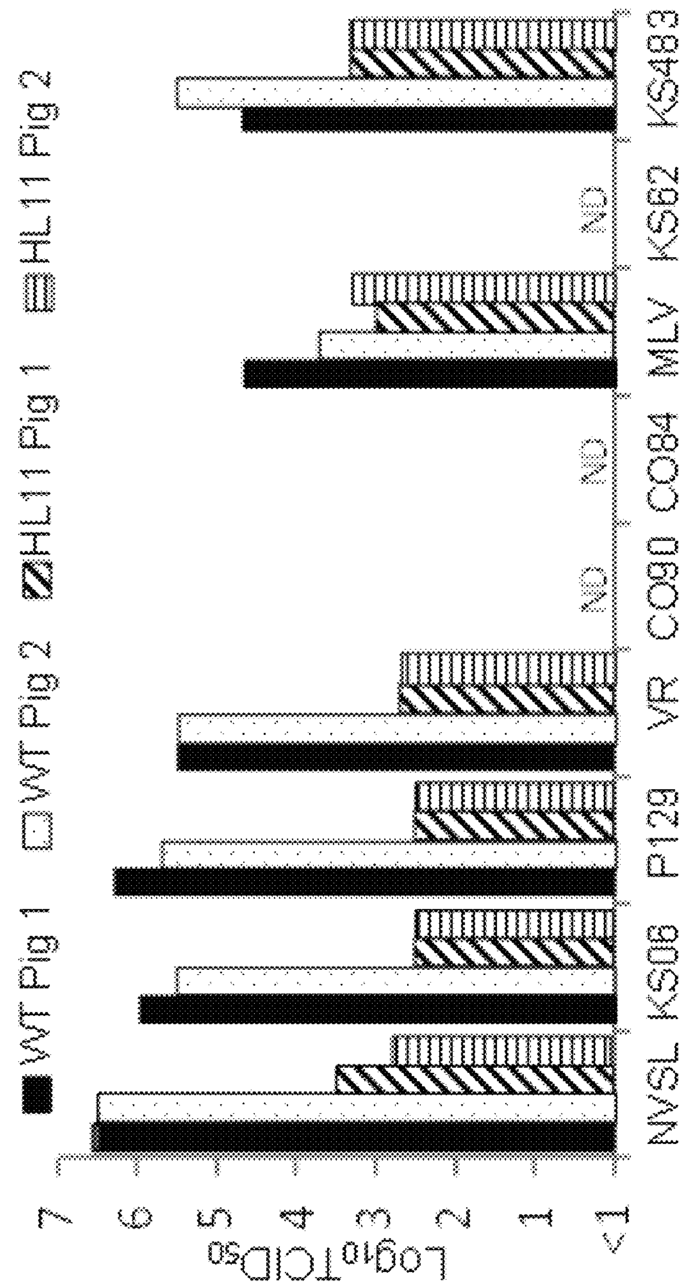

FIG. 21. Relative permissiveness of wild-type and HL11m PAMs to infection with Type 2 PRRSV isolates.

Figure 22:
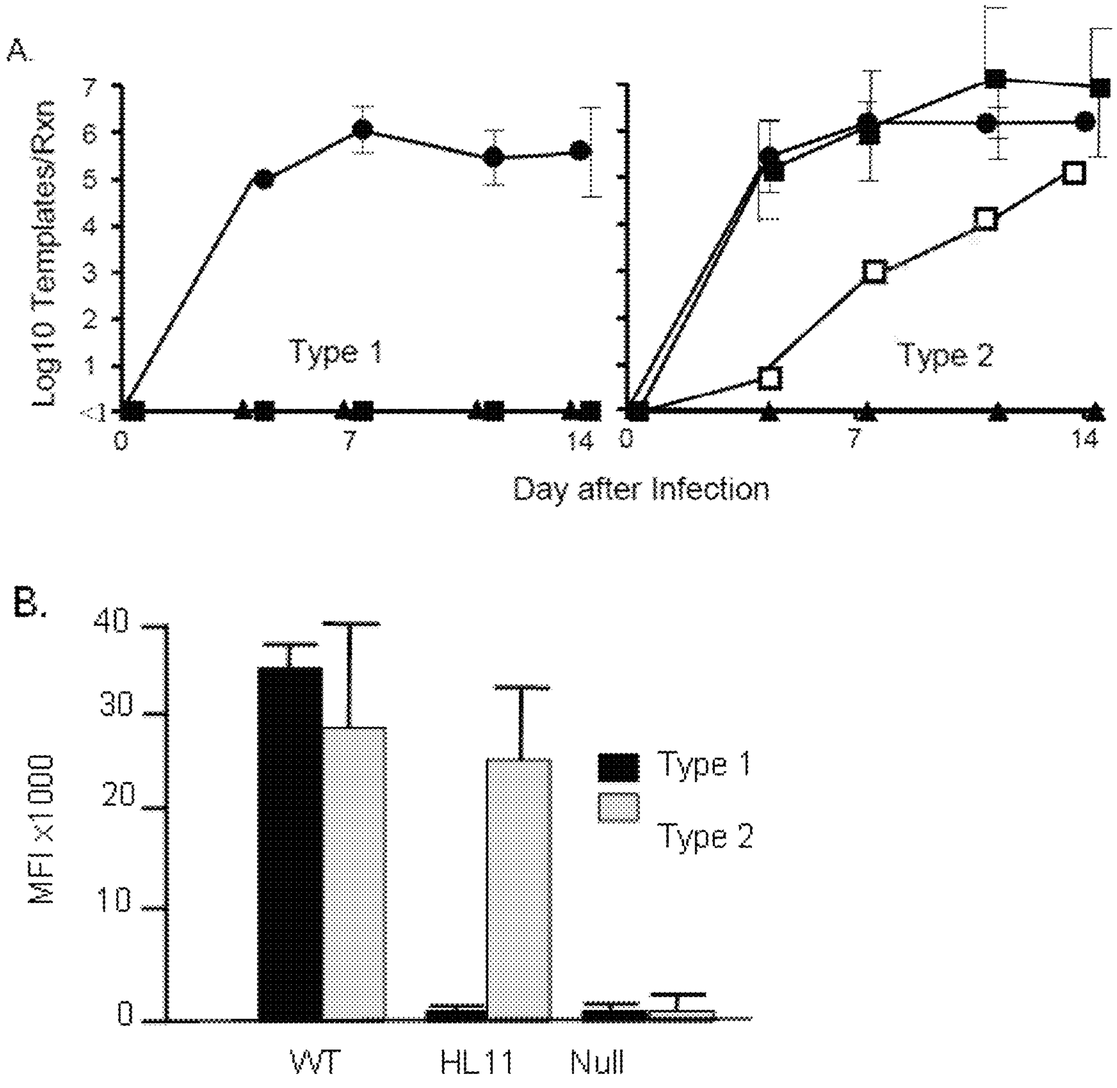

FIG. 22. Infection of CD163 modified pigs with Type 1 and Type 2 PRRSV isolates.

Figure 23:
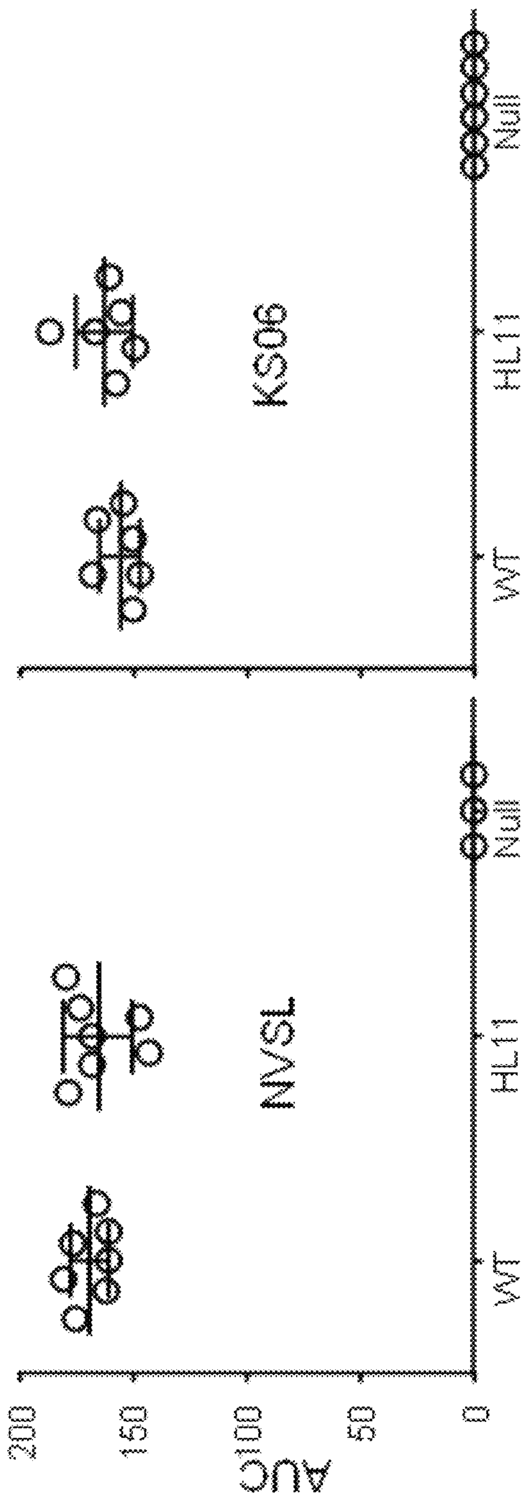

FIG. 23. Virus load for WT and CD163-modified pigs infected with Type 2 viruses.

Figure 24:
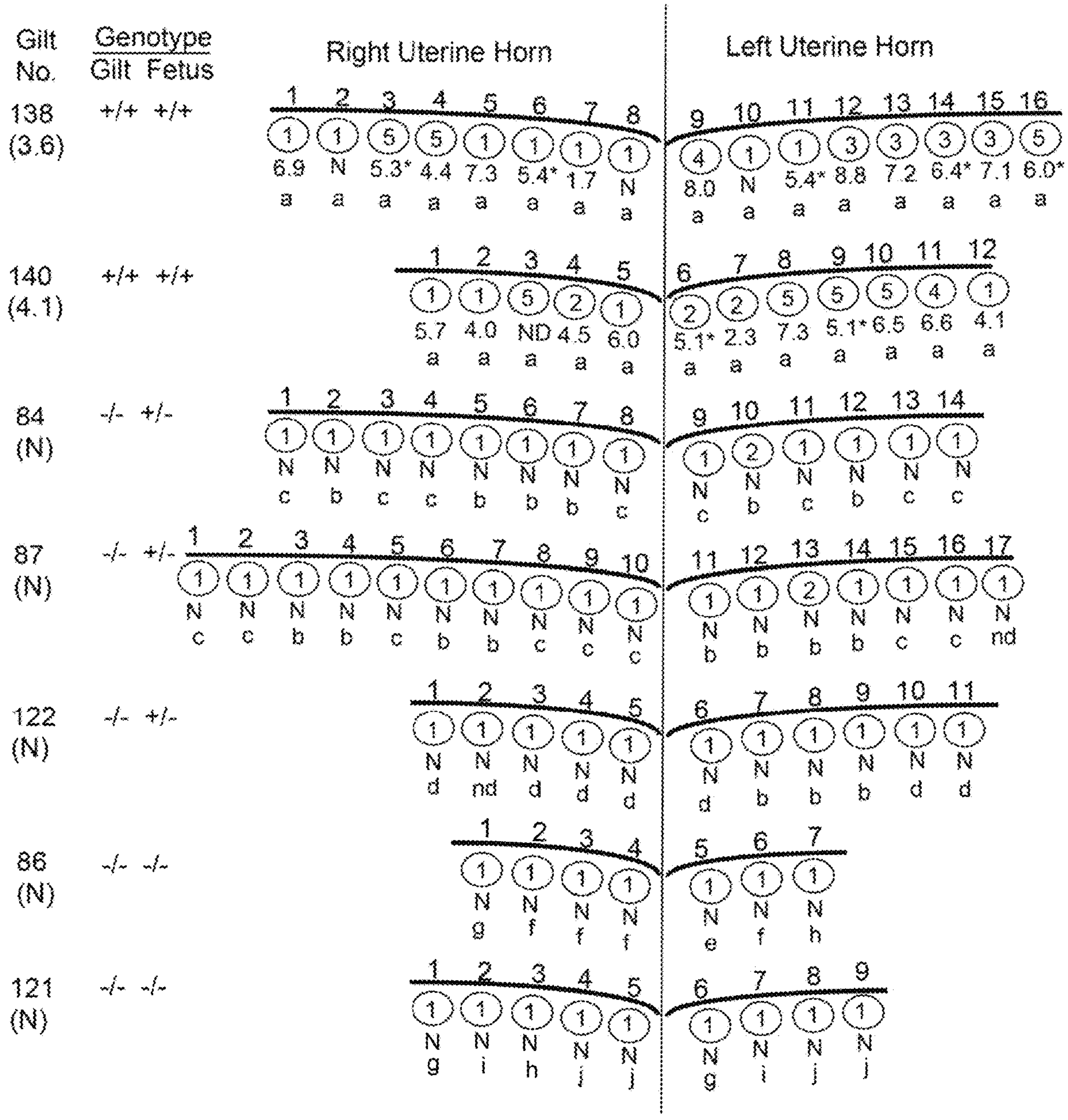

FIG. 24. Fetal outcomes following maternal infection with PRRSV. The numbers on the left identify each dam ("Dam No."; see Table 16 below). Below each dam number in parenthesis is the result for PRRS PCR in serum, measured as $\log_{10}$ templates per reaction. "N" is negative for PRRSV nucleic acid (Ct>39). Fetuses are identified by number and relative position within each uterine horn. Asterisks identify fetal PCR samples obtained from abdominal fluid. The number below each fetus is the result for PRRS PCR in fetal serum ($\log_{10}$ templates per reaction). The number within each circle refers to the presence of anatomical pathology: 1) normal fetus; 2) small fetus; 3) placenta changes such as detached placenta and/or necrosis; 4) meconium stained fetus; 5) fetus is dead and necrotic. Lower case letters identify the genotype of the individual fetuses (see Table 16). Key: a, A/A; b, C/A; c, B/A; d, E/A; e, B/C; f, B/D; g, D/C; h, D/D; i, E/C; j, E/D; ND not determined because the fetus was necrotic; nd, genotype was not determined.

DETAILED DESCRIPTION OF THE INVENTION

The present invention is directed to methods for protecting porcine fetuses from infection with porcine reproductive and respiratory syndrome virus (PRRSV). Pigs having inactivating mutations in both alleles of the CD163 gene are resistant to infection with PRRSV. It has now unexpectedly been found that CD163-positive fetuses (e.g., fetuses that have one or two wild-type CD163 alleles) can be protected from PRRSV infection while in utero so long as the dam possesses inactivating mutations in both alleles of her CD163 gene. Thus, for example, dams having inactivating mutations in both alleles of the CD163 gene can be mated males having two wild-type CD163 alleles, and the resulting heterozygous fetuses will be protected from PRRSV infection.

Definitions

When introducing elements of the present invention or the preferred embodiments(s) thereof, the articles "a", "an", "the", and "said" are intended to mean that there are one or more of the elements.

The term "and/or" means any one of the items, any combination of the items, or all of the items with which this term is associated.

The term "breeding" as used herein refers to the union of male and female gametes so that fertilization occurs. Such a union may be brought about by mating (copulation) or by in vitro or in vivo artificial methods. Such artificial methods include, but are not limited to, artificial insemination, surgical assisted artificial insemination, in vitro fertilization, intracytoplasmic sperm injection, zona drilling, in vitro culture of fertilized oocytes, ovary transfer, and ovary splitting. The term "breeding" as used herein also includes transferring of a fertilized oocyte into the reproductive tract of a female animal.

The terms "comprising", "including", and "having" are intended to be inclusive and mean that there may be additional elements other than the listed elements.

The term "CRISPR" stands for "clustered regularly interspaced short palindromic repeats." CRISPR systems include Type I, Type II, and Type III CRISPR systems.

The term "Cas" refers to "CRISPR associated protein." Cas proteins include but are not limited to Cas9 family member proteins, Cas6 family member proteins (e.g., Csy4 and Cas6), and Cas5 family member proteins.

The term "Cas9" can generally refer to a polypeptide with at least about 5%, 10%, 20%, 30%, 40%, 50%, 60%, 70%, 80%, 90%, or 100% sequence identity and/or sequence similarity to a wild-type Cas9 polypeptide (e.g., Cas9 from *S. pyogenes*). Illustrative Cas9 sequences are provided by SEQ ID NOs. 1-256 and 795-1346 of U.S. Patent Publication No. 2016/0046963. SEQ ID NOs. 1-256 and 795-1346 of U.S. Patent Publication No. 2016/0046963 are hereby incorporated herein by reference. "Cas9" can refer to can refer to a polypeptide with at most about 5%, 10%, 20%, 30%, 40%, 50%, 60%, 70%, 80%, 90%, or 100% sequence identity and/or sequence similarity to a wild type Cas9 polypeptide (e.g., from *S. pyogenes*). "Cas9" can refer to the wild-type or a modified form of the Cas9 protein that can comprise an amino acid change such as a deletion, insertion, substitution, variant, mutation, fusion, chimera, or any combination thereof.

The term "Cas5" can generally refer to can refer to a polypeptide with at least about 5%, 10%, 20%, 30%, 40%, 50%, 60%, 70%, 80%, 90%, or 100% sequence identity and/or sequence similarity to a wild type illustrative Cas5 polypeptide (e.g., Cas5 from *D. vulgaris*). Illustrative Cas5 sequences are provided in FIG. 42 of U.S. Patent Publication No. 2016/0046963. FIG. 42 of U.S. Patent Publication No. 2016/0046963 is hereby incorporated herein by reference. "Cas5" can generally refer to can refer to a polypeptide with at most about 5%, 10%, 20%, 30%, 40%, 50%, 60%, 70%, 80%, 90%, or 100% sequence identity and/or sequence similarity to a wild-type Cas5 polypeptide (e.g., a Cas5 from *D. vulgaris*). "Cas5" can refer to the wild-type or a modified form of the Cas5 protein that can comprise an amino acid change such as a deletion, insertion, substitution, variant, mutation, fusion, chimera, or any combination thereof.

The term "Cas6" can generally refer to can refer to a polypeptide with at least about 5%, 10%, 20%, 30%, 40%, 50%, 60%, 70%, 80%, 90%, or 100% sequence identity and/or sequence similarity to a wild type illustrative Cas6 polypeptide (e.g., a Cas6 from *T. thermophilus*). Illustrative Cas6 sequences are provided in FIG. 41 of U.S. Patent Publication No. 2016/0046963. FIG. 41 of U.S. Patent Publication No. 2016/0046963 is hereby incorporated herein by reference. "Cas6" can generally refer to can refer to a polypeptide with at most about 5%, 10%, 20%, 30%, 40%, 50%, 60%, 70%, 80%, 90%, or 100% sequence identity and/or sequence similarity to a wild-type Cas6 polypeptide (e.g., from *T. thermophilus*). "Cas6" can refer to the wild-type or a modified form of the Cas6 protein that can comprise an amino acid change such as a deletion, insertion, substitution, variant, mutation, fusion, chimera, or any combination thereof.

The terms "CRISPR/Cas9" or "CRISPR/Cas9 system" refer to a programmable nuclease system for genetic engineering that includes a Cas9 protein, or derivative thereof, and one or more non-coding RNAs that can provide the function of a CRISPR RNA (crRNA) and trans-activating RNA (tracrRNA) for the Cas9. The crRNA and tracrRNA can be used individually or can be combined to produce a "guide RNA" (gRNA). The crRNA or gRNA provide sequence that is complementary to the genomic target.

References herein to a deletion in a nucleotide sequence from nucleotide x to nucleotide y mean that all of the nucleotides in the range have been deleted, including x and y. Thus, for example, the phrase "an 11 base pair deletion from nucleotide 3,137 to nucleotide 3,147 as compared to SEQ ID NO: 47" means that each of nucleotides 3,317 through 3,147 have been deleted, including nucleotides 3,317 and 3,147.

"Resistance" of an animal to a disease is a characteristic of an animal, wherein the animal avoids the disease symptoms that are the outcome of animal-pathogen interactions, such as interactions between a porcine animal and PRRSV. That is, pathogens are prevented from causing animal diseases and the associated disease symptoms, or alternatively, a reduction of the incidence and/or severity of clinical signs or reduction of clinical symptoms. One of skill in the art will appreciate that the methods disclosed herein can be used with other compositions and methods available in the art for protecting animals from pathogen attack.

As used herein, "gene editing," "gene edited", "genetically edited" and "gene editing effectors" refer to the use of homing technology with naturally occurring or artificially engineered nucleases, also referred to as "molecular scissors," "homing endonucleases," or "targeting endonucleases." The nucleases create specific double-stranded chromosomal breaks (DSBs) at desired locations in the genome, which in some cases harnesses the cell's endogenous mechanisms to repair the induced break by natural processes of homologous recombination (HR) and/or non-homologous end-joining (NHEJ). Gene editing effectors include Zinc Finger Nucleases (ZFNs), Transcription Activator-Like Effector Nucleases (TALENs), Clustered Regularly Interspaced Short Palindromic Repeats (CRISPR) systems (e.g., the CRISPR/Cas9 system), and meganucleases (e.g., meganucleases re-engineered as homing endonucleases). The terms also include the use of transgenic procedures and techniques, including, for example, where the change is a deletion or relatively small insertion (typically less than 20 nt) and/or does not introduce DNA from a foreign species. The term also encompasses progeny animals such as those created by sexual crosses or asexual propagation from the initial gene edited animal.

The terms "genome engineering," "genetic engineering," "genetically engineered," "genetically altered," "genetic alteration," "genome modification," "genome modification," and "genomically modified" can refer to altering the genome by deleting, inserting, mutating, or substituting specific nucleic acid sequences. The altering can be gene or location specific. Genome engineering can use nucleases to cut a nucleic acid thereby generating a site for the alteration. Engineering of non-genomic nucleic acid is also contemplated. A protein containing a nuclease domain can bind and cleave a target nucleic acid by forming a complex with a nucleic acid-targeting nucleic acid. In one example, the cleavage can introduce double stranded breaks in the target nucleic acid. A nucleic acid can be repaired e.g. by endogenous non-homologous end joining (NHEJ) machinery. In a further example, a piece of nucleic acid can be inserted. Modifications of nucleic acid-targeting nucleic acids and site-directed polypeptides can introduce new functions to be used for genome engineering.

As used herein "homing DNA technology," "homing technology" and "homing endonuclease" include any mechanisms that allow a specified molecule to be targeted to a specified DNA sequence including Zinc Finger (ZF) proteins, Transcription Activator-Like Effectors (TALEs) meganucleases, and CRISPR systems (e.g., the CRISPR/Cas9 system).

The terms "increased resistance" and "reduced susceptibility" herein mean, but are not limited to, a statistically significant reduction of the incidence and/or severity of clinical signs or clinical symptoms which are associated with infection by pathogen. For example, "increased resistance" or "reduced susceptibility" can refer to a statistically significant reduction of the incidence and/or severity of clinical signs or clinical symptoms which are associated with infection by PRRS V in an animal comprising a modified chromosomal sequence in a CD163 gene protein as compared to a control animal having an unmodified chromosomal sequence. The term "statistically significant reduction of clinical symptoms" means, but is not limited to, the frequency in the incidence of at least one clinical symptom in the modified group of subjects is at least 10%, preferably at least 20%, more preferably at least 30%, even more preferably at least 50%, and even more preferably at least 70% lower than in the non-modified control group after the challenge with the infectious agent.

"Knock-out" means disruption of the structure or regulatory mechanism of a gene. Knock-outs may be generated through homologous recombination of targeting vectors, replacement vectors, or hit-and-run vectors or random insertion of a gene trap vector resulting in complete, partial or conditional loss of gene function.

As used herein, the term "mutation" includes alterations in the nucleotide sequence of a polynucleotide, such as for example a gene or coding DNA sequence (CDS), compared to the wild-type sequence. The term includes, without limitation, substitutions, insertions, frameshifts, deletions, inversions, translocations, duplications, splice-donor site mutations, point-mutations and the like.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, these terms encompass any clinical signs of infection, lung pathology, viremia, antibody production, reduction of pathogen load, pathogen shedding, reduction in pathogen transmission, or reduction of any clinical sign symptomatic of PRRSV. Preferably these clinical signs are reduced in one or more animals of the invention by at least 10% in comparison to subjects not having a modification in the CD163 gene and that become infected. More preferably clinical signs are reduced in subjects of the invention by at least 20%, preferably by at least 30%, more preferably by at least 40%, and even more preferably by at least 50%.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Zinc finger and TALE binding domains can be "engineered" to bind to a predetermined nucleotide sequence, for example via engineering (altering one or more amino acids) of the recognition helix region of naturally occurring zinc finger or TALE proteins. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

Various other terms are defined hereinbelow.

Methods for Protecting Porcine Fetuses from PRRSV Infection

A method for protecting a porcine fetus from infection with porcine reproductive and respiratory syndrome virus (PRRSV) is provided. The method comprises breeding a female porcine animal with a male porcine animal. The female porcine animal comprises modified chromosomal sequences in both alleles of its CD163 gene, wherein the modified chromosomal sequences reduce the susceptibility of the female porcine animal to infection by PRRSV, as compared to the susceptibility to infection by PRRSV of a female porcine animal that does not comprise any modified chromosomal sequences in the alleles of its CD163 gene. The male porcine animal comprises at least one wild-type CD163 allele.

In the methods described herein, the modified chromosomal sequences can be sequences that are altered such that a CD163 protein function as it relates to PRRSV infection is impaired, reduced, or eliminated. Thus, the female porcine animals used in the methods described herein can be referred to as a "knock-out" animal.

The male porcine animal can comprise two wild-type CD163 alleles.

The term "wild-type CD163 allele" as used herein means that the sequence of the CD163 allele is a sequence as found in nature, or that the sequence of the CD163 allele contains one or more mutations (e.g., insertions, deletions, or substitutions) that do not substantially impair CD163 activity. Thus, wild-type CD163 alleles can contain polymorphisms and/or mutations, so long as those polymorphisms or mutations do not substantially impair CD163 activity.

Using the methods described herein, the fetuses will be protected from both Type 1 and Type 2 PRRSV viruses, including various Type 1 and Type 2 PRRSV isolates.

Thus, in the methods described herein, the modified chromosomal sequences can reduce the susceptibility of the female porcine animal to a Type 1 PRRSV virus, a Type 2 PRRSV, or to both Type 1 and Type 2 PRRSV viruses.

The modified chromosomal sequences can reduce the susceptibility of the female porcine animal to a PRRSV isolate selected from the group consisting of NVSL 97-7895, KS06-72109, P129, VR2332, CO90, AZ25, MLV-ResPRRS, KS62-06274, KS483 (SD23983), CO84, SD13-15, Lelystad, 03-1059, 03-1060, SD01-08, 4353W, and combinations thereof.

The female porcine animal can comprise a genetically edited female porcine animal.

The genetically edited female porcine animal can be an animal that has been edited using a homing endonuclease. The homing endonuclease can be a naturally occurring endonuclease but is preferably a rationally designed, non-naturally occurring homing endonuclease that has a DNA recognition sequence that has been designed so that the endonuclease targets a chromosomal sequence in gene encoding a CD163 protein.

Thus, the homing endonuclease can be a designed homing endonuclease. The homing endonuclease can comprise, for example, a Clustered Regularly Interspaced Short Palindromic Repeats (CRISPR) system, a Transcription Activator-Like Effector Nuclease (TALEN), a Zinc Finger Nuclease (ZFN), a recombinase fusion protein, a meganuclease, or a combination of any thereof.

The homing nuclease preferably comprises a CRISPR system. Examples of CRISPR systems that can be used to create the female porcine animals for use in the methods described herein include, but are not limited to CRISPR/Cas9, CRISPR/Cas5, and CRISPR/Cas6. The use of CRISPR systems to generate genetically edited animals is discussed further hereinbelow.

In any of the methods described herein, the female porcine animal can comprise the same modified chromosomal sequence in both alleles of the CD163 gene.

Alternatively, the female porcine animal can comprise a first modified chromosomal sequence in a first allele of the CD163 gene and a second modified chromosomal sequence in a second allele of the CD163 gene, the first and second modified chromosomal sequences being different from each other.

In any of the methods described herein, each allele of the CD163 gene of the female porcine animal can comprise an insertion, a deletion, or a combination thereof.

For example, at least one allele of the CD163 gene of the female porcine animal can comprise a deletion.

At least one allele of the CD163 gene can comprise an in-frame deletion.

At least one allele of the CD163 gene of the female porcine animal can comprise an insertion.

In the methods described herein, the modified chromosomal sequences preferably cause CD163 protein production or activity to be reduced, as compared to CD163 protein production or activity in a female porcine animal that lacks the modified chromosomal sequences.

Preferably, the modified chromosomal sequences result in production of substantially no functional CD163 protein by the female porcine animal. By "substantially no functional CD163 protein," it is meant that the level of CD163 protein in the animal, offspring, or cell is undetectable, or if detectable, is at least about 90% lower, preferably at least about 95% lower, more preferably at least about 98%, lower, and even more preferably at least about 99% lower than the level observed in an animal, offspring, or cell that does not comprise the modified chromosomal sequences.

For example, in any of the methods described herein, the female porcine animal does not produce CD163 protein.

In any of the methods described herein, each allele of the CD163 gene of the female porcine animal can comprise a modification in exon 7, a modification in exon 8, a modification in an intron that is contiguous with exon 7 or exon 8, or a combination of any thereof.

For example, one or both alleles of the CD163 gene of the female porcine animal can comprise a modification in exon 7 of the CD163 gene.

The modification in exon 7 can comprise a deletion.

In any of the methods described herein wherein an allele of the CD163 gene of the female porcine animal comprises a deletion, the deletion can comprise an in-frame deletion.

The modification in exon 7 can comprise an insertion.

In any of the methods described herein, the modified chromosomal sequences in one or both alleles of the CD163 gene of the female porcine animal can result in a miscoding.

Where a modified chromosomal sequence results in a miscoding in an allele of the CD163 gene, the miscoding can result in a premature stop codon downstream of the miscoding in the allele of the CD163 gene.

In any of the methods described herein, at least one of the alleles of the CD163 gene in the female porcine animal comprises a modification selected from the group consisting of: an 11 base pair deletion from nucleotide 3,137 to nucleotide 3,147 as compared to reference sequence SEQ ID NO: 47; a 2 base pair insertion between nucleotides 3,149 and 3,150 as compared to reference sequence SEQ ID NO: 47, with a 377 base pair deletion from nucleotide 2,573 to nucleotide 2,949 as compared to reference sequence SEQ ID NO: 47 on the same allele; a 124 base pair deletion from nucleotide 3,024 to nucleotide 3,147 as compared to reference sequence SEQ ID NO: 47; a 123 base pair deletion from nucleotide 3,024 to nucleotide 3,146 as compared to reference sequence SEQ ID NO: 47; a 1 base pair insertion between nucleotides 3,147 and 3,148 as compared to reference sequence SEQ ID NO: 47; a 130 base pair deletion from nucleotide 3,030 to nucleotide 3,159 as compared to reference sequence SEQ ID NO: 47; a 132 base pair deletion from nucleotide 3,030 to nucleotide 3,161 as compared to reference sequence SEQ ID NO: 47; a 1506 base pair deletion from nucleotide 1,525 to nucleotide 3,030 as compared to reference sequence SEQ ID NO: 47; a 7 base pair insertion between nucleotide 3,148 and nucleotide 3,149 as compared to reference sequence SEQ ID NO: 47; a 1280 base pair deletion from nucleotide 2,818 to nucleotide 4,097 as compared to reference sequence SEQ ID NO: 47; a 1373 base pair deletion from nucleotide 2,724 to nucleotide 4,096 as compared to reference sequence SEQ ID NO: 47; a 1467 base pair deletion from nucleotide 2,431 to nucleotide 3,897 as compared to reference sequence SEQ ID NO: 47; a 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; a 28 base pair deletion from nucleotide 3,145 to nucleotide 3,172 as compared to reference sequence SEQ ID NO: 47; a 1387 base pair deletion from nucleotide 3,145 to nucleotide 4,531 as compared to reference sequence SEQ ID NO: 47; a 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; a 452 base pair deletion from nucleotide 3,015 to nucleotide 3,466 as compared to reference sequence SEQ ID NO: 47; and combinations of any thereof.

At least one of the alleles of the CD163 gene in the female porcine animal can comprise the 11 base pair deletion from nucleotide 3,137 to nucleotide 3,147 as compared to reference sequence SEQ ID NO: 47.

At least one of the alleles of the CD163 gene in the female porcine animal can comprise the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele.

Where the modification comprises the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele, and the 2 base pair insertion can comprise the dinucleotide AG.

At least one of the alleles of the CD163 gene in the female porcine animal can comprise the 124 base pair deletion from nucleotide 3,024 to nucleotide 3,147 as compared to reference sequence SEQ ID NO: 47.

At least one of the alleles of the CD163 gene in the female porcine animal can comprise the 123 base pair deletion from nucleotide 3,024 to nucleotide 3,146 as compared to reference sequence SEQ ID NO: 47.

At least one of the alleles of the CD163 gene in the female porcine animal can comprise the 1 base pair insertion between nucleotides 3,147 and 3,148 as compared to reference sequence SEQ ID NO: 47.

Where the modification comprises the 1 base pair insertion between nucleotides 3,147 and 3,148 as compared to reference sequence SEQ ID NO: 47, the 1 base pair insertion can comprise a single adenine residue.

At least one of the alleles of the CD163 gene in the female porcine animal can comprise the 130 base pair deletion from nucleotide 3,030 to nucleotide 3,159 as compared to reference sequence SEQ ID NO: 47.

At least one of the alleles of the CD163 gene in the female porcine animal can comprise the 132 base pair deletion from nucleotide 3,030 to nucleotide 3,161 as compared to reference sequence SEQ ID NO: 47.

At least one of the alleles of the CD163 gene in the female porcine animal can comprise the 1506 base pair deletion from nucleotide 1,525 to nucleotide 3,030 as compared to reference sequence SEQ ID NO: 47.

At least one of the alleles of the CD163 gene in the female porcine animal can comprise the 7 base pair insertion between nucleotide 3,148 and nucleotide 3,149 as compared to reference sequence SEQ ID NO: 47.

Where the modification comprises the 7 base pair insertion between nucleotide 3,148 and nucleotide 3,149 as compared to reference sequence SEQ ID NO: 47, the 7 base pair insertion can comprise the sequence TACTACT (SEQ ID NO: 115).

At least one of the alleles of the CD163 gene in the female porcine animal can comprise the 1280 base pair deletion from nucleotide 2,818 to nucleotide 4,097 as compared to reference sequence SEQ ID NO: 47.

At least one of the alleles of the CD163 gene in the female porcine animal can comprise the 1373 base pair deletion from nucleotide 2,724 to nucleotide 4,096 as compared to reference sequence SEQ ID NO: 47.

At least one of the alleles of the CD163 gene in the female porcine animal can comprise the 1467 base pair deletion from nucleotide 2,431 to nucleotide 3,897 as compared to reference sequence SEQ ID NO: 47.

At least one of the alleles of the CD163 gene in the female porcine animal can comprise the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47.

Where the modification comprises the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47, the 12 base pair insertion can comprise the sequence TGTGGAGAATTC (SEQ ID NO: 116).

At least one of the alleles of the CD163 gene in the female porcine animal can comprise the 28 base pair deletion from nucleotide 3,145 to nucleotide 3,172 as compared to reference sequence SEQ ID NO: 47.

At least one of the alleles of the CD163 gene in the female porcine animal can comprise the 1387 base pair deletion from nucleotide 3,145 to nucleotide 4,531 as compared to reference sequence SEQ ID NO: 47.

At least one of the alleles of the CD163 gene in the female porcine animal can comprise the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113.

Where the modification comprises the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113, the 11 base pair insertion can comprises the sequence AGCCAGCGTGC (SEQ ID NO: 117).

At least one of the alleles of the CD163 gene in the female porcine animal can comprise the 1720 base pair deletion from nucleotide 2,440 to nucleotide 4,160 as compared to reference sequence SEQ ID NO: 47.

At least one of the alleles of the CD163 gene in the female porcine animal can comprise the 452 base pair deletion from nucleotide 3,015 to nucleotide 3,466 as compared to reference sequence SEQ ID NO: 47.

For example, at least one of the alleles of the CD163 gene in the female porcine animal comprises a modification selected from the group consisting of: the 7 base pair insertion between nucleotide 3,148 and nucleotide 3,149 as compared to reference sequence SEQ ID NO: 47; the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele; the 11 base pair deletion from nucleotide 3,137 to nucleotide 3,147 as compared to reference sequence SEQ ID NO: 47; the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113; and combinations of any thereof.

The CD163 gene in the female porcine animal can comprise any combination of the modified chromosomal sequences described herein.

For example, the female porcine animal can comprise the 7 base pair insertion between nucleotide 3,148 and nucleotide 3,149 as compared to reference sequence SEQ ID NO: 47 in one allele of the CD163 gene; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47, in the other allele of the CD163 gene.

The female porcine animal can comprise the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113, in one allele of the CD163 gene; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47, in the other allele of the CD163 gene.

The female porcine animal can comprise the 7 base pair insertion between nucleotide 3,148 and nucleotide 3,149 as compared to reference sequence SEQ ID NO: 47 in one allele of the CD163 gene; and the 11 base pair deletion from nucleotide 3,137 to nucleotide 3,147 as compared to reference sequence SEQ ID NO: 47 in the other allele of the CD163 gene.

The female porcine animal can comprise the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113, in one allele of the CD163 gene; and the 11 base pair deletion from nucleotide 3,137 to nucleotide 3,147 as compared to reference sequence SEQ ID NO: 47 in the other allele of the CD163 gene.

In any of the methods described herein, the alleles of the CD163 gene of the female porcine animal can comprise a chromosomal sequence having at least 80% sequence identity to SEQ ID NO: 47 in the regions of said chromosomal sequence outside of the insertion or deletion.

The alleles of the CD163 gene of the female porcine animal can comprise a chromosomal sequence having at least 85% sequence identity to SEQ ID NO: 47 in the regions of said chromosomal sequence outside of the insertion or deletion.

The alleles of the CD163 gene of the female porcine animal can comprise a chromosomal sequence having at least 90% sequence identity to SEQ ID NO: 47 in the regions of said chromosomal sequence outside of the insertion or deletion.

The alleles of the CD163 gene of the female porcine animal can comprise a chromosomal sequence having at least 95% sequence identity to SEQ ID NO: 47 in the regions of said chromosomal sequence outside of the insertion or deletion.

The alleles of the CD163 gene of the female porcine animal can comprise a chromosomal sequence having at least 98% sequence identity to SEQ ID NO: 47 in the regions of said chromosomal sequence outside of the insertion or deletion.

The alleles of the CD163 gene of the female porcine animal can comprise a chromosomal sequence having at least 99% sequence identity to SEQ ID NO: 47 in the regions of said chromosomal sequence outside of the insertion or deletion.

The alleles of the CD163 gene of the female porcine animal can comprise a chromosomal sequence having at least 99.9% sequence identity to SEQ ID NO: 47 in the regions of said chromosomal sequence outside of the insertion or deletion.

The alleles of the CD163 gene of the female porcine animal can comprise a chromosomal sequence having 100% sequence identity to SEQ ID NO: 47 in the regions of said chromosomal sequence outside of the insertion or deletion.

In any of the methods described herein, the female porcine animal can comprise a chromosomal sequence comprising SEQ ID NO: 98, 99, 100, 101, 102, 103, 104, 105, 106, 107, 108, 109, 110, 111, 112, 113, 114, or 119 in one or both alleles of the CD163 gene.

For example, the female porcine animal can comprise a chromosomal sequence comprising SEQ ID NO: 99, 102, 103, or 113 in one or both alleles of the CD163 gene.

The alleles of the CD163 gene in the female porcine animal can comprise any combination of chromosomal sequences comprising SEQ ID NO: 98, 99, 100, 101, 102, 103, 104, 105, 106, 107, 108, 109, 110, 111, 112, 113, 114, or 119. Thus, the female porcine animal can comprise a chromosomal sequence comprising any one of SEQ ID NO: 98, 99, 100, 101, 102, 103, 104, 105, 106, 107, 108, 109, 110, 111, 112, 113, 114, or 119 in one allele of the CD163 gene and a chromosomal sequence comprising any one of SEQ ID NO: 98, 99, 100, 101, 102, 103, 104, 105, 106, 107, 108, 109, 110, 111, 112, 113, 114, or 119 in the other allele of the CD163 gene.

For example, the female porcine animal can comprise a chromosomal sequence comprising SEQ ID NO: 99 in one allele of the CD163 gene, and a chromosomal sequence comprising SEQ ID NO: 103 in the other allele of the CD163 gene.

The female porcine animal can comprise a chromosomal sequence comprising SEQ ID NO: 113 in one allele of the CD163 gene, and a chromosomal sequence comprising SEQ ID NO: 99 in the other allele of the CD163 gene.

The female porcine animal can comprise a chromosomal sequence comprising SEQ ID NO: 99 in one allele of the CD163 gene, and a chromosomal sequence comprising SEQ ID NO: 102 in the other allele of the CD163 gene.

The female porcine animal can comprise a chromosomal sequence comprising SEQ ID NO: 113 in one allele of the CD163 gene, and a chromosomal sequence comprising SEQ ID NO: 102 in the other allele of the CD163 gene.

In any of the methods described herein, the breeding will produce one or more fetuses that comprise a modified chromosomal sequence in a single allele of the CD163 gene. Since the female porcine animal used in the methods described herein comprises modified chromosomal sequences in both alleles of its CD163 gene, breeding the female porcine animal with a male porcine animal comprising at least one wild-type CD163 allele will produce fetuses that have inherited a CD163 allele comprising the modified chromosomal sequence from the female porcine animal and a wild-type CD163 allele from the male porcine animal. Thus, the breeding will produce fetuses that are heterozygous for the modified CD163 chromosomal sequence. Where the male animal comprises two wild-type CD163 alleles, all of the fetuses produced as a result of the breeding will be heterozygous for the modified CD163 chromosomal sequence.

The fetuses produced by the breeding will have reduced susceptibility to infection by PRRSV while in utero, as compared to fetuses in utero in a wild-type female porcine animal.

In any of the methods described herein, the breeding can comprise mating (copulation) of the female porcine animal with the male porcine animal.

In any of the methods described herein, the breeding can comprises artificial insemination of the female animal with sperm obtained from the male animal.

In any of the methods described herein, the breeding can comprise transferring a fertilized oocyte into the reproductive tract of the female porcine animal.

In methods where the breeding comprises transferring a fertilized oocyte into the reproductive tract of the female porcine animal, the fertilized oocyte can be generated by in vitro fertilization of the oocyte with sperm obtained from the male porcine animal.

The in vitro fertilization can comprise intracytoplasmic injection of an oocyte with sperm obtained from the male porcine animal.

Where the breeding comprises transferring a fertilized oocyte into the reproductive tract of the female porcine animal, the oocyte can be an oocyte derived from the porcine female animal, such that the oocyte comprises modified chromosomal sequences in both alleles of its CD163 gene. Alternatively, the oocyte can be an oocyte derived from a different female porcine animal comprising modified chromosomal sequences in both alleles of its CD163 gene, wherein the modified chromosomal sequences reduce the susceptibility of the animal to infection by PRRSV, as compared to the susceptibility to infection by PRRSV of a female porcine animal that does not comprise any modified chromosomal sequences in the alleles of its CD163 gene. Thus, for example, any oocyte having modified chromosomal sequences in both alleles of its CD163 gene (e.g., knockouts of both alleles of the C163 gene) can be used.

However, where the breeding comprises transferring a fertilized oocyte into the reproductive tract of the female porcine animal, the oocyte need not comprise any modified chromosomal sequences in the alleles of its CD163 gene. An oocyte containing two wild-type CD163 alleles can be used. The oocyte containing two wild-type CD163 alleles can be fertilized with sperm obtained from a male porcine animal, wherein the sperm comprises two wild-type CD163 alleles, to create a fertilized oocyte containing two wild-type CD163 alleles. If such a fertilized oocyte (containing two wild-type CD163 alleles) is transferred into the reproductive tract of the female porcine animal comprising the modified chromosomal sequences in both alleles of its CD163 gene, the resulting fetus will be protected from PRRSV infection.

Alternatively, where the breeding comprises transferring a fertilized oocyte into the reproductive tract of the female porcine animal, the fertilized oocyte can comprise a modified chromosomal sequence in a single allele of its CD163 gene. Such fertilized oocytes will also produce fetuses that are protected from PRRSV infection upon transfer of the fertilized oocyte into the reproductive tract of the female porcine animal comprising the modified chromosomal sequences in both alleles of its CD163 gene.

Thus, where the breeding comprises transferring a fertilized oocyte into the reproductive tract of the female porcine animal, the fertilized oocyte can comprise modified chromosomal sequences in both alleles of its CD163 gene (e.g., knockouts of both alleles of its CD163 gene), can comprise a modified chromosomal sequence in only one allele of its CD163 gene, or can comprise only wild-type CD163 alleles.

Affinity Tags

An "affinity tag" can be either a peptide affinity tag or a nucleic acid affinity tag. The term "affinity tag" generally refers to a protein or nucleic acid sequence that can be bound to a molecule (e.g., bound by a small molecule, protein, or covalent bond). An affinity tag can be a non-native sequence. A peptide affinity tag can comprise a peptide. A peptide affinity tag can be one that is able to be part of a split system (e.g., two inactive peptide fragments can combine together in trans to form an active affinity tag). A nucleic acid affinity tag can comprise a nucleic acid. A nucleic acid affinity tag can be a sequence that can selectively bind to a known nucleic acid sequence (e.g. through hybridization). A nucleic acid affinity tag can be a sequence that can selectively bind to a protein. An affinity tag can be fused to a native protein. An affinity tag can be fused to a nucleotide sequence.

Sometimes, one, two, or a plurality of affinity tags can be fused to a native protein or nucleotide sequence. An affinity tag can be introduced into a nucleic acid-targeting nucleic acid using methods of in vitro or in vivo transcription. Nucleic acid affinity tags can include, for example, a chemical tag, an RNA-binding protein binding sequence, a DNA-binding protein binding sequence, a sequence hybridizable to an affinity-tagged polynucleotide, a synthetic RNA aptamer, or a synthetic DNA aptamer. Examples of chemical nucleic acid affinity tags can include, but are not limited to, ribo-nucleotriphosphates containing biotin, fluorescent dyes, and digoxeginin. Examples of protein-binding nucleic acid affinity tags can include, but are not limited to, the MS2 binding sequence, the U1A binding sequence, stem-loop binding protein sequences, the boxB sequence, the eIF4A sequence, or any sequence recognized by an RNA binding protein. Examples of nucleic acid affinity-tagged oligonucleotides can include, but are not limited to, biotinylated oligonucleotides, 2, 4-dinitrophenyl oligonucleotides, fluorescein oligonucleotides, and primary amine-conjugated oligonucleotides.

A nucleic acid affinity tag can be an RNA aptamer. Aptamers can include, aptamers that bind to theophylline, streptavidin, dextran B512, adenosine, guanosine, guanine/xanthine, 7-methyl-GTP, amino acid aptamers such as aptamers that bind to arginine, citrulline, valine, tryptophan, cyanocobalamine, N-methylmesoporphyrin IX, flavin, NAD, and antibiotic aptamers such as aptamers that bind to tobramycin, neomycin, lividomycin, kanamycin, streptomycin, viomycin, and chloramphenicol.

A nucleic acid affinity tag can comprise an RNA sequence that can be bound by a site-directed polypeptide. The site-directed polypeptide can be conditionally enzymatically inactive. The RNA sequence can comprise a sequence that can be bound by a member of Type I, Type II, and/or Type III CRISPR systems. The RNA sequence can be bound by a RAMP family member protein. The RNA sequence can be bound by a Cas9 family member protein, a Cas6 family member protein (e.g., Csy4, Cas6). The RNA sequence can be bound by a Cas5 family member protein (e.g., Cas5). For example, Csy4 can bind to a specific RNA hairpin sequence with high affinity (Kd ~50 pM) and can cleave RNA at a site 3' to the hairpin.

A nucleic acid affinity tag can comprise a DNA sequence that can be bound by a site-directed polypeptide. The site-directed polypeptide can be conditionally enzymatically inactive. The DNA sequence can comprise a sequence that can be bound by a member of the Type I, Type II and/or Type III CRISPR system. The DNA sequence can be bound by an Argonaut protein. The DNA sequence can be bound by a protein containing a zinc finger domain, a TALE domain, or any other DNA-binding domain.

A nucleic acid affinity tag can comprise a ribozyme sequence. Suitable ribozymes can include peptidyl transferase 23 SrRNA, RnaseP, Group I introns, Group II introns, GIR1 branching ribozyme, Leadzyme, hairpin ribozymes, hammerhead ribozymes, HDV ribozymes, CPEB3 ribozymes, VS ribozymes, glmS ribozyme, CoTC ribozyme, and synthetic ribozymes.

Peptide affinity tags can comprise tags that can be used for tracking or purification (e.g., a fluorescent protein such as green fluorescent protein (GFP), YFP, RFP, CFP, mCherry, tdTomato; a His tag, (e.g., a 6 XHis tag); a hemagglutinin (HA) tag; a FLAG tag; a Myc tag; a GST tag; a MBP tag; a chitin binding protein tag; a calmodulin tag; a V5 tag; a streptavidin binding tag; and the like).

Both nucleic acid and peptide affinity tags can comprise small molecule tags such as biotin, or digitoxin, and fluorescent label tags, such as for example, fluoroscein, rhodamin, Alexa fluor dyes, Cyanine3 dye, Cyanine5 dye.

Nucleic acid affinity tags can be located 5' to a nucleic acid (e.g., a nucleic acid-targeting nucleic acid). Nucleic acid affinity tags can be located 3' to a nucleic acid. Nucleic acid affinity tags can be located 5' and 3' to a nucleic acid. Nucleic acid affinity tags can be located within a nucleic acid. Peptide affinity tags can be located N-terminal to a polypeptide sequence. Peptide affinity tags can be located C-terminal to a polypeptide sequence. Peptide affinity tags can be located N-terminal and C-terminal to a polypeptide sequence. A plurality of affinity tags can be fused to a nucleic acid and/or a polypeptide sequence.

Capture Agents

As used herein, "capture agent" can generally refer to an agent that can purify a polypeptide and/or a nucleic acid. A capture agent can be a biologically active molecule or material (e.g. any biological substance found in nature or synthetic, and includes but is not limited to cells, viruses, subcellular particles, proteins, including more specifically antibodies, immunoglobulins, antigens, lipoproteins, glycoproteins, peptides, polypeptides, protein complexes, (strept)avidin-biotin complexes, ligands, receptors, or small molecules, aptamers, nucleic acids, DNA, RNA, peptidic nucleic acids, oligosaccharides, polysaccharides, lipopolysaccharides, cellular metabolites, haptens, pharmacologically active substances, alkaloids, steroids, vitamins, amino acids, and sugars). In some embodiments, the capture agent can comprise an affinity tag. In some embodiments, a capture agent can preferentially bind to a target polypeptide or nucleic acid of interest. Capture agents can be free floating in a mixture. Capture agents can be bound to a particle (e.g. a bead, a microbead, a nanoparticle). Capture agents can be bound to a solid or semisolid surface. In some instances, capture agents are irreversibly bound to a target. In other instances, capture agents are reversibly bound to a target (e.g., if a target can be eluted, or by use of a chemical such as imidazole).

DNA-Binding Polypeptides

Site-specific integration can be accomplished by using factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; Tet repressors; LacI; and steroid hormone receptors.

For example, the DNA-binding polypeptide can be a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an $\alpha$-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435: 646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, Beerli et al. (2002) Nature Biotechnol. 20: 135-141; Pabo et al. (2001) Ann. Rev. Biochem. 70: 313-340; Isalan et al. (2001) Nature Biotechnol. 19:656-660; Segal et al. (2001) Curr. Opin. Biotechnol. 12: 632-637; Choo et al. (2000) Curr. Opin. Struct. Biol. 10: 411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites: ZFPs and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Where a porcine female animal for use in the methods described herein has been genetically edited using a zinc-finger nuclease, the female animal can be created using a process comprising introducing into an embryo or cell at least one RNA molecule encoding a targeted zinc finger nuclease and, optionally, at least one accessory polynucleotide. The method further comprises incubating the embryo or cell to allow expression of the zinc finger nuclease, wherein a double-stranded break introduced into the targeted chromosomal sequence by the zinc finger nuclease is repaired by an error-prone non-homologous end-joining DNA repair process or a homology-directed DNA repair process. The method of editing chromosomal sequences encoding a protein associated with germline development using targeted zinc finger nuclease technology is rapid, precise, and highly efficient.

Alternatively, the DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the upstream activation sequence (UAS)).

Native GAL4 consists of 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43(3 Pt 2): 729-36. The N-terminal 65 amino acids of GAL4 comprise the GAL4 DNA-binding domain. Keegan et al. (1986) Science 231:699-704; Johnston (1987) Nature 328:

353-5. Sequence-specific binding requires the presence of a divalent cation coordinated by six Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356: 408-14. The DNA-binding function of the protein positions C-terminal transcriptional activating domains in the vicinity of the promoter, such that the activating domains can direct transcription.

Additional DNA-binding polypeptides that can be used include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10: 3343-56; Baim et al. (1991) Proc. Natl. Acad. Sci. USA 88(12): 5072-6); a steroid hormone receptor (Elliston et al. (1990) J. Biol. Chem. 265: 11517-121); the Tet repressor (U.S. Pat. No. 6,271,341) and a mutated Tet repressor that binds to a tet operator sequence in the presence, but not the absence, of tetracycline (Tc); the DNA-binding domain of NF-kappaB; and components of the regulatory system described in Wang et al. (1994) Proc. Natl. Acad. Sci. USA 91(17):8180-4, which utilizes a fusion of GAL4, a hormone receptor, and VP16.

The DNA-binding domain of one or more of the nucleases used in the methods and compositions described herein can comprise a naturally occurring or engineered (non-naturally occurring) TAL effector DNA binding domain See, e.g., U.S. Patent Publication No. 2011/0301073.

Alternatively, the nuclease can comprise a CRISPR system. For example, the nuclease can comprise a CRISPR/Cas system.

The (CRISPR-associated) system evolved in bacteria and archaea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of a Cas protein (e.g., Cas9 protein) to the sequence in the viral genome. The Cas protein cleaves and thereby silences the viral target. Recently, the CRISPR/Cas system has been adapted for genome editing in eukaryotic cells. The introduction of site-specific double strand breaks (DSBs) enables target sequence alteration through one of two endogenous DNA repair mechanisms—either non-homologous end-joining (NHEJ) or homology-directed repair (HDR). The CRISPR/Cas system has also been used for gene regulation including transcription repression and activation without altering the target sequence. Targeted gene regulation based on the CRISPR/Cas system can, for example, use an enzymatically inactive Cas9 (also known as a catalytically dead Cas9).

CRISPR/Cas systems include a CRISPR (clustered regularly interspaced short palindromic repeats) locus, which encodes RNA components of the system, and a Cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60). CRISPR loci in microbial hosts contain a combination of Cas genes as well as non-coding RNA elements capable of programming the specificity of the CRISPR-mediated nucleic acid cleavage.

The Type II CRISPR is one of the most well characterized systems and carries out targeted DNA double-strand break in nature in four sequential steps. First, two non-coding RNAs, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

For use of the CRISPR/Cas system to create targeted insertions and deletions, the two non-coding RNAs (crRNA and the TracrRNA) can be replaced by a single RNA referred to as a guide RNA (gRNA). Activity of the CRISPR/Cas system comprises of three steps: (i) insertion of exogenous DNA sequences into the CRISPR array to prevent future attacks, in a process called "adaptation," (ii) expression of the relevant proteins, as well as expression and processing of the array, followed by (iii) RNA-mediated interference with the foreign nucleic acid. In the bacterial cell, several Cas proteins are involved with the natural function of the CRISPR/Cas system and serve roles in functions such as insertion of the foreign DNA etc.

The Cas protein can be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Where a porcine female animal for use in the methods described herein has been genetically edited using a CRISPR system, a CRISPR/Cas9 system can be used to generate the porcine female animal. To use Cas9 to edit genomic sequences, the protein can be delivered directly to a cell. Alternatively, an mRNA that encodes Cas9 can be delivered to a cell, or a gene that provides for expression of an mRNA that encodes Cas9 can be delivered to a cell. In addition, either target specific crRNA and a tracrRNA can be delivered directly to a cell or target specific gRNA(s) can be to a cell (these RNAs can alternatively be produced by a gene constructed to express these RNAs). Selection of target sites and designed of crRNA/gRNA are well known in the art. A discussion of construction and cloning of gRNAs can be found at http://www.genome-engineering.org/crispr/wp-content/uploads/2014/05/CRISPR-Reagent-Description-Rev20140509.pdf.

A DNA-binding polypeptide can specifically recognize and bind to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

Targeting Endonucleases

A DNA-binding polypeptide that specifically recognizes and binds to a target nucleotide sequence can be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. Functional polypeptides of a chimeric polypeptide can be operatively linked by their expression from a single polynucleotide encoding at least the functional polypeptides ligated to each other in-frame, so as to create a chimeric gene encoding a chimeric protein. Alternatively, the functional polypeptides of a chimeric polypeptide can be operatively linked by other means, such as by cross-linkage of independently expressed polypeptides.

A DNA-binding polypeptide, or guide RNA that specifically recognizes and binds to a target nucleotide sequence can be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR/Cas9, and meganucleases.

As used herein, the term "targeting endonuclease" refers to natural or engineered isolated proteins and mutants thereof that comprise a DNA-binding polypeptide or guide RNA and a nuclease polypeptide, as well as to chimeric polypeptides comprising a DNA-binding polypeptide or guide RNA and a nuclease. Any targeting endonuclease comprising a DNA-binding polypeptide or guide RNA that specifically recognizes and binds to a target nucleotide sequence comprised within a CD163 locus (e.g., either because the target sequence is comprised within the native sequence at the locus, or because the target sequence has been introduced into the locus, for example, by recombination) can be used.

Some examples of suitable chimeric polypeptides include, without limitation, combinations of the following polypeptides: zinc finger DNA-binding polypeptides; a Fold nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR/Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

The chimeric polypeptide can comprise a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNAse I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, the near edges of the target sites can be separated by 5-8 nucleotides or by 15-18 nucleotides. However any integral number of nucleotides, or nucleotide pairs, can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/transgenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyses double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89: 4275-4279; Li et al. (1993) Proc. Natl. Acad. Sci. USA 90: 2764-2768; Kim et al. (1994a) Proc. Natl. Acad. Sci. USA 91:883-887; Kim et al. (1994b) J. Biol. Chem. 269: 31,978-31,982. Thus, fusion proteins can comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain Thus, for targeted double-stranded cleavage and/or targeted replacement of cellular sequences using zinc finger-Fok I fusions, two fusion proteins, each comprising a Fold cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 2007/0134796. Additional restriction enzymes also contain separable binding and cleavage domains, and these are contemplated by the present disclosure. See, for example, Roberts et al. (2003) Nucleic Acids Res. 31:418-420.

The cleavage domain can comprise one or more engineered cleavage half-domain (also referred to as dimerization domain mutants) that minimize or prevent homodimerization, as described, for example, in U.S. Patent Publication Nos. 2005/0064474; 2006/0188987 and 2008/0131962.

Alternatively, nucleases may be assembled in vivo at the nucleic acid target site using so-called “split-enzyme” technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Zinc Finger Nucleases

A chimeric polypeptide can comprise a custom-designed zinc finger nuclease (ZFN) that may be designed to deliver a targeted site-specific double-strand DNA break into which an exogenous nucleic acid, or donor DNA, may be integrated (see US Patent publication 2010/0257638). ZFNs are chimeric polypeptides containing a non-specific cleavage domain from a restriction endonuclease (for example, Fold) and a zinc finger DNA-binding domain polypeptide. See, e.g., Huang et al. (1996) J. Protein Chem. 15: 481-9; Kim et al. (1997a) Proc. Natl. Acad. Sci. USA 94:3616-20; Kim et al. (1996) Proc. Natl. Acad. Sci. USA 93: 1156-60; Kim et al. (1994) Proc Natl. Acad. Sci. USA 91: 883-7; Kim et al. (1997b) Proc. Natl. Acad. Sci. USA 94: 12875-9; Kim et al. (1997c) Gene 203: 43-9; Kim et al. (1998) Biol. Chem. 379: 489-95; Nahon and Raveh (1998) Nucleic Acids Res. 26: 1233-9; Smith et al. (1999) Nucleic Acids Res. 27: 674-81. The ZFNs can comprise non-canonical zinc finger DNA binding domains (see US Patent publication 2008/0182332). The Fold restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334: 1191-7; Smith et al. (2000) Nucleic Acids Res. 28: 3361-9. Dimerization of the ZFN can be facilitated by two adjacent, oppositely oriented DNA-binding sites. Id.

A method for the site-specific integration of an exogenous nucleic acid into at least one CD163 locus of a host can comprise introducing into a cell of the host a ZFN, wherein the ZFN recognizes and binds to a target nucleotide sequence, wherein the target nucleotide sequence is comprised within at least one CD163 locus of the host. In certain examples, the target nucleotide sequence is not comprised within the genome of the host at any other position than the at least one CD163 locus. For example, a DNA-binding polypeptide of the ZFN may be engineered to recognize and bind to a target nucleotide sequence identified within the at least one CD163 locus (e.g., by sequencing the CD163 locus). A method for the site-specific integration of an exogenous nucleic acid into at least one CD163 performance locus of a host that comprises introducing into a cell of the host a ZFN may also comprise introducing into the cell an exogenous nucleic acid, wherein recombination of the exogenous nucleic acid into a nucleic acid of the host comprising the at least one CD163 locus is facilitated by site-specific recognition and binding of the ZFN to the target sequence (and subsequent cleavage of the nucleic acid comprising the CD163 locus).

Optional Exogenous Nucleic Acids for Integration at a CD163 Locus

Exogenous nucleic acids for integration at a CD163 locus include: an exogenous nucleic acid for site-specific integration in at least one CD163 locus, for example and without limitation, an ORF; a nucleic acid comprising a nucleotide sequence encoding a targeting endonuclease; and a vector comprising at least one of either or both of the foregoing. Thus, particular nucleic acids include nucleotide sequences encoding a polypeptide, structural nucleotide sequences, and/or DNA-binding polypeptide recognition and binding sites.

Optional Exogenous Nucleic Acid Molecules for Site-Specific Integration

As noted above, insertion of an exogenous sequence (also called a “donor sequence” or “donor” or “transgene”) is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient homology-directed repair (HDR) at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See e.g., U.S. Patent Publication Nos. 2010/0047805, 2011/0281361, 2011/0207221, and 2013/0326645. If introduced in linear form, the ends of the donor sequence can be protected (e.g. from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84: 4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

The donor is generally integrated so that its expression is driven by the endogenous promoter at the integration site, namely the promoter that drives expression of the endogenous gene into which the donor is integrated (e.g., CD163). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one CD163 locus, so as to modify the CD163 locus include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the CD163 gene.

An exogenous nucleic acid can be integrated at a CD163 locus, so as to modify the CD163 locus, wherein the nucleic acid comprises a nucleotide sequence encoding a polypeptide of interest, such that the nucleotide sequence is expressed in the host from the CD163 locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass.

Nucleic Acid Molecules Comprising a Nucleotide Sequence Encoding a Targeting Endonuclease A nucleotide sequence encoding a targeting endonuclease can be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. The last codon (i.e., most 3' in the nucleic acid sequence) of a first polynucleotide sequence encoding a nuclease polypeptide, and a second polynucleotide sequence encoding a DNA-binding polypeptide, can be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, consist of any sequence, such that the amino acid sequence encoded is not likely to significantly alter the translation of the targeting endonuclease. Due to the autonomous nature of known nuclease polypeptides and known DNA-binding polypeptides, intervening sequences will not interfere with the respective functions of these structures.

Other Knockout Methods

Various other techniques known in the art can be used to inactivate genes to make knock-out animals and/or to introduce nucleic acid constructs into animals to produce founder animals and to make animal lines, in which the knockout or nucleic acid construct is integrated into the genome. Such techniques include, without limitation, pronuclear microinjection (U.S. Pat. No. 4,873,191), retrovirus mediated gene transfer into germ lines (Van der Putten et al. (1985) Proc. Natl. Acad. Sci. USA 82, 6148-1652), gene targeting into embryonic stem cells (Thompson et al. (1989) Cell 56, 313-321), electroporation of embryos (Lo (1983) Mol. Cell. Biol. 3, 1803-1814), sperm-mediated gene transfer (Lavitrano et al. (2002) Proc. Natl. Acad. Sci. USA 99, 14230-14235; Lavitrano et al. (2006) Reprod. Fert. Develop. 18, 19-23), and in vitro transformation of somatic cells, such as cumulus or mammary cells, or adult, fetal, or embryonic stem cells, followed by nuclear transplantation (Wilmut et al. (1997) Nature 385, 810-813; and Wakayama et al. (1998) Nature 394, 369-374). Pronuclear microinjection, sperm mediated gene transfer, and somatic cell nuclear transfer are particularly useful techniques. An animal that is genomically modified is an animal wherein all of its cells have the modification, including its germ line cells. When methods are used that produce an animal that is mosaic in its modification, the animals may be inbred and progeny that are genomically modified may be selected. Cloning, for instance, may be used to make a mosaic animal if its cells are modified at the blastocyst state, or genomic modification can take place when a single-cell is modified. Animals that are modified so they do not sexually mature can be homozygous or heterozygous for the modification, depending on the specific approach that is used. If a particular gene is inactivated by a knock out modification, homozygosity would normally be required. If a particular gene is inactivated by an RNA interference or dominant negative strategy, then heterozygosity is often adequate.

Typically, in embryo/zygote microinjection, a nucleic acid construct or mRNA is introduced into a fertilized egg; one or two cell fertilized eggs are used as the nuclear structure containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 OOCYTE MATURATION MEDIUM (Minitube, Verona, Wis.) supplemented with 0.1 mg/mL cysteine, 10 ng/mL epidermal growth factor, 10% porcine follicular fluid, 50 μM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium, which will not contain cAMP, PMSG or hCG and incubated for an additional 22 hours. Matured oocytes can be stripped of their cumulus cells by vortexing in 0.1% hyaluronidase for 1 minute.

For swine, mature oocytes can be fertilized in 500 μl Minitube PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to 400,000 sperm. Sperm concentrations can be analyzed by computer assisted semen analysis (SPERMVISION, Minitube, Verona, Wis.). Final in vitro insemination can be performed in a 10 μl volume at a final concentration of approximately 40 motile sperm/oocyte, depending on boar. All fertilizing oocytes can be incubated at 38.7° C. in 5.0% $CO_2$ atmosphere for six hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs or mRNA can be injected into one of the pronuclei or into the cytoplasm. Then the injected eggs can be transferred to a recipient female (e.g., into the oviducts of a recipient female) and allowed to develop in the recipient female to produce the transgenic or gene edited animals. In particular, in vitro fertilized embryos can be centrifuged at 15,000×g for 5 minutes to sediment lipids allowing visualization of the pronucleus. The embryos can be injected with using an Eppendorf FEMTOJET injector and can be cultured until blastocyst formation. Rates of embryo cleavage and blastocyst formation and quality can be recorded.

Embryos can be surgically transferred into uteri of asynchronous recipients. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed.

In somatic cell nuclear transfer, a transgenic or gene edited cell such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic or gene edited cell into an enucleated oocyte arrested at meiosis 2. In some conventions, oocytes arrested at meiosis-2 are termed eggs. After producing a porcine or bovine embryo (e.g., by fusing and activating the oocyte), the embryo is transferred to the oviducts of a recipient female, about 20 to 24 hours after activation. See, for example, Cibelli et al. (1998) Science 280, 1256-1258 and U.S. Pat. Nos. 6,548,741, 7,547,816, 7,989,657, or 6,211,429. For pigs, recipient females can be checked for pregnancy approximately 20-21 days after transfer of the embryos.

Standard breeding techniques can be used to create animals that are homozygous for the inactivated gene from the initial heterozygous founder animals. Homozygosity may not be required, however. Gene edited pigs described herein can be bred with other pigs of interest.

Once gene edited animals have been generated, inactivation of an endogenous nucleic acid can be assessed using standard techniques. Initial screening can be accomplished by Southern blot analysis to determine whether or not inactivation has taken place. For a description of Southern analysis, see sections 9.37-9.52 of Sambrook et al., 1989, Molecular Cloning, A Laboratory Manual, second edition, Cold Spring Harbor Press, Plainview; N.Y. Polymerase chain reaction (PCR) techniques also can be used in the initial screening PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) Genetic Engineering News 12,1; Guatelli et al. (1990) Proc. Natl. Acad. Sci. USA 87: 1874; and Weiss (1991) Science 254:1292. At the blastocyst stage, embryos can be individually processed for analysis by PCR, Southern hybridization and splinkerette PCR (see, e.g., Dupuy et al. Proc Natl Acad Sci USA (2002) 99: 4495).

Interfering RNAs

A variety of interfering RNA (RNAi) systems are known. Double-stranded RNA (dsRNA) induces sequence-specific degradation of homologous gene transcripts. RNA-induced silencing complex (RISC) metabolizes dsRNA to small 21-23-nucleotide small interfering RNAs (siRNAs). RISC contains a double stranded RNAse (dsRNAse, e.g., Dicer) and ssRNAse (e.g., Argonaut 2 or Ago2). RISC utilizes antisense strand as a guide to find a cleavable target. Both siRNAs and microRNAs (miRNAs) are known. A method of inactivating a gene in a genetically edited animal comprises inducing RNA interference against a target gene and/or nucleic acid such that expression of the target gene and/or nucleic acid is reduced.

For example the exogenous nucleic acid sequence can induce RNA interference against a nucleic acid encoding a polypeptide. For example, double-stranded small interfering RNA (siRNA) or small hairpin RNA (shRNA) homologous to a target DNA can be used to reduce expression of that DNA. Constructs for siRNA can be produced as described, for example, in Fire et al. (1998) Nature 391: 806; Romano and Masino (1992) Mol. Microbiol. 6: 3343; Cogoni et al. (1996) EMBO J. 15: 3153; Cogoni and Masino (1999) Nature 399: 166; Misquitta and Paterson (1999) Proc. Natl. Acad. Sci. USA 96:1451; and Kennerdell and Carthew (1998) Cell 95:1017. Constructs for shRNA can be produced as described by McIntyre and Fanning (2006) BMC Biotechnology 6:1. In general, shRNAs are transcribed as a single-stranded RNA molecule containing complementary regions, which can anneal and form short hairpins.

The probability of finding a single, individual functional siRNA or miRNA directed to a specific gene is high. The predictability of a specific sequence of siRNA, for instance, is about 50% but a number of interfering RNAs may be made with good confidence that at least one of them will be effective.

In vitro cells, in vivo cells, or a genetically edited animal such as a livestock animal that express an RNAi directed against a gene encoding CD163 can be used. The RNAi may be, for instance, selected from the group consisting of siRNA, shRNA, dsRNA, RISC and miRNA.

Inducible Systems

An inducible system may be used to inactivate a CD163 gene. Various inducible systems are known that allow spatial and temporal control of inactivation of a gene. Several have been proven to be functional in vivo in porcine animals.

An example of an inducible system is the tetracycline (tet)-on promoter system, which can be used to regulate transcription of the nucleic acid. In this system, a mutated Tet repressor (TetR) is fused to the activation domain of herpes simplex virus VP 16 transactivator protein to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

The tetracycline-inducible system and the Cre/loxP recombinase system (either constitutive or inducible) are among the more commonly used inducible systems. The tetracycline-inducible system involves a tetracycline-controlled transactivator (tTA)/reverse tTA (rtTA). A method to use these systems in vivo involves generating two lines of genetically edited animals. One animal line expresses the activator (tTA, rtTA, or Cre recombinase) under the control of a selected promoter. Another line of animals expresses the acceptor, in which the expression of the gene of interest (or the gene to be altered) is under the control of the target sequence for the tTA/rtTA transactivators (or is flanked by loxP sequences). Mating the two of animals provides control of gene expression.

The tetracycline-dependent regulatory systems (tet systems) rely on two components, i.e., a tetracycline-controlled transactivator (tTA or rtTA) and a tTA/rtTA-dependent promoter that controls expression of a downstream cDNA, in a tetracycline-dependent manner. In the absence of tetracycline or its derivatives (such as doxycycline), tTA binds to tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. Administration of tetracycline or its derivatives allows temporal control of transgene expression in vivo. rtTA is a variant of tTA that is not functional in the absence of doxycycline but requires the presence of the ligand for transactivation. This tet system is therefore termed tet-ON. The tet systems have been used in vivo for the inducible expression of several transgenes, encoding, e.g., reporter genes, oncogenes, or proteins involved in a signaling cascade.

The Cre/lox system uses the Cre recombinase, which catalyzes site-specific recombination by crossover between two distant Cre recognition sequences, i.e., loxP sites. A DNA sequence introduced between the two loxP sequences (termed floxed DNA) is excised by Cre-mediated recombination. Control of Cre expression in a transgenic and/or gene edited animal, using either spatial control (with a tissue- or cell-specific promoter), or temporal control (with an inducible system), results in control of DNA excision between the two loxP sites. One application is for conditional gene inactivation (conditional knockout). Another approach is for protein over-expression, wherein a floxed stop codon is inserted between the promoter sequence and the DNA of interest. Genetically edited animals do not express the transgene until Cre is expressed, leading to excision of the floxed stop codon. This system has been applied to tissue-specific oncogenesis and controlled antigene receptor expression in B lymphocytes. Inducible Cre recombinases have also been developed. The inducible Cre recombinase is activated only by administration of an exogenous ligand. The inducible Cre recombinases are fusion proteins containing the original Cre recombinase and a specific ligand-binding domain. The functional activity of the Cre recombinase is dependent on an external ligand that is able to bind to this specific domain in the fusion protein.

In vitro cells, in vivo cells, or a genetically edited animal such as a livestock animal that comprises a CD163 gene under control of an inducible system can be used. The chromosomal modification of an animal may be genomic or mosaic. The inducible system may be, for instance, selected from the group consisting of Tet-On, Tet-Off, Cre-lox, and Hif1 alpha.

Vectors and Nucleic Acids

A variety of nucleic acids may be introduced into cells for knockout purposes, for inactivation of a gene, to obtain expression of a gene, or for other purposes. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3): 187; and Hyrup et al. (1996) Bioorgan. Med. Chem. 4: 5. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, inducible promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes or heart tissue and can include the albumin or alpha-myosin heavy chain promoters, respectively. A promoter that facilitates the expression of a nucleic acid molecule without significant tissue or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. For example, a fusion of the chicken beta actin gene promoter and the CMV enhancer can be used as a promoter. See, for example, Xu et al. (2001) Hum. Gene Ther. 12: 563; and Kiwaki et al. (1996) Hum. Gene Ther. 7: 821.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphotransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

A sequence encoding a selectable marker can be flanked by recognition sequences for a recombinase such as, e.g., Cre or Flp. For example, the selectable marker can be flanked by loxP recognition sites (34-bp recognition sites recognized by the Cre recombinase) or FRT recognition sites such that the selectable marker can be excised from the construct. See, Orban, et al., Proc. Natl. Acad. Sci. (1992) 89: 6861, for a review of Cre/lox technology, and Brand and Dymecki, Dev. Cell (2004) 6: 7. A transposon containing a Cre- or Flp-activatable transgene interrupted by a selectable marker gene also can be used to obtain animals with conditional expression of a transgene. For example, a promoter driving expression of the marker/transgene can be either ubiquitous or tissue-specific, which would result in the ubiquitous or tissue-specific expression of the marker in FO animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

The exogenous nucleic acid can encode a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™ tag (Kodak, New Haven, Conn.).

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult animal cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to an exogenous nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) Nucleic Acids Res. 31: 6873); Tol2 (Kawakami (2007) Genome Biology 8 (Suppl. 1): S7; Minos (Pavlopoulos et al. (2007) Genome Biology 8 (Suppl. 1): S2); Hsmar1 (Miskey et al. (2007)) Mol Cell Biol. 27: 4589); and Passport have been developed to introduce nucleic acids into cells, including mice, human, and pig cells. The Sleeping Beauty transposon is particularly useful. A transposase can be delivered as a protein, encoded on the same nucleic acid construct as the exogenous nucleic acid, can be introduced on a separate nucleic acid construct, or provided as an mRNA (e.g., an in vitro-transcribed and capped mRNA).

Insulator elements also can be included in a nucleic acid construct to maintain expression of the exogenous nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region-(MAR) type insulator elements and border-type insulator elements. See, for example, U.S. Pat. Nos. 6,395,549, 5,731,178, 6,100,448, and 5,610,053, and U.S. Publication No. 2004/0203158.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand).

Having described the invention in detail, it will be apparent that modifications and variations are possible without departing from the scope of the invention defined in the appended claims.

EXAMPLES

The following non-limiting examples are provided to further illustrate the present invention.

Example 1: Use of the CRISPR/Cas9 System to Produce Genetically Engineered Pigs from In Vitro-Derived Oocytes and Embryos Recent reports describing homing endonucleases, such as zinc-finger nucleases (ZFNs), transcription activator-like effector nucleases (TALENs), and components in the clustered regularly interspaced short palindromic repeat (CRISPR)/CRISPR-associated (Cas9) system suggest that genetic engineering (GE) in pigs might now be more efficient. Targeted homing endonucleases can induce double-strand breaks (DSBs) at specific locations in the genome and cause either random mutations through nonhomologous end joining (NHEJ) or stimulation of homologous recombination (HR) if donor DNA is provided. Targeted modification of the genome through HR can be achieved with homing endonucleases if donor DNA is provided along with the targeted nuclease. After introducing specific modifications in somatic cells, these cells were used to produce GE pigs for various purposes via SCNT. Thus, homing endonucleases are a useful tool in generating GE pigs. Among the different homing endonucleases, the CRISPR/Cas9 system, adapted from prokaryotes where it is used as a defense mechanism, appears to be an effective approach. In nature, the Cas9 system requires three components, an RNA (~20 bases) that contains a region that is complementary to the target sequence (cis-repressed RNA [crRNA]), an RNA that contains a region that is complementary to the crRNA (trans-activating crRNA [tracrRNA]), and Cas9, the enzymatic protein component in this complex. A single guide RNA (gRNA) can be constructed to serve the roles of the base-paired crRNA and tracrRNA. The gRNA/protein complex can scan the genome and catalyze a DSB at regions that are complementary to the crRNA/gRNA. Unlike other designed nucleases, only a short oligomer needs to be designed to construct the reagents required to target a gene of interest whereas a series of cloning steps are required to assemble ZFNs and TALENs.

Unlike current standard methods for gene disruption, the use of designed nucleases offers the opportunity to use zygotes as starting material for GE. Standard methods for gene disruption in livestock involve HR in cultured cells and subsequent reconstruction of embryos by somatic cell nuclear transfer (SCNT). Because cloned animals produced through SCNT sometimes show signs of developmental defects, progeny of the SCNT/GE founders are typically used for research to avoid confounding SCNT anomalies and phenotype that could occur if founder animals are used for experiments. Considering the longer gestation period and higher housing costs of pigs compared to rodents, there are time and cost benefits to the reduced need for breeding. A recent report demonstrated that direct injection of ZFNs and TALENs into porcine zygotes could disrupt an endogenous gene and produce piglets with the desired mutations. However, only about 10% of piglets showed biallelic modification of the target gene, and some presented mosaic genotypes. A recent article demonstrated that CRISPR/Cas9 system could induce mutations in developing embryos and produce GE pigs at a higher efficiency than ZFNs or TALENs. However, GE pigs produced from the CRISPR/Cas9 system also possessed mosaic genotypes. In addition, all the above-mentioned studies used in vivo derived zygotes for the experiments, which require intensive labor and numerous sows to obtain a sufficient number of zygotes.

The present example describes an efficient approach to use the CRISPR/Cas9 system in generating GE pigs via both injection of in vitro derived zygotes and modification of somatic cells followed by SCNT. Two endogenous genes (CD163 and CD1D) and one transgene (eGFP) were targeted, and only in vitro derived oocytes or zygotes were used for SCNT or RNA injections, respectively. CD163 appears to be required for productive infection by porcine reproductive and respiratory syndrome virus, a virus known to cause a significant economic loss to swine industry. CD1D is considered a nonclassical major histocompatibility complex protein and is involved in presentation of lipid antigens to invariant natural killer T cells. Pigs deficient in these genes were designed to be models for agriculture and biomedicine. The eGFP transgene was used as a target for preliminary proof-of-concept experiments and optimizations of methods.

Materials and Methods

Chemical and Reagents. Unless otherwise stated, all of the chemicals used in this study were purchased from Sigma.

Design of gRNAs to Build Specific CRISPRs

Guide RNAs were designed to regions within exon 7 of CD163 that were unique to the wild type CD163 and not present in the domain swap targeting vector (described below), so that the CRISPR would result in DSB within wild type CD163 but not in the domain swap targeting vector. There were only four locations in which the targeting vector would introduce a single nucleotide polymorphism (SNP) that would alter an *S. pyogenes* (Spy) protospacer adjacent motif (PAM). All four targets were selected including:

(CRISPR 10)
(SEQ ID NO: 1)
GGAAACCCAGGCTGGTTGGAgGG, (CRISPR 131)
(SEQ ID NO: 2)
GGAACTACAGTGCGGCACTGtGG,

-continued (CRISPR 256)
(SEQ ID NO: 3)
CAGTAGCACCCCGCCCTGACgGG
and (CRISPR 282)
(SEQ ID NO: 4)
TGTAGCCACAGCAGGGACGTcGG.

The PAM can be identified by the bold font in each gRNA.

For CD1D mutations, the search for CRISPR targets was arbitrarily limited to the coding strand within the first 1000 bp of the primary transcript. However, RepeatMasker [26] ("Pig" repeat library) identified a repetitive element beginning at base 943 of the primary transcript. The search for CRISPR targets was then limited to the first 942 bp of the primary transcript. The search was further limited to the first 873 bp of the primary transcript since the last Spy PAM is located at base 873. The first target (CRISPR 4800) was selected because it overlapped with the start codon located at base 42 in primary transcript (CCAGCCTCGCCCAGCGACATgGG (SEQ ID NO:5)). Two additional targets (CRISPRs 5620 and 5626) were selected because they were the most distal to the first selection within the arbitrarily selected region (CTTTCATTTATCTGAACTCAgGG (SEQ ID NO:6)) and TTATCTGAACTCAGGGTCCCcGG (SEQ ID NO:7)). These targets overlap. In relation to the start codon, the most proximal Spy PAMs were located in simple sequence that contained extensively homopolymeric sequence as determined by visual appraisal. The forth target (CRISPR 5350) was selected because, in relation to the first target selection, it was the most proximal target that did not contain extensive homopolymeric regions (CAGCTGCAGCATATATTTAAgGG (SEQ ID NO:8)). Specificity of the designed crRNAs was confirmed by searching for similar porcine sequences in GenBank. The oligonucleotides (Table 1) were annealed and cloned into the p330X vector which contains two expression cassettes, a human codon-optimized *S. pyogenes* (hSpy) Cas9 and the chimeric guide RNA. P330X was digested with BbsI (New England Biolabs) following the Zhang laboratory protocol (http://www.addgene.org/crispr/zhang/).

To target eGFP, two specific gRNAs targeting the eGFP coding sequence were designed within the first 60 bp of the eGFP start codon. Both eGFP1 and eGFP2 gRNA were on the antisense strand and eGFP1 directly targeted the start codon. The eGFP1 gRNA sequence was CTCCTCGCCCTTGCTCACCAtGG (SEQ ID NO:9) and the eGFP2 gRNA sequence was GACCAGGATGGGCACCACCCcGG (SEQ ID NO:10).

TABLE 1

Designed crRNAs. Primer 1 and primer 2 were annealed following the Zhang protocol.

| Primer | Sequence (5'-3') | SEQ ID NO. |
|---|---|---|
| CD163 101 | CACCGGAAACCCAGGCTGGTTGGA | 48 |
| CD163 102 | AAACTCCAACCAGCCTGGGTTTCC | 49 |
| CD163 131 1 | CACCGGAACTACAGTGCGGCACTG | 50 |
| CD163 131 2 | AAACCAGTGCCGCACTGTAGTTCC | Si |
| CD163 256 1 | CACCGCAGTAGCACCCCGCCCTGAC | 52 |
| CD163 256 2 | AAACGTCAGGGCGGGGTGCTACTGC | 53 |

TABLE 1-continued

Designed crRNAs. Primer 1 and primer 2 were annealed following the Zhang protocol.

| Primer | Sequence (5'-3') | SEQ ID NO. |
|---|---|---|
| CD163 282 1 | CACCGTGTAGCCACAGCAGGGACGT | 54 |
| CD163 282 2 | AAACACGTCCCTGCTGTGGCTACAC | 55 |
| CD1D 4800 1 | CACCGCCAGCCTCGCCCAGCGACAT | 56 |
| CD1D 4800 2 | AAACATGTCGCTGGGCGAGGCTGGC | 57 |
| CD1D 5350 1 | CACCGCAGCTGCAGCATATATTTAA | 58 |
| CD1D 5350 2 | AAACTTAAATATATGCTGCAGCTGC | 59 |
| CD1D 5620 1 | CACCGCTTTCATTTATCTGAACTCA | 60 |
| CD1D 5620 2 | AAACTGAGTTCAGATAAATGAAAGC | 61 |
| CD1D 5626 1 | CACCGTTATCTGAACTCAGGGTCCC | 62 |
| CD1D 5626 2 | AAACGGGACCCTGAGTTCAGATAAC | 63 |
| eGFP 1 1 | CACCGCTCCTCGCCCTTGCTCACCA | 64 |
| eGFP 1 2 | AAACTGGTGAGCAAGGGCGAGGAGC | 65 |
| eGFP 2 1 | CACCGGACCAGGATGGGCACCACCC | 66 |
| eGFP 2 2 | AAACGGGTGGTGCCCATCCTGGTCC | 67 |

Synthesis of Donor DNA for CD163 and CD1D Genes

Figure 1:
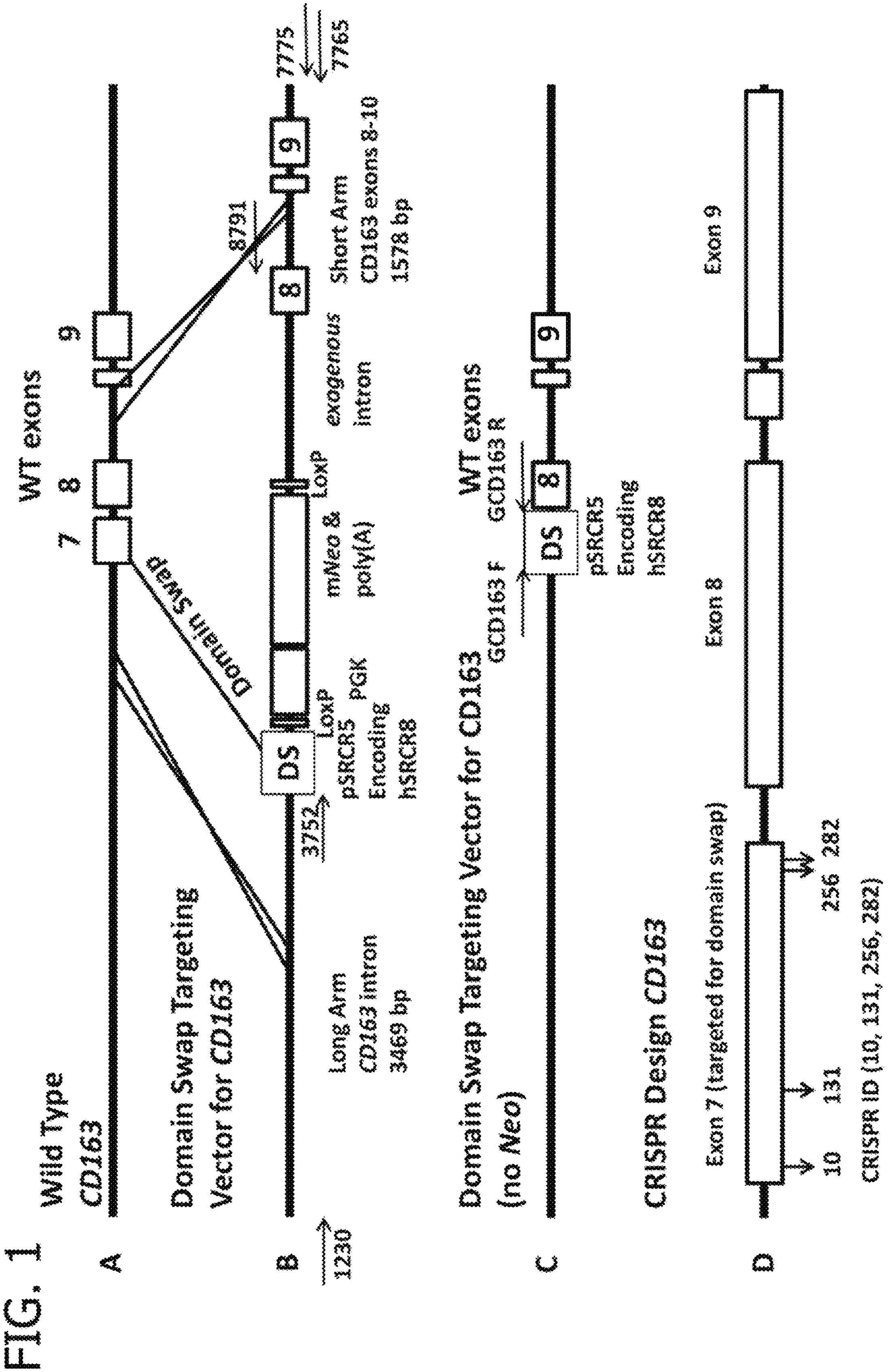
FIG. 1. Targeting vectors and CRISPRs used to modify CD163. Panel A depicts wild type exons 7, 8 and 9 of the CD163 gene that was targeted for modification using CRISPRs. Panel B shows the targeting vector designed to replace pig exon 7 (pig domain SRCR5 of CD163) with DNA that encodes human SRCR8 of CD163L. This targeting vector was used in transfections with drug selection by G418. PCR primers for the long range, left arm and right arm assay are labelled with arrows for 1230, 3752, 8791, 7765 and 7775. Panel C depicts a targeting vector identical to the one shown in panel B, but wherein the Neo cassette was removed. This targeting vector was used to target CD163 in cells that were already neomycin resistant. Primers used in small deletions assays are illustrated with arrows and labeled GCD163F and GCD163R. Panel D emphasizes the exons targeted by CRISPRs. Location of CRISPRs 10, 131, 256 and 282 are represented by the downward facing arrows on exon 7. The CRISPR numbers represent the number of base pairs from the intron-exon junction of intron 6 and exon 7.

Both porcine CD163 and CD1D were amplified by PCR from DNA isolated from the fetal fibroblasts that would be used for later transfections to ensure an isogenic match between the targeting vector and the transfected cell line. Briefly, LA taq (Clontech) using the forward primer CTCTCCCTCACTCTAACCTACTT (SEQ ID NO:11), and the reverse primer TATTTCTCTCACATGGCCAGTC (SEQ ID NO:12) were used to amplify a 9538 bp fragment of CD163. The fragment was DNA sequence validated and used to build the domain-swap targeting vector (FIG. 1). This vector included 33 point mutations within exon 7 so that it would encode the same amino acid sequence as human CD163L from exon 11. The replacement exon was 315 bp. In addition, the subsequent intron was replaced with a modified myostatin intron B that housed a selectable marker gene that could be removed with Cre-recombinase (Cre) and had previously demonstrated normal splicing when harboring the retained loxP site (Wells, unpublished results). The long arm of the construct was 3469 bp and included the domain swap DS exon. The short arm was 1578 bp and included exons 7 and 8 (FIG. 1, panel B). This plasmid was used to attempt to replace the coding region of exon 7 in the first transfection experiments and allowed for selection of targeting events via the selectable marker (G418). If targeting were to occur, the marker could be deleted by Cre-recombinase. The CD163 DS-targeting vector was then modified for use with cell lines that already contained a SIGLEC1 gene disrupted with Neo that could not be Cre deleted. In this targeting vector, the Neo cassette, loxP and myostatin intron B, were removed, and only the DS exon remained with the WT long and short arm (FIG. 1, panel C).

The genomic sequence for porcine CD1D was amplified with LA taq using the forward primer CTCTCCCT-CACTCTAACCTACTT (SEQ ID NO:13) and reverse primer GACTGGCCATGTGAGAGAAATA (SEQ ID NO:14), resulting in an 8729 bp fragment. The fragment was DNA sequenced and used to build the targeting vector shown in FIG. 2. The Neo cassette is under the control of a phosphoglycerol kinase (PGK) promoter and flanked with loxP sequences, which were introduced for selection. The long arm of the construct was 4832 bp and the short arm was 3563 bp, and included exons 6 and 7. If successful HR occurred, exons 3, 4, and 5 would be removed and replaced with the Neo cassette. If NHEJ repair occurred incorrectly, then exon 3 would be disrupted.

Fetal Fibroblast Collection

Porcine fetal tissue was collected on Day 35 of gestation to create cell lines. Two wild-type (WT) male and female fetal fibroblast cell lines were established from a large white domestic cross. Male and female fetal fibroblasts that had previously been modified to contain a Neo cassette (SIGLEC1−/− genetics) were also used in these studies. Fetal fibroblasts were collected as described with minor modifications; minced tissue from each fetus was digested in 20 ml of digestion media (Dulbecco-modified Eagle medium [DMEM] containing L-glutamine and 1 g/L D-glucose [Cellgro] supplemented with 200 units/ml collagenase and 25 Kunitz units/ml DNAseI) for 5 hours at 38.5° C. After digestion, fetal fibroblast cells were washed and cultured with DMEM, 15% fetal bovine serum (FBS), and 40 μg/ml gentamicin. After overnight culture, the cells were trypsinized and frozen at −80° C. in aliquots in FBS with 10% dimethyl sulfoxide and stored in liquid nitrogen.

Cell Transfection and Genotyping

Transfection conditions were essentially as previously reported. The donor DNA was always used at a constant amount of 1 μg with varying amounts of CRISPR/Cas9 plasmid (listed below). Donor DNA was linearized with MLUI (CD163) (NEB) or AFLII (CD1D) (NEB) prior to transfection. The gender of the established cell lines was determined by PCR as described previously prior to transfection. Both male and female cell lines were transfected, and genome modification data was analyzed together between the transfections. Fetal fibroblast cell lines of similar passage number (2-4) were cultured for 2 days and grown to 75%-85% confluency in DMEM containing L-glutamine and 1 g/L D-glucose (Cellgro) supplemented with 15% FBS, 2.5 ng/ml basic fibroblast growth factor, and 10 mg/ml gentamicin. Fibroblast cells were washed with phosphate-buffered saline (PBS) (Life Technologies) and trypsinized. As soon as cells detached, the cells were rinsed with an electroporation medium (75% cytosalts [120 mM KCl, 0.15 mM $CaCl_2$, 10 mM $K_2HPO_4$, pH 7.6, 5 Mm $MgCl_2$]) and 25% Opti-MEM (LifeTechnologies). Cell concentration was quantified by using a hemocytometer. Cells were pelleted at 600× g for 5 minutes and resuspended at a concentration of $1\times10^6$ in electroporation medium. Each electroporation used 200 μl of cells in 2 mm gap cuvettes with three (1 msec) square-wave pulses administered through a BTX ECM 2001 at 250 V. After the electroporation, cells were resuspended in DMEM described above. For selection, 600 μg/ml G418 (Life Technologies) was added 24 hours after transfection, and the medium was changed on Day 7. Colonies were picked on Day 14 after transfection. Fetal fibroblasts were plated at 10,000 cells/plate if G418 selection was used and at 50 cells/plate if no G418 selection was used. Fetal fibroblast colonies were collected by applying 10 mm autoclaved cloning cylinders sealed around each colony by autoclaved vacuum grease. Colonies were rinsed with PBS and harvested via trypsin; then resuspended in DMEM culture medium. A part (⅓) of the resuspended colony was transferred to a 96-well PCR plate, and the remaining (⅔) cells were cultured in a well of a 24-well plate. The cell pellets were resuspended in 6 μl of lysis buffer (40 mM Tris, pH 8.9, 0.9% Triton X-100, 0.4 mg/ml proteinase K [NEB]), incubated at 65° C. for 30 minutes for cell lysis, followed by 85° C. for 10 minutes to inactivate the proteinase K.

PCR Screening for DS and Large and Small Deletions

Detection of HR-directed repair. Long-range PCRs were used to identify mutations on either CD163 or CD1D. Three different PCR assays were used to identify HR events: PCR amplification of regions spanning from the CD163 or CD1D sequences in the donor DNA to the endogenous CD163 or CD1D sequences on either the right or left side and a long-range PCR that amplified large regions of CD163 or CD1D encompassing the designed donor DNAs. An increase in the size of a PCR product, either 1.8 kb (CD1D) or 3.5 kb (CD163), arising from the addition of exogenous Neo sequences, was considered evidence for HR-directed repair of the genes. All the PCR conditions included an initial denaturation of 95° C. for 2 minutes followed by 33 cycles of 30 seconds at 94° C., 30 seconds at 50° C., and 7-10 minutes at 68° C. LA taq was used for all the assays following the manufacturers' recommendations. Primers are shown in Table 2.

TABLE 2

Primers used to identify HR directed repair of CD163 and CD1D

| Primer | Sequence (5'-3') | SEQ ID NO. |
|---|---|---|
| CD163 Long Range Assay Primer 1230F | TTGTTGGAAGGCTCACTGTCCTTG | 68 |
| CD163 Long Range Assay Primer 7775 R | ACAACTAAGGTGGGGCAAAG | 69 |
| CD163 Left Arm Assay Primer 1230 F | TTGTTGGAAGGCTCACTGTCCTTG | 70 |
| CD163 Left Arm Assay Primer 8491 R | GGAGCTCAACATTCTTGGGTCCT | 71 |
| CD163 Right Arm Assay Primer 3752 F | GGCAAAATTTTCATGCTGAGGTG | 72 |
| CD163 Right Arm Assay Primer 7765 R | GCACATCACTTCGGGTTACAGTG | 73 |
| CD1D Long Range Assay Primer F 3991 F | CCCAAGTATCTTCAGTTCTGCAG | 74 |
| CD1D Long Range Assay Primer R 12806 R | TACAGGTAGGAGAGCCTGTTTTG | 75 |
| CD1D Left Arm Assay Primer F 3991 F | CCCAAGTATCTTCAGTTCTGCAG | 76 |
| CD1D Left Arm Assay Primer 7373 R | CTCAAAAGGATGTAAACCCTGGA | 77 |
| CD1D Right Arm Assay Primer 4363 F | TGTTGATGTGGTTTGTTTGCCC | 78 |
| CD1D Right Arm Assay Primer 12806 R | TACAGGTAGGAGAGCCTGTTTTG | 79 |

Small Deletions Assay (NHEJ).

Small deletions were determined by PCR amplification of CD163 or CD1D flanking a projected cutting site introduced by the CRISPR/Cas9 system. The size of the amplicons was 435 bp and 1244 bp for CD163 and CD1D, respectively. Lysates from both embryos and fetal fibroblasts were PCR amplified with LA taq. PCR conditions of the assays were an initial denaturation of 95° C. for 2 minutes followed by 33 cycles of 30 seconds at 94° C., 30 seconds at 56° C., and 1 minute at 72° C. For genotyping of the transfected cells, insertions and deletions (INDELs) were identified by separating PCR amplicons by agarose gel electrophoresis. For embryo genotyping, the resulting PCR products were subsequently DNA sequenced to identify small deletions using forward primers used in the PCR. Primer information is shown in Table 3.

TABLE 3

Primers used to identify mutations through NHEJ on CD163 and CD1D

| Primer | Sequence (5'-3') | SEQ ID NO. |
|---|---|---|
| GCD163F | GGAGGTCTAGAATCGGCTAAGCC | 80 |
| GCD163R | GGCTACATGTCCCGTCAGGG | 81 |
| GCD1DF | GCAGGCCACTAGGCAGATGAA | 82 |
| GCD1DR | GAGCTGACACCCAAGAAGTTCCT | 83 |
| eGFP1 | GGCTCTAGAGCCTCTGCTAACC | 84 |
| eGFP2 | GGACTTGAAGAAGTCGTGCTGC | 85 |

Somatic Cell Nuclear Transfer (SCNT)

To produce SCNT embryos, either sow-derived oocytes (ART, Inc.) or gilt-derived oocytes from a local slaughter house were used. The sow-derived oocytes were shipped overnight in maturation medium (TCM-199 with 2.9 mM Hepes, 5 μg/ml insulin, 10 ng/ml epidermal growth factor [EGF], 0.5 μg/ml porcine follicle-stimulating hormone [p-FSH], 0.91 mM pyruvate, 0.5 mM cysteine, 10% porcine follicular fluid, and 25 ng/ml gentamicin) and transferred into fresh medium after 24 hours. After 40-42 hours of maturation, cumulus cells were removed from the oocytes by vortexing in the presence of 0.1% hyaluronidase. The gilt-derived oocytes were matured as described below for in vitro fertilization (IVF). During manipulation, oocytes were placed in the manipulation medium (TCM-199 [Life Technologies] with 0.6 mM $NaHCO_3$, 2.9 mM Hepes, 30 mM NaCl, 10 ng/ml gentamicin, and 3 mg/ml BSA, with osmolarity of 305 mOsm) supplemented with 7.0 μg/ml cytochalasin B. The polar body along with a portion of the adjacent cytoplasm, presumably containing the metaphase II plate, was removed, and a donor cell was placed in the perivitelline space by using a thin glass capillary. The reconstructed embryos were then fused in a fusion medium (0.3 M mannitol, 0.1 mM $CaCl_2$, 0.1 mM $MgCl_2$, and 0.5 mM Hepes) with two DC pulses (1-second interval) at 1.2 kV/cm for 30 seconds using a BTX Electro Cell Manipulator (Harvard Apparatus). After fusion, fused embryos were fully activated with 200 μM thimerosal for 10 minutes in the dark and 8 mM dithiothreitol for 30 minutes. Embryos were then incubated in modified porcine zygote medium PZM3-MU1 with 0.5 μM Scriptaid (S7817; Sigma-Aldrich), a histone deacetylase inhibitor, for 14-16 hours, as described previously.

In Vitro Fertilization (IVF)

For IVF, ovaries from prepubertal gilts were obtained from an abattoir (Farmland Foods Inc.). Immature oocytes were aspirated from medium size (3-6 mm) follicles using an 18-gauge hypodermic needle attached to a 10 ml syringe. Oocytes with evenly dark cytoplasm and intact surrounding cumulus cells were then selected for maturation. Around 50 cumulus oocyte complexes were place in a well containing 500 μl of maturation medium, TCM-199 (Invitrogen) with 3.05 mM glucose, 0.91 mM sodium pyruvate, 0.57 mM cysteine, 10 ng/ml EGF, 0.5 μg/ml luteinizing hormone (LH), 0.5 μg/ml FSH, 10 ng/ml gentamicin (APP Pharm), and 0.1% polyvinyl alcohol for 42-44 hours at 38.5° C., 5% CO2, in humidified air. At the end of the maturation, the surrounding cumulus cells were removed from the oocytes by vortexing for 3 minutes in the presence of 0.1% hyaluronidase. Then, in vitro matured oocytes were placed in 50 μl droplets of IVF medium (modified Tris-buffered medium containing 113.1 mM NaCl, 3 mM KCl, 7.5 mM $CaCl_2$, 11 mM glucose, 20 mM Tris, 2 mM caffeine, 5 mM sodium pyruvate, and 2 mg/ml bovine serum albumin [BSA]) in groups of 25-30 oocytes. One 100 μl frozen semen pellet was thawed in 3 ml of Dulbecco PBS supplemented with 0.1% BSA. Either frozen WT or fresh eGFP semen was washed in 60% Percoll for 20 minutes at 650 3 g and in modified Tris-buffered medium for 10 minutes by centrifugation. In some cases, freshly collected semen heterozygous for a previously described eGFP transgene was washed three times in PBS. The semen pellet was then resuspended with IVF medium to $0.5\times10^6$ cells/ml. Fifty microliters of the semen suspension was introduced into the droplets with oocytes. The gametes were coincubated for 5 hours at 38.5° C. in an atmosphere of 5% $CO_2$ in air. After fertilization, the embryos were incubated in PZM3-MU1 at 38.5° C. and 5% $CO_2$ in air.

Embryo Transfer

Embryos generated to produce GE CD163 or CD1D pigs were transferred into surrogates either on Day 1 (SCNT) or 6 (zygote injected) after first standing estrus. For Day 6 transfer, zygotes were cultured for five additional days in PZM3-MU1 in the presence of 10 ng/ml ps48 (Stemgent, Inc.). The embryos were surgically transferred into the ampullary-isthmic junction of the oviduct of the surrogate.

In Vitro Synthesis of RNA for CRISPR/Cas9 System

Template DNA for in vitro transcription was amplified using PCR (Table 4). CRISPR/Cas9 plasmid used for cell transfection experiments served as the template for the PCR. In order to express the Cas9 in the zygotes, the mMESSAGE mMACHINE Ultra Kit (Ambion) was used to produce mRNA of Cas9. Then a poly A signal was added to the Cas9 mRNA using a Poly (A) tailing kit (Ambion). CRISPR guide RNAs were produced by MEGAshortscript (Ambion). The quality of the synthesized RNAs were visualized on a 1.5% agarose gel and then diluted to a final concentration of 10 ng/μl (both gRNA and Cas9) and distributed into 3 μl aliquots.

TABLE 4

Primers used to amplify templates for in vitro transcription.

| Primers | Sequence (5'-3') | SEQ ID NO. |
|---|---|---|
| Cas9 | F: TAATACGACTCACTATAGGGAGAATGGACTATAAGGACCACGAC | 86 |
| | R: GCGAGCTCTAGGAATTCTTAC | 87 |
| eGFP 1 | F: TTAATACGACTCACTATAGGCTCCTCGCCCTTGCTCACCA | 88 |
| | R: AAAAGCACCGACTCGGTGCC | 89 |
| CD163 10 | F: TTAATACGACTCACTATAGGAAACCCAGGCTGGTTGGA | 90 |
| | R: AAAAGCACCGACTCGGTGCC | 91 |
| CD163 131 | F: TTAATACGACTCACTATAGGAACTACAGTGCGGCACTG | 92 |
| | R: AAAAGCACCGACTCGGTGCC | 93 |
| CD1D 4800 | F: TTAATACGACTCACTATAGGCCAGCCTCGCCCAGCGACAT | 94 |
| | R: AAAAGCACCGACTCGGTGCC | 95 |
| CD1D 5350 | F: TTAATACGACTCACTATAGGCAGCTGCAGCATATATTTAA | 96 |
| | R: AAAAGCACCGACTCGGTGCC | 97 |

Microinjection of Designed CRISPR/Cas9 System in Zygotes

Messenger RNA coding for Cas9 and gRNA was injected into the cytoplasm of fertilized oocytes at 14 hours postfertilization (presumptive zygotes) using a FemtoJet microinjector (Eppendorf). Microinjection was performed in manipulation medium on the heated stage of a Nikon inverted microscope (Nikon Corporation; Tokyo, Japan). Injected zygotes were then transferred into the PZM3-MU1 with 10 ng/ml ps48 until further use.

Statistical Analysis

The number of colonies with a modified genome was classified as 1, and the colonies without a modification of the genome were classified as 0. Differences were determined by using PROC GLM (SAS) with a P-value of 0.05 being considered as significant. Means were calculated as least-square means. Data are presented as numerical means±SEM.

Results

CRISPR/Cas9-Mediated Knockout of CD163 and CD1D in Somatic Cells

Figure 3:
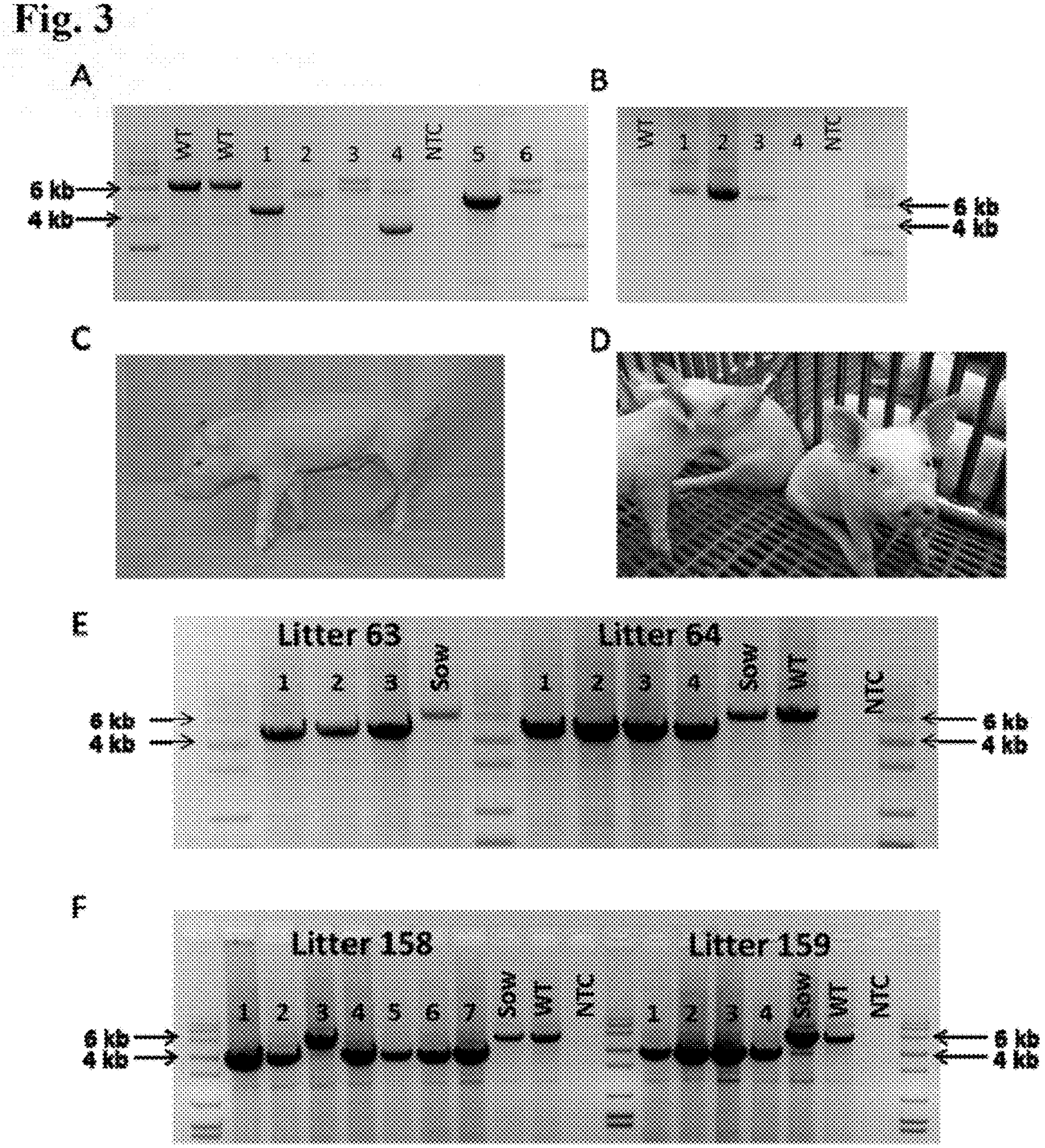
FIG. 3. Generation of CD163 and CD1D knockout pigs by CRISPR/Cas9 and SCNT. A) Targeted deletion of CD163 in somatic cells after transfection with CRISPR/Cas9 and donor DNA. A wild-type (WT) genotype results in a 6545 base pair (bp) band. Lanes 1-6 represent six different colonies from a single transfection with CRISPR 10 with Cas9 and donor DNA containing Neo. Lanes 1, 4, and 5 show a large homozygous deletion of 1500-2000 bp. Lane 2 represents a smaller homozygous deletion. Lanes 3 and 6 represent either a WT allele and a small deletion or a biallelic modification of both alleles. The exact modifications of each colony were only determined by sequencing for colonies used for SCNT. The faint WT band in some of the lanes may represent cross-contamination of fetal fibroblasts from a neighboring WT colony. NTC=no template control. B) Targeted deletion of CD1D in somatic cells after transfection with CRISPR/Cas9 and donor DNA. A WT genotype results in an 8729 bp band. Lanes 1-4 represent colonies with a 500-2000 bp deletion of CD1D. Lane 4 appears to be a WT colony. NTC=no template control. C) Image of CD163 knockout pig produced by SCNT during the study. This male piglet contains a homozygous 1506 bp deletion of CD163. D) Image of CD1D pigs produced during the study. These piglets contain a 1653 bp deletion of CD1D. E) Genotype of two SCNT litters containing the 1506 bp deletion of CD163. Lanes 1-3 (litter 63) and lanes 1-4 (litter 64) represent the genotype for each piglet from each litter. Sow indicates the recipient female of the SCNT embryos, and WT represents a WT control. NTC=no template control. F) Genotype of two SCNT litters containing the 1653 bp deletion of CD1D. Lanes 1-7 (litter 158) and lanes 1-4 (litter 159) represent the genotype for each piglet.

Efficiency of four different CRISPRs plasmids (guides 10, 131, 256, and 282) targeting CD163 was tested at an amount of 2 μg/μl of donor DNA (Table 5). CRISPR 282 resulted in significantly more average colony formation than CRISPR 10 and 256 treatments (P<0.05). From the long-range PCR assay described above, large deletions were found ranging from 503 bp to as much as 1506 bp instead of a DS through HR as was originally intended (FIG. 3, panel A). This was not expected because previous reports with other DNA-editing systems showed much smaller deletions of 6-333 bp using ZFN in pigs. CRISPR 10 and a mix of all four CRISPRs resulted in a higher number of colonies with a modified genome than CRISPR 256 and 282 (Table 5, P<0.002). Transfection with CRISPR 10 and a plasmid containing Neo but no homology to CD163 resulted in no colonies presenting the large deletion. Interestingly, one monoallelic deletion was also detected when the donor DNA was introduced without any CRISPR. This assay likely represents an underestimation of the mutation rate because any potential small deletions by sequencing which could not be detected on an agarose gel in the transfected somatic cells were not screened for.

TABLE 5

Efficiency of four different CRISPR plasmids (guides 10, 131, 256, and 282) targeting CD163. Four different CRISPRs were tested at an amount of 2 μg to 1 μg Donor DNA (shown in FIG. 1).

| Treatment* | Total No. of Colonies | Total No. of Plates | Average No. of Colonies/plate† | No. of Colonies NHEJ | Colony with HR | Percent Colonies with a Modified Genome† | Reps |
|---|---|---|---|---|---|---|---|
| 10 + Donor DNA | 76 | 102 | $0.75^{bc}$ | 11 | 1‡ | $15.79^{a}$ | 4 |
| 131 + Donor DNA | 102 | 51 | $2.00^{ab}$ | 11 | 0 | $10.78^{ab}$ | 3 |
| 256 + Donor DNA | 43 | 49 | $0.88^{c}$ | 2 | 0 | $4.65^{bc}$ | 3 |
| 282 + Donor DNA | 109 | 46 | $2.37^{a}$ | 3 | 0 | $2.75^{bc}$ | 3 |
| mix of 4 + Donor DNA | 111 | 55 | $2.02^{ab}$ | 20 | 0 | $18.02^{a}$ | 3 |
| Donor DNA | 48 | 52 | $0.92^{bc}$ | 1 | 0 | $2.08^{bc}$ | 3 |
| 10 + Neo (no CD163) | 26 | 20 | $1.3^{n/a}$ | 0 | 0 | $0.00^{c}$ | 1 |

*Mix of 4 + Donor DNA represents an equal mixing of 0.5 μg of each CRISPR with 1 μg of Donor DNA. The Donor DNA treatment served as the no CRISPR control and the 10 + Neo treatment illustrates that the large deletions observed in the CRISPR treatments were present only when the CD163 Donor DNA was also present.

†ANOVA was performed comparing the average number of colonies/plate to estimate CRISPR toxicity and on the percent colonies with a modified genome. P-values were 0.025 and 0.0002, respectively. n/a = There were no replicates for this treatment so no statistical analysis was performed.

‡The one colony with HR represents a partial HR event.

$^{a-c}$Superscript letters indicate a significant difference between treatments for both average number of colonies/plate and percent colonies with a modified genome (P < 0.05).

The initial goal was to obtain a domain swap (DS)-targeting event by HR for CD163, but CRISPRs did not increase the efficiency of targeting CD163. It should be noted that various combinations of this targeting vector had been used to modify CD163 by HR by traditional transfections and resulted in 0 targeting events after screening 3399 colonies (Whitworth and Prather, unpublished results). Two pigs were obtained with a full DS resulting from HR that contained all 33 of the mutations that were attempted to be introduced by transfection with CRISPR 10 and the DS-targeting vector as donor DNA.

Next, the efficiency of CRISPR/Cas9-induced mutations without drug selection was tested; the fetal fibroblast cell line used in this study already had an integration of the Neo resistant cassette and a knockout of SIGLEC1. Whether the ratio of CRISPR/Cas9 and donor DNA would increase genome modification or result in a toxic effect at a high concentration was also tested. CRISPR 131 was selected for this trial because in the previous experiment, it resulted in a high number of total colonies and an increased percentage of colonies possessing a modified genome. Increasing amounts of CRISPR 131 DNA from 3:1 to 20:1 did not have a significant effect on fetal fibroblast survivability. The percent of colonies with a genome modified by NHEJ was not significantly different between the various CRISPR concentrations but had the highest number of NHEJ at a 10:1 ratio (Table 6, P=0.33). Even at the highest ratio of CRISPR DNA to donor DNA (20:1), HR was not observed.

TABLE 6

Efficiency of CRISPR/Cas9-induced mutations without drug selection. Four different ratios of Donor DNA to CRISPR 131 DNA were compared in a previously modified cell line without the use of G418 selection.

| Donor DNA: CRISPR Ratio | Number Plates | Number of Colonies | Mean Number of Colonies/Plate | Number of Colonies NHEJ | Percent Colonies with NHEJ | Colony with HR | Percent Colonies with HR | Reps |
|---|---|---|---|---|---|---|---|---|
| 1:0 | 30 | 79 | 2.6 | 1 | 1.3[a] | 0 | 0.0 | 2 |
| 1:3 | 30 | 84 | 2.8 | 1 | 1.2[a] | 0 | 0.0 | 2 |
| 1:5 | 27 | 76 | 2.8 | 2 | 2.6[a] | 0 | 0.0 | 2 |
| 1:10 | 32 | 63 | 2.0 | 5 | 7.9[a] | 0 | 0.0 | 2 |
| 1:20 | 35 | 77 | 2.2 | 3 | 3.9[a] | 0 | 0.0 | 2 |

[a]Significant difference between treatments for percent colonies with NHEJ repair ($P > 0.05$).
[b]There was not a significant difference in the number of genome modified colonies with increasing concentration of CRISPR ($P > 0.33$).

Based on this experience, targeted disruption of CD1D in somatic cells was attempted. Four different CRISPRs were designed and tested in both male and female cells. Modifications of CD1D could be detected from three of the applied CRISPRs, but use of CRISPR 5350 did not result in modification of CD1D with a deletion large enough to detect by agarose gel electrophoresis (Table 7). Interestingly, no genetic changes were obtained through HR although donor DNA was provided. However, large deletions similar to the CD163 knockout experiments were observed (FIG. 3, panel B). No targeted modification of CD1D with a large deletion was detected when CRISPR/Cas9 was not used with the donor DNA. Modification of CD1D from CRISPR/Cas9-guided targeting was 4/121 and 3/28 in male and female colonies of cells, respectively. Only INDELs detectable by agarose gel electrophoresis were included in the transfection data.

TABLE 7

Figure 2:
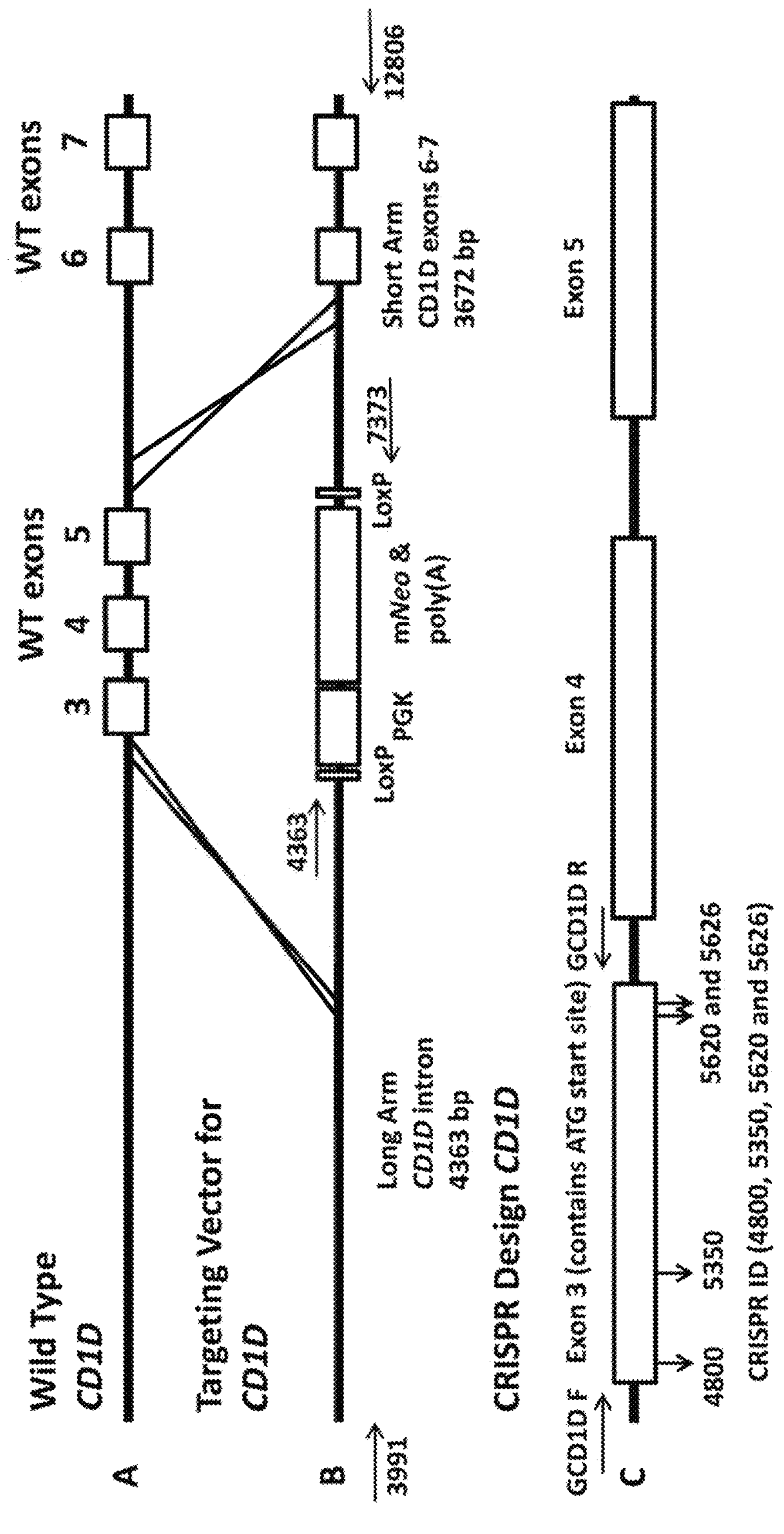
FIG. 2. Targeting vector and CRISPRs used to modify CD1D. Panel A depicts wild type exons 3, 4, 5, 6 and 7 of the CD1D gene that was targeted for modification by CRISPRs. Panel B shows the targeting vector designed to replace exon 3 with the selectable marker Neo. This targeting vector was used in combination with CRISPRs to modify CD1D. PCR primers for the long range, left arm and right arm assay are labeled with arrows for 3991, 4363, 7373 and 12806. Panel C depicts the exons targeted by CRISPRs. Locations of CRISPRs 4800, 5350, 5620 and 5626 are represented by the downward facing arrows on exon 3. Primers used in small deletions assays are illustrated with arrows and labelled GCD1DF and GCD1DR.

Four different CRISPRS were tested at an amount of 2 μg to 1 μg Donor DNA (shown in FIG. 2). The Donor DNA treatment served as the no CRISPR control.

| Gender | Treatment | Total Number of Colonies | INDEL | Efficiency (%) |
|---|---|---|---|---|
| male | 4800 + Donor DNA | 29 | 2 | 6.9 |
| male | 5350 + Donor DNA | 20 | 0 | 0 |
| male | 5620 + Donor DNA | 43 | 1 | 2.33 |
| male | 5626 + Donor DNA | 29 | 2 | 6.9 |
| male | Donor DNA | 28 | 0 | 0 |
| female | 4800 + Donor DNA | 2 | 0 | 0 |
| female | 5350 + Donor DNA | 8 | 0 | 0 |
| female | 5620 + Donor DNA | 10 | 0 | 0 |
| female | 5626 + Donor DNA | 8 | 3 | 37.5 |
| female | Donor DNA | 7 | 0 | 0 |

Production of CD163 and CD1D Pigs Through SCNT Using the GE Cells

The cells presenting modification of CD163 or CD1D were used for SCNT to produce CD163 and CD1D knockout pigs (FIG. 3). Seven embryo transfers (CD163 Table 8), six embryo transfers (CD163-No Neo), and five embryo transfers (CD1D) into recipient gilts were performed with SCNT embryos from male and female fetal fibroblasts transfected with CRISPR/Cas9 systems. Six (CD163), two (CD163-No Neo), and four (CD1D) (Table 9) of the recipient gilts remained pregnant to term resulting in pregnancy rates of 85.7%. 33.3%, and 80%, respectively. Of the CD163 recipients, five delivered healthy piglets by caesarean section. One (0044) farrowed naturally. Litter size ranged from one to eight. Four pigs were euthanized because of failure to thrive after birth. One piglet was euthanized due to a severe cleft palate. All the remaining piglets appear healthy (FIG. 3, panel C). Two litters of male piglets resulting from fetal fibroblasts transfected with CRISPR 10 and donor DNA described in FIG. 3, panel B had a 30 bp deletion in exon 7 adjacent to CRISPR 10 and an additional 1476 bp deletion of the preceding intron, thus removing the intron 6/exon 7 junction of CD163 (FIG. 3, panel E). The genotypes and predicted translations are summarized in Table 10. One male piglet and one female litter (4 piglets) were obtained from the CD163-No Neo transfection of previously modified SIGLEC1 cells. All five piglets were double knockouts for SIGLEC1 and CD163. The male piglet had a biallelic modification of CD163 with a 28 bp deletion in exon 7 on one allele and a 1387 bp deletion on the other allele that included a partial deletion of exon 7 and complete deletion of exon 8 and the proceeding intron, thus removing the intron exon junction. The female piglets had a biallelic mutation of CD163, including a 1382 bp deletion with a 11 bp insertion on one allele and a 1720 bp deletion of CD163 on the other allele. A summary of the CD163 modifications and the predicted translations can be found in Table 10. A summary of the CD1D modifications and predicted translations by CRISPR modification can be found in Table 11. Briefly, one female and two male litters were born, resulting in 13 piglets. One piglet died immediately after birth. Twelve of the 13 piglets contained either a biallelic or homozygous deletion of CD1D (FIG. 3, panel F). One piglet was WT.

TABLE 8

Embryo Transfer data for CD163.

| Pig ID | Line* | Gender | # Embryos Transferred | Oocyte Source† | Day of Estrus | Piglet Result |
|---|---|---|---|---|---|---|
| O047 | CD163 CRISPR NT | Male | 240 | ART | 2 | 4 live piglets (2 euthanized after birth) |
| O015 | CD163 CRISPR NT | Male | 267 | ART | 1 | 3 live piglets (all healthy) |
| O044 | CD163 CRISPR NT | Male | 206 | ART | 1 | 7 live piglets (1 born dead, 1 euthanized after birth) |
| O053 | CD163 CRISPR NT | Male | 224 | ART | 2 | 1 male piglet (euthanized at day 13) |
| O08 | CD163 CRISPR NT | Male | 226 | ART | 1 | 0 piglets |
| O094 | CD163 CRISPR NT | Female | 193 | MU | 2 | 8 live piglets (1 euthanized due to FTT) |
| O086 | CD163 CRISPR NT | Female | 213 | MU | 1 | 9 live piglets (2 euthanized at day 0, 2 due to FTT) |
| O082 | CRISPR Injected CD163 10/131 | Male/Female | 50 Blast | MU | 5 | 0 piglets |
| O083 | CRISPR Injected CD163 10/131 | Male | 46 Blast | MU | 5 | 4 live piglets |
| O99 | CD163 CRISPR NT-no Neo | Male | 156 | ART | 1 | 1 live piglet, 1 dead piglet |
| O128 | CD163 CRISPR NT-no Neo | Male | 196 | ART | 2 | 0 piglets |
| O100 | CD163 CRISPR NT-no Neo | Male | 261 | MU | 3 | 0 piglets |
| O134 | CD163 CRISPR NT-no Neo | Male/Female | 181 | MU | 1 | 0 piglets |
| 200889 | CD163 CRISPR NT-no Neo | Female | 202 | ART | 1 | 4 live piglets |
| O135 | CD163 CRISPR NT-no Neo | Female | 169 | ART | 2 | 0 piglets |

*The CD163 CRISPR NT line represents embryos created by NT with a fetal fibroblast line modified by transfection. CRISPR injected embryos were IVF embryos injected at the 1 cell stage with CD163 guide RNA with CAS9 RNA. CD163 CRISPR NT-no Neo fetal line represents embryos created by NT with a previously modified fetal fibroblast that was already Neo resistant line modified by transfection without the use of a selectable marker.
†MU refers to gilt oocytes that were aspirated and matured at the University of Missouri as described in the IVF se4ction of the Materials and Methods. ART refers to sow oocytes that were purchased and matured as described in the SCNT section of the Materials and Methods.

TABLE 9

Embryo transfer data for CD1D.

| Pig ID | Line* | Gender | # Embryos Transferred | Oocyte Source† | Day of Estrus | Result |
|---|---|---|---|---|---|---|
| 200888 | CD1D CRISPR NT | Male | 201 | ART | 2 | 7 live piglets |
| O61 | CD1D CRISPR NT | Male | 239 | ART | 0 | 4 live piglets |
| O164 | CD1D CRISPR NT | Female | 199 | MU | 2 | 0 piglets |
| O156 | CD1D CRISPR NT | Female | 204 | MU | 2 | 0 piglets |
| O165 | CD1D Injected 4800/5350 | Male/Female | 55 Blast | MU | 6 | 4 piglets (1 female, 3 male) |
| O127 | CD1D Injected 4800/5350 | Male/Female | 55 Blast | MU | 6 | 0 piglets |
| O121 | CD1D CRISPR NT | Female | 212 | ART | 1 | 2 live piglets |

*CD1D CRISPR NT line represents embryos created by NT with a fetal fibroblast line modified by transfection. CRISPR injected embryos were IVF embryos injected at the 1 cell stage with CD1D guide RNA with CAS9 RNA.
†MU refers to gilt oocytes that were aspirated and matured at the University of Missouri as described in the IVF se4ction of the Materials and Methods. ART refers to sow oocytes that were purchased and matured as described in the SCNT section of the Materials and Methods.

TABLE 10

Genotype and Translational Prediction for CD163 modified pigs. Some pigs contain a biallelic type of modification, but only have one allele described and another modified allele that was not amplified by PCR.

| Litter | No. of Piglets | Repair mechanism | Type | Size of INDELs | Description |
|---|---|---|---|---|---|
| 63 & 64 | 7 | NHEJ | biallelic | 1506 bp deletion<br>Other allele | 30 bp deletion in exon 7<br>Uncharacterized, unamplifiable |
| 65 | 3 | NHEJ | Bialletic | 7 pb insertion | Insertion into exon 7 |
| 65 | 2 | NHEJ | Biallelic | 503 bp deletion<br>Other allele | Partial deletion of exon 7 and 8<br>Uncharacterized |
| 65 | 2 | NHEJ | Biallelic | 1280 bp deletion<br>1373 bp deletion | Complete deletion of exons 7 and 8<br>Complete deletion of exons 7 and 8 |
| 66 | 1 | NHEJ | Homozygous | 2015 bp insertion | Insertion of targeting vector backbone into exon 7 |
| 67-1 | 1 | NHEJ | Biallelic | 11 bp deletion<br>2 bp insertion, 377 bp deletion in intron 6 | Deletion in exon 7<br>Insertion in exon 7 |
| 67-2 | 1 | NHEJ | Biallelic | 124 bp deletion<br>123 bp deletion | Deletion in exon 7<br>Deletion in exon 7 |
| 67-3 | 1 | NHEJ | Biallelic | 1 bp insertion<br>Other allele | Insertion into exon 7<br>Uncharacterized, unamplifiable |
| 67-4 | 1 | NHEJ | Biallelic | 130 bp deletion<br>132 bp deletion | Deletion in exon 7<br>Deletion in exon 7 |

TABLE 10-continued

Genotype and Translational Prediction for CD163 modified pigs. Some pigs contain a biallelic type of modification, but only have one allele described and another modified allele that was not amplified by PCR.

| | | | | | |
|---|---|---|---|---|---|
| 68 & 69 | 6 | NHEJ | Biallelic | 1467 bp deletion<br>Other allele | Complete deletion of exons 7 and 8<br>Uncharacterized, unamplifiable |
| 68 & 69 | 2 | NHEJ | Biallelic | 129 bp deletion, 1930 bp intron 6 deletion<br>other allele | Deletion in exon 7<br>Uncharacterized, unamplifiable |
| 65 & 69 | 3 | WT | | | Wild type pigs created from a mixed colony |
| 70 | 2 | NHEJ | On $SIGLEC1^{-/-}$ Biallelic | 28 bp deletion | Deletion in exon 7 |
| | | | | 1387 bp deletion | Partial deletion in exon 7 and all of exon 8 |
| 73 | 4 | NHEJ | On $SIGLEC1^{-/-}$ Biallelic | 1382 bp deletion + 11 bp insertion | Partial deletion in exon 7 and all of exon 8 |
| | | | | 1720 bp deletion | Complete deletion of exons 7 and 8 |

| Litter | No. of Piglets | Protein translation* | Premature stop codon | In reference to SEQ ID NO: 47 | SEQ ID NO† |
|---|---|---|---|---|---|
| 63 & 64 | 7 | KO or $CD163^{\Delta 422-527}$ | No | Deletion from nt 1,525 to nt 3,030 | 98 |
| 65 | 3 | KO | Yes (491) | Insertion between nt 3,148 & 3.149[a] | 99 |
| 65 | 2 | KO | Yes (491) | ** | ** |
| 65 | 2 | $CD163^{\Delta 422-631}$ | No | Deletion from nt 2,818 to nt 4,097 | 100 |
| | | $CD163^{\Delta 422-631}$ | No | Deletion from nt 2,724 to nt 4,096 | 101 |
| 66 | 1 | | | ** | ** |
| 67-1 | 1 | KO | Yes (485) | Deletion from nt 3,137 to nt 3,147 | 102 |
| | | | | 2 bp insertion between nt 3,149 & nt 3,150[b] with a 377 bp deletion from nt 2,573 to nt 2,949 | 103 |
| 67-2 | 1 | KO | Yes (464) | Deletion from nt 3,024 to nt 3,147 | 104 |
| | | $CD163^{\Delta 429-470}$ | No | Deletion from nt 3,024 to nt 3,146 | 105 |
| 67-3 | 1 | KO | Yes (489) | Insertion between nt 3,147 & 3,148[c] | 106 |
| 67-4 | 1 | KO | Yes (462) | Deletion from nt 3,030 to nt 3,159 | 107 |
| | | $CD163^{\Delta 430-474}$ | No | Deletion from nt 3,030 to nt 3,161 | 108 |
| 68 & 69 | 6 | $CD163^{\Delta 422-631}$ | No | Deletion from nt 2,431 to nt 3,897 | 109 |
| 68 & 69 | 2 | $CD163^{\Delta 435-478}$ | No | Deletion from nt 488 to nt 2,417 in exon 6, deleted sequence is replaced with a 12 bp insertion[d] starting at nt 488, & an additional 129 bp deletion from nt 3,044 to nt 3,172 | 110 |
| 65 & 69 | 3 | | | SEQ ID NO: 47 | 47 |
| 70 | 2 | KO | Yes (528) | Deletion from nt 3,145 to nt 3,172 | 111 |
| | | KO | No | Deletion from nt 3,145 to nt 4,531 | 112 |
| 73 | 4 | KO | No | Deletion from nt 3,113 to nt 4,494, deleted sequence replaced with an 11 bp insertion[e] starting at nt 3,113 | 113 |
| | | $CD163^{\Delta 422-631}$ | | Deletion from nt 2,440 to nt 4,160 | 114 |

*KO, knock-out

**Not included because piglets were euthanized.

†SEQ ID NOs. in this column refer to the SEQ ID NOs. for the sequences that show the INDELs in relation to SEQ ID NO: 47.

[a]The inserted sequence was TACTACT (SEQ ID NO: 115)

[b]The inserted sequence was AG.

[c]The inserted sequence was a single adenine (A) residue.

[d]The inserted sequence was TGTGGAGAATTC (SEQ ID NO: 116).

[e]The inserted sequence was AGCCAGCGTGC (SEQ ID NO: 117).

TABLE 11

Genotype and Translational Prediction for CD1D modified pigs

| Litter | Number of Piglets | Repair Mechanism | Type | Size of INDEL | Description | Protein Translation |
|---|---|---|---|---|---|---|
| 158, 159 | 11 | NHEJ | homozygous | 1653 bp deletion | Deletion of exon 3, 4 and 5 | KO* |
| 167 | 2 | NHEJ | homozygous | 1265 bp deletion | Deletion of exon 5 and 72 bp of exon 6 | KO |
| 166-1 | 1 | NHEJ | biallelic | 24 bp deletion | Removal of start codon in exon 3 | KO |
| | | | | 27 bp deletion | Disruption of start codon in exon 3 | |
| | | | | 362 bp deletion + 5 bp | Deletion of exon 3 | |
| 166-2 | 1 | NHEJ | biallelic | 6 bp insertion + 2 bp mismatch | Addition of 6 bp before start codon in exon 3 | $CD1D^{ko/+}$ |
| | | | | 1598 bp deletion | Removal of start codon in exon 3 and deletion of exons 4,5 | |
| 166-3 | 1 | NHEJ | biallelic | 1 bp insertion | Addition of G/T in exon 3 before start codon in exon 3 | $CD1D^{+/+}$ |
| 166-4 | 1 | NHEJ | homozygous | 1 bp insertion | Addition of A in exon 3 before start codon in exon 3 | $CD1D^{+/+}$ |

*KO, knock-out

Efficiency of CRISPR/Cas9 System in Porcine Zygotes

Figure 4:
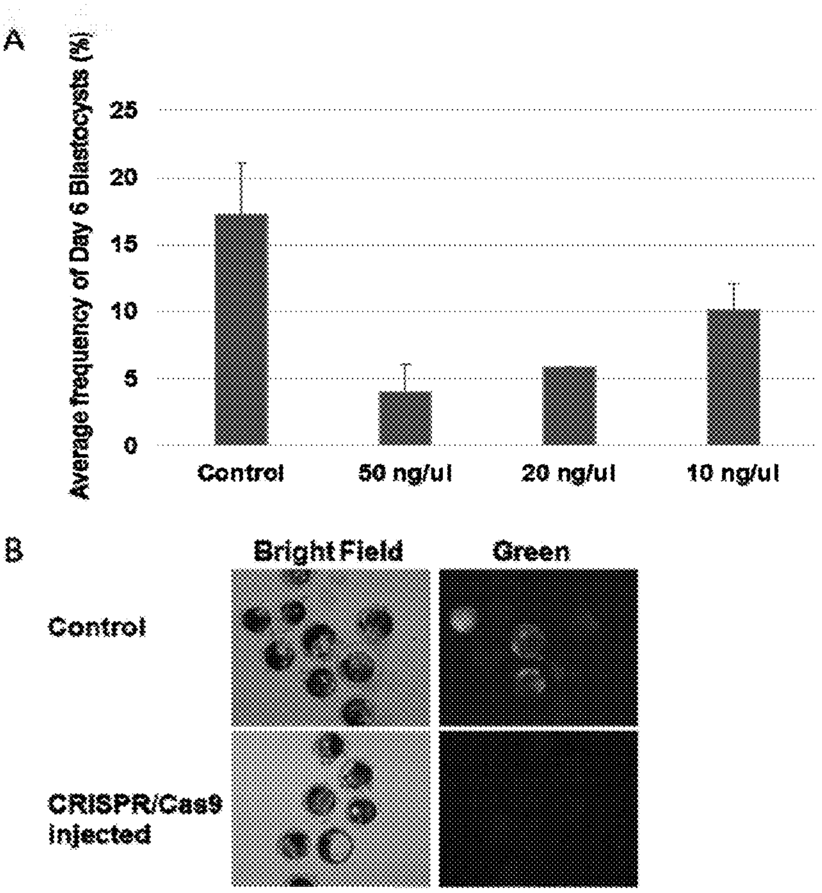
FIG. 4. Effect of CRISPR/Cas9 system in porcine embryos. A) Frequency of blastocyst formation after injection of different concentrations of CRISPR/Cas9 system into zygotes. Toxicity of the CRISPR/Cas9 system was lowest at 10 ng/μl. B) The CRISPR/Cas9 system can successfully disrupt expression of eGFP in blastocysts when introduced into zygotes. Original magnification X4. C) Types of mutations on eGFP generated using the CRISPR/Cas9 system: WT genotype (SEQ ID NO:16), #1 (SEQ ID NO:17), #2 (SEQ ID NO:18), and #3 (SEQ ID NO:19).

Based on targeted disruption of CD163 and CD1D in somatic cells using the CRISPR/Cas9 system, this approach was applied to porcine embryogenesis. First, the effectiveness of the CRISPR/Cas9 system in developing embryos was tested. CRISPR/Cas9 system targeting eGFP was introduced into zygotes fertilized with semen from a boar heterozygous for the eGFP transgene. After the injection, subsequent embryos expressing eGFP were monitored. Various concentrations of the CRISPR/Cas9 system were tested and cytotoxicity of the delivered CRISPR/Cas9 system was observed (FIG. 4, panel A); embryo development after CRISPR/Cas9 injection was lower compared to control. However, all the concentrations of CRISPR/Cas9 that were examined were effective in generating modification of eGFP because no embryos with eGFP expression were found in the CRISPR/Cas9-injected group (FIG. 4, panel B); of the noninjected control embryos 67.7% were green, indicating expression of eGFP. When individual blastocysts were genotyped, it was possible to identify small mutations near the CRISPR binding sites (FIG. 4, panel C). Based on the toxicity and effectiveness, 10 ng/μl of gRNA and Cas9 mRNA were used for the following experiments.

When CRISPR/Cas9 components designed to target CD163 were introduced into presumptive zygotes, targeted editing of the genes in the subsequent blastocysts was observed. When individual blastocysts were genotyped for mutation of CD163, specific mutations were found in all the embryos (100% GE efficiency). More importantly, while embryos could be found with homozygous or biallelic modifications (8/18 and 3/18, respectively) (FIG. 5), mosaic (monoallelic modifications) genotypes were also detected (4/18 embryos). Some embryos (8/10) from the pool were injected with 2 ng/μl Cas9 and 10 ng/μl CRISPR and no difference was found in the efficiency of mutagenesis. Next, based on the in vitro results, two CRISPRs representing different gRNA were introduced to disrupt CD163 or CD1D during embryogenesis to induce a specific deletion of the target genes. As a result, it was possible to successfully induce a designed deletion of CD163 and CD1D by introducing two guides. A designed deletion is defined as a deletion that removes the genomic sequence between the two guides introduced. Among the embryos that received two CRISPRs targeting CD163, all but one embryo resulted in a targeted modification of CD163. In addition, 5/13 embryos were found to have a designed deletion on CD163 (FIG. 6, panel A) and 10/13 embryos appeared to have modification of CD163 in either homozygous or biallelic fashion. Targeting CD1D with two CRISPRs was also effective because all the embryos (23/23) showed a modification of CD1D. However, the designed deletion of CD1D could only be found in two embryos (2/23) (FIG. 6, panel B). Five of twenty-three embryos possessing mosaic genotypes were also found, but the rest of embryos had either homozygous or biallelic modification of CD1D Finally, whether multiple genes can be targeted by the CRISPR/Cas9 system within the same embryo was tested. For this purpose, targeting both CD163 and eGFP was performed in the zygotes that were fertilized with heterozygous eGFP semen. When blastocysts from the injected embryos were genotyped for CD163 and eGFP, it was found that found that CD163 and eGFP were successfully targeted during embryogenesis. Sequencing results demonstrated that multiple genes can be targeted by introducing multiple CRISPRs with Cas9 (FIG. 6, panel C).

Production of CD163 and CD1D Mutants from CRISPR/Cas9-Injected Zygotes

Based on the success from the previous in vitro study, some CRISPR/Cas9-injected zygotes were produced and 46-55 blastocysts were transferred per recipient (because this number has been shown to be effective in producing pigs from the in vitro derived embryos). Four embryo transfers were performed, two each for CD163 and CD1D, and a pregnancy for each modification was obtained. Four healthy piglets were produced carrying modifications on CD163 (Table 8). All the piglets, litter 67 from recipient sow ID 0083 showed either homozygous or biallelic modification of CD163 (FIG. 7). Two piglets showed the designed deletion of CD163 by the two CRISPRs delivered. All the piglets were healthy. For CD1D, one pregnancy also produced four piglets (litter 166 from recipient sow identification no. 0165): one female and three males (Table 9). One piglet (166-1) did carry a mosaic mutation of CD1D, including a 362 bp deletion that completely removed exon 3 that contains the start codon (FIG. 8). One piglet contained a 6 bp insertion with a 2 bp mismatch on one allele with a large deletion on the other allele. Two additional piglets had a biallelic single bp insertion. There were no mosaic mutations detected for CD163.

DISCUSSION

An increase in efficiency of GE pig production can have a wide impact by providing more GE pigs for agriculture and biomedicine. The data described above show that by using the CRISPR/Cas9 system, GE pigs with specific mutations can be produced at a high efficiency. The CRISPR/Cas9 system was successfully applied to edit genes in both somatic cells and in preimplantation embryos.

When the CRISPR/Cas9 system was introduced into somatic cells, it successfully induced targeted disruption of the target genes by NHEJ but did not increase the ability to target by HR. Targeting efficiency of individual CRISPR/Cas9 in somatic cells was variable, which indicated that the design of the guide can affect the targeting efficiency. Specifically, it was not possible to find targeted modification of CD1D when CRISPR 5350 and Cas9 were introduced into somatic cells. This suggests that it could be beneficial to design multiple gRNAs and validate their efficiencies prior to producing pigs. A reason for the lack of HR-directed repair with the presence of donor DNA is still unclear. After screening 886 colonies (both CD163 and CD1D) transfected with CRISPR and donor DNA, only one colony had evidence for a partial HR event. The results demonstrated that the CRISPR/Cas9 system worked with introduced donor DNA to cause unexpected large deletions on the target genes but did not increase HR efficiency for these two particular targeting vectors. However, a specific mechanism for the large deletion observation is not known. Previous reports from our group suggested that a donor DNA can be effectively used with a ZFN to induce HR-directed repair. Similarly, an increase in the targeting efficiency was seen when donor DNA was used with CRISPR/Cas9 system, but complete HR directed repair was not observed. In a previous study using ZFN, it was observed that targeted modification can occur through a combination of HR and NHEJ because a partial recombination was found of the introduced donor DNA after induced DSBs by the ZFN. One explanation might be that HR and NHEJ pathways are not independent but can act together to complete the repair process after DSBs induced by homing endonucleases. Higher concentrations of CRISPRs might improve targeting efficiency in somatic cells although no statistical difference was found in these experimental results. This may suggest that CRISPR is a limiting factor in CRISPR/Cas9 system, but further validation is needed. Targeted cells were successfully used to produce GE pigs through SCNT, indicating the application of CRISPR/Cas9 does not affect the ability of the cells to be cloned. A few piglets were euthanized because of health issues; however, this is not uncommon in SCNT-derived piglets.

When the CRISPR/Cas9 system was introduced into developing embryos by zygote injection, nearly 100% of embryos and pigs contained an INDEL in the targeted gene, demonstrating that the technology is very effective during embryogenesis. The efficiency observed during this study surpasses frequencies reported in other studies utilizing homing endonucleases during embryogenesis. A decrease in the number of embryos reaching the blastocyst stage suggested that the concentration of CRISPR/Cas9 introduced in this study may be toxic to embryos. Further optimization of the delivery system may increase survivability of embryos and thus improve the overall efficiency of the process. The nearly 100% mutagenesis rate observed here was different from a previous report in CRISPR/Cas9-mediated knockout in pigs; however, the difference in efficiency between the studies could be a combination of the guide and target that was selected. In the present study, lower concentrations of CRISPR/Cas9 (10 ng/μl each) were effective in generating mutations in developing embryos and producing GE pigs. The concentration is lower than previously reported in pig zygotes (125 ng/μl of Cas9 and 12.5 ng/μl of CRISPR). The lower concentration of CRISPR/Cas9 components could be beneficial to developing embryos because introducing excess amounts of nucleic acid into developing embryos can be toxic. Some mosaic genotypes were seen in CRISPR/Cas9-injected embryos from the in vitro assays; however, only one piglet produced through the approach had a mosaic genotype. Potentially, an injection with CRISPR/Cas9 components may be more effective than introduction of other homing endonucleases because the mosaic genotype was considered to be a main hurdle of using the CRISPR/Cas9 system in zygotes. Another benefit of using the CRISPR/Cas9 system demonstrated by the present results is that no CD163 knockout pigs produced from IVF-derived zygotes injected with CRISPR/Cas9 system were lost, whereas a few piglets resulting from SCNT were euthanized after a few days. This suggests that the technology could not only bypass the need of SCNT in generating knockout pigs but could also overcome the common health issues associated with SCNT. Now that injection of CRISPR/Cas9 mRNA into zygotes has been optimized, future experiments will include coinjection of donor DNA as well.

The present study demonstrates that introducing two CRISPRs with Cas9 in zygotes can induce chromosomal deletions in developing embryos and produce pigs with an intended deletion, that is, specific deletion between the two CRISPR guides. This designed deletion can be beneficial because it is possible to specify the size of the deletion rather than relying on random events caused by NHEJ. Specifically, if there is insertion/deletion of nucleotides in a multiple of three caused by a homing endonuclease, the mutation may rather result in a hypomorphic mutation because no frame shift would occur. However, by introducing two CRISPRs, it is possible to cause larger deletions that will have a higher chance of generating non-functional protein. Interestingly, CD1D CRISPRs were designed across a greater area in the genome than CD163; there was a 124 bp distance between CD163 CRISPR 10 and 131 while there was a distance of 550 bp between CRISPR 4800 and 5350 for CD1D. The longer distance between CRISPRs was not very effective in generating a deletion as shown in the study. However, because the present study included only limited number of observations and there is a need to consider the efficacy of individual CRISPRs, which is not addressed here, further study is need to verify the relationship between the distance between CRISPRs and probability of causing intended deletions.

The CRISPR/Cas9 system was also effective in targeting two genes simultaneously within the same embryo with the only extra step being the introduction of one additional CRISPR with crRNA. This illustrates the ease of disrupting multiples genes compared to other homing endonucleases. These results suggest that this technology may be used to target gene clusters or gene families that may have a compensatory effect, thus proving difficult to determine the role of individual genes unless all the genes are disrupted. The results demonstrate that CRISPR/Cas9 technology can be applied in generating GE pigs by increasing the efficiency of gene targeting in somatic cells and by direct zygote injection.

Example 2: Increased Resistance to PRRSV in Swine Having a Modified Chromosomal Sequence in a Gene Encoding a CD163 Protein Porcine Reproductive and Respiratory Syndrome Virus (PRRSV) has ravaged the swine industry over the last quarter of a century. Speculation about the mode of viral entry has included both SIGLEC1 and CD163. While knockout of SIGLEC1 did not affect the response to a viral challenge, it is shown in the present example that CD163 null animals show no clinical signs of infection, lung pathology, viremia or antibody production that are all hallmarks of PRRSV infection. Not only has a PRRSV entry mediator been confirmed; but if similarly created animals were allowed to enter the food supply, then a strategy to prevent significant economic losses and animal suffering has been described.

Materials and Methods

Genotyping

Genotyping was based on both DNA sequencing and mRNA sequencing. The sire's genotype had an 11 bp deletion in one allele that when translated predicted 45 amino acids into domain 5, resulting in a premature stop codon at amino acid 64. In the other allele there was a 2 bp addition in exon 7 and 377 bp deletion in intron before exon 7, that when translated predicted the first 49 amino acids of domain 5, resulting in a premature stop code at amino acid 85. One sow had a 7 bp addition in one allele that when translated predicted the first 48 amino acids of domain 5, resulting in a premature stop codon at amino acid 70. The other allele was uncharacterized (A), as there was no band from exon 7 by either PCR or long range 6.3 kb PCR. The other 3 sows were clones and had a 129 bp deletion in exon 7 that is predicted to result in a deletion of 43 amino acids from domain 5. The other allele was uncharacterized (B).

Growth of PRRSV in Culture and Production of Virus Inoculum for the Infection of Pigs are Covered Under Approved IBC Application 973

A type strain of PRRSV, isolate NVSL 97-7895 (GenBank #AF325691 2001-0241), was grown as described in approved IBC protocol 973. This laboratory isolate has been used in experimental studies for about 20 years (Ladinig et al.: 2015). A second isolate was used for the $2^{nd}$ trial, KS06-72109 as described previously (Prather et al., 2013).

Infection of Pigs with PRRSV

A standardized infection protocol for PRRSV was used for the infection of pigs. Three week old piglets were inoculated with approximately $10^4$ TCID50 of PRRS virus which was administered by intramuscular (IM) and intranasal (IN) routes. Pigs were monitored daily and those exhibiting symptoms of illness are treated according to the recommendations of the CMG veterinarians. Pigs that show severe distress and are in danger of succumbing to infection are humanely euthanized and samples collected. Staff and veterinarians: were blind to the genetic status of the pigs to eliminate bias in evaluation or treatment. PRRSV is present in body fluids during infection, therefore, blood samples were collected and stored at −80° C. until measured to determine the amount or degree of viremia in each pig. At the end of the experiment, pigs were weighed and humanely euthanized, and tissues collected and fixed in 10% buffered formalin, embedded in paraffin, and processed for histopathology by a board-certified pathologist.

Phenotype Scoring of the Challenged Pigs

The phenotype of the pigs was blindly scored daily as follows: What is the attitude of the pig? Attitude Score: 0: BAR, 1: QAR, 2: Slightly depressed, 3: Depressed, 4: Moribund. What is the body condition of the pig? Body Condition Score: 1: Emaciated, 2: Thin, 3: Ideal, 4: Fat, 5: Overfat/Obese. What is the rectal temperature of the pig? Normal Body Temperature 101.6-103.6° F. (Fever considered≥104° F.). Is there any lameness (grade)? What limb? Evaluate limbs for joint swelling and hoof lesions (check bottom and sides of hoof). Lameness Score: 1: No lameness, 2: Slightly uneven when walking, appears stiff in some joints but no lameness, 3: Mild lameness, slight limp while walking, 4: Moderate lameness, obvious limp including toe touching lame, 5: Severe lameness, non-weight bearing on limb, needs encouragement to stand/walk. Is there any respiratory difficulty (grade)? Is there open mouth breathing? Is there any nasal discharge (discharge color, discharge amount: mild/moderate/severe)? Have you noticed the animal coughing? Is there any ocular discharge? Respiratory Score: 0: Normal, 1: mild dyspnea and/or tachypnea when stressed (when handled), 2: mild dyspnea and/or tachypnea when at rest, 3: moderate dyspnea and/or tachypnea when stressed (when handled), 4: moderate dyspnea and/or tachypnea when at rest, 5: severe dyspnea and/or tachypnea when stressed (when handled), 6: severe dyspnea and/or tachypnea when at rest. Is there evidence of diarrhea (grade) or vomiting? Is there any blood or mucus? Diarrhea Score: 0: no feces noted, 1: normal stool, 2: soft stool but formed (soft serve yogurt consistency, creates cow patty), 3: liquid diarrhea of brown/tan coloration with particulate fecal material, 4: liquid diarrhea of brown/tan coloration without particulate fecal material, 5: liquid diarrhea appearing similar to water.

This scoring system was developed by Dr. Megan Niederwerder at KSU and is based on the following publications (Halbur et al., 1995; Merck; Miao et al., 2009; Patience and Thacker, 1989; Winckler and Willen, 2001). Scores and temperatures were analyzed by using ANOVA separated based on genotypes as treatments.

Measurement of PRRSV Viremia

Viremia was determined via two approaches, Virus titration was performed by adding serial 1:10 dilutions of serum to confluent MARC-145 cells in a 96 well-plate. Serum was diluted in Eagle's minimum essential medium supplemented with 8% fetal bovine serum, penicillin, streptomycin, and amphotericin B as previously described (Prather et al., 2013). The cells were examined after 4 days of incubation for the presence of a cytopathic effect by using microscope. The highest dilution showing a cytopathic effect was scored as the titration endpoint. Total RNA was isolated from serum by using the Life Technologies MagMAX-96 viral RNA isolation kit for measuring viral nucleic acid. The reverse transcription polymerase chain reaction was performed by using the EZ-PRRSV MPX 4.0 kit from Tetracore on a CFX-96 real-time PCR system (Bio-Rad) according to the manufacturer's instructions. Each reaction (25 µl) contained RNA from 5.8 µl of serum. The standard curve was constructed by preparing serial dilutions of an RNA control supplied in the kit (Tetracore). The number of templates per PCR are reported.

SIGLEC1 and CD163 Staining of PAM Cells

Porcine alveolar macrophages (PAMs) were collected by excising the lungs and filling them with ~100 ml cold phosphate buffered saline. After recovering the phosphate buffered saline wash cells were pelleted and resuspended in 5 ml cold phosphate buffered saline and stored on ice. Approximately $10^7$PAMs were incubated in 5 ml of the various antibodies (anti-porcine CD169 (clone 3B11/11; AbD Serotec); anti-porcine CD163 (clone 2A10/11; AbD Serotec)) diluted in phosphate buffered saline with 5% fetal bovine serum and 0.1% sodium azide for 30 minutes on ice. Cells were washed and resuspended in 1/100 dilution of fluorescein isothiocyanate (FITC)-conjugated to goat anti-mouse IgG (life Technologies) diluted in staining buffer and incubated for 30 minutes on ice. At least $10^4$ cells were analyzed by using a FACSCalibur flow cytometer and Cell Quest software (Becton Dickinson).

Measurement of PRRSV-Specific Ig

To measure PRRSV-specific Ig recombinant PRRSV N protein was expressed in bacteria (Trible et al., 2012) and conjugated to magnetic Luminex heads by using a kit (Luminex Corporation). The N protein-coupled heads were diluted in phosphate buffered saline containing 10% goat serum to 2,500 beads/50 μl and placed into the wells of a 96-well round-bottomed polystyrene plate, Serum was diluted 1:400 in phosphate buffered saline containing 10% goat serum and 50 μl was added in duplicate wells and incubated for 30 minutes with gentle shaking at room temperature. Next the plate was washed (3×) with phosphate buffered saline containing 10% goat serum and 50 μl of biotin-SP-conjugated affinity-purified goat anti-swine secondary antibody (IgG, Jackson ImmunoResearch) or biotin-labeled affinity purified goat anti-swine IgM (KPL) diluted to 2 μg/ml in phosphate buffered saline containing 10% goat serum was added. The plates were washed (3×) after 30 minutes of incubation and then 50 μl of streptavidin-conjugated phycoerythrin (2 μg/ml (Moss, Inc.) in phosphate buffered saline containing 10% goat serum) was added. The plates were washed 30 minutes later and microspheres were resuspended in 100 μl of phosphate buffered saline containing 10% goat serum an analyzed by using the MAGPIX and the Luminex xPONENT 4.2 software. Mean fluorescence intensity (MH) is reported.

Results

Mutations in CD163 were created by using the CRISPR/Cas9 technology as described above in Example 1. Several founder animals were produced from zygote injection and from somatic cell nuclear transfer. Some of these founders were mated creating offspring to study. A single founder male was mated to females with two genotypes. The founder male (67-1) possessed an 11 bp deletion in exon 7 on one allele and a 2 bp addition in exon 7 (and 377 bp deletion in the preceding intron) of the other allele and was predicted to be a null animal ($CD163^{-/-}$). One founder female (65-1) had a 7 bp addition in exon 7 in one allele and an uncharacterized corresponding allele and was thus predicted to be heterozygous for the knockout ($CD163^{-/?}$). A second founder female genotype (3 animals that were clones) contained an as yet uncharacterized allele and an allele with a 129 bp deletion in exon 7. This deletion is predicted to result in a deletion of 43 amino acids in domain 5. Matings between these animals resulted in all piglets inheriting a null allele from the boar and either the 43 amino acid deletion or one of the uncharacterized alleles from the sows. In addition to the wild type piglets that served as positive controls for the viral challenge, this produced 4 additional genotypes (Table 12).

TABLE 12

Genotypes tested for resistance to PRRSV challenge (NVSL and KS06 strains)

| Alleles | | Resistance to PRRSV Challenge as Measured by Viremia | |
|---|---|---|---|
| Paternal | Maternal | NVSL | KS06 |
| Null | Null | Resistant | N/A |
| Null | Δ43 Amino Acids | N/A | Resistant |
| Null | Uncharacterized A | Susceptible | N/A |
| Null | Uncharacterized B | Susceptible | Susceptible |
| Wild Type | Wild Type | Susceptible | Susceptible |

Figure 9:
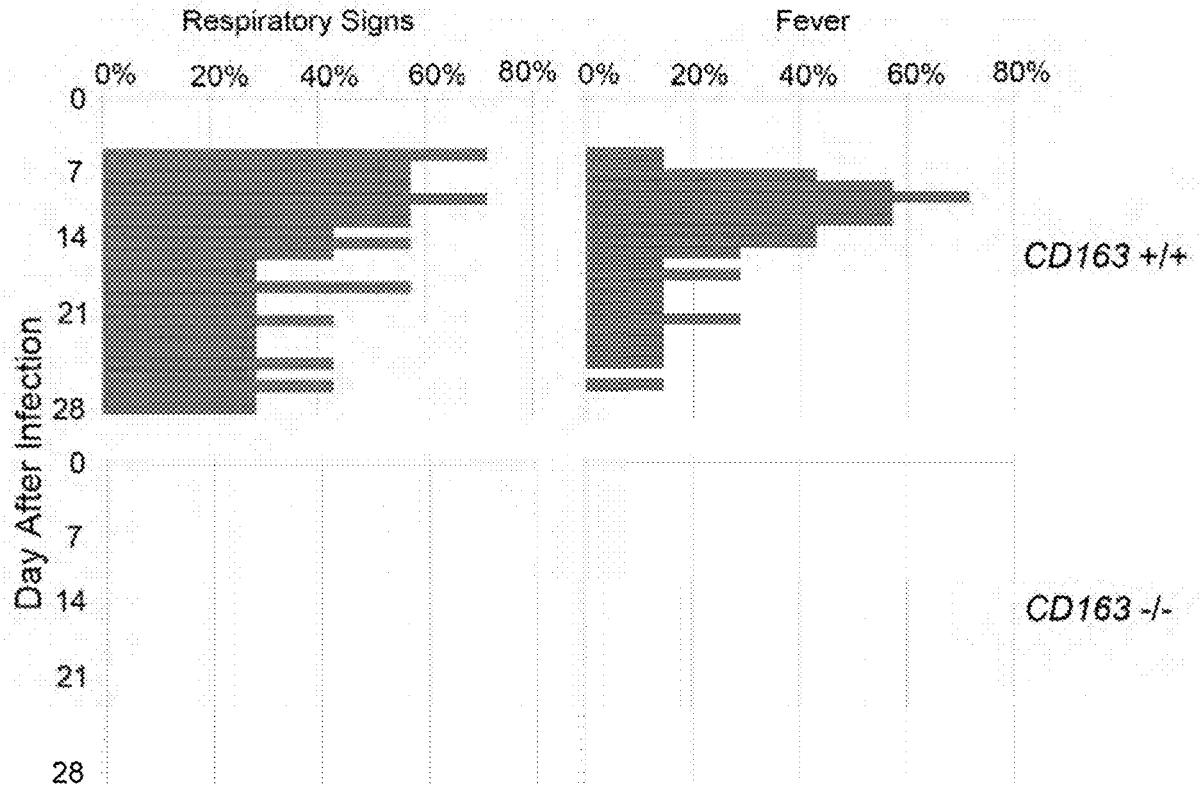
FIG. 9. Clinical signs during acute PRRSV infection. Results for daily assessment for the presence of respiratory signs and fever for CD163+/+ (n=6) and CD163−/− (n=3).
Figure 10:
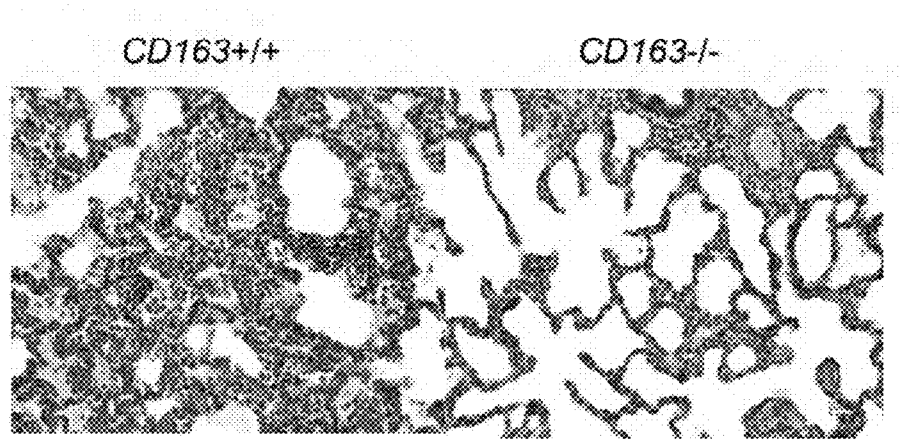
FIG. 10. Lung histopathology during acute PRRSV infection. Representative photomicrographs of H and E stained tissues from wild-type and knockout pigs. The left panel shows edema and infiltration of mononuclear cells. The right panel from a knockout pig shows lung architecture of a normal lung.

At weaning, gene edited piglets and wild type age-matched piglets were transported to Kansas State University for a PRRSV challenge. A PRRSV challenge was conducted as previously described (Prather et al., 2013). Piglets, at three weeks of age, were brought into the challenge facility and maintained as a single group. All experiments were initiated after approval of institutional animal use and biosafety committees. After acclimation, the pigs were challenged with a PRRSV isolate, NVSL 97-7895 (Ladinig et al., 2015), propagated on MARC-145 cells (Kim et al., 1993). Pigs were challenged with approximately $10^5$ $TCID_{50}$ of virus. One-half of the inoculum was delivered intramuscularly and the remaining delivered intranasally. All infected pigs were maintained as a single group, which allowed the continuous exposure of virus from infected pen mates. Blood samples were collected at various days up to 35 days after infection and at termination, day 35. Pigs were necropsied and tissues fixed in 10% buffered formalin, embedded in paraffin and processed for histopathology. PRRSV associated clinical signs recorded during the course of the infection included respiratory distress, inappetence, lethargy and fever. The results for clinical signs over the study period are summarized in FIG. 9. As expected, the wild-type Wild Type (CD163+/+) pigs showed early signs of PRRSV infection, which peaked at between days 5 and 14 and persisted in the group during the remainder of the study. The percentage of febrile pigs peaked on about day 10. In contrast, Null (CD163−/−) piglets showed no evidence of clinical signs over the entire study period. The respiratory signs during acute PRRSV infection are reflected in significant histopathological changes in the lung (Table 9). The infection of the wild type pigs showed histopathology consistent with PRRS including interstitial edema with the infiltration of mononuclear cells (FIG. 10). In contrast there was no evidence for pulmonary changes in the Null (CD163−/−) pigs. The sample size for the various genotypes is small; nevertheless the mean scores were 3.85 (n=7) for the wild type, 1.75 (n=4) for the uncharacterized A, 1.33 (n=3) for the uncharacterized B, and 0 (n=3) and for the null (CD163−/−).

TABLE 13

| Microscopic Lung evaluation | | | |
|---|---|---|---|
| Pig | Genotype | Description | Score |
| 41 | Wild Type | 100% congestion. Multifocal areas of edema. Infiltration of moderate numbers of lymphocytes and macrophages | 3 |
| 42 | Wild Type | 100% congestion. Multifocal areas of edema. Infiltration of moderate numbers of lymphocytes and macrophages | 3 |
| 47 | Wild Type | 75% multifocal infiltration with mononuclear cells and mild edema | 2 |
| 50 | Wild Type | 75% multifocal infiltration of mononuclear cells within alveolar spaces and around small blood vessels perivascular edema | 3 |
| 51 | Wild Type | 25% atelectasis with moderate infiltration of mononuclear cells | 1 |
| 52 | Wild Type | 10% of alveolar spaces collapsed with infiltration of small numbers of mononuclear cells | 1 |
| 56 | Wild Type | 100% diffuse moderate interstitial infiltration of mononuclear cells. Interalveolar septae moderately thickened by hemorrhage and edema. | 4 |
| 45 | Uncharacterized A | 75% multifocal infiltrates of mononuclear cells, especially around bronchi, blood vessels, subpleural spaces, and interalveolar septae. | 3 |
| 49 | Uncharacterized A | 75% multifocal moderate to large infiltration of mononuclear cells. Some vessels with mild edema. | 2 |
| 53 | Uncharacterized A | 10% multifocal small infiltration of mononuclear cells | 1 |
| 57 | Uncharacterized A | 15% infiltration of mononuclear cells | 1 |
| 46 | Uncharacterized B | Moderate interstitial pneumonia | 2 |
| 48 | Uncharacterized B | Perivascular edema and infiltration of mononuclear cells around small and medium sized vessels and around interalveolar septae | 2 |
| 54 | Uncharacterized B | No changes | 0 |
| 40 | Null | No changes | 0 |
| 43 | Null | No changes | 0 |
| 55 | Null | No changes | 0 |

Figure 11:
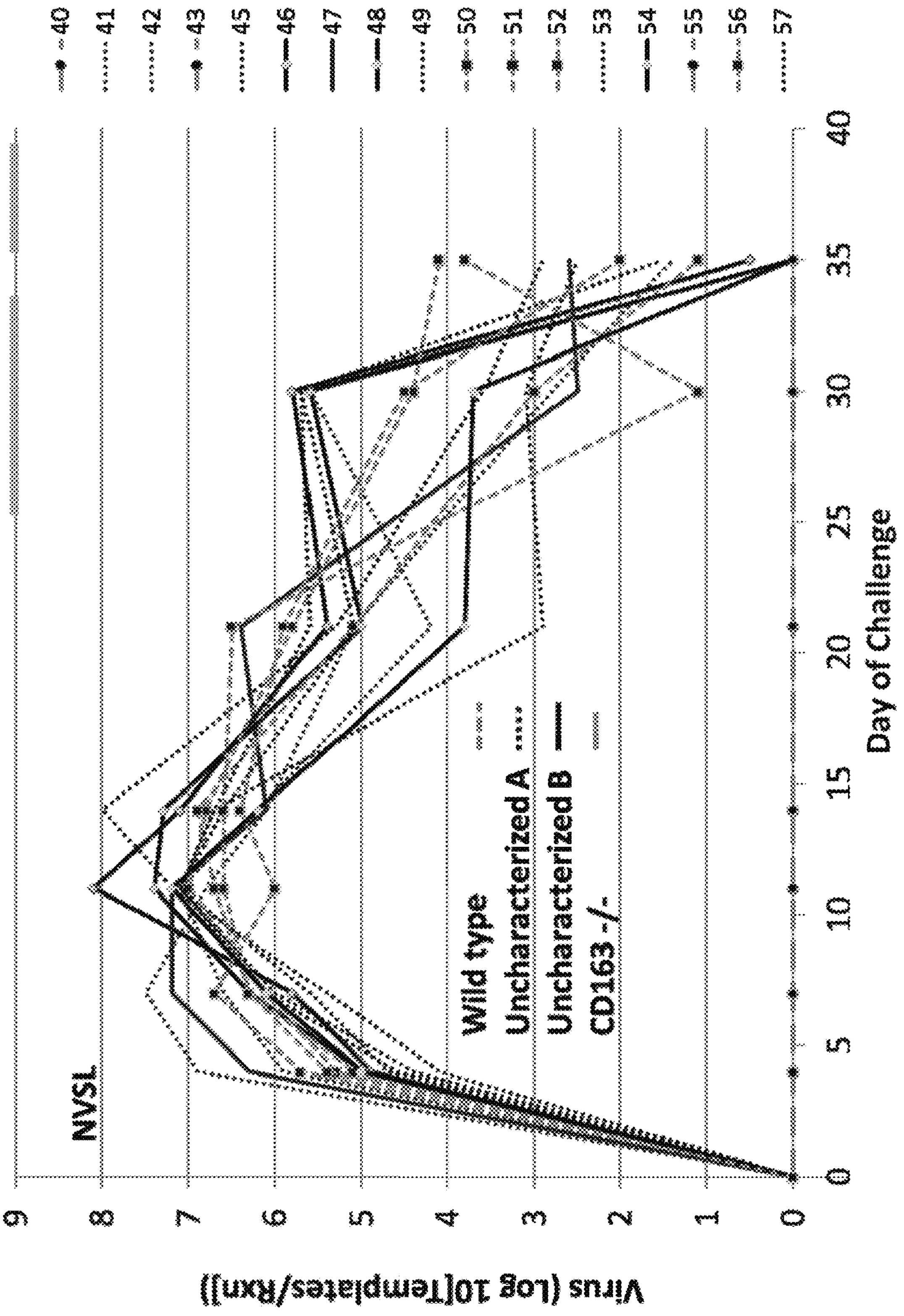
FIG. 11. Viremia in the various genotypes. Note that the CD163−/− piglet data lies along the X axis.
Figure 12:
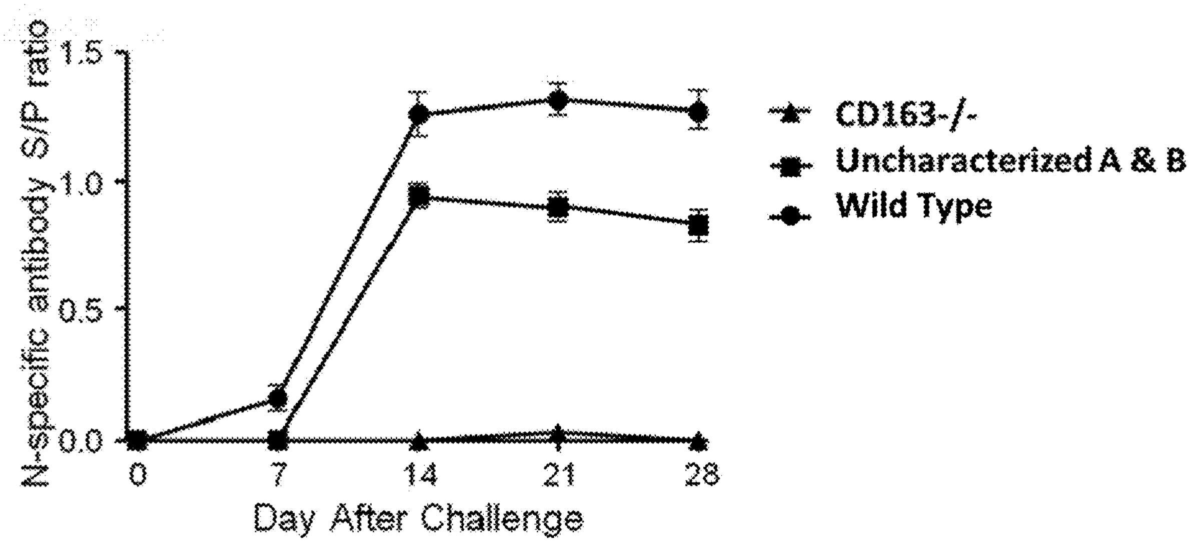
FIG. 12. Antibody production in null, wild type and uncharacterized allele pigs.

Peak clinical signs correlated with the levels of PRRSV in the blood. The measurement of viral nucleic acid was performed by isolation of total RNA from serum followed by amplification of PRRSV RNA by using a commercial reverse transcriptase real-time PRRSV PCR test (Tetracore, Rockville, MD). A standard curve was generated by preparing serial dilutions of a PRRSV RNA control, supplied in the RT-PCR kit and results were standardized as the number templates per 50 μl PCR reaction. The PRRSV isolate followed the course for PRRSV viremia in the wild type CD163+/+ pigs (FIG. 11). Viremia was apparent at day four, reached a peak at day 11 and declined until the end of the study. In contrast viral RNA was not detected in the CD163$^{-/-}$ pigs at any time point during the study period. Consistent with the viremia, antibody production by the null and uncharacterized allele pigs was detectable by 14 and increased to day 28. There was no antibody production in the null animals (FIG. 12). Together, these data show that wild type pigs support PRRSV replication with the production of clinical signs consistent with PRRS. In contrast, the knockout pigs produced no viremia and no clinical signs, even though pigs were inoculated and constantly exposed to infected pen mates.

Figure 13:
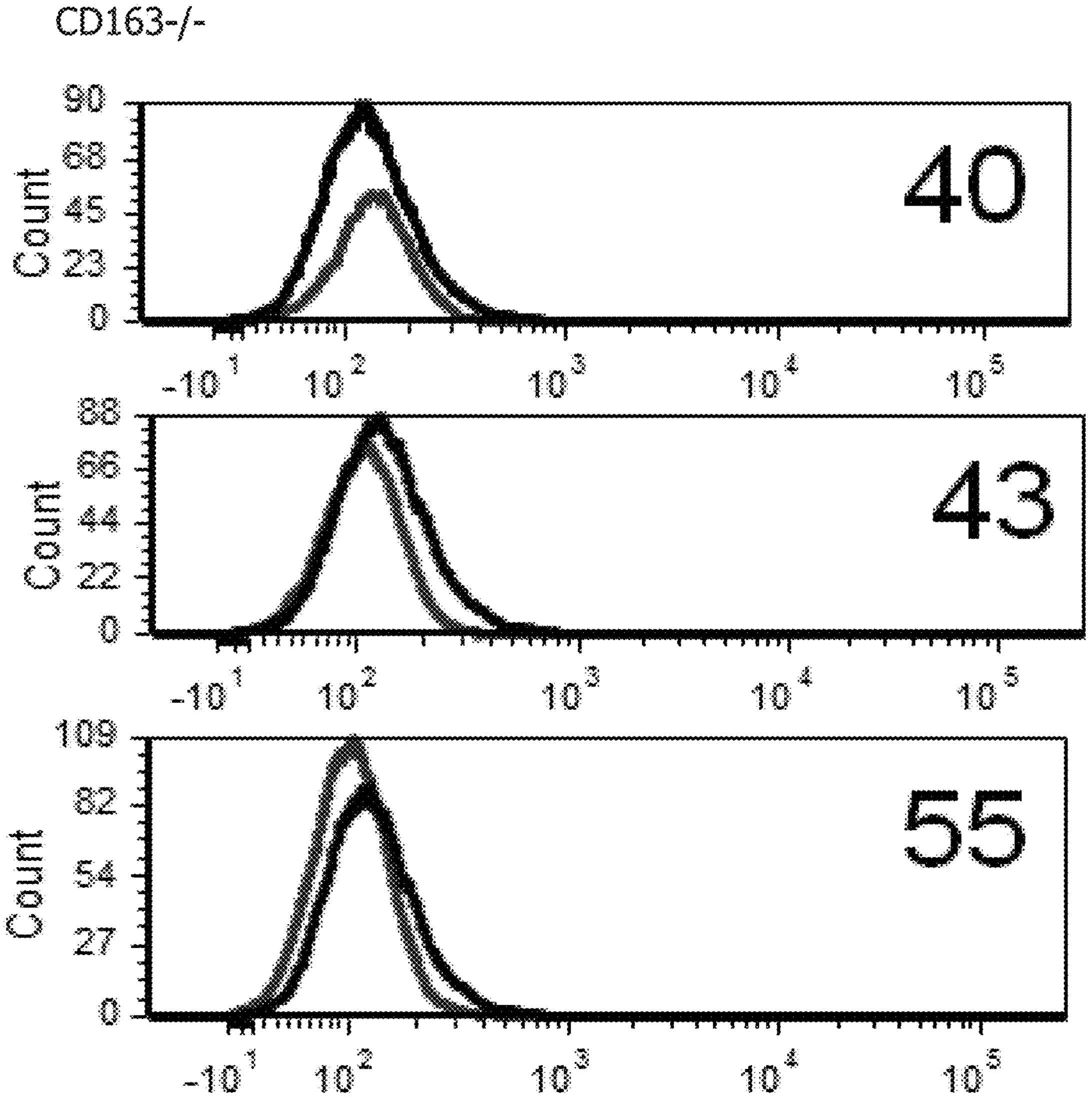
FIG. 13. Cell surface expression of CD163 in individual pigs. Lines appearing towards the right in the uncharacterized A, uncharacterized B, and CD163+/+ panels represent the CD163 antibody while the lines appearing towards the left-hand sides of these panels are the no antibody controls (background). Note that in the CD163−/− animals, the CD163 staining overlaps with the background control, and that the CD163 staining in the uncharacterized alleles is roughly half way between the WT level and the background (also note that this is a log scale, thus less than ~10%).
Figure 13:
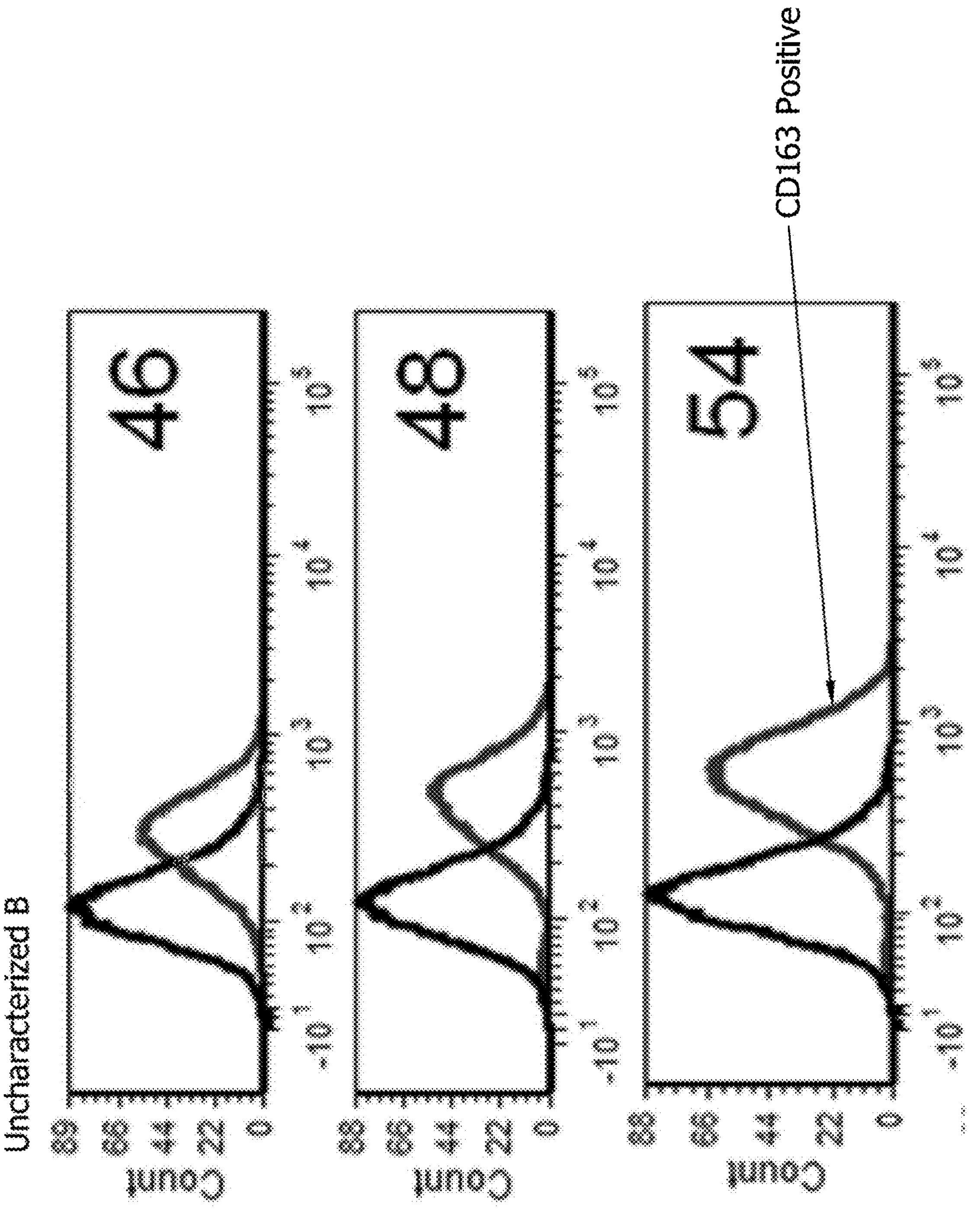
Figure 13:
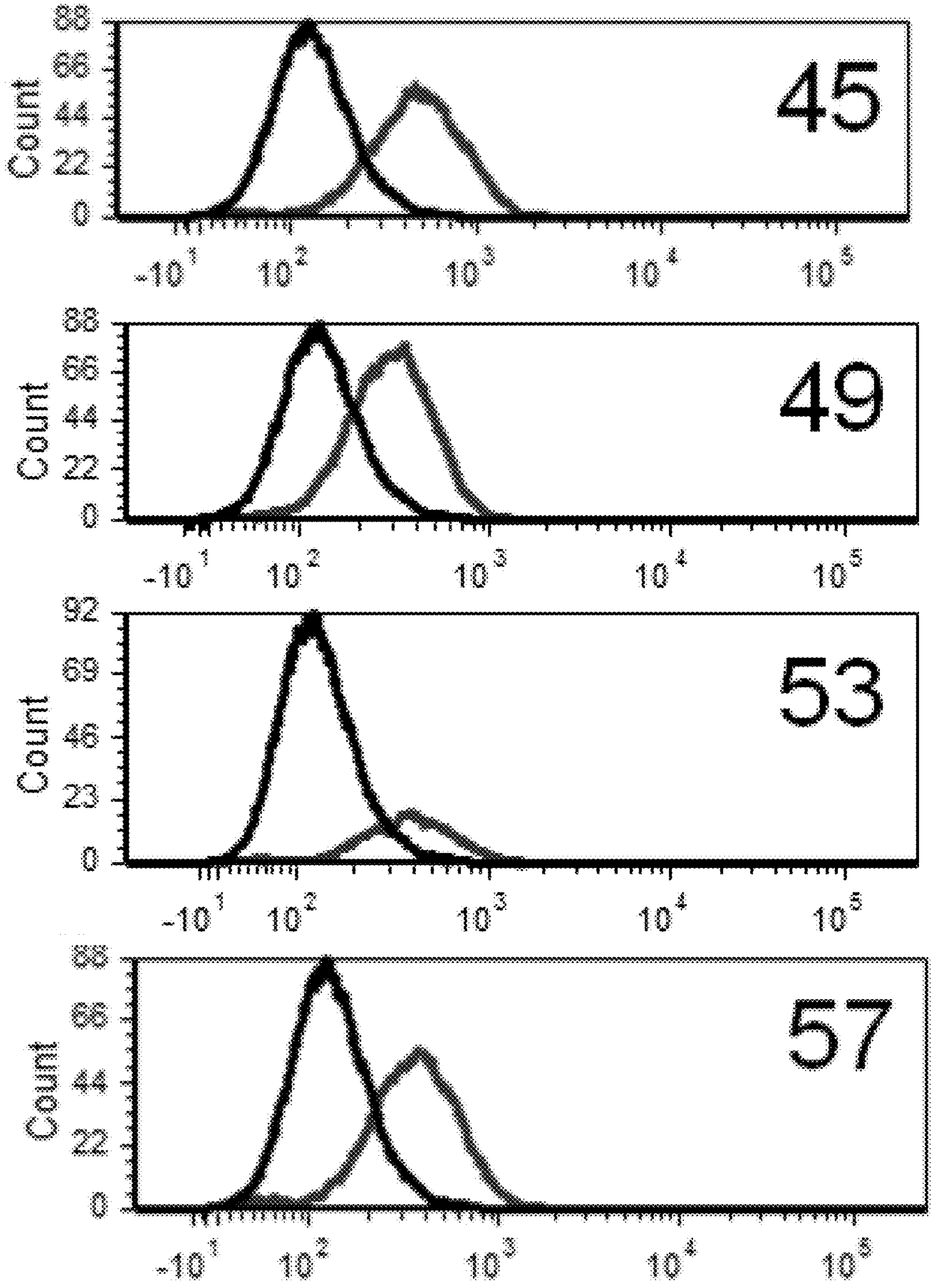
Figure 13:
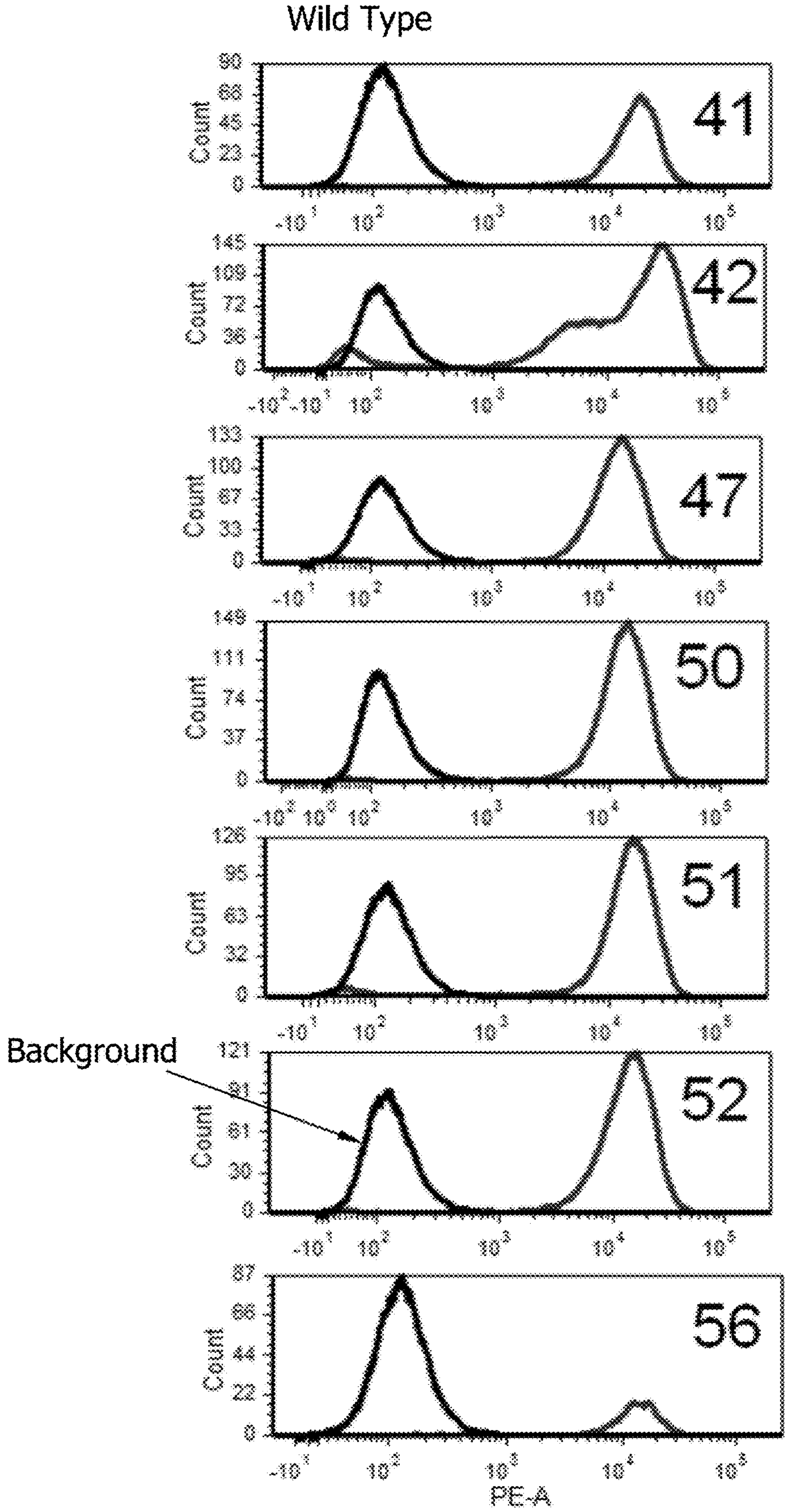
Figure 14:
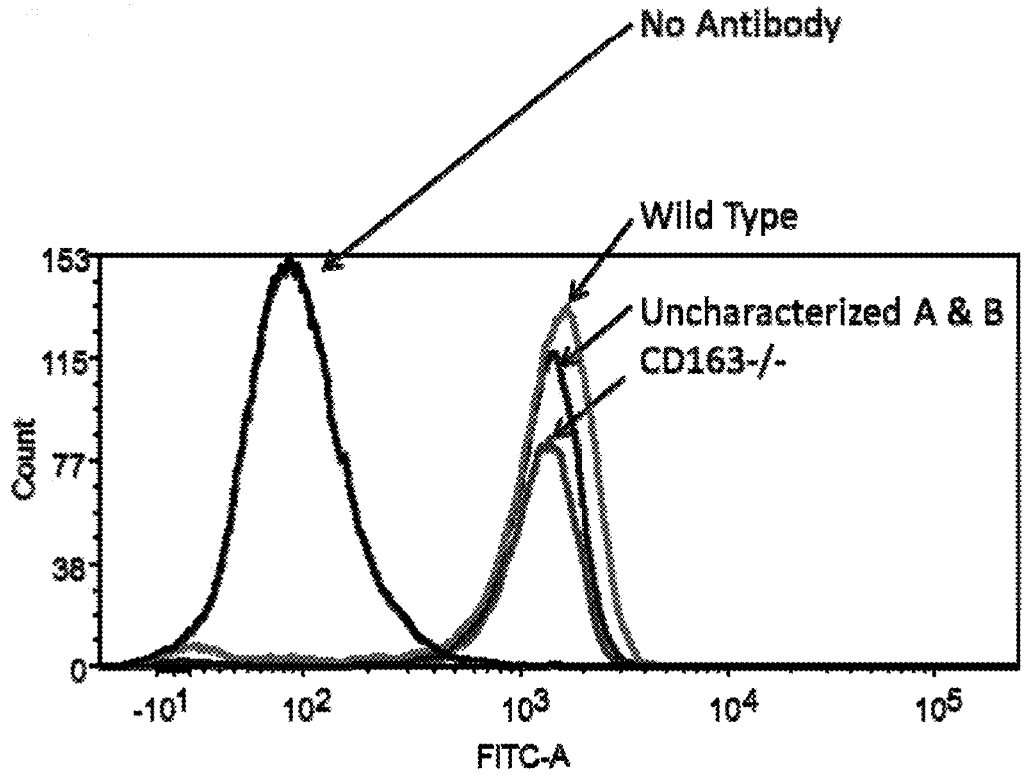
FIG. 14. Level of CD169 on alveolar macrophages from three representative pigs and the no antibody control (FITC labelled anti-CD169).

At the end of the study, porcine alveolar macrophages were removed by lung lavage and stained for surface expression of SIGLEC1 (CD169, clone 3B11/11) and CD163 (clone 2A10/11), as described previously (Prather et al., 2013). Relatively high levels of CD163 expression were detected on CD163+/+ wild type animals (FIG. 13). In contrast, CD163−/− pigs showed only background levels of anti-CD163 staining, thus confirming the knockout phenotype. Expression levels for another macrophage marker CD169 were similar for both wild type and knockout pigs (FIG. 14). Other macrophage surface markers, including MHC II and CD172 were the same for both genotypes (data not shown).

While the sample size was small the wild type pigs tended to gain less weight over the course of the experiment (average daily gain 0.81 kg±0.33, n=7) versus the pigs of the other three genotypes (uncharacterized A 1.32 kg±0.17, n=4; uncharacterized B 1.20 kg±0.16, n=3; null 1.21 kg±0.16, n=3).

Figure 15:
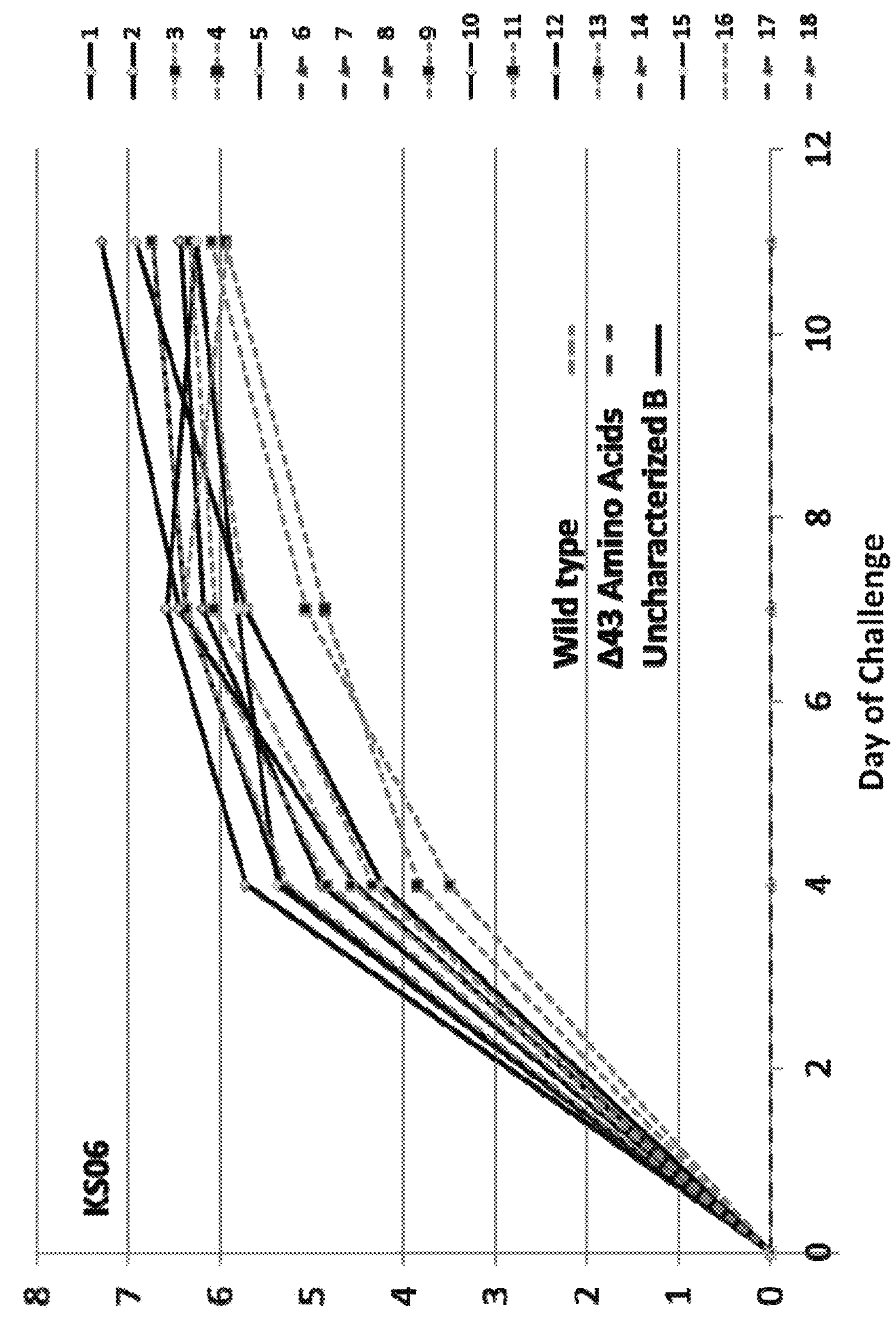
FIG. 15. Viremia in the various genotypes. Note that the 443 amino acid piglet data lies along the X-axis.

In a second trial 6 wild type, 6 Δ43 amino acids, and 6 pigs with an uncharacterized allele (B) were challenged as described above, except KS06-72109 was used to inoculate the piglets. Similar to the NVSL data the wild type and uncharacterized B piglets developed viremia. However, in the Δ43 amino acid pigs the KS06 did not result in viremia (FIG. 15; Table 7).

Implications and Conclusion

The most clinically relevant disease to the swine industry is PRRS. While vaccination programs have been successful to prevent or ameliorate most swine pathogens, the PRRSV has proven to be more of a challenge. Here CD163 is identified as an entry mediator for this viral strain. The founder boar was created by injection of CRISPR/Cas9 into zygotes (Whitworth et al., 2014) and thus there is no transgene. Additionally one of the alleles from the sow (also created by using CRISPR/Cas9) does not contain a transgene. Thus piglet #40 carries a 7 bp addition in one allele and a 11 bp deletion in the other allele, but no transgene. These virus-resistance alleles of CD163 represent minor genome edits considering that the swine genome is about 2.8 billion bp (Groenen et al., 2012). If similarly created animals were introduced into the food supply, significant economic losses could be prevented.

Example 3: Increased Resistance to Genotype 1 Porcine Reproductive and PRRS Viruses in Swine with CD163 SRCR Domain 5 Replaced with Human CD163-Like Homology SRCR Domain 8

CD163 is considered the principal receptor for porcine reproductive and respiratory syndrome virus (PRRSV). In this study, pigs were genetically edited (GE) to possess one of the following genotypes: complete knock out (KO) of CD163, deletions within CD163 scavenger receptor cysteine-rich (SRCR) domain 5, or replacement (domain swap) of SRCR domain 5 with a synthesized exon encoding a homolog of human CD163-like (hCD163L1) SRCR 8 domain Immunophenotyping of porcine alveolar macrophages (PAMs) showed that pigs with the KO or SRCR domain 5 deletions did not express CD163 and PAMs did not support PRRSV infection. PAMs from pigs that possessed the hCD163L1 domain 8 homolog expressed CD163 and supported the replication of Type 2, but not Type 1 genotype viruses. Infection of CD163-modified pigs with representative Type 1 and Type 2 viruses produced similar results. Even though Type 1 and Type 2 viruses are considered genetically and phenotypically similar at several levels, including the requirement of CD163 as a receptor, the results demonstrate a distinct difference between PRRSV genotypes in the recognition of the CD163 molecule.

Materials and Methods

Genomic Modifications of the Porcine CD163 Gene

Figure 17:
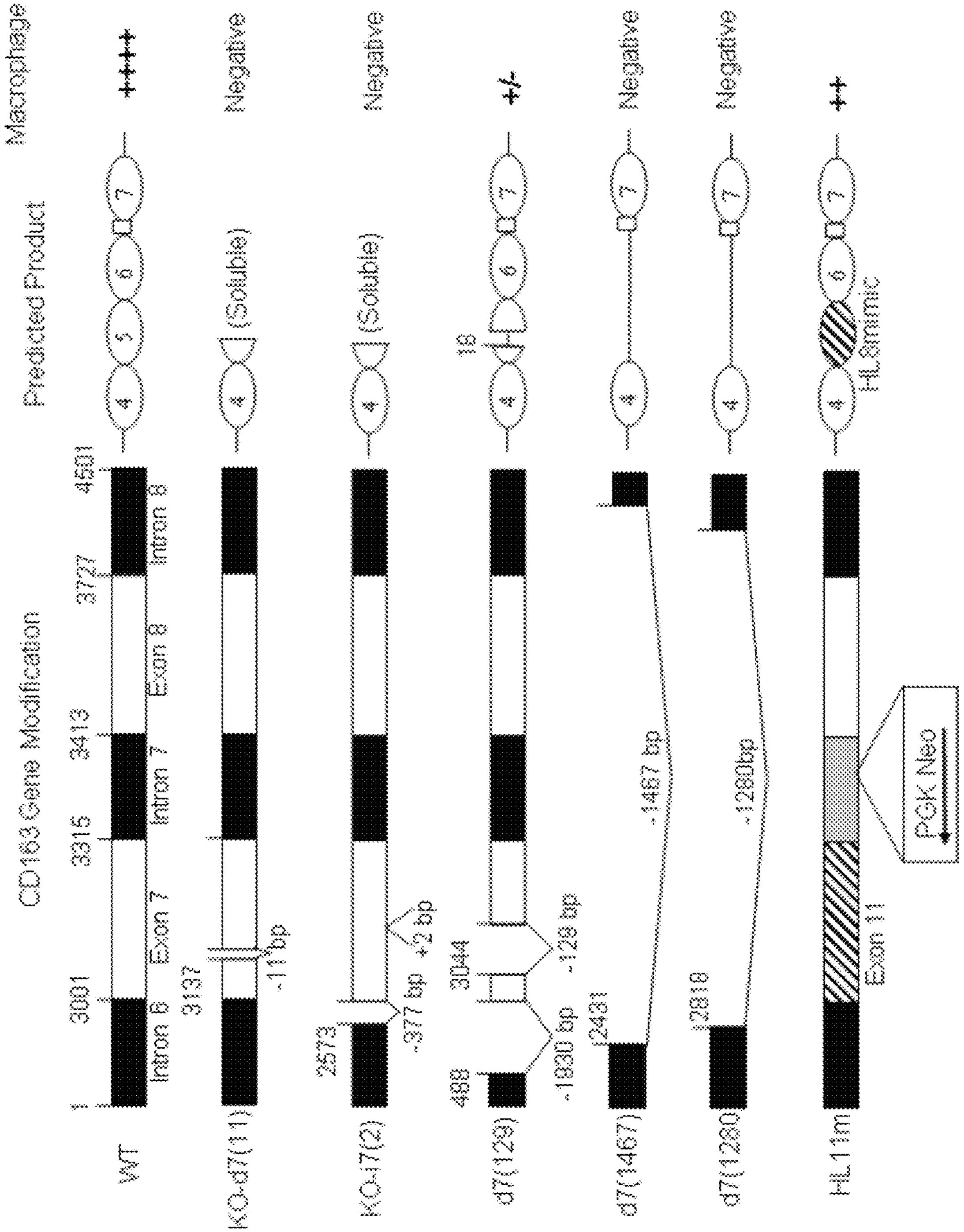
FIG. 17. Diagram of CD163 modifications illustrating several CD163 chromosomal modifications, the predicted protein product for each modification, and relative macrophage expression for each modification, as measured by the level of surface CD163 on porcine alveolar macrophages (PAMs). Black regions indicate introns and white regions indicate exons. The hatched region indicates the hCD163L1 exon 11 mimic, the homolog of porcine exon 7. The grey region indicates the synthesized intron with PGK Neo construct.

Experiments involving animals and viruses were performed in accordance with the Federation of Animal Science Societies Guide for the Care and Use of Agricultural Animals in Research and Teaching, the USDA Animal Welfare Act and Animal Welfare Regulations, and were approved by the Kansas State University and University of Missouri Institutional Animal Care and Use Committees and Institutional Biosafety Committees. Mutations in CD163 used in this study were created using the CRISPR/Cas9 technology as described hereinabove in the preceding examples. The mutations are diagrammed in FIG. 17. The diagrammed genomic region shown in FIG. 17 covers the sequence from intron 6 to intron 8 of the porcine CD163 gene. The introns and exons diagrammed in FIG. 17 are not drawn to scale. The predicted protein product is illustrated to the right of each genomic structure. Relative macrophage expression, as measured by the level of surface CD163 on PAMs, is shown on the far right of FIG. 17. The black regions indicate introns; the white regions indicate exons; the hatched region indicates hCD163L1 exon 11 mimic, the homolog of porcine exon 7; and the gray region indicates a synthesized intron with the PGK Neo construct as shown in FIG. 17.

The CD163 gene construct KO-d7(11) shown in FIG. 17 possesses an 11 base pair deletion in exon 7 from nucleotide 3,137 to nucleotide 3,147. The CD163 gene construct KO-i7 (2), possesses a 2 base pair insertion in exon 7 between nucleotides 3,149 and 3,150 as well as a 377 base pair deletion in the intron upstream of exon 7, from nucleotide 2,573 to nucleotide 2,949. These edits are predicted to cause frameshift mutations and premature stop codons, resulting in only partial translation of SRCR 5 and the KO phenotype. Three other mutations produced deletions in exon 7. The first, d7(129), has a 129 base pair deletion in exon 7 from nucleotide 3,044 to nucleotide 3,172. The d7(129) construct also has a deletion from nucleotide 488 to nucleotide 2,417 in exon 6, wherein the deleted sequence is replaced with a 12 bp insertion. The other two deletion constructs, d7(1467) and d7(1280), have complete deletions of exons 7 and 8 as illustrated in FIG. 17. d7(1467) has a 1467 base pair deletion from nucleotide 2,431 to nucleotide 3,897, and d7(1280) has a 1280 base pair deletion from nucleotide 2,818 to nucleotide 4,097. For these deletion constructs the other CD163 exons remained intact.

The last construct shown in FIG. 17, HL11 m, was produced using a targeting event that deleted exon 7 and replaced it with a synthesized exon that encoded a homolog of SRCR 8 of the human CD163-like 1 protein (hCD163L1 domain 8 is encoded by hCD163L1 exon 11). The SRCR 8 peptide sequence was created by making 33 nucleotide changes in the porcine exon 7 sequence. A neomycin cassette was included in the synthesized exon to enable screening for the modification. SEQ ID NO: 118 provides the nucleotide sequence for the HL11m construct in the region corresponding to the same region in reference sequence SEQ ID NO: 47.

Figure 18:
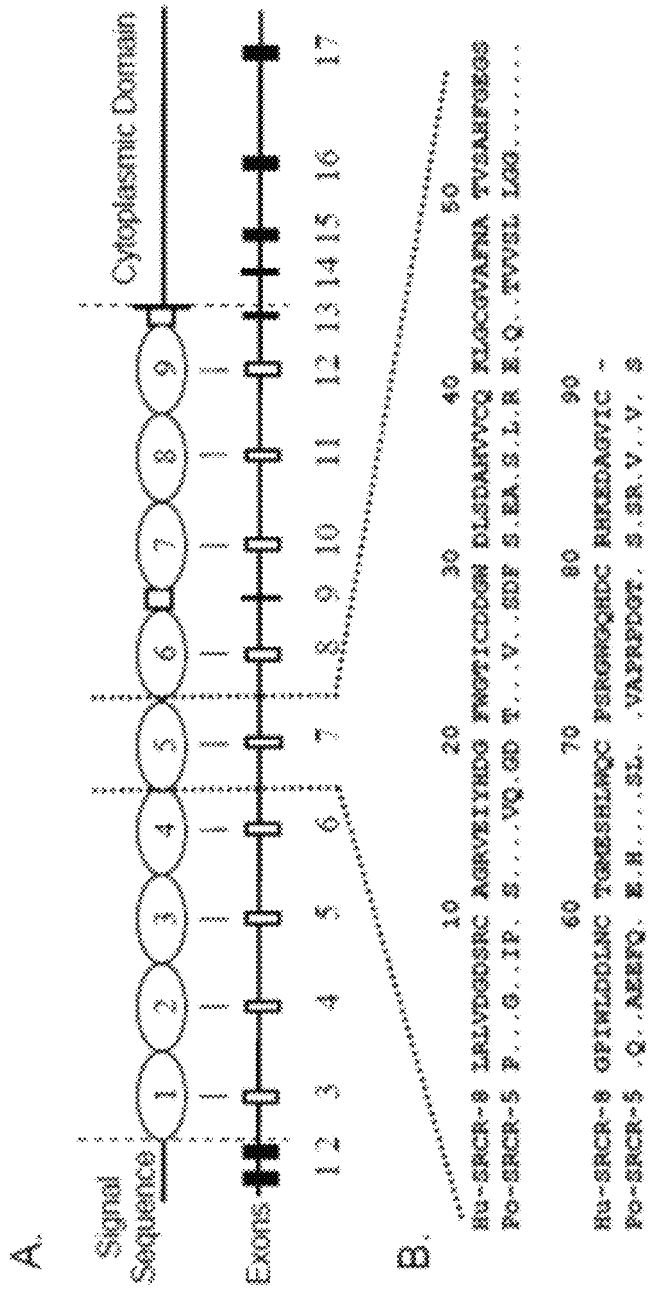
FIG. 18. Diagram of the porcine CD163 protein and gene sequence. A) CD163 protein SRCR (ovals) and PST (squares) domains along with the corresponding gene exons. B) Comparison of the porcine CD163 SRCR 5 (SEQ ID NO: 120) with the human CD163L1 SRCR 8 (SEQ ID NO: 121) homolog.

A diagram of the porcine CD163 protein and gene is provided FIG. 18. The CD163 protein SCRC (ovals) and PST (squares) domains along with the corresponding gene exons are shown in panel A of FIG. 18. A peptide sequence comparison for porcine CD163 SRCR 5 (SEQ ID NO: 120) and human CD163 SRCR 8 homolog (SEQ ID NO: 121) is shown in panel B of FIG. 18. The figure is based on GenBank accession numbers AJ311716 (pig CD163) and GQ397482 (hCD163-L1).

Viruses

The panel of viruses used in this example is listed in Table 14. Isolates were propagated and titrated on MARC-145 cells (Kim et al., 1993). For titration, each virus was serially diluted 1:10 in MEM supplemented with 7% FBS, Pen-Strep (80 Units/ml and 80 μg/ml, respectively), 3 μg/ml FUNGIZONE (amphotericin B), and 25 mM HEPES. Diluted samples were added in quadruplicate to confluent MARC-145 cells in a 96 well plate to a final volume of 200 μl per well and incubated for four days at 37° C. in 5% $CO_2$. The titration endpoint was identified as the last well with a cytopathic effect (CPE). The 50% tissue culture infectious dose ($TCID_{50}$/ml) was calculated using a method as previously described (Reed and Muench 1938).

TABLE 14

PRRSV isolates.

| Virus | Genotype | Year Isolated | GenBank No. |
|---|---|---|---|
| NVSL 97-7895 | 2 | 1997 | AY545985 |
| KS06-72109 | 2 | 2006 | KM252867 |
| P129 | 2 | 1995 | AF494042 |
| VR2332 | 2 | 1992 | AY150564 |
| CO90 | 2 | 2010 | KM035799 |
| AZ25 | 2 | 2010 | KM035800 |
| MLV-ResPRRS | 2 | NA* | AF066183 |
| KS62-06274 | 2 | 2006 | KM035798 |
| KS483 (SD23983) | 2 | 1992 | JX258843 |
| CO84 | 2 | 2010 | KM035802 |
| SD13-15 | 1 | 2013 | NA |
| Lelystad | 1 | 1991 | M96262 |
| 03-1059 | 1 | 2003 | NA |
| 03-1060 | 1 | 2003 | NA |

TABLE 14-continued

| PRRSV isolates. | | | |
|---|---|---|---|
| Virus | Genotype | Year Isolated | GenBank No. |
| SD01-08 | 1 | 2001 | DQ489311 |
| 4353PZ | 1 | 2003 | NA |

*NA, Not available

Infection of Alveolar Macrophages

The preparation and infection of macrophages were performed as previously described (Gaudreault, et al., 2009 and Patton, et al., 2008). Lungs were removed from euthanized pigs and lavaged by pouring 100 ml of cold phosphate buffered saline (PBS) into the trachea. The tracheas were clamped and the lungs gently massaged. The alveolar contents were poured into 50 ml centrifuge tubes and stored on ice. Porcine alveolar macrophages (PAMs) were sedimented by centrifugation at 1200×g for 10 minutes at 4° C. The pellets were re-suspended and washed once in cold sterile PBS. The cell pellets were re-suspended in freezing medium containing 45% RPMI 1640, 45% fetal bovine serum (FBS), and 10% dimethylsulfoxide (DMSO) and stored in liquid nitrogen until use. Frozen cells were thawed on ice, counted and adjusted to $5\times10^5$ cells/ml in media (RPMI 1640 supplemented with 10% FBS, PenStrep, and FUNGIZONE; RPMI-FBS). Approximately $10^3$ PAMs per well were added to 96 well plates and incubated overnight at 37° C. in 5% $CO_2$. The cells were gently washed to remove non-adherent cells. Serial 1:10 dilutions of virus were added to triplicate wells. After incubation overnight, the cells were washed with PBS and fixed for 10 minutes with 80% acetone. After drying, wells were stained with PRRSV N-protein specific SDOW-17 mAb (Rural Technologies Inc.) diluted 1:1000 in PBS with 1% fish gelatin (PBS-FG; Sigma Aldrich). After a 30 minute incubation at 37° C., the cells were washed with PBS and stained with ALEXAFLUOR 488-labeled anti-mouse IgG (Thermofisher Scientific) diluted 1:200 in PBS-FG. Plates were incubated for 30 minutes in the dark at 37° C., washed with PBS, and viewed under a fluorescence microscope. The 50% tissue culture infectious dose ($TCID_{50}$)/ml was calculated according to a method as previously described (Reed and Muench 1938).

Measurement of CD169 and CD163 Surface Expression on PAMs

Staining for surface expression of CD169 and CD163 was performed as described previously (Prather et al., 2013). Approximately $1\times10^6$ PAMs were placed in 12 mm×75 mm polystyrene flow cytometry (FACS) tubes and incubated for 15 minutes at room temp in 1 ml of PBS with 10% normal mouse serum to block Fc receptors. Cells were pelleted by centrifugation and re-suspended in 5 μl of FITC-conjugated mouse anti-porcine CD169 mAb (clone 3B11/11; AbD Serotec) and 5 μl of PE-conjugated mouse anti-porcine CD163 mAb (Clone: 2A10/11, AbD Serotec). After 30 minutes incubation the cells were washed twice with PBS containing 1% bovine serum albumin (BSA Fraction V; Hyclone) and immediately analyzed on a BD LSR Fortessa flow cytometer (BD Biosciences) with FCS Express 5 software (De Novo Software). A minimum of 10,000 cells were analyzed for each sample.

Measurement of PRRS Viremia

RNA was isolated from 50 μl of serum using Ambion's MagMAX 96 Viral Isolation Kit (Applied Biosystems) according to the manufacturer's instructions. PRRSV RNA was quantified using EZ-PRRSV MPX 4.0 Real Time RT-PCR Target-Specific Reagents (Tetracore) performed according to the manufacturer's instructions. Each plate contained Tetracore Quantification Standards and Control Sets designed for use with the RT-PCR reagents. PCR was carried out on a CFX96 Touch Real-Time PCR Detection System (Bio-Rad) in a 96-well format using the recommended cycling parameters. The PCR assay results were reported as login PRRSV RNA copy number per 50 μl reaction volume, which approximates the number of copies per ml of serum. The area under the curve (AUC) for viremia over time was calculated using GraphPad Prism version 6.00 for Windows.

Measurement of PRRSV Antibody

The microsphere fluorescent immunoassay (FMIA) for the detection of antibodies against the PRRSV nucleocapsid (N) protein was performed as described previously (Stephenson et al., 2015). Recombinant PRRSV N protein was coupled to carboxylated Luminex MAGPLEX polystyrene microsphere beads according to the manufacturer's directions. For FMIA, approximately 2500 antigen-coated beads, suspended in 50 μL PBS with 10% goat serum (PBS-GS), were placed in each well of a 96-well polystyrene round bottom plate. Sera were diluted 1:400 in PBS-GS and 50 μl added to each well. The plate was wrapped in foil and incubated for 30 minutes at room temperature with gentle shaking. The plate was placed on a magnet and beads were washed three times with 190 μl of PBS-GS. For the detection of IgG, 50 μl of biotin-SP-conjugated affinity purified goat anti-swine secondary antibody (IgG, Jackson ImmunoResearch) was diluted to 2 μg/ml in PBS-GS and 100 μl added to each well. The plate was incubated at room temperature for 30 minutes and washed three times followed by the addition of 50 μl of streptavidin-conjugated phycoerythrin (2 μg/ml in PBS-GS; SAPE). After 30 minutes, the microspheres were washed, resuspended in 100 μl of PBS-GS, and analyzed using a MAGPIX instrument (LUMINEX) and LUMINEX xPONENT 4.2 software. The mean fluorescence intensity (MFI) was calculated on a minimum of 100 microsphere beads.

Measurement of Haptoglobin (HP)

The amount of Hp in serum was measured using a porcine-specific Hp ELISA kit (Genway Biotech Inc.) and steps performed according to the manufacturer's instructions. Serum samples were diluted 1:10,000 in 1× diluent solution and pipetted in duplicate on a pre-coated anti-pig Hp 96 well ELISA plate, incubated at room temperature for 15 minutes, then washed three times. Anti-Hp-horseradish peroxidase (HRP) conjugate was added to each well and incubated in the dark at room temperature for 15 minutes. The plate was washed and 100 μl chromogen-substrate solution added to each well. After incubating in the dark for 10 minutes, 100 μl of stop solution was added to each well. The plate was read at 450 nm on a Fluostar Omega filter-based microplate reader (BMG Labtech).

Results

Phenotypic Properties of PAMs from CD163-Modified Pigs

The forward and side scatter properties of cells in the lung lavage material were used to gate on the mononuclear subpopulation of cells. Representative CD169 and CD163 staining results for the different chromosomal modifications shown in FIG. 17 are presented in FIG. 19. In the representative example presented in panel A of FIG. 19, greater than 91% of PAMs from the WT pigs were positive for both CD169 and CD163. Results for 12 WT pigs used in this study showed a mean of 85+/−8% of double-positive cells.

Figure 19:
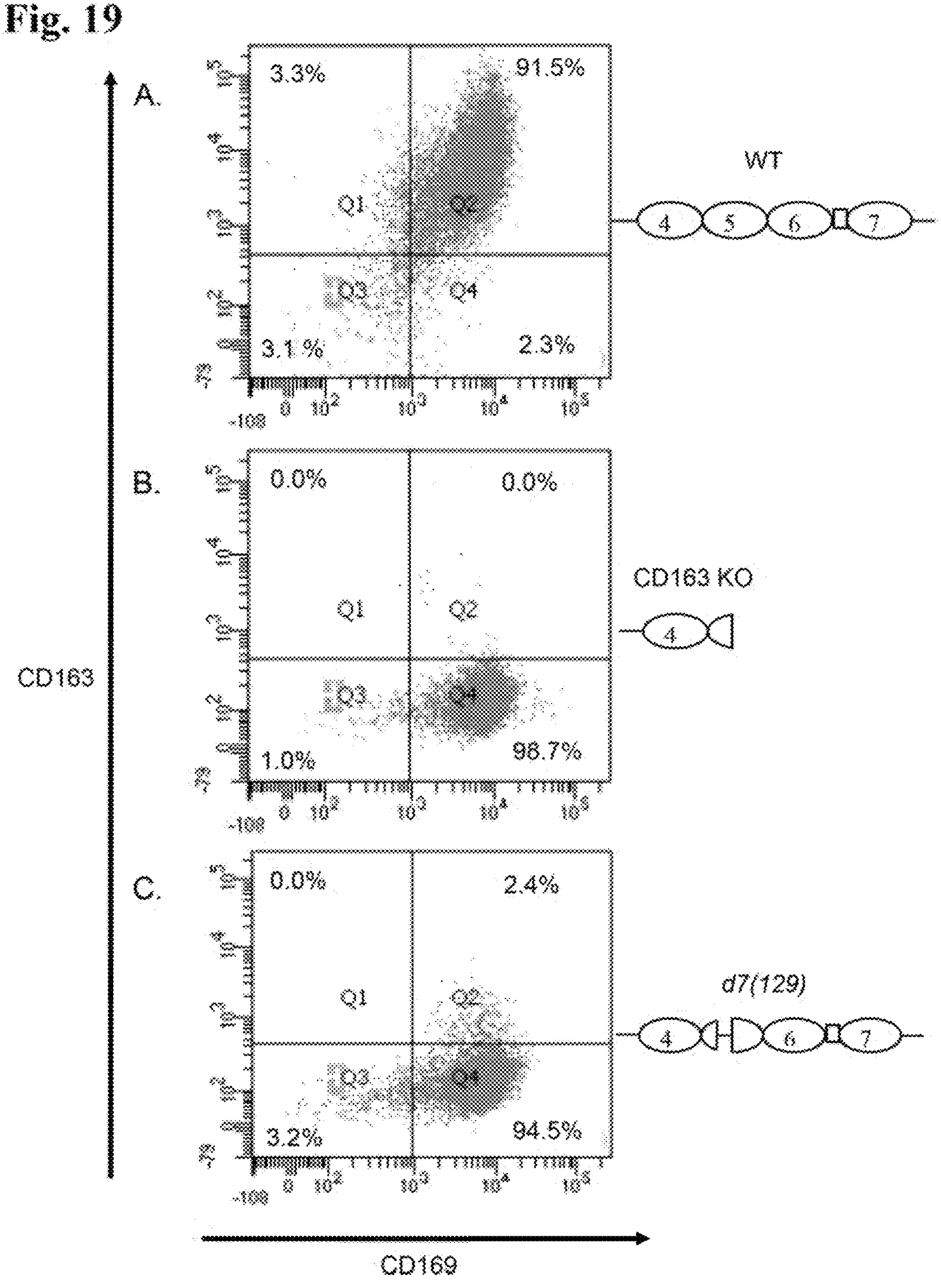
FIG. 19. Representative results for surface expression of CD163 and CD169 on PAMs from wild-type and CD163-modified pigs. Panels A-E show results for the CD163 modifications as illustrated in FIG. 17. Pooled data for d7(1467) and d7(1280) are shown in panel D.
Figure 19:
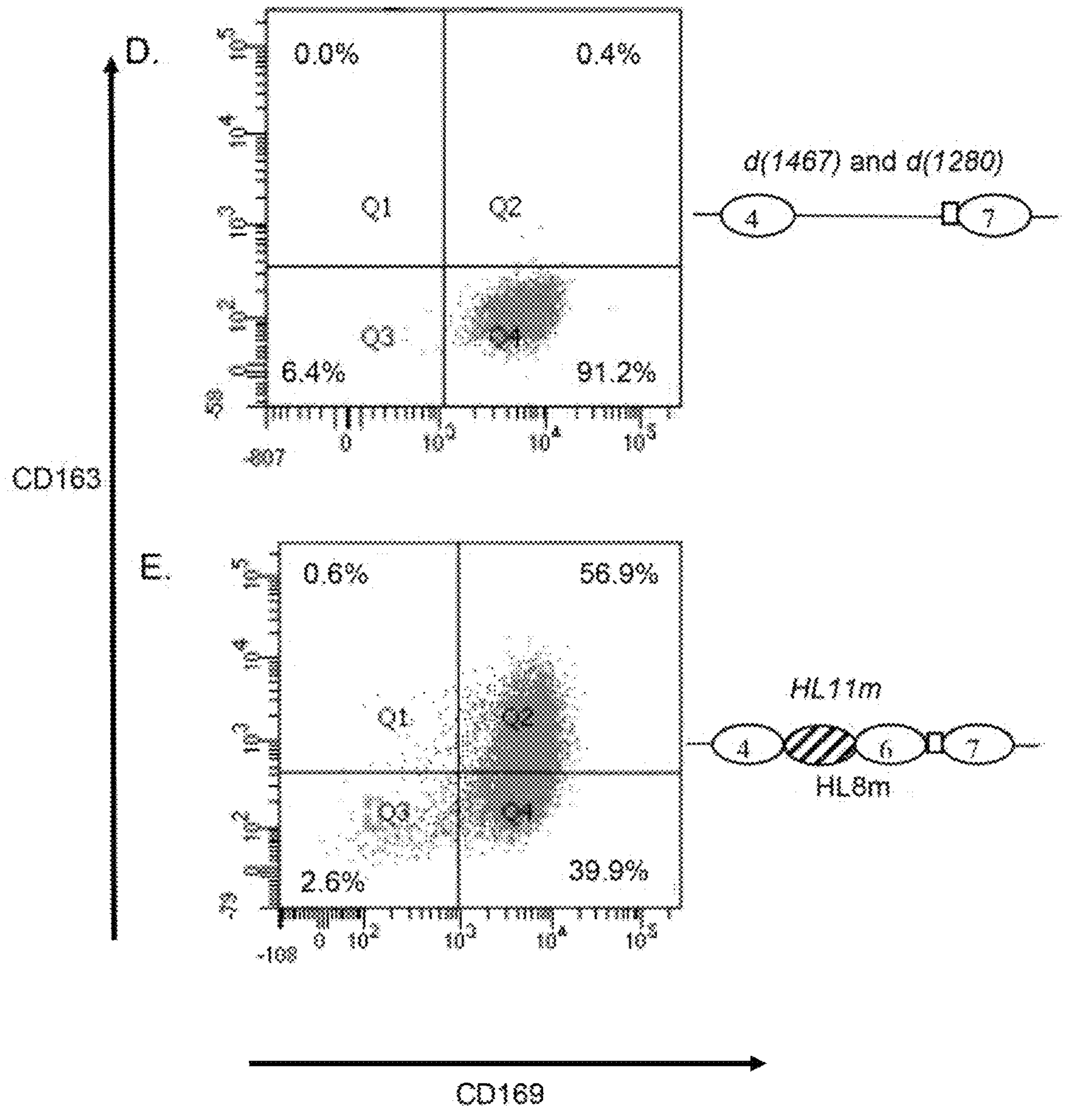

As shown in panel B of FIG. 19, PAMs from the CD163 KO pigs showed no evidence of CD163, but retained normal surface levels of CD169. Although it was predicted that the CD163 polypeptides derived from the d7(1467) and d7(1280) deletion genotypes should produce modified CD163 polypeptides anchored to the PAM surface, immunostaining results showed no surface expression of CD163 (see FIG. 19, panel D). Since MAb 2A10 recognizes an epitope located in the first three SRCR domains, the absence of detection was not the result of the deletion of an immunoreactive epitope. The d7(129) genotype was predicted to possess a 43 amino acid deletion in SRCR 5 (see FIG. 17). In the example presented in panel C of FIG. 19, only 2.4% of cells fell in the double-positive quadrant. The analysis of PAMs from nine d7(129) pigs used in this study showed percentages of double-positive cells ranging from 0% to 3.6% (mean=0.9%). The surface expression of CD169 remained similar to WT PAMs. For the purpose of this study, pigs possessing the KO, d7(1467), d7(1280), and d7(129) genotypes were all categorized as possessing a CD163-null phenotype.

The CD163 modification containing the hCD163L1 domain 8 peptide sequence HL11m, showed dual expression of $CD163^+$ and $CD169^+$ on PAMs (panel E of FIG. 19). However, in all of the HL11m pigs analyzed in this study, the surface expression of CD163 was markedly reduced compared to the WT PAMs. The levels of CD163 fell on a continuum of expression, ranging from no detectable CD163 to pigs possessing moderate levels of CD163. In the example shown in panel E of FIG. 19, approximately 60% of cells were in the double-positive quadrant while 40% of cells stained for only CD169. The analysis of PAMs from a total 24 HL11m pigs showed 38+/−12% of PAM cells were positive only for CD169 and 54+/−14% were double-positive ($CD169^+CD163^+$).

Circulating Haptoglobin Levels in WT and CD163-Modified Pigs

As a scavenging molecule, CD163 is responsible for removing HbHp complexes from the blood (Fabriek, et al., 2005; Kristiansen et al., 2001; and Madsen et al., 2004). The level of Hp in serum provides a convenient method for determining the overall functional properties of CD163-expressing macrophages. Hp levels in sera from WT, HL11m and CD163-null pigs were measured at three to four weeks of age, just prior to infection with PRRSV. The results, presented in FIG. 20, showed that sera from WT pigs had the lowest amounts of Hb (mean A450=23+/−0.18, n=10). The mean and standard deviation for each group were WT, 0.23+/−0.18, n=10; HL11m, 1.63+/−0.8, n=11; and 2.06+/−0.57, n=9, for the null group. The null group was composed of genotypes that did not express CD163 (CD163 null phenotype pigs). Hp measurements were made on a single ELISA plate. Groups with the same letter were not significantly different (p>0.05, Kruskal-Wallis one-way ANOVA with Dunnett's post-test). The mean A450 value was for WT pigs was significantly different from that of the HL11m and CD163-null pigs (p<0.05). Although the mean A450 value was lower for the HL11m group compared to the CD163-null group (A450=1.6+/−0.8 versus 2.1+/−0.6), the difference was not statistically significant. Since the interaction between HbHp and CD163 occurs through SRCR 3 (Madsen et al., 2004), increased circulating Hp in the HL11m pigs compared to WT pigs was likely not a consequence of a reduced affinity of CD163 for Hb/Hp, but the result of reduced numbers of $CD163^+$ macrophages along with reduced CD163 expression on the remaining macrophages (see panel E of FIG. 19).

Infection of PAMs with Type 1 and Type 2 Viruses

The permissiveness of the CD163-modified pigs for PRRSV was initially evaluated by infecting PAM cells in vitro with a panel of six Type 1 and nine Type 2 PRRSV isolates (see Table 14 for the list of viruses). The viruses in the panel represent different genotypes, as well as differences in nucleotide and peptide sequences, pathogenesis, and years of isolation. The data presented in Table 15 show the results form experiments using PAMs from three pigs for each CD163 genotype group. The viruses listed correspond to the PRRSV isolates listed in Table 14. The results are shown as mean+/−standard deviation of the percent of PAMs infected. The CD163-null PAMs were from pigs expressing the d7(129) allele (see FIGS. 17 and 19 for CD163 gene constructs and CD163 expression on PAMs, respectively).

TABLE 15

Infection of PAMs from wild-type and GE pigs with different PRRSV isolates

| | Genotype/Phenotype (% Infection) | | |
|---|---|---|---|
| Type 1 | WT (%) | HL11m | Null |
| 13-15 | 56 +/− 9 | 0 | 0 |
| Lelystad | 62 +/− 15 | 0 | 0 |
| 03-1059 | 50 +/− 18 | 0 | 0 |
| 03-1060 | 61 +/− 12 | 0 | 0 |
| 01-08 | 64 +/− 20 | 0 | 0 |
| 4353-PZ | 62 +/− 15 | 0 | 0 |
| Type 2 | WT (%) | HL11m | Null |
| NVSL 97 | 59 +/− 15 | 8 +/− 08 | 0 |
| KS-06 | 56 +/− 20 | 12 +/− 09 | 0 |
| P129 | 64 +/− 11 | 8 +/− 06 | 0 |
| VR2332 | 54 +/− 05 | 6 +/− 03 | 0 |
| CO 10-90 | 43 +/− 18 | 8 +/− 08 | 0 |
| CO 10-84 | 51 +/− 22 | 7 +/− 04 | 0 |
| MLV-ResP | 55 +/− 12 | 3 +/− 01 | 0 |
| KS62 | 49 +/− 03 | 10 +/− 11 | 0 |
| KS483 | 55 +/− 23 | 6 +/− 03 | 0 |

As expected, the WT PAMs were infected by all viruses. In contrast, the CD163-null phenotype pigs were negative for infection by all viruses. A marked difference was observed in the response of PAMs from the HL11m pigs. None of the Type 1 viruses were able to infect the HL11m PAMs; whereas, all viruses in the Type 2 panel infected the HL11m PAMs, albeit at much lower percentages compared to the WT PAMs.

Permissiveness was also evaluated by comparing virus titration endpoints between WT and HL11m PAMs for the same Type 2 viruses. Results are shown for two WT and two HL11m pigs (FIG. 21). The $\log_{10}TCID_{50}$ values were calculated based on the infection of macrophage cultures with the same virus sample. Infection results represent two different pigs from each genotype. Viruses used for infection are listed in Table 14. The $\log_{10}TCID_{50}$ values for PAMs from the HL11m pigs were 1-3 logs lower compared to WT PAMs infected with the same virus. The only exception was infection with a modified-live virus vaccine strain. When taken altogether, the results suggest that PAMs from HL11m pigs possess a reduced susceptibility or permissiveness to infection with Type 2 viruses.

Infection of CD163-Modified Pigs with Type 1 and Type 2 Viruses

WT (circles), HL11m (squares), and CD163-null (triangles) pigs were infected with representative Type 1 (SD13-15) (FIG. 22, panel A, left graph) and Type 2 (NVSL 97-7895) (FIG. 22, panel A, right graph) viruses. The null phenotype pigs were derived from the KO and d(1567) alleles (see FIG. 17). Pigs from the three genotypes inoculated with the same virus were co-mingled in one pen, which allowed for the continuous exposure of CD163-modified pigs to virus shed from WT pen mates. The number of pigs infected with representative Type 1 virus were: WT (n=4), HL11m (n=5), and Null (n=3); and Type 2 virus: WT (n=4), HL11m (n=4), and Null (n=3). As shown in FIG. 22, the CD163-null pigs infected with either the Type 1 or Type 2 virus were negative for viremia at all time points and did not seroconvert. As expected, the WT pigs were productively infected possessing mean viremia levels approaching $10^6$ templates per 50 μl PCR reaction at 7 days after infection for both viruses. By 14 days, all WT pigs had seroconverted (see FIG. 22, panel B). Consistent with the PAM infection results (Table 15), the five HL11m pigs infected with the Type 1 virus showed no evidence of viremia or PRRSV antibody. All HL11m pigs infected with the Type 2 isolate, NVSL, supported infection and seroconverted (FIG. 22, panel B). The presence of a reduced permissive of the HL11m pigs was unclear. Mean viremia for three of the four HL11m pigs were similar to the WT pigs. However, for one HL11m pig, #101 (open squares in FIG. 22, panel A right graph), viremia was greatly reduced compared to the other pigs in HL11 m genotype group. An explanation for the 3 to 4 log reduction in viremia for Pig #101 was not clear, but suggested that some HL11m pigs may be less permissive for PRRSV, an observation supporting the in vitro PAM infection results (Table 15). Since all pigs were inoculated with the same amount of virus and remained co-mingled with the WT pigs, the lower viremia in Pig #101 was not the result of receiving a lower amount of virus or less exposure to virus. Flow cytometry of macrophages showed that CD163 expression for Pig #101 was comparable to the other HL11m pigs (data not shown). There was no difference in the sequence in the exon 11 mimic sequence.

Additional virus infection trials were conducted using two viruses, NVSL 97-7895 and KS06-72109. Results are shown in FIG. 23. Pigs were followed for 35 days after infection and data reported as the area under the curve (AUC) for viremia measurements taken at 3, 7, 11, 14, 21, 28 and 35 days after infection. As shown in FIG. 23, for NVSL, the mean AUC value for the seven WT pigs infected with NVSL was 168+/−8 versus 165+/−15 for the seven HL11m pigs. For KS06, the mean AUC values for the six WT and six HL11m pigs were 156+/−9 and 163+/−13, respectively. For both viruses, there was no statistically significant difference between the WT and HL11m pigs (p>0.05). When taken altogether, the results showed that the HL11 m pigs failed to support infection with Type 1 PRRSV, but retained permissiveness for infection with Type 2 viruses. Even though there was a reduction in the PRRSV permissiveness of PAMs from HL11m pigs infected in vitro with the Type 2 isolates, this difference did not translate to the pig. For the results shown in FIG. 23, virus load was determined by calculating the area under the curve (AUC) for each pig over a 35 day infection period. The AUC calculation was performed using login PCR viremia measurements taken at 0, 4, 7, 10, 14, 21, 28 and 35 days after infection. The horizontal lines show mean and standard deviation. Key: WT=wild-type pigs, HL11=HL11m genotype pigs; Null=CD163-null genotype.

DISCUSSION

CD163 is a macrophage surface protein important for scavenging excess Hb from the blood and modulating inflammation in response to tissue damage. It also functions as a virus receptor. CD163 participates in both pro- and anti-inflammatory responses (Van Gorp et al., 2010). CD163-positive macrophages are placed within the alternatively activated M2 group of macrophages, which are generally described as highly phagocytic and anti-inflammatory. M2 macrophages participate in the cleanup and repair after mechanical tissue damage or infection (Stein et al., 1992). In an anti-inflammatory capacity, CD163 expression is upregulated by anti-inflammatory proteins, such as IL-10 (Sulahian, et al., 2002). During inflammation, CD163 decreases inflammation by reducing oxidative through the removal of circulating heme from the blood. Heme degradation products, such as biliverdin, bilirubin, and carbon monoxide are potent anti-inflammatory molecules (Soares and Bach, 2009 and Jeney et al., 2002). In a pro-inflammatory capacity, the crosslinking of CD163 on the macrophage surface by anti-CD163 antibody or bacteria results in the localized release of pro-inflammatory cytokines, including IL-6, GM-CSF, TNFα and IL-1β (Van den Heuvel et al., 1999 and Fabriek et al., 2009).

GE pigs that lack CD163 fail to support the replication of a Type 2 PRRSV isolate (Whitworth et al., 2016). In this study, in vitro infection trials demonstrate the resistance of CD163 null phenotype macrophages to an extensive panel of Type 1 and Type 2 PRRSV isolates, further extending resistance to potentially include all PRRSV isolates (Table 15). Resistance of the CD163-null phenotype macrophages to Type 1 and Type 2 viruses was confirmed in vivo (FIG. 22 and FIG. 23). Based on these results, the contribution of other PRRSV receptors previously described in the literature (Zhang and Yoo, 2015) can be ruled out. For example, Shanmukhappa et al. (2007) showed that non-permissive BHK cells transfected with a CD151 plasmid acquired the ability to support PRRSV replication, and incubation with a polyclonal anti-CD151 antibody was shown to significantly reduce the infection of MARC-145 cells. In addition, a simian cell line, SJPL, originally developed for use in propagating swine influenza viruses, was previously shown to support PRRSV replication (Provost, et al., 2012). Important properties of the SJPL cell line included the presence of CD151 and the absence of sialoadhesin and CD163. When taken together, these data provided convincing evidence that the presence of CD151 alone is sufficient to support PRRSV replication. The results from this study showing the absence of PRRSV infection in macrophages and pigs possessing a CD163 null phenotype indicates that CD151 as an alternative receptor for PRRSV is not biologically relevant.

The viral proteins GP2a and GP4, which form part of the GP2a, GP3, GP4 heterotrimer complex on the PRRSV surface, can be co-precipitated with CD163 in pull-down assays from cells transfected with GP2 and GP4 plasmids (Das, et al., 2009). Presumably, GP2 and GP4 form an interaction with one or more of the CD163 SRCR domains. In vitro infectivity assays incorporating a porcine CD163 cDNA backbone containing a domain swap between porcine SRCR 5 and the homolog from hCD163-L1 SRCR 8 further localized the region utilized by Type 1 viruses to SRCR 5 (Van Gorp, et al., 2010). It is interesting to speculate that the stable interaction between GP2/GP4 and CD163 occurs through SRCR 5. Additional viral glycoproteins, such as GP3 and GP5, may further stabilize the virus-receptor complex or may function as co-receptor molecules. The requirement for SRCR 5 was investigated in this study by infecting macrophages and pigs possessing the HL11m allele, which recreated the CD163L1 SRCR 8 domain swap by making 33 bp substitutions in porcine exon 7. The HL11 m allele also included a neomycin cassette for selection of cells positive for the genetic alteration (FIG. 17). The HL11m pigs expressed CD163 on PAMs, albeit at reduced levels compared to WT PAMs (FIG. 19, compare panels A and E). Reduced expression was likely due to the presence of the neomycin cassette, which was located between the exon 11 mimic and the following intron. HL11m pigs were not permissive for infection with a Type 1 virus, confirming the importance of SRCR 5. However, HL11m macrophages and HL11m pigs did support infection with Type 2 viruses. Based on virus titration and percent infection results, the PAMs from the HL11m pigs showed an overall decrease in permissiveness for virus compared to the WT macrophages (Table 15 and FIG. 17). Decreased permissiveness may be due to reduced levels of CD163 on the HL11m macrophages, combined with a reduced affinity of virus for the modified CD163 protein. Assuming that Type 2 viruses possesses a requirement of SRCR 5 and that L1 SRCR 8 can function as a suitable substitute, the lower affinity may be explained by the difference in peptide sequences between human SRCR 8 and porcine SRCR 5 (see FIG. 18, panel B). However, the reduced permissiveness of PAMs did not translate to the pig. Mean viremia for the HL11m pigs was not significantly different when compared to WT pigs (FIG. 23). In addition to PAMs, PRRSV infection of intravascular, septal and lymphoid tissue macrophages contribute to viremia (Lawson et al., 1997 and Morgan et al., 2014). The potential contributions of these and other CD163-positive cells populations in maintaining the overall virus load in HL11m pigs deserves further study.

Even though CD163 plasmids possessing deletions of SRCR domains are stably expressed in HEK cells (Van Gorp et al., 2010), the deletion of exons 7 and 8 in d7(1467) and d7(1280) resulted in a lack of detectable surface expression of CD163 (FIG. 19, panel D). Since the 2A10 mAB used for flow cytometry recognizes the three N-terminal SRCR domains (Van Gorp et al., 2010), and possibly the $7^{th}$ and $8^{th}$ domains (Sanchez, et al., 1999), the absence of detection was not due to the removal of a 2A10 epitope in the mutated proteins. While a small amount of CD163 expression could be detected on PAMs from some of the d7(129) pigs (see FIG. 19, panel C), the quantity of expressed protein was not sufficient to support PRRSV infection in PAMs or pigs. The absence of CD163 expression in the exon 7 and 8 deletion mutants is not fully understood, but is likely the result of mRNA and/or protein degradation.

In 2003, CD163 was identified as a receptor for African swine fever virus (ASFV; Sánchez-Torres et al., 2003). This conclusion was based on the observation that infected macrophages possess a mature CD163-positive phenotype, and anti-CD163 antibodies, such as 2A10, block ASFV infection of macrophages in vitro. It remains to be determined if CD163-null pigs are resistant to ASFV infection.

Cell culture models incorporating modifications to the PRRSV receptor have provided valuable insight into the mechanisms of PRRSV entry, replication and pathogenesis. One unique aspect of this study was the conduct of parallel experiment in vivo using receptor-modified pigs. This research has important impacts on the feasibility of developing preventative cures for one of the most serious diseases to ever face the global swine industry.

Example 4: Knockout of Maternal CD163 Protects Fetuses from Infection with Porcine Reproductive and Respiratory Syndrome Virus (PRRSV)

Examples 1 to 3 above demonstrate that pigs having a complete knockout (KO) of the CD163 gene lack CD163 expression on macrophages and fail to support PRRSV infection (see also Whitworth et al., 2016; Wells et al., 2017). Since CD163 expression is a dominant trait and inherited in a classic Mendelian fashion, offspring possessing normal CD163 expression and function can be derived by crossing a KO CD163$^{-/-}$ female pig with a wildtype (WT) CD163$^{+/+}$ male. For this study, CD163 KO gilts were bred with WT boars, producing heterozygous, CD163$^{+/-}$ fetuses in order to determine whether the presence of the CD163 KO genotype of the dam would be sufficient to protect fetuses following maternal infection with PRRSV. In this study, CD163-positive fetuses, recovered between 109 days of gestation or 20 days after maternal infection, were completely protected from PRRSV in dams possessing a complete knockout of the CD163 receptor. The results demonstrate a practical means to eliminate PRRSV-associated reproductive disease, a major source of economic hardship to agriculture.

Materials and Methods

CD163 gene editing. The CRISPR/Cas9 methods used to generate all of the KO alleles are described in detail in Examples 1-3 above. Wild-type animals and knockout, or heterozygous animals generated as described in Examples 1-3 and having the alleles described in Table 16 were used in the experiments described in this Example. Each of these alleles is described in Examples 1-3 and in PCT Publication No. WO 2017/023570, which is incorporated herein by reference in its entirety. The specific edits for alleles B, D and E are also described in Whitworth et al., 2014, and the specific edit in Allele C (2 bp insertion) is described in Whitworth et al., 2016. All of the alleles described in Table 16 were identified based on DNA sequencing. The knockout genotype was confirmed by the absence of CD163 expression, which was measured by staining alveolar macrophages with anti-CD163 mAb, 2A10, as described above in Example 2.

TABLE 16

CD163 alleles.

| Allele | Description | In Reference to SEQ ID NO: 47 | SEQ ID NO. |
|---|---|---|---|
| A | Wild Type | SEQ ID NO:47 (partial WT CD163 sequence including exon 7) | 47 |
| B | Knockout (7 bp insertion in exon 7) | 7 base pair insertion between nucleotide 3,148 and nucleotide 3,149 as compared to reference sequence SEQ ID NO: 47 | 99 |
| C | Knockout (2 bp insertion in exon 7) | 2 base pair insertion between nucleotides 3,149 and 3,150 as compared to reference sequence SEQ ID NO: 47, with a 377 base | 103 |

TABLE 16-continued

| CD163 alleles. | | | |
|---|---|---|---|
| Allele | Description | In Reference to SEQ ID NO: 47 | SEQ ID NO. |
| | | pair deletion from nucleotide 2,573 to nucleotide 2,949 as compared to reference sequence SEQ ID NO: 47 on the same allele | |
| D | Knockout (11 bp deletion in exon 7) | 11 base pair deletion from nucleotide 3,137 to nucleotide 3,147 as compared to reference sequence SEQ ID NO: 47. | 102 |
| E | Knockout (1382 bp deletion that included part of exon 7 and 8 with an 11 bp insertion in exon 7) | 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113 | 113 |

PRRSV infection. The PRRSV strain used in this study, NVSL 97-7895 (NVSL), is a laboratory strain isolated in 1997 from a herd in Southeast Iowa, USA that was experiencing a PRRS abortion storm (Halbur et al., 1997). The virus, maintained as a low passage isolate, was propagated and titered on MARC-145 cells. At 89 to 91 days of gestation, gilts were inoculated with $10^5$ $TCID_{50}$ of virus diluted in 5 ml of culture medium. One half of the inoculum was administered by intramuscular injection and the remainder was administered intranasally. All gilts were maintained in an environment that allowed for the continuous exposure to virus shed by infected pen mates. Blood samples were taken from the gilts prior to infection, seven days post-inoculation (dpi), and at the time of euthanasia. PRRSV nucleic acid was measured by isolation of total RNA from serum followed by reverse transcriptase real-time PRRSV PCR (Tetracore, Rockville, MD). A standard curve was generated using the quantification standards supplied in the RT-PCR kit. Results are reported as $\log_{10}$ templates per 25 µl reaction, which approximates the number of viral RNA templates per ml of blood.

Results

A detailed description of the knockout alleles used in this study is shown in Table 16 above. Each knockout allele possessed a mutation in exon 7 that was predicted to result in a codon frameshift followed by a premature stop codon in the mRNA. The matings between WT and CD163 KO parents are summarized in Table 17. The first group of three dams, which served as positive infection controls, were $CD163^{+/+}$ dams carrying $CD163^{+/+}$ fetuses (++/++ group). A second group (−−/+−) were $CD163^{-/-}$ dams carrying $CD163^{+/-}$ fetuses. In this group, the $CD163^{-/-}$ dams are unable to support PRRS replication, while the $CD163^{+/-}$ fetuses retain susceptibility to PRRS infection. And finally, a third group (−−/−−) consisted of $CD163^{-/-}$ dams carrying $CD163^{-/-}$ fetuses. For the last group, both dams and fetuses should be resistant to infection.

TABLE 17

| CD163 parental and fetal genotypes. | | | | | | |
|---|---|---|---|---|---|---|
| | CD163 Genotype | | | Collection of Fetuses | | |
| | Parents*1 | | | Day of | Day of | No. of |
| Gilt No. | Male | Dam | Fetus | Infection*2 | Gestation*3 | Fetuses |
| 138 | +/+ (A/A) | +/+ (A/A) | +/+ | 91 | 106 | 16 |
| 139*4 | +/+ (A/A) | +/+ (A/A) | +/+ | 91 | 106 | 14 |
| 140 | +/+ (A/A) | +/+ (A/A) | +/+ | 91 | 106 | 12 |
| 84 | +/+ (A/A) | −/− (B/C) | +/− | 89 | 109 | 14 |
| 87 | +/+ (A/A) | −/− (B/C) | +/− | 89 | 109 | 17 |
| 122 | +/+ (A/A) | −/− (E/C) | +/− | 89 | 109 | 11 |
| 86 | −/− (C/D) | −/− (B/D) | −/− | 90 | 109 | 7 |
| 121 | −/− (C/D) | −/− (B/D) | −/− | 90 | 109 | 9 |

*1 CD163 alleles are identified in Table 1
*2 Gestation day when dams were infected
*3 Gestation day when fetuses were removed
*4 PRRSV-infected dam aborted at 106 days of gestation Clinical signs in the infected wild-type (WT) dams included lethargy and transient inappetence. The KO dams showed no clinical signs. During the study period, one WT dam, No. 139, aborted on day 106 of gestation (15 dpi). PRRSV nucleic acid, measured at 7 dpi, showed a viremia level for Dam No. 139 of 5.5 $\log_{10}$ templates per reaction, demonstrating the presence of a productive PRRSV infection. Between 15 and 20 dpi, all remaining dams were euthanized and uterine horns immediately removed. Beginning at the tip of each horn, fetuses and placentas were removed and assessed for the presence of anatomic pathology. A blood sample was obtained from each fetus. If blood was not obtainable, a sample of fluid was collected from the abdominal cavity. The number of fetuses recovered from each dam is listed in Table 17. For the CD163 WT group++/++) (including the dam that aborted), the number of fetuses were 16, 14 and 12 (mean=14.0). The CD163 KO dams carrying the $CD163^{+/-}$ fetuses (−−/+− group) yielded 14, 17 and 11 fetuses (mean=13.6). For the CD163 KO dams carrying CD163 KO fetuses (−−/−− group), the numbers of fetuses were 7 and 9. The results for fetal viremia and gross pathology are summarized in FIG. 24 and Table 18.

TABLE 18

| Summary of fetal infection and pathology.*[1] | | | | | | |
|---|---|---|---|---|---|---|
| Gilt No. | Dam Geno-type | Fetus Geno-type | Total No. Fetuses | Dam Viremia*[2] | No. Infected Fetuses | Pathology*[3] |
| 138 | +/+ | +/+ | 16 | 3.6 | 13 (80%) | 8 (50%) |
| 139*[4] | +/+ | +/+ | 14 | 5.5 | ND | ND |
| 140 | +/+ | +/+ | 12 | 4.1 | 11 (92) | 8 (72) |
| 84 | −/− | +/− | 14 | N | 0 (0) | 1 (07) |
| 87 | −/− | +/− | 17 | N | 0 (0) | 1 (06) |
| 122 | −/− | +/− | 11 | N | 0 (0) | 0 (0) |
| 86 | −/− | −/− | 7 | N | 0 (0) | 0 (0) |
| 121 | −/− | −/− | 9 | N | 0 (0) | 0 (0) |

*[1]The table is a combined summary of the data presented in Table 17 and FIG. 24
*[2]Viremia shown as $\log_{10}$ virus nucleic templates per PCR
*[3]Fetuses showing pathology as described for FIG. 24
*[4]Gilt aborted prior to recovery of fetuses FIG. 24 depicts each of the fetal outcomes following maternal infection with PRRSV. The numbers on the left identify each dam. Below each dam in parenthesis is the result for PRRS PCR in serum, measured as $\log_{10}$ templates per reaction. "N" is negative for PRRSV nucleic acid (Ct>39). Fetuses are identified by number and relative position within each uterine horn. Asterisks identify fetal PCR samples obtained from abdominal fluid. The number below each fetus is the result for PRRS PCR in fetal serum ($\log_{10}$ templates per reaction). The number within each circle refers to the presence of anatomical pathology: 1) normal fetus; 2) small fetus; 3) placenta changes such as detached placenta and/or necrosis; 4) meconium stained fetus; 5) fetus is dead and necrotic. Lower case letters identify the genotype of the individual fetuses (see Table 17). Key: a, A/A; b, C/A; c, B/A; d, E/A; e, B/C; f, B/D; g, D/C; h, D/D; i, E/C; j, E/D; ND not determined because the fetus was necrotic; nd, genotype was not determined.

At the anatomic level, 50% and 72% of fetuses derived from the two CD163 WT (++/++) dams, No. 138 and No. 140, showed some degree of pathology, including smaller than normal fetuses (11% of all fetuses), fetuses with detached or necrotic placentas (14%), meconium staining (7%), and fetuses that were dead and necrotic (25%). The pathology observations are typical of reproductive PRRS. The same litters showed a high rate of PRRSV infection, with 92% of the fetuses testing positive for the presence of PRRSV nucleic acid. The PCR results for the fetuses from the WT dams illustrate two important properties of fetal PRRSV infection. First, there was a wide variation between fetuses in the concentration of virus detected in serum, the result of fetuses becoming infected at different times. Secondly, the level of viremia was not always correlated with pathology. For example, Fetus No. 5 from Dam No. 138 possessed a high level of viremia (7.3 $\log_{10}$ templates per reaction) and yet the fetus appeared unaffected. The reason for the discrepancy between viremia and the pathology is unclear. One possibility is that fetal pathology is the result of tissue damage that occurs on the maternal side and not related to the level of fetal viremia. In the field, these normal, but infected newborn piglets can function as "supershedders," which facilitate the rapid dissemination of PRRSV throughout a production system. For the −−/+− group (dams No. 84, 87 and 122), all fetuses appeared normal, with the minor exception of two fetuses that were smaller than the other littermates. The smaller than normal size is likely a consequence of crowding within the uterine horn that decreases the surface area of the placenta, thus restricting the growth of the developing fetus. All dams and fetuses in the −−/+− group were negative for the presence of PRRSV nucleic acid. For the last group, −−/−−, there was no visible pathology, and all dams (No. 86 and 121) and fetuses were negative for PRRSV nucleic acid.

The results from this study clearly demonstrate that the absence of CD163 in the dam is sufficient to protect the PRRSV-susceptible fetus. Although CD163-positive offspring derived from CD163 KO dams are susceptible to virus immediately after birth, the protection from PRRSV in utero provides a means to eliminate a major source of economic loss and animal suffering.

Examples disclosed herein are provided by way of exemplification and are not intended to limit the scope of the invention.

In view of the above, it will be seen that the several objects of the invention are achieved and other advantageous results attained.

As various changes could be made in the above products and methods without departing from the scope of the invention, it is intended that all matter contained in the above description and shown in the accompanying drawing[s] shall be interpreted as illustrative and not in a limiting sense.

REFERENCES

Allende R, et al., 1999. North American and European porcine reproductive and respiratory syndrome viruses differ in non-structural protein coding regions. J. Gen. Virol. 80: 307-315.

Bauer B K, et al., Arginine supplementation in vitro increases porcine embryo development and affects mRNA transcript expression. Reprod Fertil Dev 2011; 23: 107.

Beaton B P, et al., Compound transgenics: recombinase-mediated gene stacking. In: Pinkert C A (ed.). Transgenic Animal Technology: A Laboratory Handbook, 3rd ed. Waltham, MA: Elsevier; 2014: 565-578.

Benfield D A, et al., 1992. Characterization of swine infertility and respiratory syndrome (SIRS) virus (Isolate ATCC VR-2332). J Vet Diag Invest 4: 127-133.

Boddicker, et al., 2014. Genome-wide association and genomic prediction for host response to porcine reproductive and respiratory syndrome virus infection. Genetics, selection, evolution: GSE 46, 18.

Borg N A, et al., CD1d-lipid-antigen recognition by the semi-invariant NKT T-cell receptor. Nature 2007; 448: 44-49.

Brinster R L, et al., Factors affecting the efficiency of introducing foreign DNA into mice by microinjecting eggs. Proc Natl Acad Sci USA 1985; 82: 4438-4442.

Cafruny, W A, et al, Trojan Horse macrophages: studies with the murine lactate dehydrogenase-elevating virus and implications for sexually transmitted virus infection. J. Gen. Virol. 77(12): 3005-3012 (1996).

Calvert J G, et al., 2007. CD163 expression confers susceptibility to porcine reproductive and respiratory syndrome viruses. J Virol. 81: 7371-7379.

Carter D B, et al., Phenotyping of transgenic cloned piglets. Cloning Stem Cells 2002; 4: 131-145.

Cong L, et al., Multiplex genome engineering using CRISPR/Cas systems. Science 2013; 339: 819-823.

Christianson, W. T. et al. Experimental reproduction of swine infertility and respiratory syndrome in pregnant sows. American Journal of Veterinary Research 53, 485-488 (1993).

Christopher-Hennings, et al., Effects of a modified-live virus vaccine against porcine reproductive and respiratory syndrome in boars, American J. Veterinary Research 58(1), 40-45 (1997).
Dai Y, et al., Targeted disruption of the alpha1,3-galactosyltransferase gene in cloned pigs. Nat Biotechnol 2002; 20:251-255.
Das P B, et al., 2009. The minor envelope glycoproteins GP2a and GP4 of porcine reproductive and respiratory syndrome virus interact with the receptor CD163. J Virol. 84: 1731-40.
Dee et al., Elimination of porcine reproductive and respiratory syndrome virus using a test and removal process, The Veterinary Record 143, 474-476 (1998).
Delputte P L, et al., 2002. Involvement of the matrix protein in attachment of porcine reproductive and respiratory syndrome virus to a heparin-like receptor on porcine alveolar macrophages. J Virol. 76: 4312-4320.
Etzerodt, A., et al., 2013. Plasma clearance of hemoglobin and haptoglobin in mice and effect of CD163 gene targeting disruption. Antioxidants & redox signaling 18, 2254-2263.
Etzerodt, A., et al., 2013. CD163 and inflammation: biological, diagnostic, and therapeutic aspects. Antioxidants & redox signaling 18, 2352-2363.
Fabriek B O, et al., 2005. The macrophage scavenger receptor CD163. Immunobiology. 210: 153-160.
Fabriek B O, et al., 2009. The macrophage scavenger receptor CD163 functions as an innate immune sensor for bacteria. Blood. 113: 887-892.
Gaj T, et al., ZFN, TALEN, and CRISPR/Cas-based methods for genome engineering. Trends Biotechnol 2013; 31: 397-405.
Gaudreault N, et al., 2009. Factors affecting the permissiveness of porcine alveolar macrophages for porcine reproductive and respiratory syndrome virus. Archiv Virol. 154: 133-136.
Graversen, J. H., et al., 2012. Targeting the hemoglobin scavenger receptor CD163 in macrophages highly increases the anti-inflammatory potency of dexamethasone. Molecular therapy: the journal of the American Society of Gene Therapy 20, 1550-1558.
Groenen, M. A., et al., 2012. Analyses of pig genomes provide insight into porcine demography and evolution. Nature 491, 393-398.
Hai T, et al., One-step generation of knockout pigs by zygote injection of CRISPR/Cas system. Cell Res 2014; 24: 372-375.
Halbur, P. G., et al., 1995. Comparison of the pathogenicity of two U.S. porcine reproductive and respiratory syndrome virus isolates with that of the Lelystad virus. Veterinary pathology 32, 648-660.
Halbur, P. & Bush, E. B. Update on abortion storms and sow mortality. Journal of Swine Health and Production 5, 73 (1997).
Hammer R E, et al., Production of transgenic rabbits, sheep and pigs by microinjection. Nature 1985; 315: 680-683.
Hauschild J, et al., Efficient generation of a biallelic knockout in pigs using zinc-finger nucleases. Proc Natl Acad Sci USA 2011; 108: 12013-12017.
Holtkamp, D. J., et al., 2013. Assessment of the economic impact of porcine reproductive and respiratory syndrome virus on United States pork producers. Journal of Swine Health and Production 21, 72-84.
Hwang W Y, et al., Efficient genome editing in zebrafish using a CRISPR-Cas system. Nat Biotechnol 2013; 31: 227-229.
Jeney V, et al., 2002. Pro-oxidant and cytotoxic effects of circulating heme. Blood. 100: 879-887.
Keffaber, K. K., 1989. Reproductive failure of unknown etiology. American Association of Swine Practitioners Newsletter 1, 1-10.
Key, K. F. et al. Genetic variation and phylogenetic analyses of the ORFS gene of acute porcine reproductive and respiratory syndrome virus isolates. Veterinary Microbiology 83, 249-263 (2001).
Kim, H. S., et al., 1993 Enhanced replication of porcine reproductive and respiratory syndrome (PRRS) virus in a homogeneous subpopulation of MA-104 cell line. Arch Virol 133, 477-483.
Kristiansen M, et al., 2001. Identification of the haemoglobin scavenger receptor. Nature. 409: 198-201.
Kwon D N, et al., Production of biallelic CMP-Neu5Ac hydroxylase knock-out pigs. Sci Rep 2013; 3: 1981.
Ladinig, A., et al., 2015. Pathogenicity of three type 2 porcine reproductive and respiratory syndrome virus strains in experimentally inoculated pregnant gilts. Virus Res 203, 24-35.
Lai L, et al., Production of alpha-1,3-galactosyltransferase knockout pigs by nuclear transfer cloning. Science 2002; 295: 1089-1092.
Lai L, et al., Creating genetically modified pigs by using nuclear transfer. Reprod Biol Endocrinol 2003; 1: 82.
Lai L, et al., Production of cloned pigs by using somatic cells as donors. Cloning Stem Cells 2003; 5: 233-241.
Lawson S R, et al., 1997. Porcine reproductive and respiratory syndrome virus infection of gnotobiotic pigs: sites of virus replication and co-localization with MAC-387 staining at 21 days post-infection. Virus Res. 51: 105-113.
Lee K, et al., Engraftment of human iPS cells and allogeneic porcine cells into pigs with inactivated RAG2 and accompanying severe combined immunodeficiency. Proc Natl Acad Sci USA 2014; 111: 7260-7265.
Lee K, et al., Piglets produced from cloned blastocysts cultured in vitro with GM-CSF. Mol Reprod Dev 2013; 80: 145-154.
Li D, et al., Heritable gene targeting in the mouse and rat using a CRISPR-Cas system. Nat Biotechnol 2013; 31: 681-683.
Lillico S G, et al., Live pigs produced from genome edited zygotes. Sci Rep 2013; 3: 2847.
Machaty Z, et al., Complete activation of porcine oocytes induced by the sulfhydryl reagent, thimerosal. Biol Reprod 1997; 57: 1123-1127.
Madsen M, et al., 2004. Molecular characterization of the haptoglobin-hemoglobin receptor CD163. Ligand binding properties of the scavenger receptor cysteine-rich domain region. J Biol Chem. 279: 51561-51567.
Mengeling, W. L. et al. Clinical consequences of exposing pregnant gilts to strains of porcine reproductive and respiratory syndrome (PRRS) virus isolated from field cases of "atypical" PRRS. American Journal of Veterinary Research. 59, 1540-1544 (1998).
Merck, The Merck Veterinary Manual. http://www.merckmanuals.com/vet/appendixes/reference_guides/normal-_rectal_temperature_ranges.html.
Miao, Y. L., et al., 2009. Centrosome abnormalities during porcine oocyte aging. Environmental and molecular mutagenesis 50, 666-671.
Morgan S B, et al., 2014. Pathology and Virus Distribution in the Lung and Lymphoid Tissues of Pigs Experimentally Inoculated with Three Distinct Type 1 PRRS Virus Isolates of Varying Pathogenicity. Transbound Emerg Dis. November 10. pp 1-11.

Nelsen C J, et al., 1999. Porcine reproductive and respiratory syndrome virus comparison: divergent evolution on two continents. J. Virol. 73, 270-280.
Neumann E J, et al., Assessment of the economic impact of porcine reproductive and respiratory syndrome on swine production in the United States. J Am Vet Med Assoc 2005; 227: 385-392.
Niu Y, et al., Generation of gene-modified Cynomolgus monkey via Cas9/RNA-mediated gene targeting in one-cell embryos. Cell 2014; 156: 836-843.
Patience, J. F., et al., 1989. Swine Nutrition Guide, in: Center, P.S. (Ed.), University of Saskatchewan, Saskatoon, CA, pp. 149-171.
Patton J P, et al., 2008. Modulation of CD163 receptor expression and replication of porcine reproductive and respiratory syndrome virus in porcine macrophages. Virus Res. 140: 161-171.
Plagemann, P. G. W. Lactate dehydrogenase-elevating virus and related viruses. In Fields Virology, 3rd Ed, Fields, B. ed. Lippincott-Raven, Philadelphia, pp 1105-1120 (1996).
Prather R S, et al., An intact sialoadhesin (Sn/SIGLEC1/CD169) is not required for attachment/internalization of the porcine reproductive and respiratory syndrome virus. J Virol 2013; 87: 9538-9546.
Prather, R. S., et al., 2013. An intact sialoadhesin (Sn/SIGLEC1/CD169) is not required for attachment/internalization of the porcine reproductive and respiratory syndrome virus. J Virol 87, 9538-9546.
Provost C, et al., 2012. Identification of a new cell line permissive to porcine reproductive and respiratory syndrome virus infection and replication which is phenotypically distinct from MARC-145 cell line. Virol J. 9: 267.
Reed J L, et al., 1938. A simple method of estimating fifty percent endpoints. The American Journal of Hygiene 27: 493-497.
Ross J W, et al., Optimization of square-wave electroporation for transfection of porcine fetal fibroblasts. Transgenic Res 2010; 19: 611-620.
Rowland, R. R. R., et al., The evolution of porcine reproductive and respiratory syndrome virus: quasispecies and emergence of a virus subpopulation during infection of pigs with VR-2332, Virology 259, 262-266 (1999).
Rowland, R. R. R. et al. Lymphotropism of porcine reproductive and respiratory syndrome virus replication during persistent infection of pigs originally exposed to virus in utero. Veterinary Microbiology 96, 219-235 (2003).
Rowland, R. R. R. The interaction between PRRSV and the late gestation pig fetus. Virus Research 154, 114-122 (2010).
Rowland, R. R., et al., 2012. Control of porcine reproductive and respiratory syndrome (PRRS) through genetic improvements in disease resistance and tolerance. Frontiers in genetics 3, 260.
Sanchez C, et al., 1999. The porcine 2A10 antigen is homologous to human CD163 and related to macrophage differentiation. Journal of Immunology 162: 5230-5237.
Sánchez-Torres C, et al., 2003. Expression of porcine CD163 on monocytes/macrophages correlates with permissiveness to African swine fever infection. Arch Virol. 148: 2307-2323.
Schaer, C. A., et al., 2006a. Constitutive endocytosis of CD163 mediates hemoglobin-heme uptake and determines the noninflammatory and protective transcriptional response of macrophages to hemoglobin. Circulation research 99, 943-950.
Schaer, D. J., et al., 2006b. CD163 is the macrophage scavenger receptor for native and chemically modified hemoglobins in the absence of haptoglobin. Blood 107, 373-380.
Schaer, D. J., et al., 2006c. Hemophagocytic macrophages constitute a major compartment of heme oxygenase expression in sepsis. European journal of haematology 77, 432-436.
Shanmukhappa, K, et al., 2007. Role of CD151, A tetraspanin, in porcine reproductive and respiratory syndrome virus infection. Virol J. 4:62.
Shimozawa N, et al., Abnormalities in cloned mice are not transmitted to the progeny. Genesis 2002; 34: 203-207.
Shi, M. et al. Phylogeny-based evolutionary, demographical, and geographical dissection of North American type 2 porcine reproductive and respiratory syndrome viruses. Journal of Virology 84, 8700-8711 (2010).
Smit, A F A, et al., RepeatMasker Open-3.0. 1996-2010. Current Version: open-4.0.5 (RMLib: 20140131 and Dfam: 1.2). http://www.repeatmasker.org&gt. CD163: accessed Jul. 25, 2014; CD1D: accessed Aug. 27, 2013.
Soares M P, et al., 2009. Heme oxygenase-1: from biology to therapeutic potential. Trends Mol Med. 15: 50-58.
Stein M, et al., 1992. Interleukin 4 potently enhances murine macrophage mannose receptor activity: a marker of alternative immunologic macrophage activation. J Exp Med. 176: 287-292.
Stephenson R, et al., 2015. Multiplex serology for common viral infections in feral pigs in Hawaii between 2007 and 2010. Accepted for publication. J Wildlife Dis 51: 239-2343.
Sulahian TH1, et al., 2002. 2002. Human monocytes express CD163, which is upregulated by IL-10 and identical to p155. Cytokine. 2000 12: 1312-1321.
Terns M P, et al., CRISPR-based adaptive immune systems. Curr Opin Microbiol 2011; 14: 321-327.
Tian, K. et al. Emergence of fatal PRRSV variants: unparalleled outbreaks of atypical PRRS in China and molecular dissection of the unique hallmark. PLoS One. 2, e526 (2007).
Trible, B. R., et al., 2012. Recognition of the different structural forms of the capsid protein determines the outcome following infection with porcine circovirus type 2. J Virol 86, 13508-13514.
U.S. Department of Agriculture and U.S. Department of Health and Human Services. Dietary Guidelines for Americans, 2010. 7th Edition,
Van Breedam W, et al., Porcine reproductive and respiratory syndrome virus entry into the porcine macrophage. J Gen Virol 2010; 91: 1659-1667.
Van Breedam, W., et al., 2010. Porcine reproductive and respiratory syndrome virus entry into the porcine macrophage. J Gen Virol 91, 1659-1667.
Van den Heuvel M M, et al., 1999. Regulation of C D 163 on human macrophages: crosslinking of CD163 induces signaling and activation. J Leukoc Biol. 66: 858-866.
van den Hoff M J, et al., Electroporation in 'intracellular' buffer increases cell survival. Nucleic Acids Res 1992; 20:2902.
Van Gorp, H., et al., 2010. Scavenger receptor CD163, a Jack-of-all-trades and potential target for cell-directed therapy. Mol Immunol 47, 1650-1660.
Van Gorp H, et al., 2010. Identification of the CD163 protein domains involved in infection of the porcine reproductive and respiratory syndrome virus. J Virol. 84: 3101-3105.
Walters E M, et al., Advancing swine models for human health and diseases. Mo Med 2013; 110: 212-215.

Wang H, et al., One-step generation of mice carrying mutations in multiple genes by CRISPR/Cas-mediated genome engineering. Cell 2013; 153: 910-918.
Welch S K, et al., 2010. A brief review of CD163 and its role in PRRSV infection. Virus Res. 154: 98-103.
Wells, K. D., et al., 2014. Use of the CRISPR/Cas9 system to produce genetically engineered pigs from in vitro-derived oocytes and embryos. Biol Reprod 91, 78.
Wells, K. D. et al. Substitution of porcine CD163 SRCR domain 5 with a CD163-like homolog confers resistance of pigs to genotype1 but not genotype 2 porcine reproductive and respiratory syndrome (PRRS) viruses. Journal of Virology In press (2017).
Wensvoort, G., et al., 1991. Mystery swine disease in The Netherlands: the isolation of Lelystad virus. Veterinary Quarterly 13, 121-130.
Whitworth K M, et al., 2016. CD163 facilitates both entry and replication of porcine reproductive and respiratory syndrome virus. Nature Biotech. 34: 20-22.
Whitworth K M, et al., Method of oocyte activation affects cloning efficiency in pigs. Mol Reprod Dev 2009; 76: 490-500.
Whitworth et al. Use of the CRISPR/Cas9 system to produce genetically engineered pigs from in vitro-derived oocytes and embryos, Biology of Reproduction 91(3): 1-13 (2014).
Whitworth K M, et al., Activation method does not alter abnormal placental gene expression and development in cloned pigs. Mol Reprod Dev 2010; 77: 1016-1030.
Whitworth K M, et al., Scriptaid corrects gene expression of a few aberrantly reprogrammed transcripts in nuclear transfer pig blastocyst stage embryos. Cell Reprogram 2011; 13: 191-204.
Whitworth, K. M., et al., 2014. Use of the CRISPR/Cas9 system to produce genetically engineered pigs from in vitro-derived oocytes and embryos. Biol Reprod 91, 78.
Whyte J J, et al., Genetic modifications of pigs for medicine and agriculture. Mol Reprod Dev 2011; 78: 879-891.
Whyte J J, et al., Gene targeting with zinc finger nucleases to produce cloned eGFP knockout pigs. Mol Reprod Dev 2011; 78:2.
Wiedenheft B, et al., RNA-guided genetic silencing systems in bacteria and archaea. Nature 2012; 482: 331-338.
Wilkinson et al. Genome-wide analysis of the transcriptional response to porcine reproductive and respiratory syndrome virus infection at the maternal/fetal interface and in the fetus. BMC Genomics 17, 383 (2016).
Whitworth, K. M. et al. Gene-edited pigs are protected from porcine reproductive and respiratory syndrome virus. Nature Biotechnology 34, 20-22 (2016).
Winckler, C., et al., 2001. The reliability and repeatability of a lameness scoring system for use as an indicator of welfare in dairy cattle. Acta Agricultura Scandinavica Section A. Animal Science, 103-107.
Yang D, et al., Generation of PPARgamma mono-allelic knockout pigs via zinc-finger nucleases and nuclear transfer cloning. Cell Res 2011; 21:979-982.
Yoshioka K, et al., Birth of piglets derived from porcine zygotes cultured in a chemically defined medium. Biol Reprod 2002; 66:112-119.
Zhang Q, et al., 2015. PRRS virus receptors and their role for pathogenesis. Vet Microbiol. 177: 229-241.
Zhao J, et al., Histone deacetylase inhibitors improve in vitro and in vivo developmental competence of somatic cell nuclear transfer porcine embryos. Cell Reprogram 2010; 12: 75-83.
Zhao J, et al., Significant improvement in cloning efficiency of an inbred miniature pig by histone deacetylase inhibitor treatment after somatic cell nuclear transfer. Biol Reprod 2009; 81:525-530.

TABLE OF SEQUENCES

Figure 5:
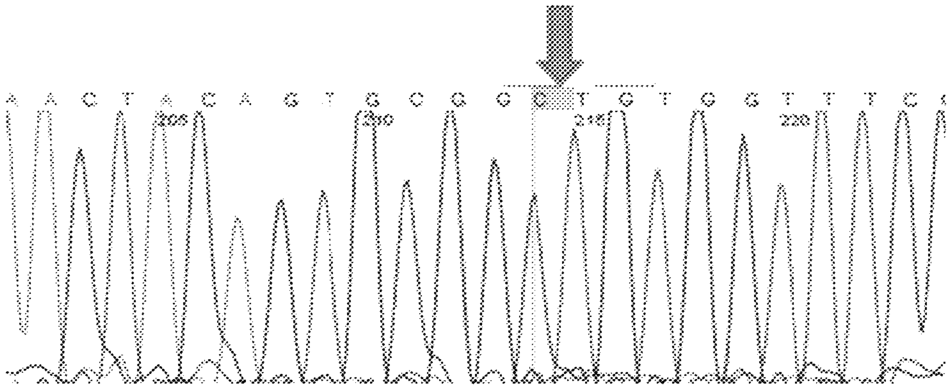
FIG. 5. Effect of CRISPR/Cas9 system in targeting CD163 in porcine embryos. A) Examples of mutations generated on CD163 by the CRISPR/Cas9 system: WT genotype (SEQ ID NO:20), #1-1 (SEQ ID NO:21), #1-4 (SEQ ID NO:22), and #2-2 (SEQ ID NO:23). All the embryos examined by DNA sequencing showed mutation on the CD163 (18/18). CRISPR 131 is highlighted in bold. B) Sequencing read of a homozygous deletion caused by the CRISPR/Cas9 system. The image represents #1-4 from panel A carrying a 2 bp deletion of CD163.

| SEQ | TYPE | DESCRIPTION |
|---|---|---|
| SEQ ID NO:1 | nucleotide | CRISPR 10 |
| SEQ ID NO:2 | nucleotide | CRISPR 131 |
| SEQ ID NO:3 | nucleotide | CRISPR 256 |
| SEQ ID NO:4 | nucleotide | CRISPR 282 |
| SEQ ID NO:5 | nucleotide | CRISPR 4800 |
| SEQ ID NO:6 | nucleotide | CRISPR 5620 |
| SEQ ID NO:7 | nucleotide | CRISPR 5626 |
| SEQ ID NO:8 | nucleotide | CRISPR 5350 |
| SEQ ID NO:9 | nucleotide | eGFP1 |
| SEQ ID NO:10 | nucleotide | eGFP2 |
| SEQ ID NO:11 | nucleotide | forward primer 9538 fragment |
| SEQ ID NO:12 | nucleotide | reverse primer 9538 fragment |
| SEQ ID NO:13 | nucleotide | forward primer 8729 fragment |
| SEQ ID NO:14 | nucleotide | forward primer 8729 fragment |
| SEQ ID NO:15 | nucleotide | WILD TYPE CD163 |
| SEQ ID NO:16 | nucleotide | FIG. 4, panel C WT |
| SEQ ID NO:17 | nucleotide | FIG. 4, panel C #1 |
| SEQ ID NO:18 | nucleotide | FIG. 4, panel C #2 |
| SEQ ID NO:19 | nucleotide | FIG. 4, panel C #3 |
| SEQ ID NO:20 | nucleotide | FIG. 5, panel A WT |
| SEQ ID NO:21 | nucleotide | FIG. 5, panel A #1-1 |
| SEQ ID NO:22 | nucleotide | FIG. 5, panel A #1-4 |
| SEQ ID NO:23 | nucleotide | FIG. 5, panel A #2-2 |
| SEQ ID NO:24 | nucleotide | FIG. 6, panel C CD163 WT |
| SEQ ID NO:25 | nucleotide | FIG. 6, panel C CD163 #1 |
| SEQ ID NO:26 | nucleotide | FIG. 6, panel C CD163 #2 |
| SEQ ID NO:27 | nucleotide | FIG. 6, panel C CD163 #3 |
| SEQ ID NO:28 | nucleotide | FIG. 6, panel C eGFP WT |
| SEQ ID NO:29 | nucleotide | FIG. 6, panel C eGFP #1-1 |
| SEQ ID NO: 30 | nucleotide | FIG. 6, panel C eGFP #1-2 |
| SEQ ID NO:31 | nucleotide | FIG. 6, panel C eGFP #2 |
| SEQ ID NO:32 | nucleotide | FIG.6, panel C eGFP #3 |
| SEQ ID NO:33 | nucleotide | FIG. 7, panel C WT |
| SEQ ID NO:34 | nucleotide | FIG. 7, panel C #67-1 |
| SEQ ID NO:35 | nucleotide | FIG. 7, panel C #67-2 al |
| SEQ ID NO:36 | nucleotide | FIG. 7, panel C #67-2 a2 |
| SEQ ID NO:37 | nucleotide | FIG. 7, panel C #67-3 |
| SEQ ID NO:38 | nucleotide | FIG. 7, panel C #67-4 al |
| SEQ ID NO:39 | nucleotide | FIG. 7, panel C #67-4 a2 |
| SEQ ID NO:40 | nucleotide | FIG. 8, panel D WT |
| SEQ ID NO:41 | nucleotide | FIG. 8, panel D #166-1.1 |
| SEQ ID NO:42 | nucleotide | FIG. 8, panel D #166-1.2 |
| SEQ ID NO:43 | nucleotide | FIG. 8, panel D #166-2 |
| SEQ ID NO:44 | nucleotide | FIG. 8, panel D #166-3.1 |
| SEQ ID NO:45 | nucleotide | FIG. 8, panel D #166-3.2 |
| SEQ ID NO:46 | nucleotide | FIG. 8, panel D #166-4 |
| SEQ ID NO:47 | nucleotide | FIG. 16 WT CD163 partial |
| SEQ ID NOs. 48-67 | nucleotide | Primer sequences (Table 1) |
| SEQ ID NOs. 68-79 | nucleotide | Primer sequences (Table 2) |
| SEQ ID NOs. 80-85 | nucleotide | Primer sequences (Table 3) |
| SEQ ID NOs. 86-97 | nucleotide | Primer sequences (Table 4) |
| SEQ ID NO: 98 | nucleotide | Allele with 1506 bp deletion |
| SEQ ID NO: 99 | nucleotide | Allele with 7 bp insertion |
| SEQ ID NO: 100 | nucleotide | Allele with 1280 bp deletion |
| SEQ ID NO: 101 | nucleotide | Allele with 1373 bp deletion |
| SEQ ID NO: 102 | nucleotide | Allele with 11 bp deletion |
| SEQ ID NO: 103 | nucleotide | Allele with 2 bp insertion & 377 bp deletion |
| SEQ ID NO: 104 | nucleotide | Allele with 124 bp deletion |
| SEQ ID NO: 105 | nucleotide | Allele with 123 bp deletion |
| SEQ ID NO: 106 | nucleotide | Allele with 1 bp insertion |
| SEQ ID NO: 107 | nucleotide | Allele with 130 bp deletion |
| SEQ ID NO: 108 | nucleotide | Allele with 132 bp deletion |
| SEQ ID NO: 109 | nucleotide | Allele with 1467 bp deletion |
| SEQ ID NO: 110 | nucleotide | Allele with 1930 bp deletion in exon 6, 129 bp deletion in exon 7, and 12 bp insertion |
| SEQ ID NO: 111 | nucleotide | Allele with 28 bp deletion |
| SEQ ID NO: 112 | nucleotide | Allele with 1387 bp deletion |
| SEQ ID NO: 113 | nucleotide | Allele with 1382 bp deletion &11 bp insertion |

-continued

TABLE OF SEQUENCES

| SEQ | TYPE | DESCRIPTION |
|---|---|---|
| SEQ ID NO: 114 | nucleotide | Allele with 1720 bp deletion |
| SEQ ID NO: 115 | nucleotide | Inserted sequence for SEQ ID NO: 99 |
| SEQ ID NO: 116 | nucleotide | Inserted sequence for SEQ ID NO: 110 |
| SEQ ID NO: 117 | nucleotide | Inserted sequence for SEQ ID NO: 113 |
| SEQ ID NO: 118 | nucleotide | Domain swap sequence |
| SEQ ID NO: 119 | nucleotide | Allele with 452 bp deletion |
| SEQ ID NO: 120 | peptide | Porcine CD163 SRCR 5 |
| SEQ ID NO: 121 | peptide | Human CD163L1 SRCR 8 homolog |

What is claimed is:

1. A method for protecting a porcine fetus from infection with porcine reproductive and respiratory syndrome virus (PRRSV) in utero, the method comprising;
   - breeding a female porcine animal with a male porcine animal, wherein
   - the female porcine animal comprises modified chromosomal sequences in both alleles of its CD163 gene, wherein the modified chromosomal sequences reduce production or activity of the CD163 protein as compared to a female porcine animal which lacks the modified CD163 sequence; and
   - the male porcine animal comprises at least one wild-type CD163 allele;
   - wherein the porcine fetus is protected from infection with PRRSV in utero, as compared to a porcine fetus in utero in a wild-type female porcine animal.

2. The method of claim 1, wherein the male porcine animal comprises two wild-type CD163 alleles.

3. The method of claim 1, wherein the female porcine animal comprises a genetically edited female porcine animal.

4. The method of claim 1, wherein the female porcine animal comprises the same modified chromosomal sequence in both alleles of the CD163 gene.

5. The method of claim 1, wherein the female porcine animal comprises a first modified chromosomal sequence in a first allele of the CD163 gene and a second modified chromosomal sequence in a second allele of the CD163 gene, the first and second modified chromosomal sequences being different from each other.

6. The method of claim 1, wherein each allele of the CD163 gene of the female porcine animal comprises an insertion, a deletion, or a combination thereof.

7. The method of claim 1, wherein each allele of the CD163 gene of the female porcine animal comprises a modification in exon 7, a modification in exon 8, a modification in an intron that is contiguous with exon 7 or exon 8, or a combination of any thereof.

8. The method of claim 1, wherein at least one of the alleles of the CD163 gene in the female porcine animal comprises a modification selected from the group consisting of:
   - an 11 base pair deletion from nucleotide 3,137 to nucleotide 3,147 as compared to reference sequence SEQ ID NO: 47;
   - a 2 base pair insertion between nucleotides 3,149 and 3,150 as compared to reference sequence SEQ ID NO: 47, with a 377 base pair deletion from nucleotide 2,573 to nucleotide 2,949 as compared to reference sequence SEQ ID NO: 47 on the same allele;
   - a 124 base pair deletion from nucleotide 3,024 to nucleotide 3,147 as compared to reference sequence SEQ ID NO: 47;
   - a 123 base pair deletion from nucleotide 3,024 to nucleotide 3,146 as compared to reference sequence SEQ ID NO: 47;
   - a 1 base pair insertion between nucleotides 3,147 and 3,148 as compared to reference sequence SEQ ID NO: 47;
   - a 130 base pair deletion from nucleotide 3,030 to nucleotide 3,159 as compared to reference sequence SEQ ID NO: 47;
   - a 132 base pair deletion from nucleotide 3,030 to nucleotide 3,161 as compared to reference sequence SEQ ID NO: 47;
   - a 1506 base pair deletion from nucleotide 1,525 to nucleotide 3,030 as compared to reference sequence SEQ ID NO: 47;
   - a 7 base pair insertion between nucleotide 3,148 and nucleotide 3,149 as compared to reference sequence SEQ ID NO: 47;
   - a 1280 base pair deletion from nucleotide 2,818 to nucleotide 4,097 as compared to reference sequence SEQ ID NO: 47;
   - a 1373 base pair deletion from nucleotide 2,724 to nucleotide 4,096 as compared to reference sequence SEQ ID NO: 47;
   - a 1467 base pair deletion from nucleotide 2,431 to nucleotide 3,897 as compared to reference sequence SEQ ID NO: 47;
   - a 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47;
   - a 28 base pair deletion from nucleotide 3,145 to nucleotide 3,172 as compared to reference sequence SEQ ID NO: 47;
   - a 1387 base pair deletion from nucleotide 3,145 to nucleotide 4,531 as compared to reference sequence SEQ ID NO: 47;
   - a 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113;
   - a 1720 base pair deletion from nucleotide 2,440 to nucleotide 4,160 as compared to reference sequence SEQ ID NO: 47;

a 452 base pair deletion from nucleotide 3,015 to nucleotide 3,466 as compared to reference sequence SEQ ID NO: 47;

and combinations of any thereof.

9. The method of claim 8, wherein:

the modification comprises the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele, and the 2 base pair insertion comprises the dinucleotide AG;

the modification comprises the 1 base pair insertion between nucleotides 3,147 and 3,148 as compared to reference sequence SEQ ID NO: 47, and the 1 base pair insertion comprises a single adenine residue;

the modification comprises the 7 base pair insertion between nucleotide 3,148 and nucleotide 3,149 as compared to reference sequence SEQ ID NO: 47, and the 7 base pair insertion comprises the sequence TACTACT (SEQ ID NO: 115);

the modification comprises the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47, and wherein the 12 base pair insertion comprises the sequence TGTGGAGAATTC (SEQ ID NO: 116); or the modification comprises the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113, and the 11 base pair insertion comprises the sequence AGCCAGCGTGC (SEQ ID NO: 117).

10. The method of claim 8, wherein at least one of the alleles of the CD163 gene in the female porcine animal comprises a modification selected from the group consisting of:

the 7 base pair insertion between nucleotide 3,148 and nucleotide 3,149 as compared to reference sequence SEQ ID NO: 47;

the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele;

the 11 base pair deletion from nucleotide 3,137 to nucleotide 3,147 as compared to reference sequence SEQ ID NO: 47;

the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113;

and combinations of any thereof.

11. The method of claim 10, wherein the female porcine animal comprises:

(a) the 7 base pair insertion between nucleotide 3,148 and nucleotide 3,149 as compared to reference sequence SEQ ID NO: 47 in one allele of the CD163 gene; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47, in the other allele of the CD163 gene;

(b) the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113, in one allele of the CD163 gene; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47, in the other allele of the CD163 gene;

(c) the 7 base pair insertion between nucleotide 3,148 and nucleotide 3,149 as compared to reference sequence SEQ ID NO: 47 in one allele of the CD163 gene; and the 11 base pair deletion from nucleotide 3,137 to nucleotide 3,147 as compared to reference sequence SEQ ID NO: 47 in the other allele of the CD163 gene; or (d) the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113, in one allele of the CD163 gene; and the 11 base pair deletion from nucleotide 3, 137 to nucleotide 3,147 as compared to reference sequence SEQ ID NO: 47 in the other allele of the CD163 gene.

12. The method of claim 11, wherein the female porcine animal comprises:

(a) the 7 base pair insertion between nucleotide 3,148 and nucleotide 3,149 as compared to reference sequence SEQ ID NO: 47 in one allele of the CD163 gene; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47, in the other allele of the CD163 gene; or (b) the 1382 base pair deletion from nucleotide 3,113 to nucleotide 4,494 as compared to reference sequence SEQ ID NO: 47, wherein the deleted sequence is replaced with the 11 base pair insertion beginning at nucleotide 3,113, in one allele of the CD163 gene; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47, in the other allele of the CD163 gene.

13. The method of claim 1, wherein the female porcine animal comprises:

(a) a chromosomal sequence comprising SEQ ID NO: 99 in one allele of the CD163 gene, and a chromosomal sequence comprising SEQ ID NO: 103 in the other allele of the CD163 gene;

(b) a chromosomal sequence comprising SEQ ID NO: 113 in one allele of the CD163 gene, and a chromosomal sequence comprising SEQ ID NO: 99 in the other allele of the CD163 gene;

(c) a chromosomal sequence comprising SEQ ID NO: 99 in one allele of the CD163 gene, and a chromosomal sequence comprising SEQ ID NO: 102 in the other allele of the CD163 gene; or (d) a chromosomal sequence comprising SEQ ID NO: 113 in one allele of the CD163 gene, and a chromosomal sequence comprising SEQ ID NO: 102 in the other allele of the CD163 gene.

14. The method of claim 13, wherein the female porcine animal comprises:

(a) a chromosomal sequence comprising SEQ ID NO: 99 in one allele of the CD163 gene, and a chromosomal sequence comprising SEQ ID NO: 103 in the other allele of the CD163 gene; or (b) a chromosomal sequence comprising SEQ ID NO: 113 in one allele of the CD163 gene, and a chromosomal sequence comprising SEQ ID NO: 99 in the other allele of the CD163 gene.

15. The method of claim 1, wherein the breeding produces one or more fetuses that comprise a modified chromosomal sequence in a single allele of the CD163 gene.

16. The method of claim 1, wherein the breeding comprises mating of the female porcine animal with the male porcine animal.

17. The method of claim 1, wherein the breeding comprises artificial insemination of the female animal with sperm obtained from the male animal.

18. The method of claim 1, wherein the breeding comprises transferring a fertilized oocyte into the reproductive tract of the female porcine animal.

19. The method of claim 18, wherein the fertilized oocyte has been generated by in vitro fertilization of the oocyte with sperm obtained from the male porcine animal.

20. The method of claim 19, wherein the in vitro fertilization comprises intracytoplasmic injection of an oocyte with sperm obtained from the male porcine animal.

* * * * *

SEQUENCE LISTING

```
<160> NUMBER OF SEQ ID NOS: 121

<210> SEQ ID NO 1
<211> LENGTH: 23
<212> TYPE: DNA
<213> ORGANISM: Sus scrofa

<400> SEQUENCE: 1

ggaaacccag gctggttgga ggg                                              23


<210> SEQ ID NO 2
<211> LENGTH: 23
<212> TYPE: DNA
<213> ORGANISM: Sus scrofa

<400> SEQUENCE: 2

ggaactacag tgcggcactg tgg                                              23


<210> SEQ ID NO 3
<211> LENGTH: 23
<212> TYPE: DNA
<213> ORGANISM: Sus scrofa

<400> SEQUENCE: 3

cagtagcacc ccgccctgac ggg                                              23


<210> SEQ ID NO 4
<211> LENGTH: 23
<212> TYPE: DNA
<213> ORGANISM: Sus scrofa

<400> SEQUENCE: 4

tgtagccaca gcagggacgt cgg                                              23


<210> SEQ ID NO 5
<211> LENGTH: 23
<212> TYPE: DNA
<213> ORGANISM: Sus scrofa

<400> SEQUENCE: 5

ccagcctcgc ccagcgacat ggg                                              23


<210> SEQ ID NO 6
<211> LENGTH: 23
<212> TYPE: DNA
<213> ORGANISM: Sus scrofa

<400> SEQUENCE: 6

ctttcattta tctgaactca ggg                                              23
```

<210> SEQ ID NO 7
<211> LENGTH: 23
<212> TYPE: DNA
<213> ORGANISM: Sus scrofa

<400> SEQUENCE: 7
ttatctgaac tcagggtccc cgg 23

<210> SEQ ID NO 8
<211> LENGTH: 23
<212> TYPE: DNA
<213> ORGANISM: Sus scrofa

<400> SEQUENCE: 8
cagctgcagc atatatttaa ggg 23

<210> SEQ ID NO 9
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 9
ctcctcgccc ttgctcacca tgg 23

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
gaccaggatg ggcaccaccc cgg 23

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
ctctccctca ctctaaccta ctt 23

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
tatttctctc acatggccag tc 22

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 13
ctctccctca ctctaaccta ctt 23

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
gactggccat gtgagagaaa ta 22

<210> SEQ ID NO 15
<211> LENGTH: 27767
<212> TYPE: DNA
<213> ORGANISM: Sus scrofa

<400> SEQUENCE: 15
atacaagtgc cttttacaga caatctgcac aagttatttg ttagacatat ttgattatag 60
aattaatatt aaaaggggtt ataacaatca agcattgata atttaattat gtttgcctat 120
tttactttag ttttttgaca taactgtgta actattgcga tttttttatt cctaatgtaa 180
ttagttcaaa acaaagtgca gaaatttaaa atattcaatt caacaacagt atataagtca 240
atattccccc cttaaatttt tacaaatctt tagggagtgt ttctcaattt ctcaatttct 300
ttggttgttt catgtcccat atggaagaaa acatgggtgt gaaagggaag cttactcttt 360
tgattacttc ccttttctgg ttgactccac ctccattatg aagcctttct gtatttttgt 420
ggaagtgaaa tgatttttag aattcttagt ggttctcttc ttcaggagaa catttctagg 480
taataataca agaagattta aatggcataa aaccttggaa tggacaaact cagaatggtg 540
ctacatgaaa actctggatc tgcaggtaaa atcttctcat ttattctata tttacctttt 600
aaatagagtg tagcaatatt ccgacagtca atcaatctga tttaatagtg attggcatct 660
ggagaagaag taacagggaa aaaggcaata agctttataa ggggaacttt tatcttccat 720
agactcaaaa ttgaagacgt gactagaaga ttgctagatt tggcatcagt tttgtaaaat 780
tgctgaggtg aaattaagta agggatgaaa attaactaaa ttgtgttgag tatgaaacta 840
gtagttgtta gaaaagatag aacatgaagg aatgaatatt gattgaaagt tgatgaccta 900
gaggacattt agactaacac ctctgagtgt caaagtctaa tttatgattt acatcgatgc 960
gttaaactca tttaacattc ttactttttt cccctcaagc atttaagctg aagtataaca 1020
tttcacatga aagcctggat tataaatgca cagttcagtg acctatctca gaggagtgac 1080
tgccatagca tttttttgt ctttttgcct tcagagccac agcaacgcgg gatccgaagc 1140
cgcgtctgcg acccacacca cagctcacgg caatgccgga tctttaaccc actgagcgag 1200
gccggggatc gaacccgcag tctcatggtt cctagtagga ttcgttaacc actgcgccac 1260
gacgggaact cctaccatag catttttact tttaagttac tgttggttta gagtaagaag 1320
gagaaatgag agtgatggag cgtttgctat atttggagac aaggtcctat attggaggtt 1380
ctcaaatata aattttgtcg ctttttcctc caatgtattg ttcaactact atttagcagg 1440
ccactgtgcc aggtactggt gaaactggtg aacatgatag atgtaattca ttccctcatg 1500
gaactttcca tctaacaatg tggatcaggt aggcttggag atgagaatgc cagtggttga 1560
ctatgactct gtggctgaag ggagagctac tcacttcgta gtttcatcaa tgtcttttg 1620 gttttccagg ttttaagccc tgctcttgca attcttttcc cttctccaac tttcttctaa 1680
tttctcaccc ctaggatgcc tataaacatg agtattttca aagctacttc actgaggtta 1740
tatgatcctg gtgtgaattt ttcctgcctg acttgccatt tagaaggaag tgtttcctgg 1800

-continued

```
aatttccatt gtggcttggt ggttaaagac cctgcattgt ctctgtgagg atgtgggttc   1860
aatctctggc ctcattcagt gagtgggtta aggatctggt gtcgctgcaa gctgtggcta   1920
agatcccaca ttgccatgtc tgtggtgtag actggcacct ggagctctga tttgaccaca   1980
atcttaggaa cttcagatgt ggccataaaa aggaaaaaaa agttaggaag ggttttctgt   2040
cttgtttgga ccttcgttaa tctcaaacct ttggaaccat ctctcctcca aaacctcctt   2100
tgggtaagac tgtatgtttg ccctctctct tcttttcgca gactttagaa gatgttctgc   2160
ccatttaagt tccttcactt tggctgtagt cgctgttctc agtgcctgct tggtcactag   2220
ttctcttggt gagtactttg acaaatttac ttgtaaccga gcccaactgt gacaagaaac   2280
actgaaaagc aaataattgc tcctgaagtc tagatagcat ctaaaaacat gcttcatggt   2340
ttcaaggatc atatattgaa accccaggga tcctctagag tcgacctgca gcatgcaggg   2400
gggggggggg gggggggggg gggggggggg gggggggggg gggggggggg gggggggggg   2460
gggggggggg gggggggggg gggggggggg gggggggggg gtgcataagg aaagactatc   2520
tcaacgtctt attcctcagc ttacattaga tttgaaactc tagtcaccta aaatgcaaat   2580
ctcatttact taccatcaga gatattaatg acctatagaa ttcagcataa ataaagtttc   2640
atgtatggat attagcttat ggttctagtc actgctaatt gaaacctgtg atattgctgt   2700
ttgttttgac tcctatgaaa taacattctc ccattgtacc atggatgggt ccagaaacat   2760
ttctcaaatc ctggcttgaa aaaataaata agtaatctaa agaataataa ttctctactt   2820
gctctttgaa tcttgaccaa ttgctgcatt tacctattgt tacaggagga aaagacaagg   2880
agctgaggct aacgggtggt gaaaacaagt gctctggaag agtggaggtg aaagtgcagg   2940
aggagtgggg aactgtgtgt aataatggct gggacatgga tgtggtctct gttgtttgta   3000
ggcagctggg atgtccaact gctatcaaag ccactggatg ggctaatttt agtgcaggtt   3060
ctggacgcat ttggatggat catgtttctt gtcgagggaa tgagtcagct ctctgggact   3120
gcaaacatga tggatgggga aagcataact gtactcacca acaggatgct ggagtaacct   3180
gctcaggtaa gacatacaca aataagtcaa gcctatacat gaaatgcttt gtgggaaaaa   3240
atgtatagat gagttaaaaa caaaaaggaa ccagttttct ataagtcatc tagtccatgt   3300
ataaaattac ccaatccatt actaaaagac cacttctggt attttacaca tgacaaagcc   3360
catattaaaa aaaaaaaatt cagaagagat tctgaatgct ataataaatg agcaagtgac   3420
tagcttcaat tttatattag gtcattctac cttctacttc tacatgaaaa tatcataatg   3480
tctaagttaa ttccttgtcc cctttcccaa taaagcactg ctttcatgca ctggcctatg   3540
aatcatgaac tttttgccct ttaactgatg atcaacttac caaatcaaga aataaatatt   3600
cttagcactg atccttttt gttgttgttg gaggaagaat gttttgcaaa gtagaattgc   3660
tttttctgt ttaacagtgc tattcatttc atttacatgg tcgttttaat ttataaaaca   3720
tttcataagt ttcacctcat atgcccttac aataactcag gaagttatat gttagacctt   3780
tctgctgaca aatcccagag tcatgtttct gacccagttc agattccttg gcttcccatt   3840
tctctttgct catgtcattg acctttatgc agccctctta cctcccacct ttctattaca   3900
gaccatctcc tccataggac tggtgttaga aagtactaat ctctacccag gcattgtggt   3960
gcaatgtggg cagcacaggc tggtatctag aaaaatgctg aagtgaattc cagctcagct   4020
gctcgttaat actatcgttt taagtaagct gttcaatcct ttgaaattca ctttctgagc   4080
actcagtgat ataataaatg tagagctact ggtacactgt ctggtatgta ataggtgtta   4140
```

ccaattaacc ttagtttcct catgggtcac tggttctcat tacctagaca actcatttct 4200
ctttcttcct ctttctcttt ctccattctc ctcctccttc ttcctcttct tcttgtctgt 4260
tattgttata tcattttgct gagaaagtta agaaataaca actctaacct ctacatcgac 4320
cacctagagc aaagttaaaa ataataataa accttgccag actcttacta taattgttgc 4380
tgtctataga gttgactgtt taagttaaga catcagtata tatttttaat ttttgtgttt 4440
ttttttcat actttttacat gaggatcctt tatataagga tgagttaaac aaacttgatt 4500
tttgaagttt ataccccctga ggctcaactg cataataata gaaagggatc catagcctct 4560
caaggactta actagtttca tgagttttca gaatctgaat ttctgagatt ctccacccca 4620
attaaagctc aagcctcaga acatatatcc ttctcttggt aaattctatt cttatcacat 4680
gcgtaataat aaaaaagaga gatgttggag acagattttt ttcctcacat tctgtctcta 4740
ctgttttcta ggtgtttgat tctgtgttat ttaacctcag tttgcttatc tgtgaagtag 4800
ggattatggt aataacatat aatgctttat gttgtaaaga ctaaagaaga tagcatatgt 4860
aacacatttg gaacagggaa tgcatatttt gattgtgagc tcttattatt attaccattc 4920
agccctaata aaaatcttgg taagtggaag gctttggatt tcagaacttt taaaatctaa 4980
ttactttttc aaaaaagaac ttcttagggt tttttttttt taaccacaaa gtgtttctat 5040
tttttaggtg tcccaaaatt tcgttccaaa tatctttttc tcagatattt tagtcctcat 5100
agaacaccta gggatagtgg atagagaaaa ttttctttat taaaaagctg ttctttgcta 5160
aaaattgtag caggtacttt tgggaggggg gaaaactttg attcagaaac tgctaagaca 5220
tggagtgttt tgactaattt ttcctcaatt tttaatgttt tttataccat agggtacttt 5280
tgcaaactat tatgcatact tatatatttt tactttttc ctgtctttta acttccaaat 5340
tcaacttcag acaattattc atgcactaaa ctgtttgtag taagaaagat taaaattaaa 5400
aaattaacca ttcaacaaat gactggtttg ccatttttac tactttgttg tatgaacaat 5460
tttttttct acaaatgaat actttgagtc tgatttatcc attcctacat aaaagttttt 5520
actatatctt agtattggaa ggaaacaaaa caaaacacaa tgtaaatttt aatctataaa 5580
ttttgggggg gtaaatatac atagatgaaa gtcttaacca ttaattagag tcaaaagatt 5640
aaaattctcc aatatgtgaa cttaggctgc atccaaaatg aagcatcatt tttaaggaca 5700
gcatcaaaag tgaccagagg aattttactt tctttctttt tttttttttt gaattttagt 5760
ttctaaactc acttctgaat aaatacaact tctaaattct cgtcttttct ctactctaga 5820
tggatctgat ttagagatga ggctggtgaa tggaggaaac cggtgcttag gaagaataga 5880
agtcaaattt caaggaacgt ggggaacagt gtgtgatgat cacttcaaca taaatcatgc 5940
ttctgtggtt tgtaaacaac ttgaatgtgg aagtgctgtc agtttctctg gttcagctaa 6000
ttttggagaa ggttctggac caatctggtt tgatgatctt gtatgcaatg gaaatgagtc 6060
agctctctgg aactgcaaac atgaaggatg ggaaaagcac aattgcgatc atgctgagga 6120
tgctggagtg atttgcttaa gtaaggactg acctgggttt gttctgttct ccatgagagg 6180
gcaaaaaaag gggagtaaaa gtcttaaaag ctcaaactgt taaaaacata atgatgattg 6240
cttcttttat catcttatta ttatctaatt tcaggtcgaa attctagtac ctgtgcagtt 6300
ttttacctta actgaaatta agataaatag gatagggagg aaggatgagc agtgacattt 6360
aggtccaagt catgaggtta gaaggaaatg ttcagagaat agcccattcc ctcagccctc 6420
aaagaaagaa agaaagaaaa agaaaaaaaa aaagaaagct taactagaaa attttgttct 6480
ctggatgttt tagaggcaaa ccatcccttt atcattccta cctacaaagc cttctcttaa 6540

```
tcacattacc caccctttcc tactatagtc aggggggggg gggggggggg gggggggggg   6600
gggggggggg gggggggggg gggggggggg gggggggggg gggggggggg gggggggggg   6660
gggggggggg gtgaaaaaag aaccaaacaa tttcaacaaa aaaccaaaca attccaacaa   6720
aattggtcca ataagcaaac ctctagataa atttcagtgc cctggatgtt ttgttaggaa   6780
ctcttcctac aatgcgtgct ttccattctg aaaagtccta tctacttgcc tgatccactt   6840
ctccttccat cctaaacgat tttcagtggt agtatattac tgttgtctct gtctctactt   6900
atatatcttc cccttttcac tcactcctct caggtacagc tcttcagttt gcccttattc   6960
ttgtttcctt gtcaatgact tgttttgtgt ccctcttaca gatggagcag acctgaaact   7020
gagagtggta gatggagtca ctgaatgttc aggaagattg gaagtgaaat tccaaggaga   7080
atggggaaca atctgtgatg atggctggga tagtgatgat gccgctgtgg catgtaagca   7140
actgggaggt ccaactgctg tcactgccat tgtcgagtta acgccagtga gggactggac   7200
acattggctc acacacatac agccatgaca cgatctgctc tatggtccga tgattaaagg   7260
gggggggggg gggggggggg gggggggggg gggggggggg gggggggggg gggggggggg   7320
gggggggggg gggggggggg gggggggggg ggggggggag aagagctggt ggacatttct   7380
ggaaaggaac caaaacccgg aagggccttg ttcttcagga tttgggatgg attggggagg   7440
gagaaaattg tttctaatat ttcttggtgg gaattctttt acagttgtga caaatctttc   7500
acatattctt catttgagta gtttggaggg ttgtctgact gttttctata ataaatgtcc   7560
caagtgctat gaggtaccac atttcaaatt ctaattctac ctgaagctcc aaaaagacaa   7620
aatgttatag gtcttttctt tatatctaat ttgcttatgg tttttagcca ttgacaattt   7680
tttttcttta actcttgaaa ctataaccct atttctaacc aaattcatgt tctatactgg   7740
ctcttcaaaa acccaggaga tgggaaagcc agaatctcca gtgtttcagc ttctgggaag   7800
gagcaagttt ttaaaaatac cctctgggag ctaaattcca catgtatcta tggcctaagt   7860
gtatgtttat tttgcagatg gatcagatct ggaactgaga cttaaaggtg gaggcagcca   7920
ctgtgctggg acagtggagg tggaaattca gaaactggta ggaaaagtgt gtgatagaag   7980
ctggggactg aaagaagctg atgtggtttg caggcagctg ggatgtggat ctgcactcaa   8040
aacatcatat caagtttatt ccaaaaccaa ggcaacaaac acatggctgt ttgtaagcag   8100
ctgtaatgga aatgaaactt ctctttggga ctgcaagaat tggcagtggg gtggacttag   8160
ttgtgatcac tatgacgaag ccaaaattac ctgctcaggt aagaatttca atcaatgtgt   8220
taggaaattg cattctactt tcttttacat gtagctgtcc agttttccca gcaccacttg   8280
ttgaagagac tgtcttttct tcatcatata gtcctacatc ctttgtcata aattaattga   8340
ccataggtgt gtgggtttat atctgggctc tctattctgt tcctttgatc tatatgtctg   8400
tttttatgcc agcaccatgc tgttttgatt actatagctt tgtagtatca tctgaagtca   8460
ggaaacatga ttcctccagc tttgttcttc tttctcaaga ttgttttgtc tattcagagt   8520
ttatgttccc atgcagattt aatttttaaa tttatttaat ttttattttt tatttttaat   8580
ttaaattaat ttaaattttt tatttcccaa cgtacagcca agggggccag ggtaaccttt   8640
acatgtatac attaaaaatt tcaggttttt cccccaccca tttctttctg ttggcaagta   8700
aatttttgaa caaagtttcc caatgctttt taaggggaat tcccttgggg gggggggggg   8760
gggggggggg gggggggggg gggggggggg gggggggggg gggggggggg gggggggggg   8820
gggggggggg gggggggggg gggggggggg gggggggggg agacgaaatt gactatattt   8880
```

```
tctttgttgg gaatctttta cagttgtgac aaatctttca catattcttc atttgagtag   8940
tttggagggt tgtctgactg ttttctataa taaatgtccc aagtgctatg aggtaccaca   9000
tttcaaattc taattctacc tgaagctcca aaaagacaaa atgttatagg tcttttcttt   9060
atatctaatt tgcttatggt ttttagccat tgacaatttt tttttcttaa ctcttgaaac   9120
tataacccta tttctaacca aattcatgtt ctatactggc tcttcaaaaa cccaggagat   9180
gggaaagcca gaatctccag tgtttcagct tctgggaagg agcaagtttt taaaaatacc   9240
ctctgggagc taaattccac atgtatctat ggcctaagtg tatgtttatt ttgcagatgg   9300
atcagatctg gaactgagac ttaaaggtgg aggcagccac tgtgctggga cagtggaggt   9360
ggaaattcag aaactggtag gaaaagtgtg tgatagaagc tggggactga aagaagctga   9420
tgtggtttgc aggcagctgg gatgtggatc tgcactcaaa acatcatatc aagtttattc   9480
caaaaccaag gcaacaaaca catggctgtt tgtaagcagc tgtaatggaa atgaaacttc   9540
tctttgggac tgcaagaatt ggcagtgggg tggacttagt tgtgatcact atgacgaaac   9600
caaaattacc tgctcaggta agaatttcaa tcaatgtgtt aggaaaaattg cattctactt   9660
tcttttacat gtagctgtcc agttttccca gcaccacttg ttgaaaaaac tgtctttttc   9720
ttcatcatat agtcctacat cccttggcca taaattaatt gaccataagg ggtgtgggtt   9780
taatatccgg ggctcctcaa ttcgggtccc ttggatccta aaagccggtt ttataacccg   9840
acacatggcc tgtttttgac taaataaaac ctttggaaaa caatcccgaa ggtcgaggaa   9900
catggaatcc ccccaacaaa ggaccttctt tccccaaaaa tgcggctcag ccaactcaaa   9960
aagattttat gaatcacaaa ccgcacatta tcttcctaaa attactattc ctatgtttta  10020
atttgcaaag tcattccgat atagttggcg cagagtaact catttagata tccaccccac  10080
cagttcctca ctcaagtaag gggggggggg gggggggggg gggggggggg gggggggggg  10140
gggggggggg gggggggggg gggggggggg gggggggggg gggggggggg gggggggggc  10200
ccccatgtga gattttgtgt gtcctttaag agtggagtct ctatttccca ctgctctctg  10260
gttctcccca aagtaagccc tgctggcttt caaaacttct gggagcttgc cttcttggta  10320
taggactcct gggctaggga gtctaatgtt tggcttagac cccttactgc ttgggaagaa  10380
tctctgcaac tgtaatgaat tatcttccta tttgtgggtt gctgaggata tggtcttaac  10440
tgttctgtgt tctacccctc ctatccatct tgttgtggtt ccttctttat atctttagtt  10500
gtagaaaagt ttttcttatc aacagttgct ctgtaaattg taacttgggt gtacacctag  10560
taggaggtga gctcagggtc ttcctactct gccatcttgg ccatgtcctc taaacatttt  10620
ggtgtatttc actgcaacct ttttaaaaat ctcaaaagtg agctgtgatt ggctagtctt  10680
gtggataatc tctagcattt gatgctaatc atatttatac aaatactttg ttgaaaagtg  10740
atgccttttt aactattatt aaaaaacgta ttgacataac tattgctatt atactgaaaa  10800
gaaagacctt agagaaaata gcataagagc aaaaccatta aacatggaga catctagtca  10860
tagggtggaa attttatgtg gtccatatcc cctaaccagt ggctttacac caggcacatc  10920
ctaactaaga tctgctccca agtgtcttcc ctgatgcttt aaattgtgtt acatggaaac  10980
tatcctttga tgaagaaatg caacctttta aaatacaaca ttgaaacttt tgtgctttaa  11040
ttttgctttt caacattttt tctttttaaa agaagaaatt tatttgtttt tttaaatttt  11100
aatggccacg gcatatggaa gttctcaggc cagggataga attcaagcca caggtgcgac  11160
ccatgccaca actgctgcaa caccagatcc tttaacccac tgcaccaggc cagggattga  11220
agccttgcct tactgacaat ctgagccact tcagtcagat aaagaaattt cttcattaag  11280
```

```
cagagtattc acatggttta aacttcaaaa tattaaagtg taaactcttt ccccaccact  11340
gtccccagct caccaactct acttaccaca gacaactgat gtggttaggg tatttaaata  11400
gtaaatccaa gaaaatataa acaaatccgt atatataggt ttcaccccat tttattatcc  11460
taatgttgca tatcatataa actatactgt cccttgggta ttcacttagt aaaatatttt  11520
gatcataatt tcctatcagt atttaaagag ctttctgaaa ttatttctgt ataacatttc  11580
ttttctcatc ggtagggggg gggggggggg gggggggggg gggggggggg gggggggggg  11640
gggggggggg gggggggggg gggggggggg gggggggggg gggggggggg ggggaatggg  11700
aagaaaaaac caccatggtt aatttttttt atccctctac acccgggaaa attacccttg  11760
gggccacact tttctataga aaggggatta tttaaaaggg tctgaaaaag aatttttttt  11820
tcgaaagggg aaatatttgg cctaacttag tcacataagc catgttctct ggcaagttag  11880
gtaacataca tttttgtcat tgggggcaac aaaaacaatt ttccttttgg acctttttggg  11940
actccgcatt ggttagggaa ggggaagtat attggaattc ggaaaattcc ttccaaatta  12000
aaaaaggttt gttattttca tattaaccta tttcatatta attagcatga attccagcgc  12060
cattaaaagg gaaaacacct ggagtggtaa gaaaaaagtt ttttttctc tttttttttt  12120
ttttttttta atggccacat ctgtggcatg tgaagttccc aggctagggg tcgaatagga  12180
gctacagctg ccagcttgca ccacagccac aacaatgcca gagccaagcc tcatctgcga  12240
cctataccac aactcatggc aatgctggtt ccttaacccc ctgagtgagg cctggggtca  12300
aacccacatc ctcatggata ctaaccggct ttgttaccgc tgagccatga gggaaactcc  12360
ctttttctca ttgaaaataa gtcaaataga taagcagctt aaggctgttt gggtgattct  12420
gtggtccagt aattatcaaa tcctactgga caagaataga gaatgtgcaa atgagggaac  12480
gtgttggtga gatcaggctc tgcccactga gctatcctct gtcatgggcc ctgtgctgtt  12540
ctcagagctg tacttcctag ggcattgttc tcatttcaat tctgagttca gtgtggagag  12600
tatacgtgtg tgggggctgc acgcttttca caacccactt tctgctgata ctgatttagg  12660
gatccttgga ttgctttaca gttgagtcat cattaactag tgtcacttgc cttcaaagtc  12720
agcaaaataa ttgtctccaa actagtaggc ttctagtgta tttgctttaa tccaatgcca  12780
tgtgaaagta acatggtcaa agaataagtt atataccttg acctaccctg tgaccaggct  12840
cttcctctta atttattgac cactgcctta aggtcatttg aaaccatggg tttgggagga  12900
aggcaaggcc taaatcccgt ctttgttgga aggctcactg tccttgtctt tagagcatca  12960
ttttttttta aactggggta cagtttattt acagtgttgt gtcaatttct gctgtacagc  13020
acagtgaccc agtcatacac atacatacat tctttttctc atactatctt caattttatt  13080
ttctgctaag tctgccattt tatcatcacc tcagtttgaa ggacaggata tttagagttt  13140
gttttttttt tccccccaat cctgcaattt ctaaattata agactctcaa ttagccgtat  13200
ataacagctg caggcacagg atgtctccct cacaaaattg gtatttttcc ttccatttct  13260
tcttgcagtt tggctatttc ttgtctgagt tcatctctct ttttaagtgt taaaaagggc  13320
aaggaggatt catgctatgt caacattatg attttttctt ttctatactt gataagagta  13380
tacttttccc aaatgtcatc caacttttca gcatcagttt ggacatggtt ttcttttcaa  13440
ggtggtattt ctctaatgtc acttgaataa caagactcgt tagttctcca ggctacaata  13500
tcctagtctg agtatattct gcatgttaat tctattcagc cacatccata atttaggttt  13560
tattcctgga acacctcact tttttttttt tttttggtct ttttatagcc ataaccatgg  13620
```

```
catatggagg ttcccaggct aggggtctaa tctgagcttt agccactggc ccatgccaca  13680
gccacagcca tgccacatct gagccacatc tgtgaccttt tccacagctc acagaaacac  13740
cagatcccta acccactgag tgaggccagg ggtcaaacct gtaacccttc catggttcct  13800
agtcagattc gttcctctgt accacgatgg gaattcctaa tacctcactt atgataacac  13860
attctgaatt atttaggatt ctattatact gcatgtaata gaaatcccaa atagcaaaat  13920
ttgcaactta aggcaggttc ctgtctttac aaaatcatgt tttcctttgc tatatgtgca  13980
ctttgctttc ctctgtgaat tcccttttt gttatatttc tatagctttt ggaaacactt  14040
ttacttattt gggggggcct agatttttaa ccctctcctt gtttttctag aaatagagtt  14100
tataatttta tttcttcatt tacttgatac tttcaagaga ttcccaggaa aaaaattatg  14160
gaaatactgt ctctgtgcct gccaagttca aactaagaat tgtataatct gttttaattc  14220
ttaagcattt atagatgaca aggctttgtg tctgataggg gccagcgaac tcagtaaaga  14280
gggaagatga gaaagataat ggcaagaatt tatccctgaa gtgtagtttt gacaaaccag  14340
tcacaaagag gtctaagaaa ttttggtcac aaagttgttt tgaatcccag gcattttatt  14400
tgcaatgatt gcatatgttc tggaaaggac atctgaacct aagaaatagt tcatttgcat  14460
tgtgttatat tttactaagg tctgagaaat aatcttgaga tgagaatgaa ctctacttct  14520
tcagagtctg gaaggaataa attatgaaaa tgtattaatg cttctttaaa ccatattgta  14580
tatttatcta ttactaaaca aaaagaagta gctctattta tttatttatt tatttattta  14640
tttatgtctt ttgtctcttt agggccacac ctgtggcata tggaggttcc caggctagag  14700
gtccaattgg agatgtagca gccagcctat gccagagcca ccgcaacacg ggatctgagc  14760
cacgtctgtg acttacacca cagctcacag caacgcctga tcctcaaccc actgagcgag  14820
gccagggatc gaacccatgt cctcatggat gctagttggg ttcgttaact gctgagccat  14880
gatgggaact ccaaattaat tatttcttat atttgttctt catatattca tttctataga  14940
aagaaataaa tacagattca gttaatgatg gcaggtaaaa gcttaactta ttaatcaaag  15000
gagttaatcc aggcacaaaa attcaattca tggctctctg ttaaaattta ggtataggtt  15060
tagcaggaag aaaaggttag tagatgcaga ctattacatt tagaatggat ggacaatgaa  15120
gtcctactat acagcacagg gaactatatc caatctcttg ggatagaata tgatggaaga  15180
caaaatcaga acaagagagt atatatatat gtgtgtgtgt gtgtgtgtgt gtgtgtgtgt  15240
gtgtgtgtgt gtgtgactgg gtcaccctgc ggcacagcag aaattggcag aacattgtaa  15300
atcaactata ctttaatagg aaaaatactt ttaagggcta aatttccaat attctaacca  15360
tgtacacaga gtaaatgtca taaggatgcc agtctgtgta gagattgatg tgttactagc  15420
agattcatga aataaaggct gaggatgtag tccccaagtc acttctgagt ggaagaattt  15480
ctcctttgtc ctggactcaa atattttagg ataaaggaaa aaagaagata tttatagaag  15540
ggacttgttt tcaagtactt gacaaaattt caccattaaa gagaaatttg tgggagttcc  15600
catcgtggct cagtggaaac aaatccaact aggaaccatg aggttgtggg tttgatccct  15660
ggcctcactc agtgggttaa ggatccggtg ttgccgtgag ctgtggtgta ggttgcagac  15720
acggttctga tcctgcgttg ctgtggctgt ggctgtggtg taggccagca gcaaacagct  15780
ctgattagac ccctagcctg gaaacctcca tatgccacag gtgcagccct aaaaagacaa  15840
aaaaagagaa aagacaaaaa aaaaaaaaaa aaaaaaaaaa aaaaaaaaaa aaaaaaaaag  15900
aacccccaga ggtatttatt tgtttttgcc ttttttcact gactgttctt tgtttgtttg  15960
tttgagactg atctagaaga ctagagatta caagaaatat ggatttggct cactctaaga  16020
```

```
aactgctttc attccaaggt ttgggtctat ccaaaagtgg aatagaatca tatgaatact  16080
agtttatgag tatttagtga gaggaatttc aagctcaaat aatgattcag caagattaaa  16140
ttaaggaggg aattttcctt gtggctgagt gggttaagga cccaatgttg tctctgtgag  16200
gatgtaggtt ccatcctggg ctttgctcat taggttaagg atctggcatt gctgcagctc  16260
agacccagtg ctgccctggt tgtggcttag gccaaagctg cagctccaat tcaatctctg  16320
gcctgggaac ctccatgtgc tacaaggtgc ggccttaaaa ggaaaaaaaa aaaattaaat  16380
caaggactca agagtctttc attatttgtg ttgtggaagc tatatttgtt ttaaagtctt  16440
agttgtgttt agaaagcaag atgttcttca actcaaattt gggagggaac ttgtttcata  16500
catttttaat ggataagtgg caaaattttc atgctgaggt gatctatagt gttgtaatgc  16560
agaatatagt cagatcttga acattttagg aagttggtga gggccaattg tgtatctgtg  16620
ccatgctgat aagaatgtca agggatcaca agaattcgtg ttatttgaca gcagtcatct  16680
ttaaaaggca tttgagaaag tccaatttca aatgcatttc ctttctttaa aagataaatt  16740
gaagaaaata agtctttatt tcccaagtaa attgaattgc ctctcagtct gttaaaagaa  16800
actcttacct tgatgattgc gctcttaacc tggcaaagat tgtctttaaa atctgagctc  16860
catgtcttct gctttatttc tggtgtgcct ttgactccag attacagtaa atggaggact  16920
gagtataggg ctaaaaagta gagagaatgg atgcatatta tctgtggtct ccaatgtgat  16980
gaatgaagta ggcaaatact caaaggaaag agaaagcatg ctccaagaat tatgggttcc  17040
agaaggcaaa gtcccagaat tgtctccagg gaaggacagg gaggtctaga atcggctaag  17100
cccactgtag gcagaaaaac caagaggcat gaatggcttc cctttctcac ttttcactct  17160
ctggcttact cctatcatga aggaaaatat tggaatcata ttctccctca ccgaaatgct  17220
atttttcagc ccacaggaaa cccaggctgg ttggagggga cattccctgc tctggtcgtg  17280
ttgaagtaca acatggagac acgtggggca ccgtctgtga ttctgacttc tctctggagg  17340
cggccagcgt gctgtgcagg gaactacagt gcggcactgt ggtttccctc ctggggggag  17400
ctcactttgg agaaggaagt ggacagatct gggctgaaga attccagtgt gaggggcacg  17460
agtcccacct ttcactctgc ccagtagcac cccgccctga cgggacatgt agccacagca  17520
gggacgtcgg cgtagtctgc tcaagtgaga cccagggaat gtgttcactt tgttcccatg  17580
ccatgaagag ggtagggtta ggtagtcaca gacatctttt taaagccctg tctccttcca  17640
ggatacacac aaatccgctt ggtgaatggc aagaccccat gtgaaggaag agtggagctc  17700
aacattcttg ggtcctgggg gtccctctgc aactctcact gggacatgga agatgcccat  17760
gttttatgcc agcagcttaa atgtggagtt gccctttcta tcccgggagg agcacctttt  17820
gggaaaggaa gtgagcaggt ctggaggcac atgtttcact gcactgggac tgagaagcac  17880
atgggagatt gttccgtcac tgctctgggc gcatcactct gttcttcagg gcaagtggcc  17940
tctgtaatct gctcaggtaa gagaataagg gcagccagtg atgagccact catgacggtg  18000
ccttaagagt gggtgtacct aggagttccc attgtggctc agtggtaaca aactcgactg  18060
gtatccatga gggtatgggt ttgatccctg gccttgctca atgggttaag gatccagcat  18120
tgctgtgagc tgtggtatag gttgcagact ctgctcaggt cccatgttgc tgtgattgtg  18180
gtgtaggctg actgctgcag cttcaatttg acccctagcc cgggaatttc cataggccac  18240
acgtgcagca ctaaggaagg aaaaaaagaa aaaaaaaaaa aaagagtggg tgtgcctata  18300
gtgaagaaca gatgtaaaag ggaagtgaaa gggattcccc cattctgagg gattgtgaga  18360
```

agtgtgccag aatattaact tcatttgact tgttacaggg aaagtaaact tgactttcac 18420
ggacctccta gttacctggt gcttactata tgtcttctca gagtacctga ttcattccca 18480
gcctggttga cccatccccc tatctctatg gctatgttta tccagagcac atctatctaa 18540
cactccagct gatcttcctg acacagctgt ggcaaccctg gatcctttaa ccaactgtgc 18600
caggctggag atcaaaccta agcctctgca gcaacccaag ctgctgcagt cagattttta 18660
accccctgtg ccactgtggg tatctccgat attttgtatc ttctgtgact gagtggtttg 18720
ctgtttgcag ggaaccagag tcagacacta tccccgtgca attcatcatc ctcggaccca 18780
tcaagctcta ttatttcaga agaaaatggt gttgcctgca taggtgagaa tcagtgacca 18840
acctatgaaa atgatctcaa tcctctgaaa tgcattttat tcatgtttta tttcctcttt 18900
gcagggagtg gtcaacttcg cctggtcgat ggaggtggtc gttgtgctgg gagagtagag 18960
gtctatcatg agggctcctg gggcaccatc tgtgatgaca gctgggacct gaatgatgcc 19020
catgtggtgt gcaaacagct gagctgtgga tgggccatta atgccactgg ttctgctcat 19080
tttggggaag gaacagggcc catttggctg gatgagataa actgtaatgg aaaagaatct 19140
catatttggc aatgccactc acatggttgg gggcggcaca attgcaggca taaggaggat 19200
gcaggagtca tctgctcggg taagttctgc acatcacttc gggttacagt gatttaagaa 19260
acaactaagg tggggcaaag ggtagtgagg catatccatc agagcaaatt ccttgaaata 19320
cggactcaga gggaaccatt gtgagattga ggttcccaga ggtgtggatt taatgaatta 19380
gtgttacctc atgtacaagg tagtatacta ccagaaagat aaaaattcag aagcgagttt 19440
gcagcaaaac tcatagggag aacttctttt ataaataata tgaagctgga tatttagtgc 19500
accacctgat gaccacttta ttaataaata aagagttcct gttgtggcgc agcggaaatg 19560
aatccgacaa ataatcatga gtttgcgggt ttgatccctg acctcgctca gtgggttggg 19620
gatctggtgt tgccatgagc tgtggtgtag gtcgcagatg ctgcttggat cctgctttgc 19680
tgtggctgtg gtataggctt gtggctacag ctccgatttg accgctagcc tgggaacctc 19740
catatgctgc gggggtggcc ctcaaaagaa aaataaataa ataagtaaat aaataagtag 19800
tttaaaaagg acaagaagaa atatatttgg tgttatattc tacagagaca aagataatca 19860
ccatgcccga ttgatttttc aaggcatata aatgagacgt catgggagca aaaatggtca 19920
taatacaatg cccttgtttt gtgtacatgg taagatttta gaaagcattg tgaggtaaaa 19980
aagtgtactc agttataata tattggggaa aacagtacta tgagaagtaa aaaaatctac 20040
atgccggaag ttattttttt aatgtctctt ttagagtcgc acatgcggca tatggaggtt 20100
cccaggctag gggtcgaatc agagctatag ccactggctt atggcacagc cacaacaaca 20160
ctagatctga gccacatcag cgacctatac tatagctcat ggcaatgcca gatccttaac 20220
ctactgagcc aagccatggg tcaaatccag gtcctcacgg atcctaggca aattcatttc 20280
tgctgagcca cgaagggaac tcctcagaag tgattttgat gttactttct tttcatgaca 20340
aatctggtaa agtacataca catagaaact gaagtgtcag aaagggaaat atttcatttt 20400
aaggtaatgt atacaaaaca gtggttttac catctgagta tctcgctaaa ttttaactat 20460
caaggacaat tgccaaaaaa aaaaaaaaaa gagagagaga gagaacagaa tagggttatg 20520
aagctaaaat cacagggtta tgaagctaaa atcacagtaa tttagggaga aaaaaatcca 20580
aagcatgtaa ttgataaaag gttctgagcc tttgtttgag atttagaatt caacttagaa 20640
ataccggtgg tattttaaag cagtccataa gtataaaatc caaggctaaa aaaccagaag 20700
gtatttgtag aacaaatata ttttaataag ctctaccaag tcatccagaa gctattaaag 20760
aattactggt cactgacata gtgtacctgt tttcaaggcc attcttacat cagaataaag 20820
ggagagcacc ctctgaatct tcagaaaaga tgtgaaagtg ctaattctct atttcatccc 20880
agagttcatg tctctgagac tgatcagtga aaacagcaga gagacctgtg cagggcgcct 20940
ggaagttttt tacaacggag cttggggcag cgttggcaag aatagcatgt ctccagccac 21000
agtgggggtg gtatgcaggc agctaggctg tgcagacaga ggggacatca gccctgcatc 21060
ttcagacaag acagtgtcca ggcacatgtg ggtggacaat gttcagtgtc ctaaaggacc 21120
tgacacacta tggcagtgcc catcatctcc atggaagaag agactggcca gcccctcaga 21180
ggagacatgg atcacatgtg ccagtgagta tccattcttt agcgccactg ttatcttctg 21240
atctacctaa gcagaagttt tataatctgt agttaatccc tattctacct ggatgatggg 21300
attcattctg tttaatttgg tgtgcaggta ttcagcatca gtgatcattt tcccaaagac 21360
catcatgctc tgatggtctt ctcaaaagtt ctaatcagtt gcttcctccg tgaacagttg 21420
aggagcagag aatatgtaat tcagaatttg actattgaat catcccattt ttctttcaca 21480
tagtcttttg ttgcactgaa tataaggaga gaagcagtca gaaagatcaa tcctgaatta 21540
tttctccatt ctacatctgt tttaaatttc aaaaaaaaaa attgttatag gtgatttaca 21600
atgtctgtca atttctgctc tacagcaaag tgacccagtt atttacatat acattctgtt 21660
tctcatattt ttaaaccagg agatttctat ctgcctggcg gtttgaggga atttaacatt 21720
atgcatttat gttaacttta ttcacctgat gttttctaag tcatactgag attcttatgc 21780
ccaggatgga atacacctgg tttgctggaa agacatgtgc tttcataaag acgaattttg 21840
gaaaaaatat aaaatttaaa aggcccatta aataagcaaa gttttaagag atttcaaaaa 21900
aaatttcatc tctctctttt cctctttgac ctcttgggca cgttcatctt ctcaaatatg 21960
atcttggtgt ttctgacttt tcagacaaaa taagacttca agaaggaaac actaattgtt 22020
ctggacgtgt ggagatctgg tacggaggtt cctggggcac tgtgtgtgac gactcctggg 22080
accttgaaga tgctcaggtg gtgtgccgac agctgggctg tggctcagct ttggaggcag 22140
gaaaagaggc cgcatttggc caggggactg ggcccatatg gctcaatgaa gtgaagtgca 22200
aggggaatga aacctccttg tgggattgtc ctgccagatc ctggggccac agtgactgtg 22260
gacacaagga ggatgctgct gtgacgtgtt caggtgaggg cagagagtct ggattgagct 22320
tggaagctct ggcagcaaag agagggtggg cggtgacctg cattgggtaa agattggaag 22380
gtccagccta aggatctggt ggtgggggga gacatgatgt ttcagtctga agaatgatga 22440
aaacctgtgt ggttacgcat gggccttcgc cgaggaaagg gacataacta ccatgtatcc 22500
tcctgcagag ggaggaagaa ctaggggatt ctagttttgt gtgggaagga gcagtttact 22560
tggctcagga ggcactaaag gctcagatag gaaacagaga tctgttccat tcttactccc 22620
agaactgatt ctcttctctt ttctcctaca gaaattgcaa agagccgaga atccctacat 22680
gccacaggta tatcaaaaag tttaagaaca tgggacccat tgtctgcatt ttgtggaatc 22740
cctcttatta agacattctg ggtcagaagt tctgaggatt tgacatttac ttcagctatc 22800
tgttatctta cccaagagag ggatggtaac taggaaccca ggtcttttag ctaagacatt 22860
atcacctctt gtgatgttta cttgttctca ggtcgctcat cttttgttgc acttgcaatc 22920
tttggggtca ttctgttggc ctgtctcatc gcattcctca tttggactca gaagcgaaga 22980
cagaggcagc ggctctcagg tctgaacaaa attacggtct ctctaatgtt tctatgggag 23040
aagaagcctc tctggataat aaaacaaaaa aattacattc aagtatcagt tggccagaaa 23100
gagggaacct agaagaggtt taagcagttt ctccgaaaca gggaacaaga attcagagaa 23160
gaaaaggcac attggctgta ctgatgatac ctgcactcgc tatgtatgtt taatggggga 23220
cagtagagaa ttgatagttt agaaggagta tgcttatatg gttctggatg aatcctgtat 23280
ccccccaaac atttattttc tcttactata tacttattac taatttaact cttctgtcaa 23340
gccatgtgct aggttctgaa gatggttcag acttggataa ccaagtgctt ttgttttcat 23400
ggaatttcca gtttagtgga agagataaat atgtaaacaa ataaatgggg gggggggggg 23460
gggggggggg gggggggggg gggggggggg gggggggggg gggggggggg gggggggggg 23520
gggggggggg gggggggggg gggggggggg gggggggggg gggggggggg gggggggggg 23580
gggggggggg gggggggggg gggggggggg gggggggggg gggggggggg gggggggggg 23640
gggggggggg gggggggggg gggggggggg gggggggggg gggggggggg gggggggggg 23700
gggggggggg gggggggggg gggggggggg gggggggggg gggggggggg gggggggggg 23760
gggggggggg gggggggggg gggggggggg gggggggggg gggggggggg gggggggggg 23820
gggggggggg gggggggggg gggggggggg gggggggggg gggggggggg gggggggggg 23880
gggggggggg gggggggggg gggggggggg gggggggggg gggggggggg gggggggggg 23940
gggggggggg gggggggggg gggggggggg gggggggggg gggggggggg gggggggggg 24000
gggggggggg gggggggggg gggggggggg gggggggggg ggggggggtt ggcgggcccc 24060
cctcgaggtc gacggtatcg ataagcttga tatcgaattc gtgagccaga ggacgagact 24120
agagatggat gatgactacg ttatgcttgc actgctgggg aaaagcacac atagggaggg 24180
aacgttttat tatgacccag tccctaacct atgacctctg ttatcagttt tctcaggagg 24240
agagaattct gtccatcaaa ttcaataccg ggagatgaat tcttgcctga aagcagatga 24300
aacggatatg ctaaatccct caggtccgtg ggttctttga ggggctgtag ccctggggtt 24360
cagatcagca gctgcagttg aggttgaggc atgctacttt gcatagcagt agaaagaaat 24420
ctcaactgta ataggaagct tgggatgcat atgaggaaga aaggcaagaa tgaactacaa 24480
attattctta gggaagataa aaattgcagt catggggaga cctctggctg agagggccgt 24540
gattatttct gacagaggga ttatggagta gaatatgatg gcttggacct tttttcacta 24600
aaacaagtca gtcttctcaa aggtagttta gcttttcata tatctttcac agtttcttcc 24660
attcccattt cctgccattt tcctttctct aacttttatt tattatattt tttcctaaaa 24720
gtttaaattt tctatatctt tatcccttca gaagccatcc ctagtcacag gactagtctc 24780
atttcccatt atgtaatgct tctttctctg tctgttgact tctatttaga accagtgcac 24840
taaatctgcc tttaggaaca tacctctgct aggttgcaag aaatatccca ttccccactc 24900
actctgtgaa gactcaatgc ttctcaatat tccttacctc ctgagaggga cttgcctcac 24960
ttctttaatc caagggactc gatttttgcc aaaactaagt caggaaaacc tacataagac 25020
ataggaaaga cttgctgtgc ttcttaaacc ccactgtttg ttttcctaat tgtgaacagt 25080
atttttaaag ttaacaagag agcttctaag gcacttgagg ggagatctga tttatttccc 25140
agtaattatt ttcttccttt cagaaaattc cactgaataa gatggtttta acggatgtgg 25200
gactaatttt tgtgtctaaa tctcttccta tttctggatg aaaaaaagga gaccactctg 25260
aagtacaatg aaaaggaaaa tgggaattat aacctggtga ggtgagtagg aagaatttat 25320
tcatcattgc tgaaaacagg tacattcctt ttgaaagttg agaactcctc tggtattaga 25380
aaaaaaaaaa gaacgtatat acacatatat ttccatgtct atgtttatgt ttgtaaatcc 25440
atattcagaa tatgcaacaa ctttttataa ctatgacttc agtccatctt ttagttacat 25500
atatattcta aacaacaact attgctaaga gaagctgggt aagtaaatgt gaataaatct 25560
tctaaagata ttacaggaag ttcctgctgc ggctcagtgg gttaaagact tgatgtcttt 25620
gtgaagatga gggctcgagc cctggcctca ctcagtgagt taaggatcta gcattgctgt 25680
aagctgcagc gtaggttgca gatagggctc agatccagtg ttgctgtggc tgtggcctca 25740
gttgcagctc tgattcaacc cttaggcgag gaacttccat atgcagcaaa tgtggccatt 25800
aaaaaaaaaa aaaacattat aggagtcatt tcataaaaga gataagacgt ttctatagtt 25860
atatagtgca tactctggta aagatagtat aggatactat aggaatatag aaagcttgcc 25920
tatgaaaatt tgggaagatt gtggaaaaga catctcaaaa tatggcatag aaaagaatca 25980
tatctttgag gaacagtaag tttttcattc aaaaccgtgt attgaacata cttgtggtga 26040
caagtggtgt cctgagtact aaaaattcag tgataaaaga tgctcttgac aaagacatgg 26100
ctgttgaata gaaggtctca ctgtcaatgt gtgggaatta tggacagcct atgtggacac 26160
agggaataga tgagactcta ggctggaagg ctgcattgag cccaataatg aatggtcctg 26220
tctgatatat ttcatgctca tattttattt tagggactat tggggaggtg gtgggttttg 26280
gaagattaag ctgaggcaag acacaatcag attgcctttt ataatttact ttcaggagga 26340
aagtctaact aaaaaaagaa ttcgatatca agcttatcga taccgtcgac ctcgaggagg 26400
cccgcctgcc cttttggggg gggggggggg gggggggggg gggggggggg gggggggggg 26460
gggggggggg gggggggggg gggggggggg gggggggggg gggggggggg gggggcagca 26520
ccaattttat tattggcggg aataaagaga aaaatgtaat ttcaaagatt gctgttggaa 26580
atgaggggtg tggtagcttt tggagaaagc attctggaga cttctattaa tttttttttt 26640
ttaagtgctt caaagatcct ttgatccaac aattctactc ctaaaaattt cttccataca 26700
gataaagcca tttgtctgta tataacaaat agaagagaat tcctttttgc agccttgtta 26760
gtagtgcccc caaactggaa acaaagtgaa tatcagtcag tggggtagcg gctggaaaaa 26820
ttttagtgca cccaaccaac aaagaaaaac catgcacaaa aattcaataa atatcatctc 26880
acttttgtgt tcatgttatt gaatataatt aaacataatg tttacatcta taaaattatc 26940
atatgtatac atgtaaagaa acattaaaac atttttaaca gactgtaaac ttgaggactg 27000
tgaatgactt ttgattgata atctcaaaca tatggatact attctgatgt aataaataat 27060
gattaaattt tttccctaaa gagtaatcac tactgaatcg ttgcctcaga atcatatgga 27120
ggtgctttta aaaaaggcat ttctgcactg ttgttctctg gaatagaagt aattcttatg 27180
tacactgaag tttgaaaatc attgcattta agtgttctgt tcaggaaagt agtgtgcttt 27240
ttaatatttg tgagtgaatg agtaacacaa tacattatat cacattttaa tgtaattcta 27300
cacatgtgca tatgaagaga aaagtaacat ttttttctat ttatgtcttt agttcagcct 27360
ttaagatacc ttgatgaaga cctggactat tgaatgagca agaatctgcc tcttacactg 27420
aagattacaa tacagtcctc tgtctcctgg tattccaaag actgctgttg aatttctaaa 27480
aaatagattg gtgaatgtga ctactcaaag ttgtatgtaa gactttcaag ggcattaaat 27540
aaaaaagaat attgctgatt cttgttcttg attttctgaa tttctgaatc tcttattggg 27600
cttctaattt aaaaaaaaat atctgggcgc ccgcagatat cgaactcttg ggcagtgtga 27660
ccaaacgaag acatatccaa tcaagcatgc aaatggacca gcccactgta ctagcacgct 27720
gtggcagcca atctgaccga gaaagcagac aaccgcaggg agcaacg 27767

<210> SEQ ID NO 16

<211> LENGTH: 55
<212> TYPE: DNA
<213> ORGANISM: Sus scrofa

<400> SEQUENCE: 16
ggtcgccacc atggtgagca agggcgagga gctgttcacc ggggtggtgc ccatc 55

<210> SEQ ID NO 17
<211> LENGTH: 54
<212> TYPE: DNA
<213> ORGANISM: Sus scrofa

<400> SEQUENCE: 17
ggtcgccacc atggccatga gcaagggcga ggagctgttc accggggtgg tgcc 54

<210> SEQ ID NO 18
<211> LENGTH: 48
<212> TYPE: DNA
<213> ORGANISM: Sus scrofa

<400> SEQUENCE: 18
ggtcgccacc atggtgagca agggcgagga gctgttcacc ggggtggt 48

<210> SEQ ID NO 19
<211> LENGTH: 55
<212> TYPE: DNA
<213> ORGANISM: Sus scrofa

<400> SEQUENCE: 19
ggtcgccacc atggttgagc aagggcgagg agctgttcac cggggtggtg cccat 55

<210> SEQ ID NO 20
<211> LENGTH: 43
<212> TYPE: DNA
<213> ORGANISM: Sus scrofa

<400> SEQUENCE: 20
tgcagggaac tacagtgcgg cactgtggtt tccctcctgg ggg 43

<210> SEQ ID NO 21
<211> LENGTH: 60
<212> TYPE: DNA
<213> ORGANISM: Sus scrofa

<400> SEQUENCE: 21
tgcagggaac tacagtgcgg cactgtaaac cactactact gtggtttccc tcctgggggg 60

<210> SEQ ID NO 22
<211> LENGTH: 41
<212> TYPE: DNA
<213> ORGANISM: Sus scrofa

<400> SEQUENCE: 22
tgcagggaac tacagtgcgg ctgtggtttc cctcctgggg g 41

<210> SEQ ID NO 23
<211> LENGTH: 46
<212> TYPE: DNA
<213> ORGANISM: Sus scrofa

<400> SEQUENCE: 23
tgcagggaac tacagtgcgg aactactgtg gtttccctcc tggggg 46

<210> SEQ ID NO 24
<211> LENGTH: 31
<212> TYPE: DNA
<213> ORGANISM: Sus scrofa

<400> SEQUENCE: 24
gaaacccagg ctggttggag gggacattcc c 31

<210> SEQ ID NO 25
<211> LENGTH: 24
<212> TYPE: DNA
<213> ORGANISM: Sus scrofa

<400> SEQUENCE: 25
gaaacccagg ctggggacat tccc 24

<210> SEQ ID NO 26
<211> LENGTH: 13
<212> TYPE: DNA
<213> ORGANISM: Sus scrofa

<400> SEQUENCE: 26
aggggacatt ccc 13

<210> SEQ ID NO 27
<211> LENGTH: 13
<212> TYPE: DNA
<213> ORGANISM: Sus scrofa

<400> SEQUENCE: 27
gaaacccatt ccc 13

<210> SEQ ID NO 28
<211> LENGTH: 31
<212> TYPE: DNA
<213> ORGANISM: Sus scrofa

<400> SEQUENCE: 28
ggtcgccacc atggtgagca agggcgagga g 31

<210> SEQ ID NO 29
<211> LENGTH: 32
<212> TYPE: DNA
<213> ORGANISM: Sus scrofa

<400> SEQUENCE: 29
ggtcgccacc atggctgagc aagggcgagg ag 32

<210> SEQ ID NO 30
<211> LENGTH: 29
<212> TYPE: DNA
<213> ORGANISM: Sus scrofa

<400> SEQUENCE: 30
ggtcgccacc atggtgagag ggcgaggag 29

<210> SEQ ID NO 31
<211> LENGTH: 32
<212> TYPE: DNA
<213> ORGANISM: Sus scrofa

<400> SEQUENCE: 31
ggtcgccacc atggttgagc aagggcgagg ag 32

<210> SEQ ID NO 32
<211> LENGTH: 48
<212> TYPE: DNA
<213> ORGANISM: Sus scrofa

<400> SEQUENCE: 32
ggtcgccacc atggtgagca agggcgagga gaacccaggc tggttgga 48

<210> SEQ ID NO 33
<211> LENGTH: 49
<212> TYPE: DNA
<213> ORGANISM: Sus scrofa

<400> SEQUENCE: 33
tgctgtgcag ggaactacag tgcggcactg tggtttccct cctgggggg 49

<210> SEQ ID NO 34
<211> LENGTH: 38
<212> TYPE: DNA
<213> ORGANISM: Sus scrofa

<400> SEQUENCE: 34
tgctgtgcag ggaactctgt ggtttccctc ctgggggg 38

<210> SEQ ID NO 35
<211> LENGTH: 22
<212> TYPE: DNA
<213> ORGANISM: Sus scrofa

<400> SEQUENCE: 35
ctgtggtttc cctcctgggg gg 22

<210> SEQ ID NO 36
<211> LENGTH: 23
<212> TYPE: DNA
<213> ORGANISM: Sus scrofa

<400> SEQUENCE: 36
actgtggttt ccctcctggg ggg 23

<210> SEQ ID NO 37
<211> LENGTH: 50
<212> TYPE: DNA
<213> ORGANISM: Sus scrofa

<400> SEQUENCE: 37
tgctgtgcag ggaactacag tgcggcaact gtggtttccc tcctgggggg 50

<210> SEQ ID NO 38
<211> LENGTH: 10
<212> TYPE: DNA
<213> ORGANISM: Sus scrofa

<400> SEQUENCE: 38
tcctgggggg 10

<210> SEQ ID NO 39
<211> LENGTH: 8
<212> TYPE: DNA
<213> ORGANISM: Sus scrofa

<400> SEQUENCE: 39 ctgggggg 8

<210> SEQ ID NO 40
<211> LENGTH: 52
<212> TYPE: DNA
<213> ORGANISM: Sus scrofa

<400> SEQUENCE: 40
agagagcaga gccagcgact cgcccagcga catggggtac ctgccgtttg tg 52

<210> SEQ ID NO 41
<211> LENGTH: 33
<212> TYPE: DNA
<213> ORGANISM: Sus scrofa

<400> SEQUENCE: 41
agagagcaga gccagcgact cgcccagcga gat 33

<210> SEQ ID NO 42
<211> LENGTH: 30
<212> TYPE: DNA
<213> ORGANISM: Sus scrofa

<400> SEQUENCE: 42
agagagcaga gccagcgact cgcccagcga 30

<210> SEQ ID NO 43
<211> LENGTH: 50
<212> TYPE: DNA
<213> ORGANISM: Sus scrofa

<400> SEQUENCE: 43
agagccagcc tcgcccagca ggggtaccat ggggtacctg ccgtttgtgt 50

<210> SEQ ID NO 44
<211> LENGTH: 53
<212> TYPE: DNA
<213> ORGANISM: Sus scrofa

<400> SEQUENCE: 44
agagagcaga gccagcgact cgcccagcga gcagtgggta cctgccgttt gtg 53

<210> SEQ ID NO 45
<211> LENGTH: 53
<212> TYPE: DNA
<213> ORGANISM: Sus scrofa

<400> SEQUENCE: 45
agagagcaga gccagcgact cgcccagcga tcagtgggta cctgccgttt gtg 53

<210> SEQ ID NO 46
<211> LENGTH: 53
<212> TYPE: DNA
<213> ORGANISM: Sus scrofa

<400> SEQUENCE: 46
agagagcaga gccagcgact cgcccagcga acatggggta cctgccgttt gtg 53

<210> SEQ ID NO 47
<211> LENGTH: 4990
<212> TYPE: DNA
<213> ORGANISM: Sus scrofa

<400> SEQUENCE: 47

```
tatagatgac aaggctttgt gtctgatagg ggccagcgaa ctcagtaaag agggaagatg     60
agaaagataa tggcaagaat ttatccctga agtgtagttt tgacaaacca gtcacaaaga    120
ggtctaagaa attttggtca caaagttgtt ttgaatccca ggcattttat ttgcaatgat    180
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaacccccag   1680
aggtatttat ttgtttttgc ctttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
```

tggataagtg gcaaaatttt catgctgagg tgatctatag tgttgtaatg cagaatatag 2340
tcagatcttg aacattttag gaagttggtg agggccaatt gtgtatctgt gccatgctga 2400
taagaatgtc aagggatcac aagaattcgt gttatttgac agcagtcatc tttaaaaggc 2460
atttgagaaa gtccaatttc aaatgcattt cctttcttta aaagataaat tgaagaaaat 2520
aagtctttat ttcccaagta aattgaattg cctctcagtc tgttaaaaga aactcttacc 2580
ttgatgattg cgctcttaac ctggcaaaga ttgtctttaa aatctgagct ccatgtcttc 2640
tgctttattt ctggtgtgcc tttgactcca gattacagta aatggaggac tgagtatagg 2700
gctaaaaagt agagagaatg gatgcatatt atctgtggtc tccaatgtga tgaatgaagt 2760
aggcaaatac tcaaaggaaa gagaaagcat gctccaagaa ttatgggttc cagaaggcaa 2820
agtcccagaa ttgtctccag ggaaggacag ggaggtctag aatcggctaa gcccactgta 2880
ggcagaaaaa ccaagaggca tgaatggctt ccctttctca cttttcactc tctggcttac 2940
tcctatcatg aaggaaaata ttggaatcat attctccctc accgaaatgc tatttttcag 3000
cccacaggaa acccaggctg gttggagggg acattccctg ctctggtcgt gttgaagtac 3060
aacatggaga cacgtggggc accgtctgtg attctgactt ctctctggag gcggccagcg 3120
tgctgtgcag ggaactacag tgcggcactg tggtttccct cctgggggga gctcactttg 3180
gagaaggaag tggacagatc tgggctgaag aattccagtg tgaggggcac gagtcccacc 3240
tttcactctg cccagtagca ccccgccctg acgggacatg tagccacagc agggacgtcg 3300
gcgtagtctg ctcaagtgag acccagggaa tgtgttcact ttgttcccat gccatgaaga 3360
gggtagggtt aggtagtcac agacatcttt ttaaagccct gtctccttcc aggatacaca 3420
caaatccgct tggtgaatgg caagacccca tgtgaaggaa gagtggagct caacattctt 3480
gggtcctggg ggtccctctg caactctcac tgggacatgg aagatgccca tgttttatgc 3540
cagcagctta aatgtggagt tgccctttct atcccgggag gagcaccttt tgggaaagga 3600
agtgagcagg tctggaggca catgtttcac tgcactggga ctgagaagca catgggagat 3660
tgttccgtca ctgctctggg cgcatcactc tgttcttcag ggcaagtggc ctctgtaatc 3720
tgctcaggta agagaataag ggcagccagt gatgagccac tcatgacggt gccttaagag 3780
tgggtgtacc taggagttcc cattgtggct cagtggtaac aaactcgact ggtatccatg 3840
agggtatggg tttgatccct ggccttgctc aatgggttaa ggatccagca ttgctgtgag 3900
ctgtggtata ggttgcagac tctgctcagg tcccatgttg ctgtgattgt ggtgtaggct 3960
gactgctgca gcttcaattt gacccctagc ccgggaattt ccataggcca cacgtgcagc 4020
actaaggaag gaaaaaaaga aaaaaaaaaa aaaagagtgg gtgtgcctat agtgaagaac 4080
agatgtaaaa gggaagtgaa agggattccc ccattctgag ggattgtgag aagtgtgcca 4140
gaatattaac ttcatttgac ttgttacagg gaaagtaaac ttgactttca cggacctcct 4200
agttacctgg tgcttactat atgtcttctc agagtacctg attcattccc agcctggttg 4260
acccatcccc ctatctctat ggctatgttt atccagagca catctatcta acactccagc 4320
tgatcttcct gacacagctg tggcaaccct ggatccttta accaactgtg ccaggctgga 4380
gatcaaacct aagcctctgc agcaacccaa gctgctgcag tcagattttt aaccccctgt 4440
gccactgtgg gtatctccga tattttgtat cttctgtgac tgagtggttt gctgtttgca 4500
gggaaccaga gtcagacact atccccgtgc aattcatcat cctcggaccc atcaagctct 4560
attatttcag aagaaaatgg tgttgcctgc ataggtgaga atcagtgacc aacctatgaa 4620
aatgatctca atcctctgaa atgcatttta ttcatgtttt atttcctctt tgcagggagt 4680
ggtcaacttc gcctggtcga tggaggtggt cgttgtgctg ggagagtaga ggtctatcat 4740
gagggctcct ggggcaccat ctgtgatgac agctgggacc tgaatgatgc ccatgtggtg 4800
tgcaaacagc tgagctgtgg atgggccatt aatgccactg gttctgctca ttttggggaa 4860
ggaacagggc ccatttggct ggatgagata aactgtaatg gaaaagaatc tcatatttgg 4920
caatgccact cacatggttg gggcggcac aattgcaggc ataaggagga tgcaggagtc 4980
atctgctcgg 4990

<210> SEQ ID NO 48
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 48
caccggaaac ccaggctggt tgga 24

<210> SEQ ID NO 49
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 49
aaactccaac cagcctgggt ttcc 24

<210> SEQ ID NO 50
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 50
caccggaact acagtgcggc actg 24

<210> SEQ ID NO 51
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 51
aaaccagtgc cgcactgtag ttcc 24

<210> SEQ ID NO 52
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 52
caccgcagta gcaccccgcc ctgac 25

<210> SEQ ID NO 53
<211> LENGTH: 25
<212> TYPE: DNA
<213> ORGANISM: Artificial sequence
<220> FEATURE:

<223> OTHER INFORMATION: Synthetic oligonucleotide

<400> SEQUENCE: 53
aaacgtcagg gcggggtgct actgc 25

<210> SEQ ID NO 54
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 54
caccgtgtag ccacagcagg gacgt 25

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 55
aaacacgtcc ctgctgtggc tacac 25

<210> SEQ ID NO 56
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 56
caccgccagc ctcgcccagc gacat 25

<210> SEQ ID NO 57
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 57
aaacatgtcg ctgggcgagg ctggc 25

<210> SEQ ID NO 58
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 58
caccgcagct gcagcatata tttaa 25

<210> SEQ ID NO 59
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 59
aaacttaaat atatgctgca gctgc 25

<210> SEQ ID NO 60
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 60
caccgctttc atttatctga actca 25

<210> SEQ ID NO 61
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 61
aaactgagtt cagataaatg aaagc 25

<210> SEQ ID NO 62
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 62
caccgttatc tgaactcagg gtccc 25

<210> SEQ ID NO 63
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 63
aaacgggacc ctgagttcag ataac 25

<210> SEQ ID NO 64
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 64
caccgctcct cgcccttgct cacca 25

<210> SEQ ID NO 65
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 65
aaactggtga gcaagggcga ggagc 25

<210> SEQ ID NO 66
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 66
caccggacca ggatgggcac caccc 25

<210> SEQ ID NO 67
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 67
aaacgggtgg tgcccatcct ggtcc 25

<210> SEQ ID NO 68
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 68
ttgttggaag gctcactgtc cttg 24

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
acaactaagg tggggcaaag 20

<210> SEQ ID NO 70
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 70
ttgttggaag gctcactgtc cttg 24

<210> SEQ ID NO 71
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 71
ggagctcaac attcttgggt cct 23

<210> SEQ ID NO 72
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 72
ggcaaaattt tcatgctgag gtg 23

<210> SEQ ID NO 73
<211> LENGTH: 23

<212> TYPE: DNA
<213> ORGANISM: Artificial sequence
<220> FEATURE:
<223> OTHER INFORMATION: Synthetic oligonucleotide

<400> SEQUENCE: 73
gcacatcact tcgggttaca gtg 23

<210> SEQ ID NO 74
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 74
cccaagtatc ttcagttctg cag 23

<210> SEQ ID NO 75
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 75
tacaggtagg agagcctgtt ttg 23

<210> SEQ ID NO 76
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 76
cccaagtatc ttcagttctg cag 23

<210> SEQ ID NO 77
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 77
ctcaaaagga tgtaaaccct gga 23

<210> SEQ ID NO 78
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 78
tgttgatgtg gtttgtttgc cc 22

<210> SEQ ID NO 79
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 79
tacaggtagg agagcctgtt ttg 23

<210> SEQ ID NO 80
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 80
ggaggtctag aatcggctaa gcc 23

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ggctacatgt cccgtcaggg 20

<210> SEQ ID NO 82
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 82
gcaggccact aggcagatga a 21

<210> SEQ ID NO 83
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 83
gagctgacac ccaagaagtt cct 23

<210> SEQ ID NO 84
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 84
ggctctagag cctctgctaa cc 22

<210> SEQ ID NO 85
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 85
ggacttgaag aagtcgtgct gc 22

<210> SEQ ID NO 86

<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 86
taatacgact cactataggg agaatggact ataaggacca cgac 44

<210> SEQ ID NO 87
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 87
gcgagctcta ggaattctta c 21

<210> SEQ ID NO 88
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 88
ttaatacgac tcactatagg ctcctcgccc ttgctcacca 40

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
aaaagcaccg actcggtgcc 20

<210> SEQ ID NO 90
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 90
ttaatacgac tcactatagg aaacccaggc tggttgga 38

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
aaaagcaccg actcggtgcc 20

<210> SEQ ID NO 92
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 92
ttaatacgac tcactatagg aactacagtg cggcactg 38

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
aaaagcaccg actcggtgcc 20

<210> SEQ ID NO 94
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 94
ttaatacgac tcactatagg ccagcctcgc ccagcgacat 40

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
aaaagcaccg actcggtgcc 20

<210> SEQ ID NO 96
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 96
ttaatacgac tcactatagg cagctgcagc atatatttaa 40

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
aaaagcaccg actcggtgcc 20

<210> SEQ ID NO 98
<211> LENGTH: 3484
<212> TYPE: DNA
<213> ORGANISM: Sus scrofa

<400> SEQUENCE: 98
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180

```
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggcacattc cctgctctgg tcgtgttgaa gtacaacatg   1560
gagacacgtg gggcaccgtc tgtgattctg acttctctct ggaggcggcc agcgtgctgt   1620
gcagggaact acagtgcggc actgtggttt ccctcctggg gggagctcac tttggagaag   1680
gaagtggaca gatctgggct gaagaattcc agtgtgaggg gcacgagtcc cacctttcac   1740
tctgcccagt agcaccccgc cctgacggga catgtagcca cagcagggac gtcggcgtag   1800
tctgctcaag tgagacccag ggaatgtgtt cactttgttc ccatgccatg aagagggtag   1860
ggttaggtag tcacagacat ctttttaaag ccctgtctcc ttccaggata cacacaaatc   1920
cgcttggtga atggcaagac cccatgtgaa ggaagagtgg agctcaacat tcttgggtcc   1980
tgggggtccc tctgcaactc tcactgggac atggaagatg cccatgtttt atgccagcag   2040
cttaaatgtg gagttgccct ttctatcccg ggaggagcac cttttgggaa aggaagtgag   2100
caggtctgga ggcacatgtt tcactgcact gggactgaga agcacatggg agattgttcc   2160
gtcactgctc tgggcgcatc actctgttct tcagggcaag tggcctctgt aatctgctca   2220
ggtaagagaa taagggcagc cagtgatgag ccactcatga cggtgcctta agagtgggtg   2280
tacctaggag ttcccattgt ggctcagtgg taacaaactc gactggtatc catgagggta   2340
tgggtttgat ccctggcctt gctcaatggg ttaaggatcc agcattgctg tgagctgtgg   2400
tataggttgc agactctgct caggtcccat gttgctgtga ttgtggtgta ggctgactgc   2460
tgcagcttca atttgacccc tagcccggga atttccatag gccacacgtg cagcactaag   2520
gaaggaaaaa aagaaaaaaa aaaaaaaaga gtgggtgtgc ctatagtgaa gaacagatgt   2580
```

aaaagggaag tgaaagggat tcccccattc tgagggattg tgagaagtgt gccagaatat 2640
taacttcatt tgacttgtta cagggaaagt aaacttgact ttcacggacc tcctagttac 2700
ctggtgctta ctatatgtct tctcagagta cctgattcat tcccagcctg gttgacccat 2760
ccccctatct ctatggctat gtttatccag agcacatcta tctaacactc cagctgatct 2820
tcctgacaca gctgtggcaa ccctggatcc tttaaccaac tgtgccaggc tggagatcaa 2880
acctaagcct ctgcagcaac ccaagctgct gcagtcagat ttttaacccc ctgtgccact 2940
gtgggtatct ccgatatttt gtatcttctg tgactgagtg gtttgctgtt tgcagggaac 3000
cagagtcaga cactatcccc gtgcaattca tcatcctcgg acccatcaag ctctattatt 3060
tcagaagaaa atggtgttgc ctgcataggt gagaatcagt gaccaaccta tgaaaatgat 3120
ctcaatcctc tgaaatgcat tttattcatg ttttatttcc tctttgcagg gagtggtcaa 3180
cttcgcctgg tcgatggagg tggtcgttgt gctgggagag tagaggtcta tcatgagggc 3240
tcctggggca ccatctgtga tgacagctgg gacctgaatg atgcccatgt ggtgtgcaaa 3300
cagctgagct gtggatgggc cattaatgcc actggttctg ctcattttgg ggaaggaaca 3360
gggcccattt ggctggatga gataaactgt aatggaaaag aatctcatat ttggcaatgc 3420
cactcacatg gttgggggcg gcacaattgc aggcataagg aggatgcagg agtcatctgc 3480
tcgg 3484

<210> SEQ ID NO 99
<211> LENGTH: 4997
<212> TYPE: DNA
<213> ORGANISM: Sus scrofa

<400> SEQUENCE: 99
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140

-continued

```
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccag    1680
aggtatttat ttgtttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttggagggg acattccctg ctctggtcgt gttgaagtac   3060
aacatggaga cacgtggggc accgtctgtg attctgactt ctctctggag gcggccagcg   3120
tgctgtgcag ggaactacag tgcggctact actactgtgg tttccctcct ggggggagct   3180
cactttggag aaggaagtgg acagatctgg gctgaagaat tccagtgtga ggggcacgag   3240
tcccaccttt cactctgccc agtagcaccc cgccctgacg ggacatgtag ccacagcagg   3300
gacgtcggcg tagtctgctc aagtgagacc cagggaatgt gttcactttg ttcccatgcc   3360
atgaagaggg tagggttagg tagtcacaga catcttttta aagccctgtc tccttccagg   3420
atacacacaa atccgcttgg tgaatggcaa gaccccatgt gaaggaagag tggagctcaa   3480
cattcttggg tcctgggggt ccctctgcaa ctctcactgg gacatggaag atgcccatgt   3540
```

tttatgccag cagcttaaat gtggagttgc cctttctatc ccgggaggag cacctttttgg 3600 gaaaggaagt gagcaggtct ggaggcacat gtttcactgc actgggactg agaagcacat 3660
gggagattgt tccgtcactg ctctgggcgc atcactctgt tcttcagggc aagtggcctc 3720
tgtaatctgc tcaggtaaga gaataagggc agccagtgat gagccactca tgacggtgcc 3780
ttaagagtgg gtgtacctag gagttcccat tgtggctcag tggtaacaaa ctcgactggt 3840
atccatgagg gtatgggttt gatccctggc cttgctcaat gggttaagga tccagcattg 3900
ctgtgagctg tggtataggt tgcagactct gctcaggtcc catgttgctg tgattgtggt 3960
gtaggctgac tgctgcagct tcaatttgac ccctagcccg ggaatttcca taggccacac 4020
gtgcagcact aaggaaggaa aaaaagaaaa aaaaaaaaaa agagtgggtg tgcctatagt 4080
gaagaacaga tgtaaaaggg aagtgaaagg gattccccca ttctgaggga ttgtgagaag 4140
tgtgccagaa tattaacttc atttgacttg ttacagggaa agtaaacttg actttcacgg 4200
acctcctagt tacctggtgc ttactatatg tcttctcaga gtacctgatt cattcccagc 4260
ctggttgacc catcccccta tctctatggc tatgtttatc cagagcacat ctatctaaca 4320
ctccagctga tcttcctgac acagctgtgg caaccctgga tcctttaacc aactgtgcca 4380
ggctggagat caaacctaag cctctgcagc aacccaagct gctgcagtca gatttttaac 4440
cccctgtgcc actgtgggta tctccgatat tttgtatctt ctgtgactga gtggtttgct 4500
gtttgcaggg aaccagagtc agacactatc cccgtgcaat tcatcatcct cggacccatc 4560
aagctctatt atttcagaag aaaatggtgt tgcctgcata ggtgagaatc agtgaccaac 4620
ctatgaaaat gatctcaatc ctctgaaatg cattttattc atgttttatt tcctctttgc 4680
agggagtggt caacttcgcc tggtcgatgg aggtggtcgt tgtgctggga gagtagaggt 4740
ctatcatgag ggctcctggg gcaccatctg tgatgacagc tgggacctga atgatgccca 4800
tgtggtgtgc aaacagctga gctgtggatg ggccattaat gccactggtt ctgctcattt 4860
tggggaagga acagggccca tttggctgga tgagataaac tgtaatggaa aagaatctca 4920
tatttggcaa tgccactcac atggttgggg gcggcacaat tgcaggcata aggaggatgc 4980
aggagtcatc tgctcgg 4997

<210> SEQ ID NO 100
<211> LENGTH: 3710
<212> TYPE: DNA
<213> ORGANISM: Sus scrofa

<400> SEQUENCE: 100
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600

```
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaacccccag   1680
aggtatttat ttgtttttgc ctttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaagggaa   2820
agggattccc ccattctgag ggattgtgag aagtgtgcca gaatattaac ttcatttgac   2880
ttgttacagg gaaagtaaac ttgactttca cggacctcct agttacctgg tgcttactat   2940
atgtcttctc agagtacctg attcattccc agcctggttg acccatcccc ctatctctat   3000
```

ggctatgttt atccagagca catctatcta acactccagc tgatcttcct gacacagctg 3060
tggcaaccct ggatccttta accaactgtg ccaggctgga gatcaaacct aagcctctgc 3120
agcaacccaa gctgctgcag tcagattttt aaccccctgt gccactgtgg gtatctccga 3180
tattttgtat cttctgtgac tgagtggttt gctgtttgca gggaaccaga gtcagacact 3240
atccccgtgc aattcatcat cctcggaccc atcaagctct attatttcag aagaaaatgg 3300
tgttgcctgc ataggtgaga atcagtgacc aacctatgaa aatgatctca atcctctgaa 3360
atgcatttta ttcatgtttt atttcctctt tgcagggagt ggtcaacttc gcctggtcga 3420
tggaggtggt cgttgtgctg ggagagtaga ggtctatcat gagggctcct ggggcaccat 3480
ctgtgatgac agctgggacc tgaatgatgc ccatgtggtg tgcaaacagc tgagctgtgg 3540
atgggccatt aatgccactg gttctgctca ttttggggaa ggaacagggc ccatttggct 3600
ggatgagata aactgtaatg gaaaagaatc tcatatttgg caatgccact cacatggttg 3660
ggggcggcac aattgcaggc ataaggagga tgcaggagtc atctgctcgg 3710

<210> SEQ ID NO 101
<211> LENGTH: 3617
<212> TYPE: DNA
<213> ORGANISM: Sus scrofa

<400> SEQUENCE: 101
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140
agtaaatgtc ataaggatgc cagtctgtgt agagattgat gtgttactag cagattcatg 1200
aaataaaggc tgaggatgta gtccccaagt cacttctgag tggaagaatt tctcctttgt 1260
cctggactca aatattttag gataaaggaa aaaagaagat atttatagaa gggacttgtt 1320
ttcaagtact tgacaaaatt tcaccattaa agagaaattt gtgggagttc ccatcgtggc 1380

```
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaacccccag   1680
aggtatttat ttgtttttgc ctttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gattgaaagg gattccccca ttctgaggga ttgtgagaag   2760
tgtgccagaa tattaacttc atttgacttg ttacagggaa agtaaacttg actttcacgg   2820
acctcctagt tacctggtgc ttactatatg tcttctcaga gtacctgatt cattcccagc   2880
ctggttgacc catcccccta tctctatggc tatgtttatc cagagcacat ctatctaaca   2940
ctccagctga tcttcctgac acagctgtgg caaccctgga tcctttaacc aactgtgcca   3000
ggctggagat caaacctaag cctctgcagc aacccaagct gctgcagtca gatttttaac   3060
cccctgtgcc actgtgggta tctccgatat tttgtatctt ctgtgactga gtggtttgct   3120
gtttgcaggg aaccagagtc agacactatc cccgtgcaat tcatcatcct cggacccatc   3180
aagctctatt atttcagaag aaaatggtgt tgcctgcata ggtgagaatc agtgaccaac   3240
ctatgaaaat gatctcaatc ctctgaaatg cattttattc atgttttatt tcctctttgc   3300
agggagtggt caacttcgcc tggtcgatgg aggtggtcgt tgtgctggga gagtagaggt   3360
ctatcatgag ggctcctggg gcaccatctg tgatgacagc tgggacctga atgatgccca   3420
tgtggtgtgc aaacagctga gctgtggatg ggccattaat gccactggtt ctgctcattt   3480
tggggaagga acagggccca tttggctgga tgagataaac tgtaatggaa aagaatctca   3540
tatttggcaa tgccactcac atggttgggg gcggcacaat tgcaggcata aggaggatgc   3600
aggagtcatc tgctcgg                                                  3617
```

<210> SEQ ID NO 102
<211> LENGTH: 4979

<212> TYPE: DNA
<213> ORGANISM: Sus scrofa

<400> SEQUENCE: 102
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140
agtaaatgtc ataaggatgc cagtctgtgt agagattgat gtgttactag cagattcatg 1200
aaataaaggc tgaggatgta gtccccaagt cacttctgag tggaagaatt tctcctttgt 1260
cctggactca aatattttag gataaaggaa aaaagaagat atttatagaa gggacttgtt 1320
ttcaagtact tgacaaaatt tcaccattaa agagaaattt gtgggagttc ccatcgtggc 1380
tcagtggaaa caaatccaac taggaaccat gaggttgtgg gtttgatccc tggcctcact 1440
cagtgggtta aggatccggt gttgccgtga gctgtggtgt aggttgcaga cacggttctg 1500
atcctgcgtt gctgtggctg tggctgtggt gtaggccagc agcaaacagc tctgattaga 1560
cccctagcct ggaaacctcc atatgccaca ggtgcagccc taaaaagaca aaaaaagaga 1620
aaagacaaaa aaaaaaaaaa aaaaaaaaaa aaaaaaaaaa aaaaaaaaaa gaacccccag 1680
aggtatttat ttgtttttgc cttttttcac tgactgttct ttgtttgttt gtttgagact 1740
gatctagaag actagagatt acaagaaata tggatttggc tcactctaag aaactgcttt 1800
cattccaagg tttgggtcta tccaaaagtg gaatagaatc atatgaatac tagtttatga 1860
gtatttagtg agaggaattt caagctcaaa taatgattca gcaagattaa attaaggagg 1920
gaattttcct tgtggctgag tgggttaagg acccaatgtt gtctctgtga ggatgtaggt 1980
tccatcctgg gctttgctca ttaggttaag gatctggcat tgctgcagct cagacccagt 2040
gctgccctgg ttgtggctta ggccaaagct gcagctccaa ttcaatctct ggcctgggaa 2100
cctccatgtg ctacaaggtg cggccttaaa aggaaaaaaa aaaaattaaa tcaaggactc 2160
aagagtcttt cattatttgt gttgtggaag ctatatttgt tttaaagtct tagttgtgtt 2220

-continued

```
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttggagggg acattccctg ctctggtcgt gttgaagtac   3060
aacatggaga cacgtggggc accgtctgtg attctgactt ctctctggag gcggccagcg   3120
tgctgtgcag ggaactctgt ggtttccctc ctggggggag ctcactttgg agaaggaagt   3180
ggacagatct gggctgaaga attccagtgt gaggggcacg agtcccacct ttcactctgc   3240
ccagtagcac cccgccctga cgggacatgt agccacagca gggacgtcgg cgtagtctgc   3300
tcaagtgaga cccagggaat gtgttcactt tgttcccatg ccatgaagag ggtagggtta   3360
ggtagtcaca gacatctttt taaagccctg tctccttcca ggatacacac aaatccgctt   3420
ggtgaatggc aagaccccat gtgaaggaag agtggagctc aacattcttg ggtcctgggg   3480
gtccctctgc aactctcact gggacatgga agatgcccat gttttatgcc agcagcttaa   3540
atgtggagtt gccctttcta tcccgggagg agcacctttt gggaaaggaa gtgagcaggt   3600
ctggaggcac atgtttcact gcactgggac tgagaagcac atgggagatt gttccgtcac   3660
tgctctgggc gcatcactct gttcttcagg gcaagtggcc tctgtaatct gctcaggtaa   3720
gagaataagg gcagccagtg atgagccact catgacggtg ccttaagagt gggtgtacct   3780
aggagttccc attgtggctc agtggtaaca aactcgactg gtatccatga gggtatgggt   3840
ttgatccctg gccttgctca atgggttaag gatccagcat tgctgtgagc tgtggtatag   3900
gttgcagact ctgctcaggt cccatgttgc tgtgattgtg gtgtaggctg actgctgcag   3960
cttcaatttg accccctagcc cgggaatttc cataggccac acgtgcagca ctaaggaagg   4020
aaaaaaagaa aaaaaaaaaa aaagagtggg tgtgcctata gtgaagaaca gatgtaaaag   4080
ggaagtgaaa gggattcccc cattctgagg gattgtgaga agtgtgccag aatattaact   4140
tcatttgact tgttacaggg aaagtaaact tgactttcac ggacctccta gttacctggt   4200
gcttactata tgtcttctca gagtacctga ttcattccca gcctggttga cccatccccc   4260
tatctctatg gctatgttta tccagagcac atctatctaa cactccagct gatcttcctg   4320
acacagctgt ggcaaccctg gatcctttaa ccaactgtgc caggctggag atcaaaccta   4380
agcctctgca gcaacccaag ctgctgcagt cagattttta accccctgtg ccactgtggg   4440
tatctccgat attttgtatc ttctgtgact gagtggtttg ctgtttgcag ggaaccagag   4500
tcagacacta tccccgtgca attcatcatc ctcggaccca tcaagctcta ttatttcaga   4560
agaaaatggt gttgcctgca taggtgagaa tcagtgacca acctatgaaa atgatctcaa   4620
```

```
tcctctgaaa tgcattttat tcatgtttta tttcctcttt gcagggagtg gtcaacttcg   4680

cctggtcgat ggaggtggtc gttgtgctgg gagagtagag gtctatcatg agggctcctg   4740

gggcaccatc tgtgatgaca gctgggacct gaatgatgcc catgtggtgt gcaaacagct   4800

gagctgtgga tgggccatta atgccactgg ttctgctcat tttggggaag gaacagggcc   4860

catttggctg gatgagataa actgtaatgg aaaagaatct catatttggc aatgccactc   4920

acatggttgg gggcggcaca attgcaggca taaggaggat gcaggagtca tctgctcgg    4979
```

<210> SEQ ID NO 103
<211> LENGTH: 4615
<212> TYPE: DNA
<213> ORGANISM: Sus scrofa

<400> SEQUENCE: 103

```
tatagatgac aaggctttgt gtctgatagg ggccagcgaa ctcagtaaag agggaagatg     60

agaaagataa tggcaagaat ttatccctga agtgtagttt tgacaaacca gtcacaaaga    120

ggtctaagaa attttggtca caaagttgtt ttgaatccca ggcattttat ttgcaatgat    180

tgcatatgtt ctggaaagga catctgaacc taagaaatag ttcatttgca ttgtgttata    240

ttttactaag gtctgagaaa taatcttgag atgagaatga actctacttc ttcagagtct    300

ggaaggaata aattatgaaa atgtattaat gcttctttaa accatattgt atatttatct    360

attactaaac aaaaagaagt agctctattt atttatttat ttatttattt atttatgtct    420

tttgtctctt tagggccaca cctgtggcat atggaggttc ccaggctaga ggtccaattg    480

gagatgtagc agccagccta tgccagagcc accgcaacac gggatctgag ccacgtctgt    540

gacttacacc acagctcaca gcaacgcctg atcctcaacc cactgagcga ggccagggat    600

cgaacccatg tcctcatgga tgctagttgg gttcgttaac tgctgagcca tgatgggaac    660

tccaaattaa ttatttctta tatttgttct tcatatattc atttctatag aaagaaataa    720

atacagattc agttaatgat ggcaggtaaa agcttaactt attaatcaaa ggagttaatc    780

caggcacaaa aattcaattc atggctctct gttaaaattt aggtataggt ttagcaggaa    840

gaaaaggtta gtagatgcag actattacat ttagaatgga tggacaatga agtcctacta    900

tacagcacag ggaactatat ccaatctctt gggatagaat atgatggaag acaaaatcag    960

aacaagagag tatatatata tgtgtgtgtg tgtgtgtgtg tgtgtgtgtg tgtgtgtgtg   1020

tgtgtgactg ggtcaccctg cggcacagca gaaattggca gaacattgta aatcaactat   1080

actttaatag gaaaaatact tttaagggct aaatttccaa tattctaacc atgtacacag   1140

agtaaatgtc ataaggatgc cagtctgtgt agagattgat gtgttactag cagattcatg   1200

aaataaaggc tgaggatgta gtccccaagt cacttctgag tggaagaatt tctcctttgt   1260

cctggactca aatattttag gataaaggaa aaaagaagat atttatagaa gggacttgtt   1320

ttcaagtact tgacaaaatt tcaccattaa agagaaattt gtgggagttc ccatcgtggc   1380

tcagtggaaa caaatccaac taggaaccat gaggttgtgg gtttgatccc tggcctcact   1440

cagtgggtta aggatccggt gttgccgtga gctgtggtgt aggttgcaga cacggttctg   1500

atcctgcgtt gctgtggctg tggctgtggt gtaggccagc agcaaacagc tctgattaga   1560

cccctagcct ggaaacctcc atatgccaca ggtgcagccc taaaaagaca aaaaaagaga   1620

aaagacaaaa aaaaaaaaaa aaaaaaaaaa aaaaaaaaaa aaaaaaaaaa gaacccccag   1680

aggtatttat ttgtttttgc ctttttttcac tgactgttct ttgtttgttt gtttgagact   1740
```

```
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aagaaggaaa   2580
atattggaat catattctcc ctcaccgaaa tgctattttt cagcccacag gaaacccagg   2640
ctggttggag gggacattcc ctgctctggt cgtgttgaag tacaacatgg agacacgtgg   2700
ggcaccgtct gtgattctga cttctctctg gaggcggcca gcgtgctgtg cagggaacta   2760
cagtgcggca cagtgtggtt tccctcctgg ggggagctca ctttggagaa ggaagtggac   2820
agatctgggc tgaagaattc cagtgtgagg ggcacgagtc ccacctttca ctctgcccag   2880
tagcaccccg ccctgacggg acatgtagcc acagcaggga cgtcggcgta gtctgctcaa   2940
gtgagaccca gggaatgtgt tcactttgtt cccatgccat gaagagggta gggttaggta   3000
gtcacagaca tctttttaaa gccctgtctc cttccaggat acacacaaat ccgcttggtg   3060
aatggcaaga ccccatgtga aggaagagtg gagctcaaca ttcttgggtc ctgggggtcc   3120
ctctgcaact ctcactggga catggaagat gcccatgttt tatgccagca gcttaaatgt   3180
ggagttgccc tttctatccc gggaggagca ccttttggga aaggaagtga gcaggtctgg   3240
aggcacatgt ttcactgcac tgggactgag aagcacatgg gagattgttc cgtcactgct   3300
ctgggcgcat cactctgttc ttcagggcaa gtggcctctg taatctgctc aggtaagaga   3360
ataagggcag ccagtgatga gccactcatg acggtgcctt aagagtgggt gtacctagga   3420
gttcccattg tggctcagtg gtaacaaact cgactggtat ccatgagggt atgggtttga   3480
tccctggcct tgctcaatgg gttaaggatc cagcattgct gtgagctgtg gtataggttg   3540
cagactctgc tcaggtccca tgttgctgtg attgtggtgt aggctgactg ctgcagcttc   3600
aatttgaccc ctagcccggg aatttccata ggccacacgt gcagcactaa ggaaggaaaa   3660
aaagaaaaaa aaaaaaaaag agtgggtgtg cctatagtga agaacagatg taaaagggaa   3720
gtgaaaggga ttccccccatt ctgagggatt gtgagaagtg tgccagaata ttaacttcat   3780
ttgacttgtt acagggaaag taaacttgac tttcacggac ctcctagtta cctggtgctt   3840
actatatgtc ttctcagagt acctgattca ttcccagcct ggttgaccca tccccctatc   3900
tctatggcta tgtttatcca gagcacatct atctaacact ccagctgatc ttcctgacac   3960
agctgtggca accctggatc ctttaaccaa ctgtgccagg ctggagatca aacctaagcc   4020
tctgcagcaa cccaagctgc tgcagtcaga tttttaaccc cctgtgccac tgtgggtatc   4080
tccgatattt tgtatcttct gtgactgagt ggtttgctgt ttgcagggaa ccagagtcag   4140
```

acactatccc cgtgcaattc atcatcctcg gacccatcaa gctctattat ttcagaagaa 4200
aatggtgttg cctgcatagg tgagaatcag tgaccaacct atgaaaatga tctcaatcct 4260
ctgaaatgca ttttattcat gttttatttc ctctttgcag ggagtggtca acttcgcctg 4320
gtcgatggag gtggtcgttg tgctgggaga gtagaggtct atcatgaggg ctcctggggc 4380
accatctgtg atgacagctg ggacctgaat gatgcccatg tggtgtgcaa acagctgagc 4440
tgtggatggg ccattaatgc cactggttct gctcattttg gggaaggaac agggcccatt 4500
tggctggatg agataaactg taatggaaaa gaatctcata tttggcaatg ccactcacat 4560
ggttgggggc ggcacaattg caggcataag gaggatgcag gagtcatctg ctcgg 4615

<210> SEQ ID NO 104
<211> LENGTH: 4866
<212> TYPE: DNA
<213> ORGANISM: Sus scrofa

<400> SEQUENCE: 104
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140
agtaaatgtc ataaggatgc cagtctgtgt agagattgat gtgttactag cagattcatg 1200
aaataaaggc tgaggatgta gtccccaagt cacttctgag tggaagaatt tctcctttgt 1260
cctggactca aatattttag gataaaggaa aaaagaagat atttatagaa gggacttgtt 1320
ttcaagtact tgacaaaatt tcaccattaa agagaaattt gtgggagttc ccatcgtggc 1380
tcagtggaaa caaatccaac taggaaccat gaggttgtgg gtttgatccc tggcctcact 1440
cagtgggtta aggatccggt gttgccgtga gctgtggtgt aggttgcaga cacggttctg 1500
atcctgcgtt gctgtggctg tggctgtggt gtaggccagc agcaaacagc tctgattaga 1560
cccctagcct ggaaacctcc atatgccaca ggtgcagccc taaaaagaca aaaaaagaga 1620

```
aaagacaaaa aaaaaaaaaa aaaaaaaaaa aaaaaaaaaa aaaaaaaaaa gaacccccag   1680
aggtatttat ttgtttttgc ctttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttctgtggt ttccctcctg gggggagctc actttggaga   3060
aggaagtgga cagatctggg ctgaagaatt ccagtgtgag gggcacgagt cccacctttc   3120
actctgccca gtagcacccc gccctgacgg gacatgtagc cacagcaggg acgtcggcgt   3180
agtctgctca agtgagaccc agggaatgtg ttcactttgt tcccatgcca tgaagagggt   3240
agggttaggt agtcacagac atctttttaa agccctgtct ccttccagga tacacacaaa   3300
tccgcttggt gaatggcaag accccatgtg aaggaagagt ggagctcaac attcttgggt   3360
cctgggggtc cctctgcaac tctcactggg acatggaaga tgcccatgtt ttatgccagc   3420
agcttaaatg tggagttgcc ctttctatcc cgggaggagc accttttggg aaaggaagtg   3480
agcaggtctg gaggcacatg tttcactgca ctgggactga gaagcacatg ggagattgtt   3540
ccgtcactgc tctgggcgca tcactctgtt cttcagggca agtggcctct gtaatctgct   3600
caggtaagag aataagggca gccagtgatg agccactcat gacggtgcct taagagtggg   3660
tgtacctagg agttcccatt gtggctcagt ggtaacaaac tcgactggta tccatgaggg   3720
tatgggtttg atccctggcc ttgctcaatg ggttaaggat ccagcattgc tgtgagctgt   3780
ggtataggtt gcagactctg ctcaggtccc atgttgctgt gattgtggtg taggctgact   3840
gctgcagctt caatttgacc cctagcccgg gaatttccat aggccacacg tgcagcacta   3900
aggaaggaaa aaaagaaaaa aaaaaaaaaa gagtgggtgt gcctatagtg aagaacagat   3960
gtaaaaggga agtgaaaggg attcccccat tctgagggat tgtgagaagt gtgccagaat   4020
```

attaacttca tttgacttgt tacagggaaa gtaaacttga ctttcacgga cctcctagtt 4080
acctggtgct tactatatgt cttctcagag tacctgattc attcccagcc tggttgaccc 4140
atccccctat ctctatggct atgtttatcc agagcacatc tatctaacac tccagctgat 4200
cttcctgaca cagctgtggc aaccctggat cctttaacca actgtgccag gctggagatc 4260
aaacctaagc ctctgcagca acccaagctg ctgcagtcag atttttaacc ccctgtgcca 4320
ctgtgggtat ctccgatatt ttgtatcttc tgtgactgag tggtttgctg tttgcaggga 4380
accagagtca gacactatcc ccgtgcaatt catcatcctc ggacccatca agctctatta 4440
tttcagaaga aaatggtgtt gcctgcatag gtgagaatca gtgaccaacc tatgaaaatg 4500
atctcaatcc tctgaaatgc attttattca tgttttattt cctctttgca gggagtggtc 4560
aacttcgcct ggtcgatgga ggtggtcgtt gtgctgggag agtagaggtc tatcatgagg 4620
gctcctgggg caccatctgt gatgacagct gggacctgaa tgatgcccat gtggtgtgca 4680
aacagctgag ctgtggatgg gccattaatg ccactggttc tgctcatttt ggggaaggaa 4740
cagggcccat ttggctggat gagataaact gtaatggaaa agaatctcat atttggcaat 4800
gccactcaca tggttggggg cggcacaatt gcaggcataa ggaggatgca ggagtcatct 4860
gctcgg 4866

<210> SEQ ID NO 105
<211> LENGTH: 4867
<212> TYPE: DNA
<213> ORGANISM: Sus scrofa

<400> SEQUENCE: 105
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140
agtaaatgtc ataaggatgc cagtctgtgt agagattgat gtgttactag cagattcatg 1200

```
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccag    1680
aggtatttat ttgtttttgc ctttttcac tgactgttct ttgtttgttt gtttgagact    1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttactgtgg tttccctcct gggggggagct cactttggag  3060
aaggaagtgg acagatctgg gctgaagaat tccagtgtga ggggcacgag tcccaccttt   3120
cactctgccc agtagcaccc cgccctgacg ggacatgtag ccacagcagg gacgtcggcg   3180
tagtctgctc aagtgagacc cagggaatgt gttcactttg ttcccatgcc atgaagaggg   3240
tagggttagg tagtcacaga catcttttta aagccctgtc tccttccagg atacacacaa   3300
atccgcttgg tgaatggcaa gaccccatgt gaaggaagag tggagctcaa cattcttggg   3360
tcctgggggt ccctctgcaa ctctcactgg gacatggaag atgcccatgt tttatgccag   3420
cagcttaaat gtggagttgc cctttctatc ccgggaggag caccttttgg gaaaggaagt   3480
gagcaggtct ggaggcacat gtttcactgc actgggactg agaagcacat gggagattgt   3540
tccgtcactg ctctgggcgc atcactctgt tcttcagggc aagtggcctc tgtaatctgc   3600
```

tcaggtaaga gaataagggc agccagtgat gagccactca tgacggtgcc ttaagagtgg 3660
gtgtacctag gagttcccat tgtggctcag tggtaacaaa ctcgactggt atccatgagg 3720
gtatgggttt gatccctggc cttgctcaat gggttaagga tccagcattg ctgtgagctg 3780
tggtataggt tgcagactct gctcaggtcc catgttgctg tgattgtggt gtaggctgac 3840
tgctgcagct tcaatttgac ccctagcccg ggaatttcca taggccacac gtgcagcact 3900
aaggaaggaa aaaaagaaaa aaaaaaaaaa agagtgggtg tgcctatagt gaagaacaga 3960
tgtaaaaggg aagtgaaagg gattccccca ttctgaggga ttgtgagaag tgtgccagaa 4020
tattaacttc atttgacttg ttacagggaa agtaaacttg actttcacgg acctcctagt 4080
tacctggtgc ttactatatg tcttctcaga gtacctgatt cattcccagc ctggttgacc 4140
catcccccta tctctatggc tatgtttatc cagagcacat ctatctaaca ctccagctga 4200
tcttcctgac acagctgtgg caaccctgga tcctttaacc aactgtgcca ggctggagat 4260
caaacctaag cctctgcagc aacccaagct gctgcagtca gatttttaac cccctgtgcc 4320
actgtgggta tctccgatat tttgtatctt ctgtgactga gtggtttgct gtttgcaggg 4380
aaccagagtc agacactatc cccgtgcaat tcatcatcct cggacccatc aagctctatt 4440
atttcagaag aaaatggtgt tgcctgcata ggtgagaatc agtgaccaac ctatgaaaat 4500
gatctcaatc ctctgaaatg cattttattc atgttttatt tcctctttgc agggagtggt 4560
caacttcgcc tggtcgatgg aggtggtcgt tgtgctggga gagtagaggt ctatcatgag 4620
ggctcctggg gcaccatctg tgatgacagc tgggacctga atgatgccca tgtggtgtgc 4680
aaacagctga gctgtggatg ggccattaat gccactggtt ctgctcattt tggggaagga 4740
acagggccca tttggctgga tgagataaac tgtaatggaa aagaatctca tatttggcaa 4800
tgccactcac atggttgggg gcggcacaat tgcaggcata aggaggatgc aggagtcatc 4860
tgctcgg 4867

<210> SEQ ID NO 106
<211> LENGTH: 4991
<212> TYPE: DNA
<213> ORGANISM: Sus scrofa

<400> SEQUENCE: 106
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780

-continued

```
caggcacaaa aattcaattc atggctctct gttaaaattt aggtataggt ttagcaggaa     840
gaaaaggtta gtagatgcag actattacat ttagaatgga tggacaatga agtcctacta     900
tacagcacag ggaactatat ccaatctctt gggatagaat atgatggaag acaaaatcag     960
aacaagagag tatatatata tgtgtgtgtg tgtgtgtgtg tgtgtgtgtg tgtgtgtgtg    1020
tgtgtgactg ggtcaccctg cggcacagca gaaattggca gaacattgta aatcaactat    1080
actttaatag gaaaaatact tttaagggct aaatttccaa tattctaacc atgtacacag    1140
agtaaatgtc ataaggatgc cagtctgtgt agagattgat gtgttactag cagattcatg    1200
aaataaaggc tgaggatgta gtccccaagt cacttctgag tggaagaatt tctcctttgt    1260
cctggactca aatattttag gataaaggaa aaaagaagat atttatagaa gggacttgtt    1320
ttcaagtact tgacaaaatt tcaccattaa agagaaattt gtgggagttc ccatcgtggc    1380
tcagtggaaa caaatccaac taggaaccat gaggttgtgg gtttgatccc tggcctcact    1440
cagtgggtta aggatccggt gttgccgtga gctgtggtgt aggttgcaga cacggttctg    1500
atcctgcgtt gctgtggctg tggctgtggt gtaggccagc agcaaacagc tctgattaga    1560
cccctagcct ggaaacctcc atatgccaca ggtgcagccc taaaaagaca aaaaaagaga    1620
aaagacaaaa aaaaaaaaaa aaaaaaaaaa aaaaaaaaaa aaaaaaaaaa gaacccccag    1680
aggtatttat ttgtttttgc cttttttcac tgactgttct ttgtttgttt gtttgagact    1740
gatctagaag actagagatt acaagaaata tggatttggc tcactctaag aaactgcttt    1800
cattccaagg tttgggtcta tccaaaagtg gaatagaatc atatgaatac tagtttatga    1860
gtatttagtg agaggaattt caagctcaaa taatgattca gcaagattaa attaaggagg    1920
gaattttcct tgtggctgag tgggttaagg acccaatgtt gtctctgtga ggatgtaggt    1980
tccatcctgg gctttgctca ttaggttaag gatctggcat tgctgcagct cagacccagt    2040
gctgccctgg ttgtggctta ggccaaagct gcagctccaa ttcaatctct ggcctgggaa    2100
cctccatgtg ctacaaggtg cggccttaaa aggaaaaaaa aaaaattaaa tcaaggactc    2160
aagagtcttt cattatttgt gttgtggaag ctatatttgt tttaaagtct tagttgtgtt    2220
tagaaagcaa gatgttcttc aactcaaatt tgggagggaa cttgtttcat acatttttaa    2280
tggataagtg gcaaaatttt catgctgagg tgatctatag tgttgtaatg cagaatatag    2340
tcagatcttg aacattttag gaagttggtg agggccaatt gtgtatctgt gccatgctga    2400
taagaatgtc aagggatcac aagaattcgt gttatttgac agcagtcatc tttaaaaggc    2460
atttgagaaa gtccaatttc aaatgcattt cctttcttta aaagataaat tgaagaaaat    2520
aagtctttat ttcccaagta aattgaattg cctctcagtc tgttaaaaga aactcttacc    2580
ttgatgattg cgctcttaac ctggcaaaga ttgtctttaa aatctgagct ccatgtcttc    2640
tgctttattt ctggtgtgcc tttgactcca gattacagta aatggaggac tgagtatagg    2700
gctaaaaagt agagagaatg gatgcatatt atctgtggtc tccaatgtga tgaatgaagt    2760
aggcaaatac tcaaaggaaa gagaaagcat gctccaagaa ttatgggttc cagaaggcaa    2820
agtcccagaa ttgtctccag ggaaggacag ggaggtctag aatcggctaa gcccactgta    2880
ggcagaaaaa ccaagaggca tgaatggctt ccctttctca cttttcactc tctggcttac    2940
tcctatcatg aaggaaaata ttggaatcat attctccctc accgaaatgc tatttttcag    3000
cccacaggaa acccaggctg gttggagggg acattccctg ctctggtcgt gttgaagtac    3060
aacatggaga cacgtggggc accgtctgtg attctgactt ctctctggag gcggccagcg    3120
tgctgtgcag ggaactacag tgcggcaact gtggtttccc tcctgggggg agctcacttt    3180
```

```
ggagaaggaa gtggacagat ctgggctgaa gaattccagt gtgaggggca cgagtcccac   3240
ctttcactct gcccagtagc accccgccct gacgggacat gtagccacag cagggacgtc   3300
ggcgtagtct gctcaagtga gacccaggga atgtgttcac tttgttccca tgccatgaag   3360
agggtagggt taggtagtca cagacatctt tttaaagccc tgtctccttc caggatacac   3420
acaaatccgc ttggtgaatg gcaagacccc atgtgaagga agagtggagc tcaacattct   3480
tgggtcctgg gggtccctct gcaactctca ctgggacatg gaagatgccc atgttttatg   3540
ccagcagctt aaatgtggag ttgccctttc tatcccggga ggagcacctt ttgggaaagg   3600
aagtgagcag gtctggaggc acatgtttca ctgcactggg actgagaagc acatgggaga   3660
ttgttccgtc actgctctgg gcgcatcact ctgttcttca gggcaagtgg cctctgtaat   3720
ctgctcaggt aagagaataa gggcagccag tgatgagcca ctcatgacgg tgccttaaga   3780
gtgggtgtac ctaggagttc ccattgtggc tcagtggtaa caaactcgac tggtatccat   3840
gagggtatgg gtttgatccc tggccttgct caatgggtta aggatccagc attgctgtga   3900
gctgtggtat aggttgcaga ctctgctcag gtcccatgtt gctgtgattg tggtgtaggc   3960
tgactgctgc agcttcaatt tgacccctag cccgggaatt tccataggcc acacgtgcag   4020
cactaaggaa ggaaaaaaag aaaaaaaaaa aaaaagagtg ggtgtgccta tagtgaagaa   4080
cagatgtaaa agggaagtga aagggattcc cccattctga gggattgtga gaagtgtgcc   4140
agaatattaa cttcatttga cttgttacag ggaaagtaaa cttgactttc acggacctcc   4200
tagttacctg gtgcttacta tatgtcttct cagagtacct gattcattcc cagcctggtt   4260
gacccatccc cctatctcta tggctatgtt tatccagagc acatctatct aacactccag   4320
ctgatcttcc tgacacagct gtggcaaccc tggatccttt aaccaactgt gccaggctgg   4380
agatcaaacc taagcctctg cagcaaccca agctgctgca gtcagatttt taaccccctg   4440
tgccactgtg ggtatctccg atattttgta tcttctgtga ctgagtggtt tgctgtttgc   4500
agggaaccag agtcagacac tatccccgtg caattcatca tcctcggacc catcaagctc   4560
tattatttca gaagaaaatg gtgttgcctg cataggtgag aatcagtgac caacctatga   4620
aaatgatctc aatcctctga aatgcatttt attcatgttt tatttcctct ttgcagggag   4680
tggtcaactt cgcctggtcg atggaggtgg tcgttgtgct gggagagtag aggtctatca   4740
tgagggctcc tggggcacca tctgtgatga cagctgggac ctgaatgatg cccatgtggt   4800
gtgcaaacag ctgagctgtg gatgggccat taatgccact ggttctgctc attttgggga   4860
aggaacaggg cccatttggc tggatgagat aaactgtaat ggaaaagaat ctcatatttg   4920
gcaatgccac tcacatggtt gggggcggca caattgcagg cataaggagg atgcaggagt   4980
catctgctcg g                                                        4991
```

<210> SEQ ID NO 107
<211> LENGTH: 4860
<212> TYPE: DNA
<213> ORGANISM: Sus scrofa

<400> SEQUENCE: 107

```
tatagatgac aaggctttgt gtctgatagg ggccagcgaa ctcagtaaag agggaagatg     60
agaaagataa tggcaagaat ttatccctga agtgtagttt tgacaaacca gtcacaaaga    120
ggtctaagaa attttggtca caaagttgtt ttgaatccca ggcattttat ttgcaatgat    180
tgcatatgtt ctggaaagga catctgaacc taagaaatag ttcatttgca ttgtgttata    240
```

```
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaacccccag   1680
aggtatttat ttgtttttgc ctttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
```

tgctttattt ctggtgtgcc tttgactcca gattacagta aatggaggac tgagtatagg 2700
gctaaaaagt agagagaatg gatgcatatt atctgtggtc tccaatgtga tgaatgaagt 2760
aggcaaatac tcaaaggaaa gagaaagcat gctccaagaa ttatgggttc cagaaggcaa 2820
agtcccagaa ttgtctccag ggaaggacag ggaggtctag aatcggctaa gcccactgta 2880
ggcagaaaaa ccaagaggca tgaatggctt ccctttctca cttttcactc tctggcttac 2940
tcctatcatg aaggaaaata ttggaatcat attctccctc accgaaatgc tatttttcag 3000
cccacaggaa acccaggctg gttggagggt cctgggggga gctcactttg gagaaggaag 3060
tggacagatc tgggctgaag aattccagtg tgaggggcac gagtcccacc tttcactctg 3120
cccagtagca ccccgccctg acgggacatg tagccacagc agggacgtcg gcgtagtctg 3180
ctcaagtgag acccagggaa tgtgttcact ttgttcccat gccatgaaga gggtagggtt 3240
aggtagtcac agacatcttt ttaaagccct gtctccttcc aggatacaca caaatccgct 3300
tggtgaatgg caagacccca tgtgaaggaa gagtggagct caacattctt gggtcctggg 3360
ggtccctctg caactctcac tgggacatgg aagatgccca tgttttatgc cagcagctta 3420
aatgtggagt tgccctttct atcccgggag gagcaccttt tgggaaagga agtgagcagg 3480
tctggaggca catgtttcac tgcactggga ctgagaagca catgggagat tgttccgtca 3540
ctgctctggg cgcatcactc tgttcttcag ggcaagtggc ctctgtaatc tgctcaggta 3600
agagaataag ggcagccagt gatgagccac tcatgacggt gccttaagag tgggtgtacc 3660
taggagttcc cattgtggct cagtggtaac aaactcgact ggtatccatg agggtatggg 3720
tttgatccct ggccttgctc aatgggttaa ggatccagca ttgctgtgag ctgtggtata 3780
ggttgcagac tctgctcagg tcccatgttg ctgtgattgt ggtgtaggct gactgctgca 3840
gcttcaattt gacccctagc ccgggaattt ccataggcca cacgtgcagc actaaggaag 3900
gaaaaaaaga aaaaaaaaaa aaaagagtgg gtgtgcctat agtgaagaac agatgtaaaa 3960
gggaagtgaa agggattccc ccattctgag ggattgtgag aagtgtgcca gaatattaac 4020
ttcatttgac ttgttacagg gaaagtaaac ttgactttca cggacctcct agttacctgg 4080
tgcttactat atgtcttctc agagtacctg attcattccc agcctggttg acccatcccc 4140
ctatctctat ggctatgttt atccagagca catctatcta acactccagc tgatcttcct 4200
gacacagctg tggcaaccct ggatccttta accaactgtg ccaggctgga gatcaaacct 4260
aagcctctgc agcaacccaa gctgctgcag tcagattttt aaccccctgt gccactgtgg 4320
gtatctccga tattttgtat cttctgtgac tgagtggttt gctgtttgca gggaaccaga 4380
gtcagacact atccccgtgc aattcatcat cctcggaccc atcaagctct attatttcag 4440
aagaaaatgg tgttgcctgc ataggtgaga atcagtgacc aacctatgaa aatgatctca 4500
atcctctgaa atgcatttta ttcatgtttt atttcctctt tgcagggagt ggtcaacttc 4560
gcctggtcga tggaggtggt cgttgtgctg ggagagtaga ggtctatcat gagggctcct 4620
ggggcaccat ctgtgatgac agctgggacc tgaatgatgc ccatgtggtg tgcaaacagc 4680
tgagctgtgg atgggccatt aatgccactg gttctgctca ttttggggaa ggaacagggc 4740
ccatttggct ggatgagata aactgtaatg gaaaagaatc tcatatttgg caatgccact 4800
cacatggttg gggcggcac aattgcaggc ataaggagga tgcaggagtc atctgctcgg 4860

<210> SEQ ID NO 108
<211> LENGTH: 4858
<212> TYPE: DNA

<213> ORGANISM: Sus scrofa

<400> SEQUENCE: 108
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140
agtaaatgtc ataaggatgc cagtctgtgt agagattgat gtgttactag cagattcatg 1200
aaataaaggc tgaggatgta gtccccaagt cacttctgag tggaagaatt tctcctttgt 1260
cctggactca aatattttag gataaaggaa aaaagaagat atttatagaa gggacttgtt 1320
ttcaagtact tgacaaaatt tcaccattaa agagaaattt gtgggagttc ccatcgtggc 1380
tcagtggaaa caaatccaac taggaaccat gaggttgtgg gtttgatccc tggcctcact 1440
cagtgggtta aggatccggt gttgccgtga gctgtggtgt aggttgcaga cacggttctg 1500
atcctgcgtt gctgtggctg tggctgtggt gtaggccagc agcaaacagc tctgattaga 1560
cccctagcct ggaaacctcc atatgccaca ggtgcagccc taaaaagaca aaaaaagaga 1620
aaagacaaaa aaaaaaaaaa aaaaaaaaaa aaaaaaaaaa aaaaaaaaaa gaaccccag 1680
aggtatttat ttgtttttgc cttttttcac tgactgttct ttgtttgttt gtttgagact 1740
gatctagaag actagagatt acaagaaata tggatttggc tcactctaag aaactgcttt 1800
cattccaagg tttgggtcta tccaaaagtg gaatagaatc atatgaatac tagtttatga 1860
gtatttagtg agaggaattt caagctcaaa taatgattca gcaagattaa attaaggagg 1920
gaattttcct tgtggctgag tgggttaagg acccaatgtt gtctctgtga ggatgtaggt 1980
tccatcctgg gctttgctca ttaggttaag gatctggcat tgctgcagct cagacccagt 2040
gctgccctgg ttgtggctta ggccaaagct gcagctccaa ttcaatctct ggcctgggaa 2100
cctccatgtg ctacaaggtg cggccttaaa aggaaaaaaa aaaaattaaa tcaaggactc 2160
aagagtcttt cattatttgt gttgtggaag ctatatttgt tttaaagtct tagttgtgtt 2220
tagaaagcaa gatgttcttc aactcaaatt tgggagggaa cttgtttcat acatttttaa 2280

```
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttggagggc tggggggagc tcactttgga gaaggaagtg   3060
gacagatctg ggctgaagaa ttccagtgtg aggggcacga gtcccacctt tcactctgcc   3120
cagtagcacc ccgccctgac gggacatgta gccacagcag ggacgtcggc gtagtctgct   3180
caagtgagac ccagggaatg tgttcacttt gttcccatgc catgaagagg gtagggttag   3240
gtagtcacag acatcttttt aaagccctgt ctccttccag gatacacaca aatccgcttg   3300
gtgaatggca agaccccatg tgaaggaaga gtggagctca acattcttgg gtcctggggg   3360
tccctctgca actctcactg ggacatggaa gatgcccatg ttttatgcca gcagcttaaa   3420
tgtggagttg ccctttctat cccgggagga gcaccttttg ggaaaggaag tgagcaggtc   3480
tggaggcaca tgtttcactg cactgggact gagaagcaca tgggagattg ttccgtcact   3540
gctctgggcg catcactctg ttcttcaggg caagtggcct ctgtaatctg ctcaggtaag   3600
agaataaggg cagccagtga tgagccactc atgacggtgc cttaagagtg ggtgtaccta   3660
ggagttccca ttgtggctca gtggtaacaa actcgactgg tatccatgag ggtatgggtt   3720
tgatccctgg ccttgctcaa tgggttaagg atccagcatt gctgtgagct gtggtatagg   3780
ttgcagactc tgctcaggtc ccatgttgct gtgattgtgg tgtaggctga ctgctgcagc   3840
ttcaatttga cccctagccc gggaatttcc ataggccaca cgtgcagcac taaggaagga   3900
aaaaaagaaa aaaaaaaaaa aagagtgggt gtgcctatag tgaagaacag atgtaaaagg   3960
gaagtgaaag ggattccccc attctgaggg attgtgagaa gtgtgccaga atattaactt   4020
catttgactt gttacaggga aagtaaactt gactttcacg gacctcctag ttacctggtg   4080
cttactatat gtcttctcag agtacctgat tcattcccag cctggttgac ccatccccct   4140
atctctatgg ctatgtttat ccagagcaca tctatctaac actccagctg atcttcctga   4200
cacagctgtg gcaaccctgg atcctttaac caactgtgcc aggctggaga tcaaacctaa   4260
gcctctgcag caacccaagc tgctgcagtc agatttttaa ccccctgtgc cactgtgggt   4320
atctccgata ttttgtatct tctgtgactg agtggtttgc tgtttgcagg gaaccagagt   4380
cagacactat ccccgtgcaa ttcatcatcc tcggacccat caagctctat tatttcagaa   4440
gaaaatggtg ttgcctgcat aggtgagaat cagtgaccaa cctatgaaaa tgatctcaat   4500
cctctgaaat gcattttatt catgttttat ttcctctttg cagggagtgg tcaacttcgc   4560
ctggtcgatg gaggtggtcg ttgtgctggg agagtagagg tctatcatga gggctcctgg   4620
```

ggcaccatct gtgatgacag ctgggacctg aatgatgccc atgtggtgtg caaacagctg 4680
agctgtggat gggccattaa tgccactggt tctgctcatt ttggggaagg aacagggccc 4740
atttggctgg atgagataaa ctgtaatgga aaagaatctc atatttggca atgccactca 4800
catggttggg ggcggcacaa ttgcaggcat aaggaggatg caggagtcat ctgctcgg 4858

<210> SEQ ID NO 109
<211> LENGTH: 3523
<212> TYPE: DNA
<213> ORGANISM: Sus scrofa

<400> SEQUENCE: 109
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140
agtaaatgtc ataaggatgc cagtctgtgt agagattgat gtgttactag cagattcatg 1200
aaataaaggc tgaggatgta gtccccaagt cacttctgag tggaagaatt tctcctttgt 1260
cctggactca aatattttag gataaaggaa aaaagaagat atttatagaa gggacttgtt 1320
ttcaagtact tgacaaaatt tcaccattaa agagaaattt gtgggagttc ccatcgtggc 1380
tcagtggaaa caaatccaac taggaaccat gaggttgtgg gtttgatccc tggcctcact 1440
cagtgggtta aggatccggt gttgccgtga gctgtggtgt aggttgcaga cacggttctg 1500
atcctgcgtt gctgtggctg tggctgtggt gtaggccagc agcaaacagc tctgattaga 1560
cccctagcct ggaaacctcc atatgccaca ggtgcagccc taaaaagaca aaaaaagaga 1620
aaagacaaaa aaaaaaaaaa aaaaaaaaaa aaaaaaaaaa aaaaaaaaaa gaacccccag 1680
aggtatttat ttgtttttgc cttttttcac tgactgttct ttgtttgttt gtttgagact 1740
gatctagaag actagagatt acaagaaata tggatttggc tcactctaag aaactgcttt 1800
cattccaagg tttgggtcta tccaaaagtg gaatagaatc atatgaatac tagtttatga 1860
gtatttagtg agaggaattt caagctcaaa taatgattca gcaagattaa attaaggagg 1920

```
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gagctgtggt ataggttgca gactctgctc   2460
aggtcccatg ttgctgtgat tgtggtgtag gctgactgct gcagcttcaa tttgacccct   2520
agcccgggaa tttccatagg ccacacgtgc agcactaagg aaggaaaaaa agaaaaaaaa   2580
aaaaaaagag tgggtgtgcc tatagtgaag aacagatgta aaagggaagt gaaagggatt   2640
cccccattct gagggattgt gagaagtgtg ccagaatatt aacttcattt gacttgttac   2700
agggaaagta aacttgactt tcacggacct cctagttacc tggtgcttac tatatgtctt   2760
ctcagagtac ctgattcatt cccagcctgg ttgacccatc cccctatctc tatggctatg   2820
tttatccaga gcacatctat ctaacactcc agctgatctt cctgacacag ctgtggcaac   2880
cctggatcct ttaaccaact gtgccaggct ggagatcaaa cctaagcctc tgcagcaacc   2940
caagctgctg cagtcagatt tttaaccccc tgtgccactg tgggtatctc cgatattttg   3000
tatcttctgt gactgagtgg tttgctgttt gcagggaacc agagtcagac actatccccg   3060
tgcaattcat catcctcgga cccatcaagc tctattattt cagaagaaaa tggtgttgcc   3120
tgcataggtg agaatcagtg accaacctat gaaaatgatc tcaatcctct gaaatgcatt   3180
ttattcatgt tttatttcct ctttgcaggg agtggtcaac ttcgcctggt cgatggaggt   3240
ggtcgttgtg ctgggagagt agaggtctat catgagggct cctggggcac catctgtgat   3300
gacagctggg acctgaatga tgcccatgtg gtgtgcaaac agctgagctg tggatgggcc   3360
attaatgcca ctggttctgc tcattttggg gaaggaacag ggcccatttg gctggatgag   3420
ataaactgta atggaaaaga atctcatatt tggcaatgcc actcacatgg ttgggggcgg   3480
cacaattgca ggcataagga ggatgcagga gtcatctgct cgg                     3523
```

<210> SEQ ID NO 110
<211> LENGTH: 3603
<212> TYPE: DNA
<213> ORGANISM: Sus scrofa

<400> SEQUENCE: 110

```
tatagatgac aaggctttgt gtctgatagg ggccagcgaa ctcagtaaag agggaagatg     60
agaaagataa tggcaagaat ttatccctga agtgtagttt tgacaaacca gtcacaaaga    120
ggtctaagaa attttggtca caaagttgtt ttgaatccca ggcattttat ttgcaatgat    180
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
```

```
gagatgttgt ggagaattcc acaagaattc gtgttatttg acagcagtca tctttaaaag    540
gcatttgaga aagtccaatt tcaaatgcat ttcctttctt taaaagataa attgaagaaa    600
ataagtcttt atttcccaag taaattgaat tgcctctcag tctgttaaaa gaaactctta    660
tatagatgac aaggctttgt gtctgatagg ggccagcgaa ctcagtaaag agggaagatg    720
agaaagataa tggcaagaat ttatccctga agtgtagttt tgacaaacca gtcacaaaga    780
ggtctaagaa attttggtca caaagttgtt ttgaatccca ggcattttat ttgcaatgat    840
tgcatatgtt ctggaaagga catctgaacc taagaaatag ttcatttgca ttgtgttata    900
ttttactaag gtctgagaaa taatcttgag atgagaatga actctacttc ttcagagtct    960
ggaaggaata aattatgaaa atgtattaat gcttctttaa accatattgt atatttatct   1020
attactaaac aaaaagaagt agctctattt atttatttat ttatttattt atttatgtct   1080
tttgtctctt tagggccaca cctgtggcat atggaggttc ccaggctaga ggtccaattg   1140
gagatgttgt ggagaattcc acaagaattc gtgttatttg acagcagtca tctttaaaag   1200
gcatttgaga aagtccaatt tcaaatgcat ttcctttctt taaaagataa attgaagaaa   1260
ataagtcttt atttcccaag taaattgaat tgcctctcag tctgttaaaa gaaactctta   1320
ccttgatgat tgcgctctta acctggcaaa gattgtcttt aaaatctgag ctccatgtct   1380
tctgctttat ttctggtgtg cctttgactc cagattacag taaatggagg actgagtata   1440
gggctaaaaa gtagagagaa tggatgcata ttatctgtgg tctccaatgt gatgaatgaa   1500
gtaggcaaat actcaaagga aagagaaagc atgctccaag aattatgggt tccagaaggc   1560
aaagtcccag aattgtctcc agggaaggac agggaggtct agaatcggct aagcccactg   1620
taggcagaaa aaccaagagg catgaatggc ttccctttct cacttttcac tctctggctt   1680
actcctatca tgaaggaaaa tattggaatc atattctccc tcaccgaaat gctatttttc   1740
agcccacagg aaacccaggc tggttggagg ggacattccc tgctctcact ttggagaagg   1800
aagtggacag atctgggctg aagaattcca gtgtgagggg cacgagtccc acctttcact   1860
ctgcccagta gcaccccgcc ctgacgggac atgtagccac agcagggacg tcggcgtagt   1920
ctgctcaagt gagacccagg gaatgtgttc actttgttcc catgccatga agagggtagg   1980
gttaggtagt cacagacatc tttttaaagc cctgtctcct tccaggatac acacaaatcc   2040
gcttggtgaa tggcaagacc ccatgtgaag gaagagtgga gctcaacatt cttgggtcct   2100
gggggtccct ctgcaactct cactgggaca tggaagatgc ccatgtttta tgccagcagc   2160
ttaaatgtgg agttgccctt tctatcccgg gaggagcacc ttttgggaaa ggaagtgagc   2220
aggtctggag gcacatgttt cactgcactg ggactgagaa gcacatggga gattgttccg   2280
tcactgctct gggcgcatca ctctgttctt cagggcaagt ggcctctgta atctgctcag   2340
gtaagagaat aagggcagcc agtgatgagc cactcatgac ggtgccttaa gagtgggtgt   2400
acctaggagt tcccattgtg gctcagtggt aacaaactcg actggtatcc atgagggtat   2460
gggtttgatc cctggccttg ctcaatgggt taaggatcca gcattgctgt gagctgtggt   2520
ataggttgca gactctgctc aggtcccatg ttgctgtgat tgtggtgtag gctgactgct   2580
gcagcttcaa tttgacccct agcccgggaa tttccatagg ccacacgtgc agcactaagg   2640
aaggaaaaaa agaaaaaaaa aaaaaaagag tgggtgtgcc tatagtgaag aacagatgta   2700
aaagggaagt gaaagggatt cccccattct gagggattgt gagaagtgtg ccagaatatt   2760
aacttcattt gacttgttac agggaaagta aacttgactt tcacggacct cctagttacc   2820
tggtgcttac tatatgtctt ctcagagtac ctgattcatt cccagcctgg ttgacccatc   2880
```

```
cccctatctc tatggctatg tttatccaga gcacatctat ctaacactcc agctgatctt   2940
cctgacacag ctgtggcaac cctggatcct ttaaccaact gtgccaggct ggagatcaaa   3000
cctaagcctc tgcagcaacc caagctgctg cagtcagatt tttaacccc  tgtgccactg   3060
tgggtatctc cgatattttg tatcttctgt gactgagtgg tttgctgttt gcagggaacc   3120
agagtcagac actatccccg tgcaattcat catcctcgga cccatcaagc tctattattt   3180
cagaagaaaa tggtgttgcc tgcataggtg agaatcagtg accaacctat gaaaatgatc   3240
tcaatcctct gaaatgcatt ttattcatgt tttatttcct ctttgcaggg agtggtcaac   3300
ttcgcctggt cgatggaggt ggtcgttgtg ctgggagagt agaggtctat catgagggct   3360
cctggggcac catctgtgat gacagctggg acctgaatga tgcccatgtg gtgtgcaaac   3420
agctgagctg tggatgggcc attaatgcca ctggttctgc tcattttggg gaaggaacag   3480
ggcccatttg gctggatgag ataaactgta atggaaaaga atctcatatt tggcaatgcc   3540
actcacatgg ttgggggcgg cacaattgca ggcataagga ggatgcagga gtcatctgct   3600
cgg                                                                  3603
```

<210> SEQ ID NO 111
<211> LENGTH: 4962
<212> TYPE: DNA
<213> ORGANISM: Sus scrofa

<400> SEQUENCE: 111

```
tatagatgac aaggctttgt gtctgatagg ggccagcgaa ctcagtaaag agggaagatg     60
agaaagataa tggcaagaat ttatccctga agtgtagttt tgacaaacca gtcacaaaga    120
ggtctaagaa attttggtca caaagttgtt ttgaatccca ggcattttat ttgcaatgat    180
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
```

ttcaagtact tgacaaaatt tcaccattaa agagaaattt gtgggagttc ccatcgtggc 1380
tcagtggaaa caaatccaac taggaaccat gaggttgtgg gtttgatccc tggcctcact 1440
cagtgggtta aggatccggt gttgccgtga gctgtggtgt aggttgcaga cacggttctg 1500
atcctgcgtt gctgtggctg tggctgtggt gtaggccagc agcaaacagc tctgattaga 1560
cccctagcct ggaaacctcc atatgccaca ggtgcagccc taaaaagaca aaaaaagaga 1620
aaagacaaaa aaaaaaaaaa aaaaaaaaaa aaaaaaaaaa aaaaaaaaaa gaacccccag 1680
aggtatttat ttgtttttgc ctttttcac tgactgttct ttgtttgttt gtttgagact 1740
gatctagaag actagagatt acaagaaata tggatttggc tcactctaag aaactgcttt 1800
cattccaagg tttgggtcta tccaaaagtg gaatagaatc atatgaatac tagtttatga 1860
gtatttagtg agaggaattt caagctcaaa taatgattca gcaagattaa attaaggagg 1920
gaattttcct tgtggctgag tgggttaagg acccaatgtt gtctctgtga ggatgtaggt 1980
tccatcctgg gctttgctca ttaggttaag gatctggcat tgctgcagct cagacccagt 2040
gctgccctgg ttgtggctta ggccaaagct gcagctccaa ttcaatctct ggcctgggaa 2100
cctccatgtg ctacaaggtg cggccttaaa aggaaaaaaa aaaaattaaa tcaaggactc 2160
aagagtcttt cattatttgt gttgtggaag ctatatttgt tttaaagtct tagttgtgtt 2220
tagaaagcaa gatgttcttc aactcaaatt tgggagggaa cttgtttcat acatttttaa 2280
tggataagtg gcaaaatttt catgctgagg tgatctatag tgttgtaatg cagaatatag 2340
tcagatcttg aacattttag gaagttggtg agggccaatt gtgtatctgt gccatgctga 2400
taagaatgtc aagggatcac aagaattcgt gttatttgac agcagtcatc tttaaaaggc 2460
atttgagaaa gtccaatttc aaatgcattt cctttcttta aaagataaat tgaagaaaat 2520
aagtctttat ttcccaagta aattgaattg cctctcagtc tgttaaaaga aactcttacc 2580
ttgatgattg cgctcttaac ctggcaaaga ttgtctttaa aatctgagct ccatgtcttc 2640
tgctttattt ctggtgtgcc tttgactcca gattacagta aatggaggac tgagtatagg 2700
gctaaaaagt agagagaatg gatgcatatt atctgtggtc tccaatgtga tgaatgaagt 2760
aggcaaatac tcaaaggaaa gagaaagcat gctccaagaa ttatgggttc cagaaggcaa 2820
agtcccagaa ttgtctccag ggaaggacag ggaggtctag aatcggctaa gcccactgta 2880
ggcagaaaaa ccaagaggca tgaatggctt ccctttctca cttttcactc tctggcttac 2940
tcctatcatg aaggaaaata ttggaatcat attctccctc accgaaatgc tatttttcag 3000
cccacaggaa acccaggctg gttggagggg acattccctg ctctggtcgt gttgaagtac 3060
aacatggaga cacgtggggc accgtctgtg attctgactt ctctctggag gcggccagcg 3120
tgctgtgcag ggaactacag tgcgtcactt tggagaagga agtggacaga tctgggctga 3180
agaattccag tgtgaggggc acgagtccca cctttcactc tgcccagtag caccccgccc 3240
tgacgggaca tgtagccaca gcagggacgt cggcgtagtc tgctcaagtg agacccaggg 3300
aatgtgttca ctttgttccc atgccatgaa gagggtaggg ttaggtagtc acagacatct 3360
ttttaaagcc ctgtctcctt ccaggataca cacaaatccg cttggtgaat ggcaagaccc 3420
catgtgaagg aagagtggag ctcaacattc ttgggtcctg gggtccctc tgcaactctc 3480
actgggacat ggaagatgcc catgttttat gccagcagct taaatgtgga gttgcccttt 3540
ctatcccggg aggagcacct tttgggaaag gaagtgagca ggtctggagg cacatgtttc 3600
actgcactgg gactgagaag cacatgggag attgttccgt cactgctctg ggcgcatcac 3660
tctgttcttc agggcaagtg gcctctgtaa tctgctcagg taagagaata agggcagcca 3720
gtgatgagcc actcatgacg gtgccttaag agtgggtgta cctaggagtt cccattgtgg 3780
ctcagtggta acaaactcga ctggtatcca tgagggtatg ggtttgatcc ctggccttgc 3840
tcaatgggtt aaggatccag cattgctgtg agctgtggta taggttgcag actctgctca 3900
ggtcccatgt tgctgtgatt gtggtgtagg ctgactgctg cagcttcaat ttgacccta 3960 gcccgggaat ttccataggc cacacgtgca gcactaagga aggaaaaaaa gaaaaaaaaa 4020
aaaaaagagt gggtgtgcct atagtgaaga acagatgtaa aagggaagtg aaagggattc 4080
ccccattctg agggattgtg agaagtgtgc cagaatatta acttcatttg acttgttaca 4140
gggaaagtaa acttgacttt cacggacctc ctagttacct ggtgcttact atatgtcttc 4200
tcagagtacc tgattcattc ccagcctggt tgacccatcc ccctatctct atggctatgt 4260
ttatccagag cacatctatc taacactcca gctgatcttc ctgacacagc tgtggcaacc 4320
ctggatcctt taaccaactg tgccaggctg gagatcaaac ctaagcctct gcagcaaccc 4380
aagctgctgc agtcagattt ttaacccct gtgccactgt gggtatctcc gatattttgt 4440
atcttctgtg actgagtggt ttgctgtttg cagggaacca gagtcagaca ctatccccgt 4500
gcaattcatc atcctcggac ccatcaagct ctattatttc agaagaaaat ggtgttgcct 4560
gcataggtga gaatcagtga ccaacctatg aaaatgatct caatcctctg aaatgcattt 4620
tattcatgtt ttatttcctc tttgcaggga gtggtcaact tcgcctggtc gatggaggtg 4680
gtcgttgtgc tgggagagta gaggtctatc atgagggctc ctggggcacc atctgtgatg 4740
acagctggga cctgaatgat gcccatgtgg tgtgcaaaca gctgagctgt ggatgggcca 4800
ttaatgccac tggttctgct cattttgggg aaggaacagg gcccatttgg ctggatgaga 4860
taaactgtaa tggaaaagaa tctcatattt ggcaatgcca ctcacatggt tgggggcggc 4920
acaattgcag gcataaggag gatgcaggag tcatctgctc gg 4962

<210> SEQ ID NO 112
<211> LENGTH: 3603
<212> TYPE: DNA
<213> ORGANISM: Sus scrofa

<400> SEQUENCE: 112
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840

```
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaacccccag   1680
aggtatttat ttgtttttgc ctttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttggagggg acattccctg ctctggtcgt gttgaagtac   3060
aacatggaga cacgtggggc accgtctgtg attctgactt ctctctggag gcggccagcg   3120
tgctgtgcag ggaactacag tgcgattcat catcctcgga cccatcaagc tctattattt   3180
cagaagaaaa tggtgttgcc tgcataggtg agaatcagtg accaacctat gaaaatgatc   3240
```

```
tcaatcctct gaaatgcatt ttattcatgt tttatttcct ctttgcaggg agtggtcaac   3300

ttcgcctggt cgatggaggt ggtcgttgtg ctgggagagt agaggtctat catgagggct   3360

cctggggcac catctgtgat gacagctggg acctgaatga tgcccatgtg gtgtgcaaac   3420

agctgagctg tggatgggcc attaatgcca ctggttctgc tcattttggg gaaggaacag   3480

ggcccatttg gctggatgag ataaactgta atggaaaaga atctcatatt tggcaatgcc   3540

actcacatgg ttgggggcgg cacaattgca ggcataagga ggatgcagga gtcatctgct   3600

cgg                                                                 3603
```

<210> SEQ ID NO 113
<211> LENGTH: 3619
<212> TYPE: DNA
<213> ORGANISM: Sus scrofa

<400> SEQUENCE: 113

```
tatagatgac aaggctttgt gtctgatagg ggccagcgaa ctcagtaaag agggaagatg     60

agaaagataa tggcaagaat ttatccctga agtgtagttt tgacaaacca gtcacaaaga    120

ggtctaagaa attttggtca caaagttgtt ttgaatccca ggcattttat ttgcaatgat    180

tgcatatgtt ctggaaagga catctgaacc taagaaatag ttcatttgca ttgtgttata    240

ttttactaag gtctgagaaa taatcttgag atgagaatga actctacttc ttcagagtct    300

ggaaggaata aattatgaaa atgtattaat gcttctttaa accatattgt atatttatct    360

attactaaac aaaaagaagt agctctattt atttatttat ttatttattt atttatgtct    420

tttgtctctt tagggccaca cctgtggcat atggaggttc ccaggctaga ggtccaattg    480

gagatgtagc agccagccta tgccagagcc accgcaacac gggatctgag ccacgtctgt    540

gacttacacc acagctcaca gcaacgcctg atcctcaacc cactgagcga ggccagggat    600

cgaacccatg tcctcatgga tgctagttgg gttcgttaac tgctgagcca tgatgggaac    660

tccaaattaa ttatttctta tatttgttct tcatatattc atttctatag aaagaaataa    720

atacagattc agttaatgat ggcaggtaaa agcttaactt attaatcaaa ggagttaatc    780

caggcacaaa aattcaattc atggctctct gttaaaattt aggtataggt ttagcaggaa    840

gaaaaggtta gtagatgcag actattacat ttagaatgga tggacaatga agtcctacta    900

tacagcacag ggaactatat ccaatctctt gggatagaat atgatggaag acaaaatcag    960

aacaagagag tatatatata tgtgtgtgtg tgtgtgtgtg tgtgtgtgtg tgtgtgtgtg   1020

tgtgtgactg ggtcaccctg cggcacagca gaaattggca gaacattgta aatcaactat   1080

actttaatag gaaaaatact tttaagggct aaatttccaa tattctaacc atgtacacag   1140

agtaaatgtc ataaggatgc cagtctgtgt agagattgat gtgttactag cagattcatg   1200

aaataaaggc tgaggatgta gtccccaagt cacttctgag tggaagaatt tctcctttgt   1260

cctggactca aatattttag gataaaggaa aaaagaagat atttatagaa gggacttgtt   1320

ttcaagtact tgacaaaatt tcaccattaa agagaaattt gtgggagttc ccatcgtggc   1380

tcagtggaaa caaatccaac taggaaccat gaggttgtgg gtttgatccc tggcctcact   1440

cagtgggtta aggatccggt gttgccgtga gctgtggtgt aggttgcaga cacggttctg   1500

atcctgcgtt gctgtggctg tggctgtggt gtaggccagc agcaaacagc tctgattaga   1560

cccctagcct ggaaacctcc atatgccaca ggtgcagccc taaaaagaca aaaaaagaga   1620

aaagacaaaa aaaaaaaaaa aaaaaaaaaa aaaaaaaaaa aaaaaaaaaa gaacccccag   1680
```

aggtatttat ttgtttttgc ctttttcac tgactgttct ttgtttgttt gtttgagact 1740
gatctagaag actagagatt acaagaaata tggatttggc tcactctaag aaactgcttt 1800
cattccaagg tttgggtcta tccaaaagtg gaatagaatc atatgaatac tagtttatga 1860
gtatttagtg agaggaattt caagctcaaa taatgattca gcaagattaa attaaggagg 1920
gaattttcct tgtggctgag tgggttaagg acccaatgtt gtctctgtga ggatgtaggt 1980
tccatcctgg gctttgctca ttaggttaag gatctggcat tgctgcagct cagacccagt 2040
gctgccctgg ttgtggctta ggccaaagct gcagctccaa ttcaatctct ggcctgggaa 2100
cctccatgtg ctacaaggtg cggccttaaa aggaaaaaaa aaaaattaaa tcaaggactc 2160
aagagtcttt cattatttgt gttgtggaag ctatatttgt tttaaagtct tagttgtgtt 2220
tagaaagcaa gatgttcttc aactcaaatt tgggagggaa cttgtttcat acatttttaa 2280
tggataagtg gcaaaatttt catgctgagg tgatctatag tgttgtaatg cagaatatag 2340
tcagatcttg aacattttag gaagttggtg agggccaatt gtgtatctgt gccatgctga 2400
taagaatgtc aagggatcac aagaattcgt gttatttgac agcagtcatc tttaaaaggc 2460
atttgagaaa gtccaatttc aaatgcattt cctttcttta aaagataaat tgaagaaaat 2520
aagtctttat ttcccaagta aattgaattg cctctcagtc tgttaaaaga aactcttacc 2580
ttgatgattg cgctcttaac ctggcaaaga ttgtctttaa aatctgagct ccatgtcttc 2640
tgctttattt ctggtgtgcc tttgactcca gattacagta aatggaggac tgagtatagg 2700
gctaaaaagt agagagaatg gatgcatatt atctgtggtc tccaatgtga tgaatgaagt 2760
aggcaaatac tcaaaggaaa gagaaagcat gctccaagaa ttatgggttc cagaaggcaa 2820
agtcccagaa ttgtctccag ggaaggacag ggaggtctag aatcggctaa gcccactgta 2880
ggcagaaaaa ccaagaggca tgaatggctt ccctttctca cttttcactc tctggcttac 2940
tcctatcatg aaggaaaata ttggaatcat attctccctc accgaaatgc tatttttcag 3000
cccacaggaa acccaggctg gttggagggg acattccctg ctctggtcgt gttgaagtac 3060
aacatggaga cacgtggggc accgtctgtg attctgactt ctctctggag gcagccagcg 3120
tgctttgcag ggaaccagag tcagacacta tccccgtgca attcatcatc ctcggaccca 3180
tcaagctcta ttatttcaga agaaaatggt gttgcctgca taggtgagaa tcagtgacca 3240
acctatgaaa atgatctcaa tcctctgaaa tgcattttat tcatgtttta tttcctcttt 3300
gcagggagtg gtcaacttcg cctggtcgat ggaggtggtc gttgtgctgg gagagtagag 3360
gtctatcatg agggctcctg gggcaccatc tgtgatgaca gctgggacct gaatgatgcc 3420
catgtggtgt gcaaacagct gagctgtgga tgggccatta atgccactgg ttctgctcat 3480
tttggggaag gaacagggcc catttggctg gatgagataa actgtaatgg aaaagaatct 3540
catatttggc aatgccactc acatggttgg gggcggcaca attgcaggca taaggaggat 3600
gcaggagtca tctgctcgg 3619

<210> SEQ ID NO 114
<211> LENGTH: 3270
<212> TYPE: DNA
<213> ORGANISM: Sus scrofa

<400> SEQUENCE: 114
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180

```
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaacccccag   1680
aggtatttat ttgtttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac ttgttacagg gaaagtaaac   2460
ttgactttca cggacctcct agttacctgg tgcttactat atgtcttctc agagtacctg   2520
```

attcattccc agcctggttg acccatcccc ctatctctat ggctatgttt atccagagca 2580
catctatcta acactccagc tgatcttcct gacacagctg tggcaaccct ggatccttta 2640
accaactgtg ccaggctgga gatcaaacct aagcctctgc agcaacccaa gctgctgcag 2700
tcagattttt aaccccctgt gccactgtgg gtatctccga tattttgtat cttctgtgac 2760
tgagtggttt gctgtttgca gggaaccaga gtcagacact atccccgtgc aattcatcat 2820
cctcggaccc atcaagctct attatttcag aagaaaatgg tgttgcctgc ataggtgaga 2880
atcagtgacc aacctatgaa aatgatctca atcctctgaa atgcatttta ttcatgtttt 2940
atttcctctt tgcagggagt ggtcaacttc gcctggtcga tggaggtggt cgttgtgctg 3000
ggagagtaga ggtctatcat gagggctcct ggggcaccat ctgtgatgac agctgggacc 3060
tgaatgatgc ccatgtggtg tgcaaacagc tgagctgtgg atgggccatt aatgccactg 3120
gttctgctca ttttggggaa ggaacagggc ccatttggct ggatgagata aactgtaatg 3180
gaaaagaatc tcatatttgg caatgccact cacatggttg gggcggcac aattgcaggc 3240 ataaggagga tgcaggagtc atctgctcgg 3270

<210> SEQ ID NO 115
<211> LENGTH: 7
<212> TYPE: DNA
<213> ORGANISM: Sus scrofa

<400> SEQUENCE: 115 tactact 7

<210> SEQ ID NO 116
<211> LENGTH: 12
<212> TYPE: DNA
<213> ORGANISM: Sus scrofa

<400> SEQUENCE: 116
tgtggagaat tc 12

<210> SEQ ID NO 117
<211> LENGTH: 11
<212> TYPE: DNA
<213> ORGANISM: Sus scrofa

<400> SEQUENCE: 117
agccagcgtg c 11

<210> SEQ ID NO 118
<211> LENGTH: 8532
<212> TYPE: DNA
<213> ORGANISM: Sus scrofa

<400> SEQUENCE: 118
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480

```
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccag   1680
aggtatttat ttgtttttgc ctttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
```

```
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttggagctg acatgccctg ctctggtcgt gttgaagtaa   3060
aacatgcaga cacgtggggc tccgtctgtg attctgactt ctctctgcat gcggccaacg   3120
tgctgtgcag ggaactaaat tgcggcgatg cgatttccct ctcggtggga gatcactttg   3180
gaaaaggaaa tggactgacc tgggctgaaa aattccagtg tgaggggagc gagacccacc   3240
ttgcactctg cccaatagta caacaccctg aagacacatg tatccacagc agggaagtcg   3300
gcgtagtctg ctcaagtaag agtttactga aaataacact cttaaaatct tgttatgttt   3360
ttattcataa tgtgaatgag tagtagtgga aaataactac cagtttccta agcttataac   3420
ttcgtatagc atacattata cgaagttata agcctgcagg aattctaccg ggtaggggag   3480
gcgcttttcc caaggcagtc tggagcatgc gctttagcag ccccgctggg cacttggcgc   3540
tacacaagtg gcctctggcc tcgcacacat tccacatcca ccggtaggcg ccaaccggct   3600
ccgttctttg gtggcccctt cgcgccacct tctactcctc ccctagtcag gaagttcccc   3660
cccgccccgc agctcgcgtc gtgcaggacg tgacaaatgg aagtagcacg tctcactagt   3720
ctcgtgcaga tggacagcac cgctgagcaa tggaagcggg taggcctttg gggcagcggc   3780
caatagcagc tttgctcctt cgctttctgg gctcagaggc tgggaagggg tgggtccggg   3840
ggcgggctca ggggcgggct caggggcggg gcgggcgccc gaaggtcctc cggaggcccg   3900
gcattctgca cgcttcaaaa gcgcacgtct gccgcgctgt tctcctcttc ctcatctccg   3960
ggcctttcga cctgcagcca ccatggccat gattgaacag gatggcctgc atgcaggttc   4020
tccagctgcc tgggtggaga gactgtttgg ctatgactgg gcacagcaga ccattggttg   4080
ctctgatgca gcagtgttca gactgtcagc ccagggcagg ccagtcctgt ttgtgaagac   4140
agacctcagt ggggctctca atgagctgca ggatgaggct gccagactct cctggctggc   4200
aacaactggg gtcccctgtg cagctgtcct ggatgtggtc acagaagctg gaagggactg   4260
gctcctgctg ggtgaggtgc ctgggcagga cctcctgtcc tctcacctgg ctccagctga   4320
gaaagtgtca atcatggctg atgccatgag aagactccac accctggacc cagccacctg   4380
cccctttgac caccaggcca agcacaggat tgagagggcc agaaccagga tggaggctgg   4440
cctggtggac caggatgacc tggatgaaga acaccagggc ctggcccctg ctgaactgtt   4500
tgccaggctc aaggcatcca tgccagatgg tgaggacctg gtggtgactc atggggatgc   4560
ctgcctgccc aacatcatgg tggaaaatgg aaggttctct ggcttcattg actgtggcag   4620
gctgggagtg gctgacaggt accaggacat tgccctggca accagggaca ttgcagaaga   4680
gctgggggga gaatgggcag acaggttcct ggtgctctat ggcattgcag cccctgactc   4740
ccagagaatt gccttctaca gactgctgga tgagttcttc taaatcgatt ataatcagcc   4800
ataccacatt tgtagaggtt ttacttgctt taaaaaacct cccacacctc cccctgaacc   4860
tgaaacataa aatgaatgca atgttgttgt taaacttgtt tattgcagct tataatggtt   4920
acaaataaag caatagcatc acaaatttca caaataaagc atttttttca ctgcattcta   4980
gttgtggttt gtccaaactc atcaatgtgg aaaataacta ccagtttcct aagcttataa   5040
cttcgtatag catacattat acgaagttat aagctagaca aaagtatctt accccaatgg   5100
tagccctgta cccaataaaa gtaggtgttc agtttcatat cctatgaaat accctcttga   5160
tacttttact ttgcatgagg atttagaaga aaaaagtttt actataatcc ttaacttagg   5220
```

aaattctttt gaattggaaa tgaaacacaa attgcttttc attgatatgc catatgatta 5280
tatgaataaa acatgaaatc ttcatattgg attctagtat atacccaagt aaatattttt 5340
tccctagaag agtgccaagt gtgttaaaac cttttggttt aataaagcag aaaaaaataa 5400
actctaaaaa tcataattaa aaatgaaatg cttttattta tagcaattaa ctacaacatg 5460
tttagactta catactatta aatataatat atttaagatc ccctcatgat aaatatgttc 5520
attattttgt aggctgttga tgcactaata tgtatgtaga ttactttgtg aattgccctt 5580
aataaaattt aaaactttag gctagtaaac ctgtaacact caacttagtt ctgaactatc 5640
tcactattct tttgcaagaa tttacttagg taatgccaac taatttattc caaggccaaa 5700
aagatgacaa tgtcttatat attataaaaa ctaataaaaa ccattttaaa acctagtata 5760
aatttaaagg tacttgctct tctggttcat ctcttctttt gtttacttct gctttcaaaa 5820
acttatttat tgtgaccata ttctttactt ccatttattg ttataattta taagatacta 5880
tacttgcaag caataaatgt tatcttttta gcttttaaat ggtctcattt gaaaagaata 5940
tataattagt aagtcatagc tactttaaat aaaaacttat tctttaagag attaaacact 6000
tctccaagtg atctgttttt ctttaattaa aacgttatta actcccaaaa tgatgttatt 6060
gtttttttat aatcttaaat accaataatt accaggtcta ttttgatttt gatacaggat 6120
aaaaactact attaattact taagaatgtg ttctttttta tatgtaccat tttcatgatc 6180
aaagttggtg atatgactga ggttttgatt attattaaac agatagttaa tatgatatat 6240
tcctcatttt tccaaatgaa aggaaaaatg tcttatatgg aggaaaagat tggggcaggg 6300
ggattagtaa attattactt aaatatctga ataggaggat ttttcaatga aaggataaag 6360
gaagaatgat tgtatcatct gaatctttcc ctccctttcc tggagtttgt cctttcaacc 6420
cagtatacct accactccct tcatcaccta ctttcccatt acagtcccta tgtgttgggt 6480
ggtaactatt ttgttttggt gttaatatcc aagtttccct taataacacc tagtgaatgg 6540
aggaaggatg agcataccta cccatcagac atatttagcc accatattta atcaacaagc 6600
atgaagaaag gaagctagcc tctccccttc ctttcctcct gcctctctct ctcttctctg 6660
tcctcgctcc ctttcttccc atcaatattt tcagagcacc tcttatgcgc caggcattgg 6720
gatactcaaa ctggaggaaa caagaaaaaa aaaaaaaaaa ggcgaagacc tcagggaaat 6780
ttatattgct gctatatttt tttgagccta gtgtaaatta aaattcctta atgctgtgcc 6840
ttttaaaaac acaaataagc aaaatagttt atttcttcaa cagttaaatc cttagggtag 6900
gaaagtgatt caggatctat tgctactatt aactcttctt tcattttcac acaggataca 6960
cacaaatccg cttggtgaat ggcaagaccc catgtgaagg aagagtggag ctcaacattc 7020
ttgggtcctg gggtccctc tgcaactctc actgggacat ggaagatgcc catgttttat 7080
gccagcagct taaatgtgga gttgcccttt ctatcccggg aggagcacct tttgggaaag 7140
gaagtgagca ggtctggagg cacatgtttc actgcactgg gactgagaag cacatgggag 7200
attgttccgt cactgctctg ggcgcatcac tctgttcttc agggcaagtg gcctctgtaa 7260
tctgctcagg taagagaata agggcagcca gtgatgagcc actcatgacg gtgccttaag 7320
agtgggtgta cctaggagtt cccattgtgg ctcagtggta acaaactcga ctggtatcca 7380
tgagggtatg ggtttgatcc ctggccttgc tcaatgggtt aaggatccag cattgctgtg 7440
agctgtggta taggttgcag actctgctca ggtcccatgt tgctgtgatt gtggtgtagg 7500
ctgactgctg cagcttcaat ttgacccta gcccgggaat ttccataggc cacacgtgca 7560
gcactaagga aggaaaaaaa gaaaaaaaaa aaaaaagagt gggtgtgcct atagtgaaga 7620
acagatgtaa aagggaagtg aaagggattc cccattctg agggattgtg agaagtgtgc 7680
cagaatatta acttcatttg acttgttaca gggaaagtaa acttgacttt cacggacctc 7740
ctagttacct ggtgcttact atatgtcttc tcagagtacc tgattcattc ccagcctggt 7800
tgacccatcc ccctatctct atggctatgt ttatccagag cacatctatc taacactcca 7860
gctgatcttc ctgacacagc tgtggcaacc ctggatcctt taaccaactg tgccaggctg 7920
gagatcaaac ctaagcctct gcagcaaccc aagctgctgc agtcagattt ttaaccccct 7980
gtgccactgt gggtatctcc gatattttgt atcttctgtg actgagtggt ttgctgtttg 8040
cagggaacca gagtcagaca ctatccccgt gcaattcatc atcctcggac ccatcaagct 8100
ctattatttc agaagaaaat ggtgttgcct gcataggtga gaatcagtga ccaacctatg 8160
aaaatgatct caatcctctg aaatgcattt tattcatgtt ttatttcctc tttgcaggga 8220
gtggtcaact tcgcctggtc gatggaggtg gtcgttgtgc tgggagagta gaggtctatc 8280
atgagggctc ctggggcacc atctgtgatg acagctggga cctgaatgat gcccatgtgg 8340
tgtgcaaaca gctgagctgt ggatgggcca ttaatgccac tggttctgct cattttgggg 8400
aaggaacagg gcccatttgg ctggatgaga taaactgtaa tggaaaagaa tctcatattt 8460
ggcaatgcca ctcacatggt tgggggcggc acaattgcag gcataaggag gatgcaggag 8520
tcatctgctc gg 8532

<210> SEQ ID NO 119
<211> LENGTH: 4538
<212> TYPE: DNA
<213> ORGANISM: Sus scrofa

<400> SEQUENCE: 119
tatagatgac aaggctttgt gtctgatagg ggccagcgaa ctcagtaaag agggaagatg 60
agaaagataa tggcaagaat ttatccctga agtgtagttt tgacaaacca gtcacaaaga 120
ggtctaagaa attttggtca caaagttgtt ttgaatccca ggcattttat ttgcaatgat 180
tgcatatgtt ctggaaagga catctgaacc taagaaatag ttcatttgca ttgtgttata 240
ttttactaag gtctgagaaa taatcttgag atgagaatga actctacttc ttcagagtct 300
ggaaggaata aattatgaaa atgtattaat gcttctttaa accatattgt atatttatct 360
attactaaac aaaaagaagt agctctattt atttatttat ttatttattt atttatgtct 420
tttgtctctt tagggccaca cctgtggcat atggaggttc ccaggctaga ggtccaattg 480
gagatgtagc agccagccta tgccagagcc accgcaacac gggatctgag ccacgtctgt 540
gacttacacc acagctcaca gcaacgcctg atcctcaacc cactgagcga ggccagggat 600
cgaacccatg tcctcatgga tgctagttgg gttcgttaac tgctgagcca tgatgggaac 660
tccaaattaa ttatttctta tatttgttct tcatatattc atttctatag aaagaaataa 720
atacagattc agttaatgat ggcaggtaaa agcttaactt attaatcaaa ggagttaatc 780
caggcacaaa aattcaattc atggctctct gttaaaattt aggtataggt ttagcaggaa 840
gaaaaggtta gtagatgcag actattacat ttagaatgga tggacaatga agtcctacta 900
tacagcacag ggaactatat ccaatctctt gggatagaat atgatggaag acaaaatcag 960
aacaagagag tatatatata tgtgtgtgtg tgtgtgtgtg tgtgtgtgtg tgtgtgtgtg 1020
tgtgtgactg ggtcaccctg cggcacagca gaaattggca gaacattgta aatcaactat 1080
actttaatag gaaaaatact tttaagggct aaatttccaa tattctaacc atgtacacag 1140

```
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccccag   1680
aggtatttat ttgtttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccagctca acattcttgg gtcctggggg tccctctgca actctcactg   3060
ggacatggaa gatgcccatg ttttatgcca gcagcttaaa tgtggagttg ccctttctat   3120
cccgggagga gcaccttttg ggaaaggaag tgagcaggtc tggaggcaca tgtttcactg   3180
cactgggact gagaagcaca tgggagattg ttccgtcact gctctgggcg catcactctg   3240
ttcttcaggg caagtggcct ctgtaatctg ctcaggtaag agaataaggg cagccagtga   3300
tgagccactc atgacggtgc cttaagagtg ggtgtaccta ggagttccca ttgtggctca   3360
gtggtaacaa actcgactgg tatccatgag ggtatgggtt tgatccctgg ccttgctcaa   3420
tgggttaagg atccagcatt gctgtgagct gtggtatagg ttgcagactc tgctcaggtc   3480
```

```
ccatgttgct gtgattgtgg tgtaggctga ctgctgcagc ttcaatttga cccctagccc   3540

gggaatttcc ataggccaca cgtgcagcac taaggaagga aaaaaagaaa aaaaaaaaaa   3600

aagagtgggt gtgcctatag tgaagaacag atgtaaaagg gaagtgaaag ggattccccc   3660

attctgaggg attgtgagaa gtgtgccaga atattaactt catttgactt gttacaggga   3720

aagtaaactt gactttcacg gacctcctag ttacctggtg cttactatat gtcttctcag   3780

agtacctgat tcattcccag cctggttgac ccatccccct atctctatgg ctatgtttat   3840

ccagagcaca tctatctaac actccagctg atcttcctga cacagctgtg gcaaccctgg   3900

atcctttaac caactgtgcc aggctggaga tcaaacctaa gcctctgcag caacccaagc   3960

tgctgcagtc agatttttaa ccccctgtgc cactgtgggt atctccgata ttttgtatct   4020

tctgtgactg agtggtttgc tgtttgcagg gaaccagagt cagacactat ccccgtgcaa   4080

ttcatcatcc tcggacccat caagctctat tatttcagaa gaaaatggtg ttgcctgcat   4140

aggtgagaat cagtgaccaa cctatgaaaa tgatctcaat cctctgaaat gcattttatt   4200

catgttttat ttcctctttg cagggagtgg tcaacttcgc ctggtcgatg gaggtggtcg   4260

ttgtgctggg agagtagagg tctatcatga gggctcctgg ggcaccatct gtgatgacag   4320

ctgggacctg aatgatgccc atgtggtgtg caaacagctg agctgtggat gggccattaa   4380

tgccactggt tctgctcatt ttggggaagg aacagggccc atttggctgg atgagataaa   4440

ctgtaatgga aaagaatctc atatttggca atgccactca catggttggg ggcggcacaa   4500

ttgcaggcat aaggaggatg caggagtcat ctgctcgg                           4538
```

```
<210> SEQ ID NO 120
<211> LENGTH: 101
<212> TYPE: PRT
<213> ORGANISM: Sus scrofa

<400> SEQUENCE: 120

Pro Arg Leu Val Gly Gly Asp Ile Pro Cys Ser Gly Arg Val Glu Val
1               5                   10                  15

Gln His Gly Asp Thr Trp Gly Thr Val Cys Asp Ser Asp Phe Ser Leu
            20                  25                  30

Glu Ala Ala Ser Val Leu Cys Arg Glu Leu Gln Cys Gly Thr Val Val
        35                  40                  45

Ser Leu Leu Gly Gly Ala His Phe Gly Glu Gly Ser Gly Gln Ile Trp
    50                  55                  60

Ala Glu Glu Phe Gln Cys Glu Gly His Glu Ser His Leu Ser Leu Cys
65                  70                  75                  80

Pro Val Ala Pro Arg Pro Asp Gly Thr Cys Ser His Ser Arg Asp Val
                85                  90                  95

Gly Val Val Cys Ser
            100


<210> SEQ ID NO 121
<211> LENGTH: 100
<212> TYPE: PRT
<213> ORGANISM: Homo sapiens

<400> SEQUENCE: 121

Leu Arg Leu Val Asp Gly Asp Ser Arg Cys Ala Gly Arg Val Glu Ile
1               5                   10                  15

Tyr His Asp Gly Phe Trp Gly Thr Ile Cys Asp Asp Gly Trp Asp Leu
            20                  25                  30
```

-continued

```
Ser Asp Ala His Val Val Cys Gln Lys Leu Gly Cys Gly Val Ala Phe
        35                  40                  45

Asn Ala Thr Val Ser Ala His Phe Gly Glu Gly Ser Gly Pro Ile Trp
    50                  55                  60

Leu Asp Asp Leu Asn Cys Thr Gly Met Glu Ser His Leu Trp Gln Cys
65                  70                  75                  80

Pro Ser Arg Gly Trp Gly Gln His Asp Cys Arg His Lys Glu Asp Ala
                85                  90                  95

Gly Val Ile Cys
            100
```